United States Patent
Newman et al.

(10) Patent No.: US 12,031,183 B2
(45) Date of Patent: *Jul. 9, 2024

(54) METHODS AND SYSTEMS FOR DETERMINING PROPORTIONS OF DISTINCT CELL SUBSETS

(71) Applicant: The Board of Trustees of the Leland Stanford Junior University, Stanford, CA (US)

(72) Inventors: Aaron M. Newman, San Mateo, CA (US); Arash Ash Alizadeh, San Mateo, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1256 days.

This patent is subject to a terminal disclaimer.

(21) Appl. No.: 16/226,270

(22) Filed: Dec. 19, 2018

(65) Prior Publication Data

US 2019/0338364 A1    Nov. 7, 2019

Related U.S. Application Data

(63) Continuation of application No. 15/004,611, filed on Jan. 22, 2016, now Pat. No. 10,167,514.

(60) Provisional application No. 62/106,601, filed on Jan. 22, 2015.

(51) Int. Cl.
| | |
|---|---|
| *C12Q 1/6886* | (2018.01) |
| *C12Q 1/6809* | (2018.01) |
| *C12Q 1/6881* | (2018.01) |
| *G01N 33/50* | (2006.01) |
| *G16B 25/00* | (2019.01) |
| *G16B 25/10* | (2019.01) |
| *G16B 40/10* | (2019.01) |
| *G16C 20/20* | (2019.01) |

(52) U.S. Cl.
CPC ......... *C12Q 1/6886* (2013.01); *C12Q 1/6809* (2013.01); *C12Q 1/6881* (2013.01); *G01N 33/5005* (2013.01); *G16B 25/00* (2019.02); *G16B 25/10* (2019.02); *G16B 40/10* (2019.02); *G16C 20/20* (2019.02); *C12Q 2600/106* (2013.01); *C12Q 2600/158* (2013.01)

(58) Field of Classification Search
CPC ............ C12Q 2600/158; C12Q 1/6886; C12Q 2600/106; C12Q 2600/118; C12Q 2600/112; G16B 40/00; G16B 20/00; G16B 40/20; G16B 25/10; G16B 5/20; G16B 40/30; G16B 30/00; G16B 45/00; G16B 50/00; G16B 20/10; G16B 20/40; G16B 50/30; G16B 50/10; G16B 35/20; G16H 50/20; G16H 50/30; G16H 50/70; G16H 20/10; G16H 20/00; G16H 10/60; G16H 70/20; G16H 70/40; G16H 15/00; G06N 20/00; G06N 3/08; G06N 7/005; G06N 5/003; G06N 5/02; G06N 3/0472; G06N 3/0481; G06N 3/088; G06N 5/025; G16C 20/70; G06F 17/18; G06F 16/285; G06F 17/10; G06F 30/27; G06F 17/15; G06F 17/16

See application file for complete search history.

(56) References Cited

U.S. PATENT DOCUMENTS

| | | | |
|---|---|---|---|
| 6,661,004 B2 | 12/2003 | Aumond et al. | |
| 10,167,514 B2* | 1/2019 | Newman | C12Q 1/6886 |
| 11,802,314 B2* | 10/2023 | Newman | C12Q 1/6886 |
| 2005/0108753 A1 | 5/2005 | Saidi et al. | |
| 2013/0110756 A1 | 5/2013 | Zhang et al. | |
| 2016/0217253 A1 | 7/2016 | Newman et al. | |
| 2016/0341731 A1 | 11/2016 | Sood et al. | |
| 2019/0233898 A1* | 8/2019 | Newman | G16B 40/10 |
| 2019/0338364 A1* | 11/2019 | Newman | G16B 40/10 |

(Continued)

FOREIGN PATENT DOCUMENTS

| | | |
|---|---|---|
| CN | 103217411 | 7/2013 |
| JP | 2014-517954 | 7/2014 |
| WO | WO 2007/035613 | 3/2007 |

OTHER PUBLICATIONS

Rivenbark et al. Molecular and cellular heterogeneity in breast cancer: challenges for personalized medicine. Am J Pathology vol. 183 No. 4, 23 pages. (Year: 2013).*

(Continued)

*Primary Examiner* — Mary K Zeman
(74) *Attorney, Agent, or Firm* — Edward J. Baba; Bozicevic, Field & Francis LLP

(57) ABSTRACT

Methods of deconvolving a feature profile of a physical system are provided herein. The present method may include: optimizing a regression between a) a feature profile of a first plurality of distinct components and b) a reference matrix of feature signatures for a second plurality of distinct components, wherein the feature profile is modeled as a linear combination of the reference matrix, and wherein the optimizing includes solving a set of regression coefficients of the regression, wherein the solution minimizes 1) a linear loss function and 2) an $L_2$-norm penalty function; and estimating the fractional representation of one or more distinct components among the second plurality of distinct components present in the sample based on the set of regression coefficients. Systems and computer readable media for performing the subject methods are also provided.

23 Claims, 67 Drawing Sheets

Specification includes a Sequence Listing.

(56) References Cited

U.S. PATENT DOCUMENTS

2021/0040442 A1  2/2021  Rajagopal et al.

OTHER PUBLICATIONS

Gaiteri et al. Beyond modules and hubs: the potential of gene coexpression networks for investigating molecular mechanisms of complex brain disorders. Genes, Brain and Behavior vol. 13, p. 13-24. (Year: 2013).*

Yin (2013) identification of differential gene pathways with sparse principal component analysis. Georgia State University, 26 pages. (Year: 2013).*

Smola (2004) a tutorial on support vector regression. Statistics and computing vol. 14, pp. 199-222. (Year: 2004).*

Newman et al. (2014) Identifying stem cell gene expression patterns and phenotypic networks with AutoSOME. IN Kidder (eds) Stem Cell Transcriptional Networks: Methods and Protocols, Methods in Molecular Biology vol. 1150, chapter 6, p. 115-130. (Year: 2014).*

Sotiriou et al. (2009) Gene-expression patterns in Breast Cancer. The New England Journal of Medicine vol. 360 pp. 790-800. (Year: 2009).*

Mackey et al. (2011) "Divide-and-Conquer Matrix Factorization" Advances in Neural Information Processing Systems 24, edited by J. Shawe-Taylor et al. Proceedings from the conference, "Neural information Processing Systems" 2011 [online]. [Retrieved on Oct. 19, 2018] Retrieved from the internet <URL: https:/lwww.cs.cmu.edu/-atalwalk!dfc.pdf > pp. 1-21.

Wang et al. (2013) "Non-negative matrix factorization by maximizing correntropy for cancer clustering" BMC Bioinformatics 14(107): 107 (pp. 1-11).

Thiebaut, (2002) "Optimization issues in blind deconvolution algorithms", Proc. SPIE 4847, Astronomical Data Analysis II, 1-9.

Zheng et al., (2014) "Deconvolution of High Dimensional Mixtures via Boosting, with Application to Diffusion-Weighted MRI of Human Brain", Advances in Neural Information Processing Systems, 27: 2699-2707.

Cobos et al., (2018) "Computational deconvolution of transcriptomics data from mixed cell populations", Bioinformatics, vol. 34(11), pp. 1969-1779.

Krishnan et al., (2011) "Quantitative Analysis of Sub-Epithelial Connective Tissue Cell Population of Oral Submucous Fibrosis Using Support Vector Machine", Journal of Medical Imaging and Health Informatics, vol. 1, No. 1, pp. 4-12.

Newman et al., (2015) "Robust enumeration of cell subsets from tissue expression profiles", Nature Methods, vol. 12, No. 5, pp. 453-457.

Le et al. (2020) "A Review of Digital Cytometry Methods: Estimating the Relative Abundance of Cell Types in a Bulk of Cells", Briefings in Bioinformatics: 1-12.

Li et al. (2016) "Comprehensive Analyses of Tumor Immunity: Implications for Cancer Immunotherapy", Genome Biology, 2016, vol. 17, No. 1: 1-16.

Newman et al. (2017) "Data Normalization Considerations for Digital Tumor Dissection", Genome Biology, 2017, vol. 18, No. 1: 1-6.

Newman et al. (2019) "Determining Cell Type Abundance and Expression From Bulk Tissues with Digital Cytometry", Nature Biotechnology, vol. 37, No. 7: 773-782.

Steen et al. (2020) "Profiling Cell Type Abundance and Expression in Bulk Tissues with CIBERSORTx", Methods Mol Bio, vol. 2117: 135-157.

Newman et al. (2014) "An ultrasensitive method for quantitating circulating tumor DNA with broad patient coverage" Nature Medicine 20: 548-554.

Abbas et al., "Immune response in silico (IRIS): immune-specific genes identified from a compendium of microarray expression data" Genes and Immunity, 2005, pp. 319-331, vol. 6, No. 4.

Abbas et al., "Deconvolution of Blood Microarray Data Identifies Cellular Activation Patterns in Systematic Kupus Erythematosus", PLOS One, Jul. 2009, p. e6098, vol. 4, No. 7.

Ahn et al., "DeMix: deconvolution for mixed cancer transcriptomes using raw measured data" Bioinformatics, 2013, pp. 1865-1871, vol. 29, No. 15.

Benita et al., "Gene enrichment profiles reveal T-cell development, differentiation, and lineage-specific transcription factors including ZBTB25 as a novel NF-AT repressor", Blood, 2010, pp. 5376-5384, vol. 115.

Burdick and Murray, "Deconvolution of gene expression from cell populations across the C. elegans lineage", BMC Bioinformatics, Jun. 22, 2012, p. 204, vol. 14.

Cherlassky et al., "Practical selection of SVM parameters and noise estimation for SVM regression", Neural Netk, 2004, pp. 113-126, vol. 17.

Coussens et al., "Neutralizing tumor-promoting chronic inflammation: a magic bullet?", Science, 2013, pp. 286-291, vol. 339.

Drucker et al., "Support Vector Regression Machines", MIT Press, 1997, pp. 155-161, vol. 9.

Farrar et al., "Multicollinearity in Regression Analysis: The Problem Revisited", R. R. Rev. Econ. Stat., 1967, pp. 92-107, vol. 49.

Gaujoux and Seoighe, "CellMix: a comprehensive toolbox for gene expression deconvolution", Bioinformatics, 2013, pp. 2211-2212, vol. 29, No. 17.

Gong and Szutakowski, "DeconRNASeq: a statistical framework for deconvolution of heterogeneous tissue samples based on mRNA-Seq data", Bioinformatics, 2013, pp. 1083-1085, vol. 29, No. 8.

Gong et al., "Optimal Deconvolution of Transcriptional Profiling Data Using Quadratic Programming with Application to Complex Clinical Blood Samples", PLOS One, Nov. 2011, p. e27156.

Hanahan et al., "Hallmarks of Cancer: The Next Generation", Cell, 2011, pp. 646-674, vol. 144.

Kuhn et al., "Population-specific expression analysis (PSEA) reveals molecular changes in diseased brain", Nat Methods, 2011, pp. 945-947, vol. 8.

Levy et al., "Active Idiotypic Vaccination Versus Control Immunotherapy for Folicular Lymphoma", J Clin. Oncol., 2014, pp. 1797-1803, vol. 32.

Liebner et al., "MMAD: microarray microdissection with analysis of difference is a computational tool for deconvoluting cell type= speficic contributions from tissue samples", Bioinformatics, 2014, pp. 682-689, vol. 30, No. 5.

Lu et al., "Expression deconvolution: A reinterpretation of DNA microarray data reveals dynamic changes in cell populations", PNAS, 2003, pp. 10370-10375, vol. 100, No. 18.

Lukk et al., "A global map of human gene expression", NAt. Biotechnol, 2010, pp. 322-324, vol. 28.

Qiao et al., "PERT: A Method for Expression Deconvolution of Human Blood Samples from Varied Microenvironmental and Developmental Conditions", PLOS Comput. Biol., 2012, p. e1002838, vol. 8.

Scholkopf et al., "New Support Vector Algorithms", Neural Comput., 2000, pp. 1207-1245, vol. 12.

Shen-Orr and Gajoux, "Computational deconvolution: extracting cell type-specific information from heterogeneous samples", Curr. Opin. Immunol., 2013, pp. 571-578, vol. 25.

Shen-Orr et al., "Cell type-specific gene expression differences in complex tissues", Nat. Methods., 2010, pp. 287-289, vol. 7.

Storey et al., "Statistical significance for genomewide studies", Proc. Natl. Acad. Sci. U. S. A., 2003, pp. 9440-9445, vol. 100.

Wang et al., "The doubly regularized support vector machine", Statistica Sinica, 2006, pp. 589-615, vol. 16, No. 2.

Yoshihara et al., "Inferring tumour purity and stromal and immune cell a dmixture from expression data", Nat. Commun., 2013, p. 2612, vol. 4.

Zhong and Liu, "Gene expression deconvolution in linear space", Nat. Methods., 2012, pp. 8-9, vol. 9.

Zhong et al., "Digital sorting of complex tissues for cell type-specific gene expression profiles", BMC Bioinformatics, 2013, p. 89, vol. 14.

(56) References Cited

OTHER PUBLICATIONS

Zuckerman (2013) PLOS Computational Biology 9:e1003189.
Johnson et al. (2007) "Adjusting batch effects in microarray expression data using empirical Bayes methods" Biostatistics 8(1): 118-127.
Wilhelm-Benartzi et al. (2013) "Review of processing and analysis methods for DNA methylation array data" British J of Cancer 109(6): 1394-1402.
Chen et al. (2017) "Inference of immune cell composition on the expression profiles of mouse tissue." Scientific reports 7: 1-11.
Ju et al. (2013) "Defining cell-type specificity at the transcriptional level in human disease." Genome research 23: 1862-1873.
Sun et al. (2010) "Combined feature selection and cancer prognosis using support vector machine regression." IEEE/ACM transactions on computational biology and bioinformatics 8(6): 1671-1677.
Caicedo, J.C. et al., (2017) Data-analysis strategies for image-based cell profiling. Nature Methods, vol. 14, No. 9, p. 849-863. (Aug. 11, 2017).
Chen, C. et al, (2011) Removing batch effects in analysis of expression microarray data: an evaluation of six batch adjustment methods. PLOS One vol. 6, issue 2, e17238, 10 pages.
Definition of normal distribution, Wikipedia.com downloaded Jan. 2024 (Year: 2024).
Definition of sampling, and random sampling, Wikipedia.com, downloaded Jan. 2024 (Year: 2024).
Definition of simple random sampling, Wikipedia.com downloaded Jan. 2024 (Year: 2024).
Goh et al., (2017) Why batch effects matter in Omics data and how to avoid them. Trends in Biotechnology, vol. 25, No. 6, p. 498-507 (Jun. 2017).
Meng et al., (2013) Scalable simple random sampling and stratified sampling, Proceedings of the 30th int conf on machine learning atlanta georgia, vol. 28.
Tung et al., (2017) Batch effects and the effective design of single cell gene expression studies. Scientific reports, vol. 7, e39921, 15 pages (Jan. 2017).
Wagner et al., (2016) Revealing the vectors of cellular identify with single cell genomics. Nature Biotechnology vol. 14, No. 11, p. 1145-1168.

* cited by examiner

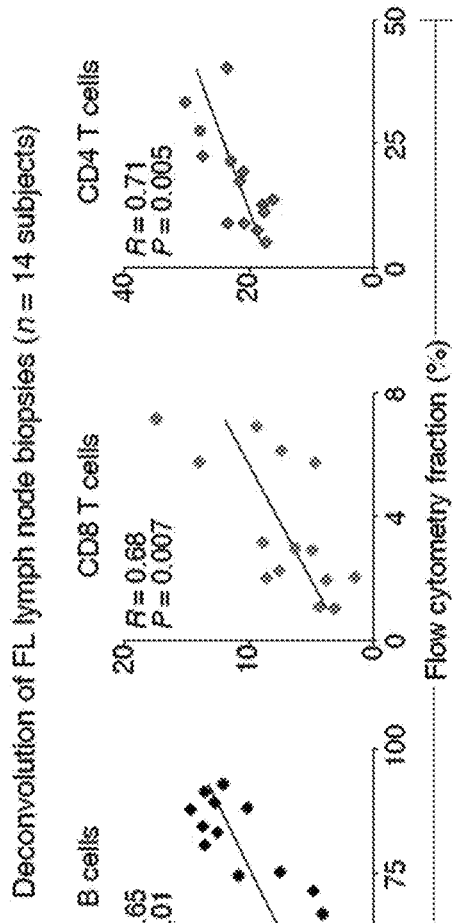
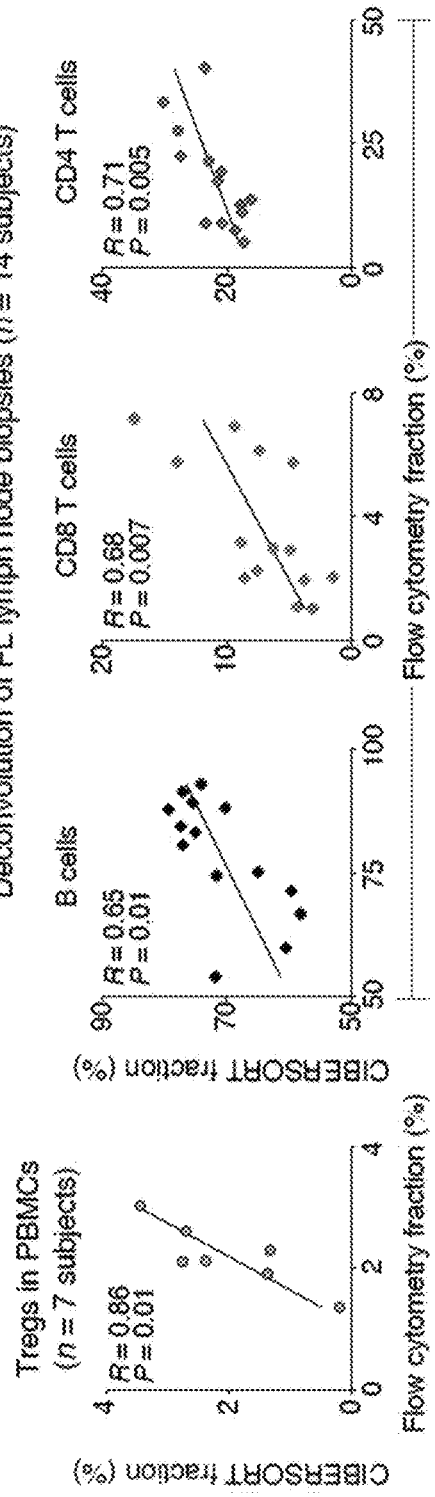
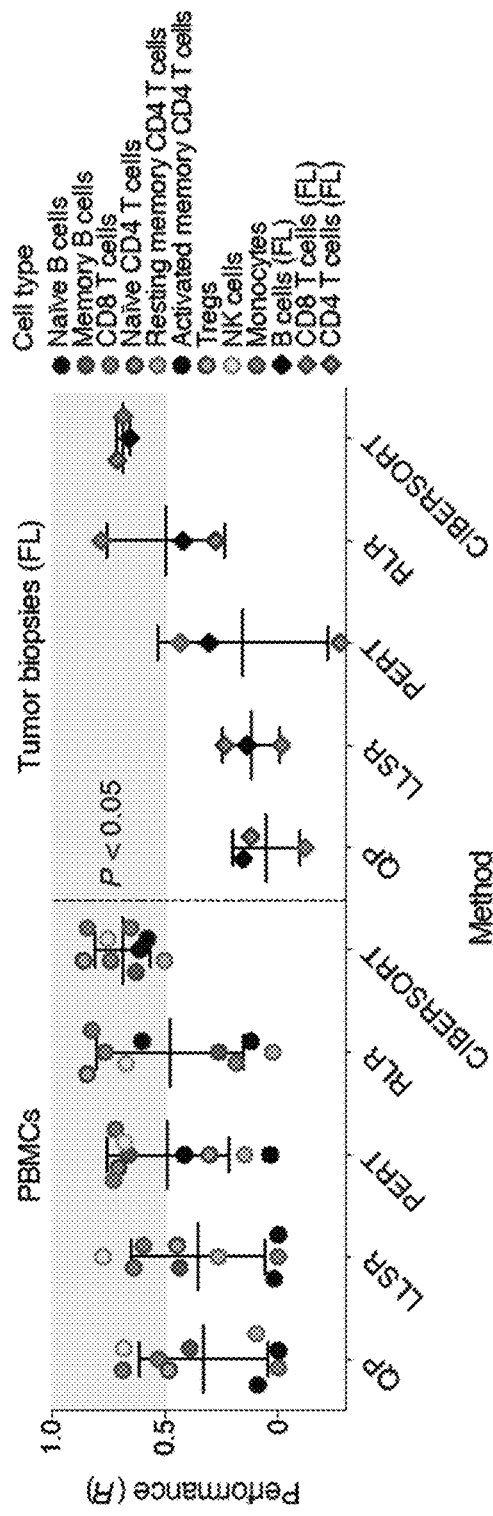

Fig. 4b
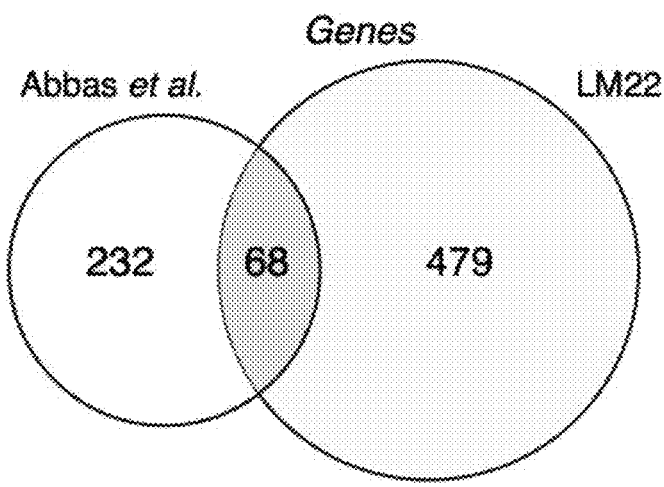
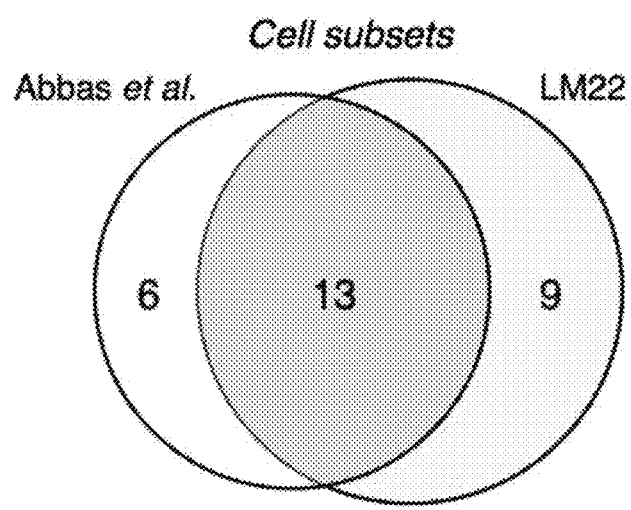
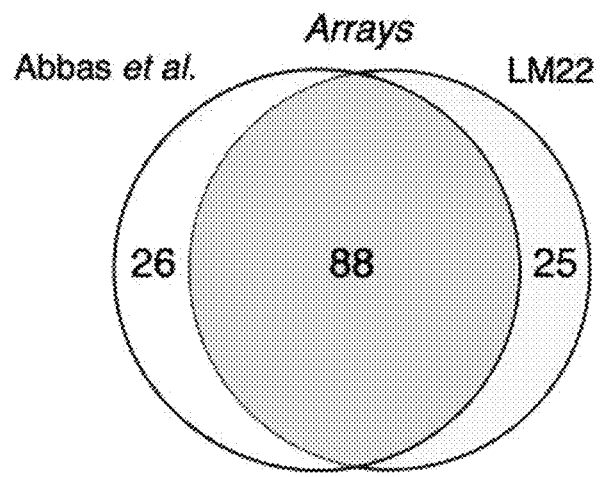

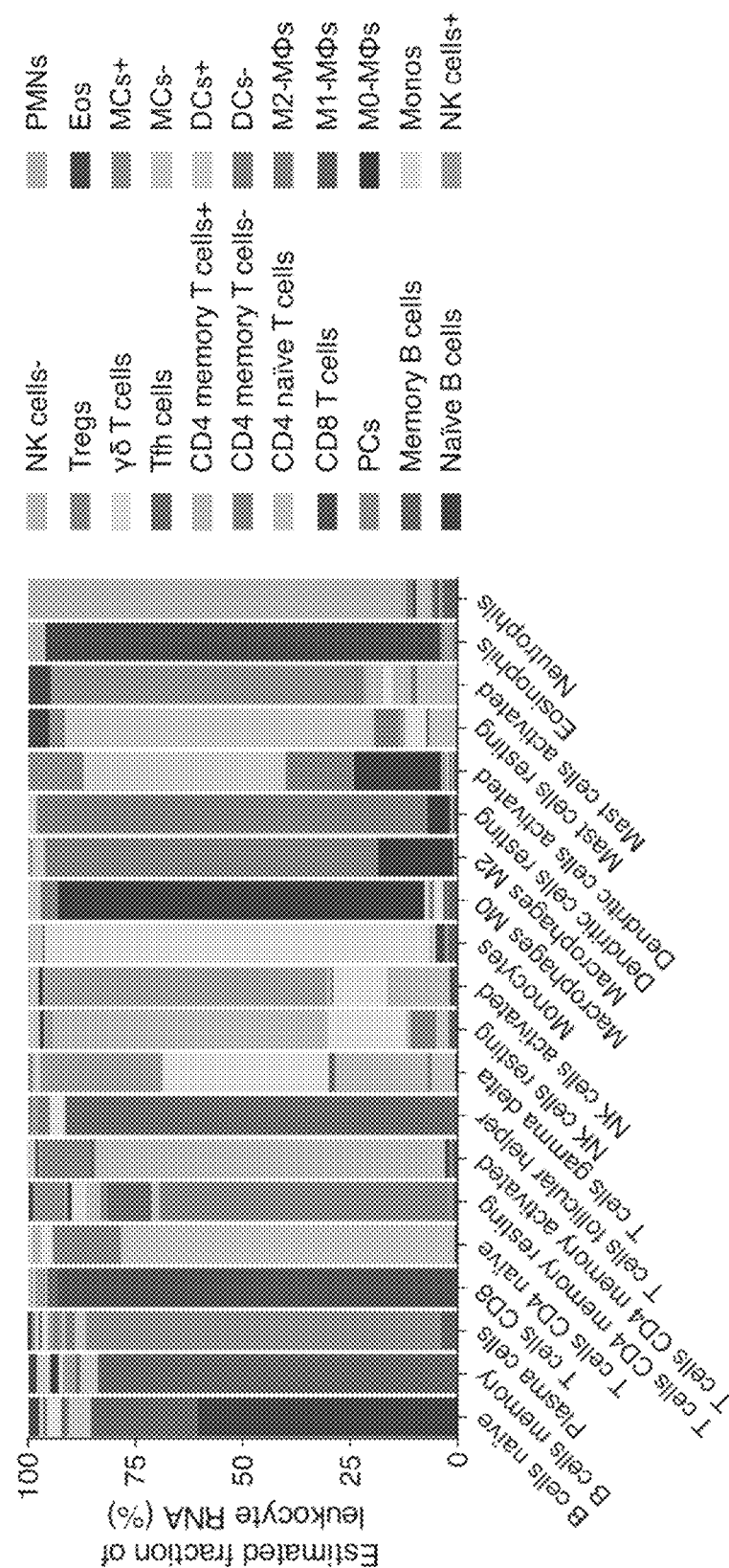

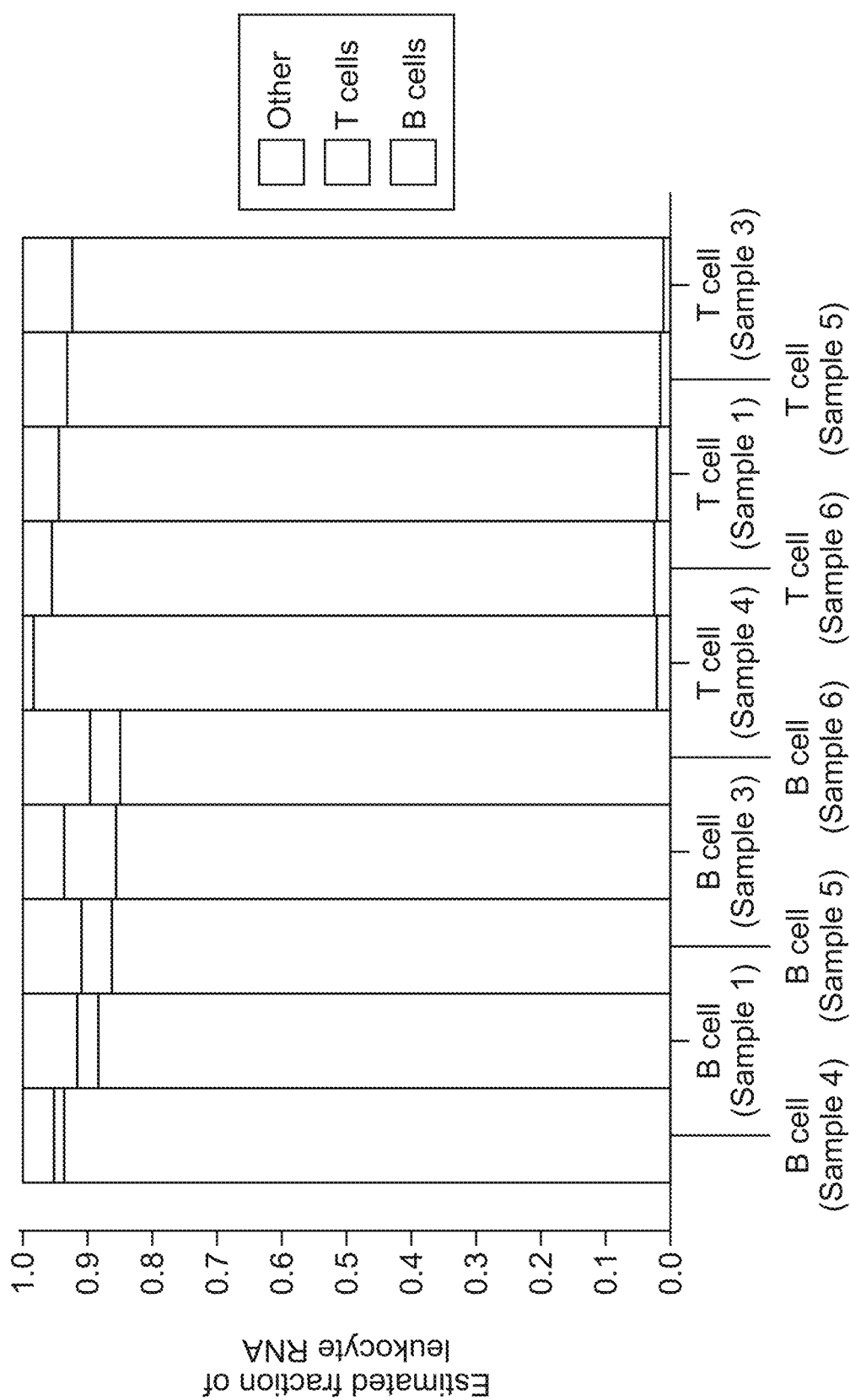

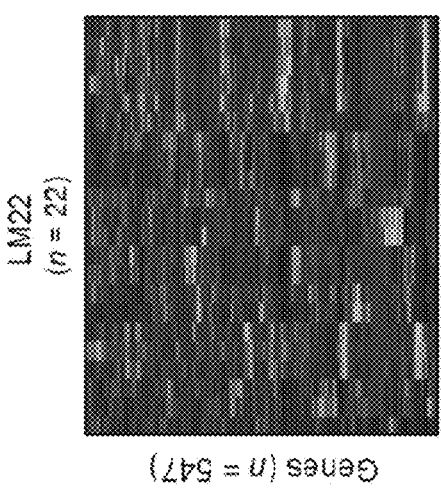
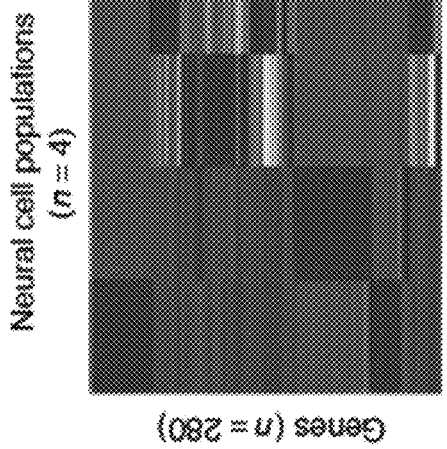
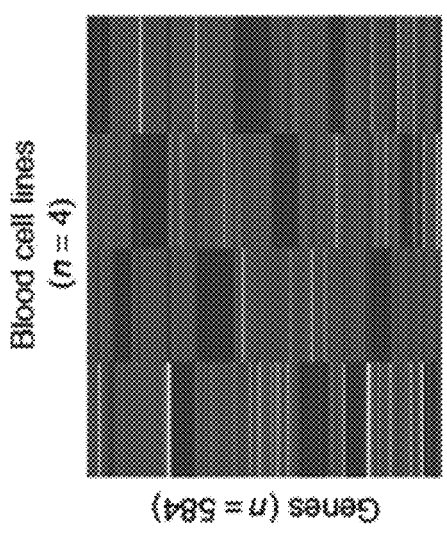

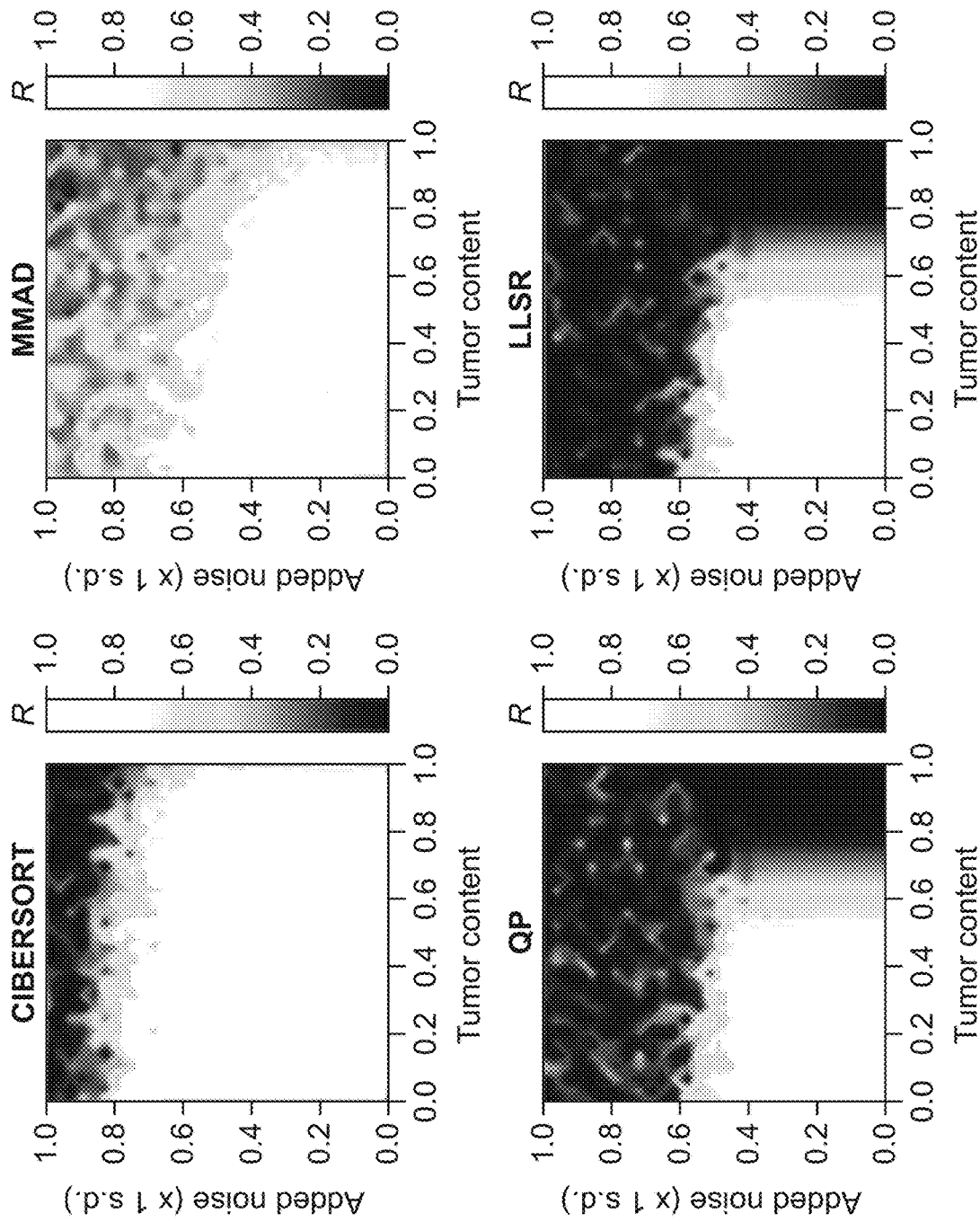

Fig. 10a
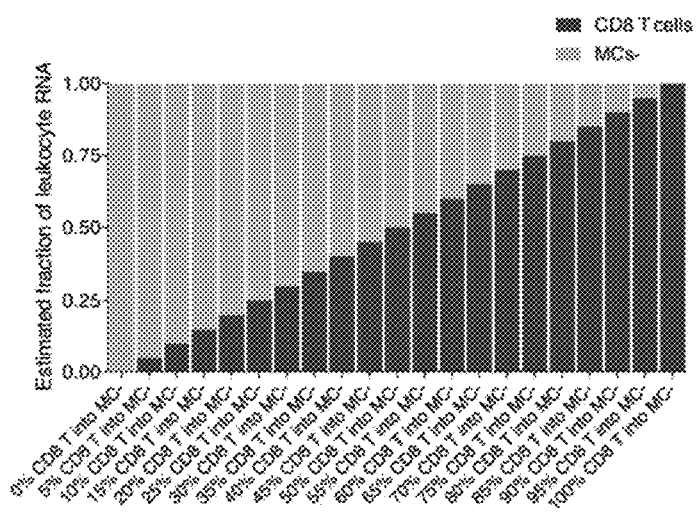
Fig. 10b
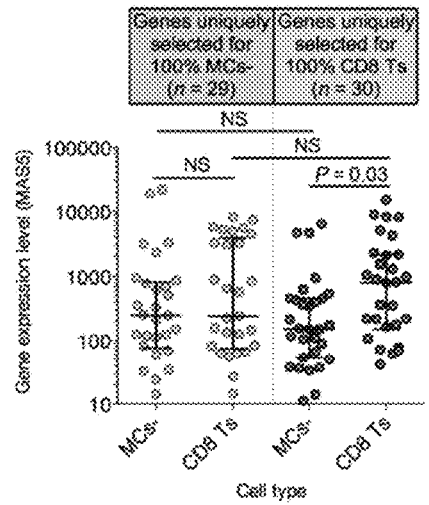
Fig. 10c
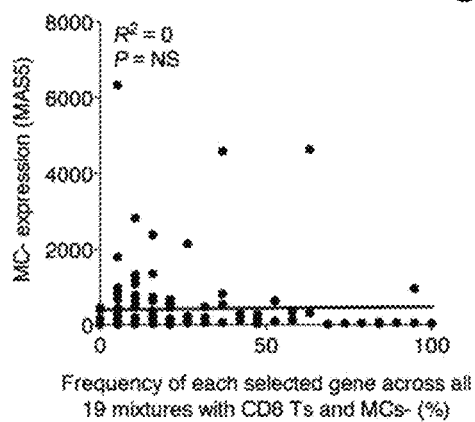
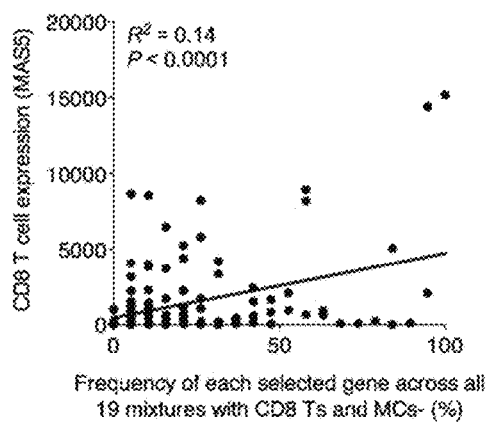
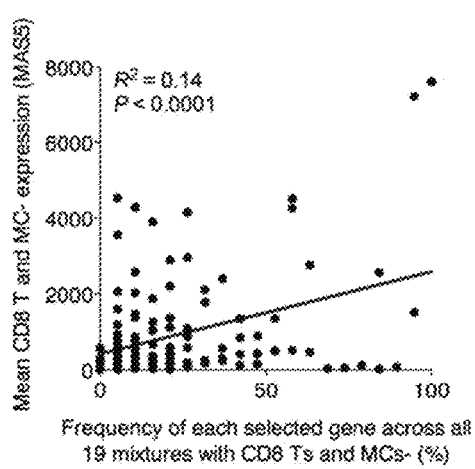
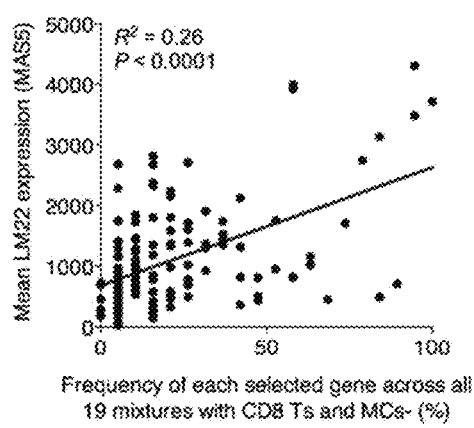

Fig. 13b
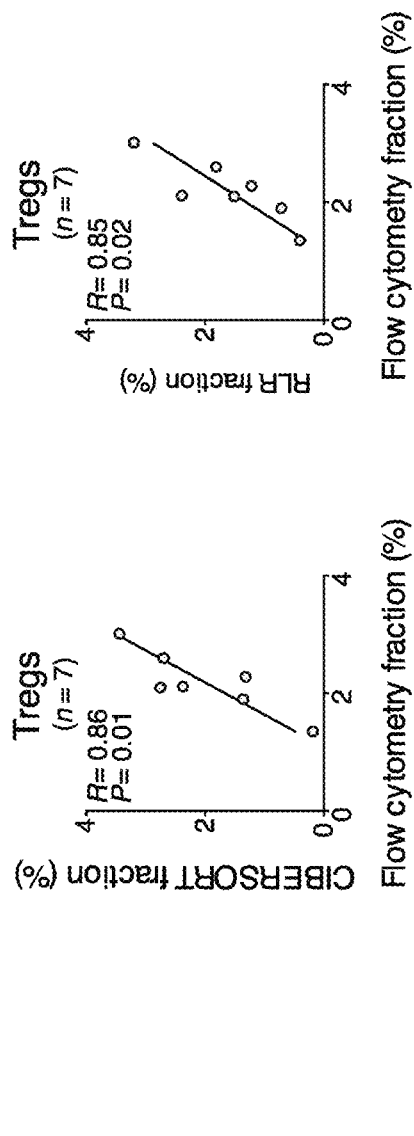
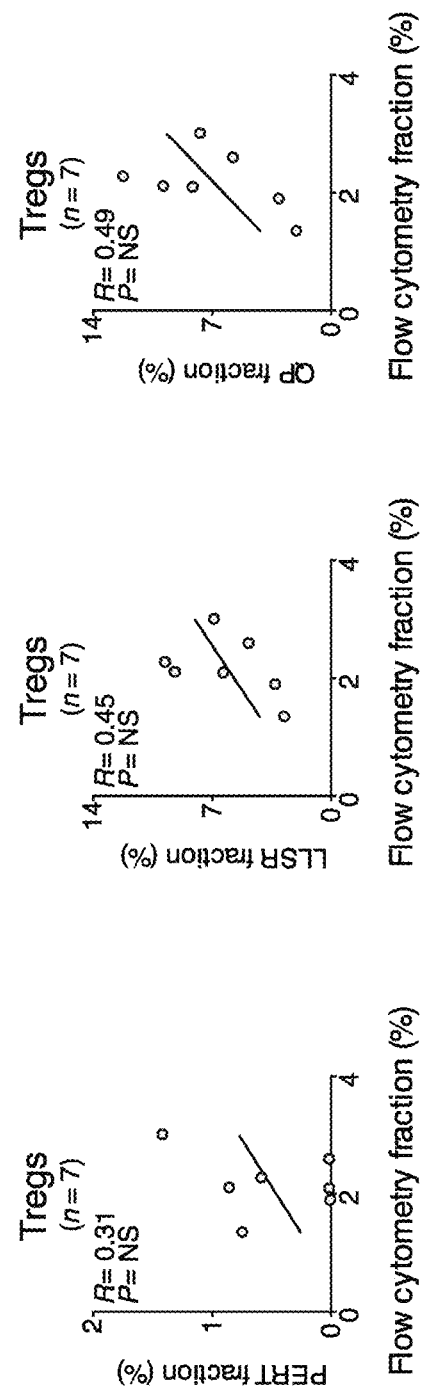

| Data set | PubMed ID | Sample ID | Sample type | Population | Abbreviated name |
|---|---|---|---|---|---|
| Chtanova et al. (2004) J Immunol 173: 68; Chtanova et al. (2005) J Immunol 175:7837 | 16339519 | A_LW_mastcellctl_U133A | A_LW_mastcellctl_U133A | Mast cells unstimulated | MCs- |
| Chtanova et al. (2004) J Immunol 173: 68; Chtanova et al. (2005) J Immunol 175:7837 | 16339519 | A_LW_mastcellgE_U133A | A_LW_mastcellgE_U133A | Mast cells stimulated | MCs+ |
| Chtanova et al. (2004) J Immunol 173: 68; Chtanova et al. (2005) J Immunol 175:7837 | 16339519 | A_LW_neutrophil_U133A | A_LW_neutrophil_U133A | Neutrophils | PMNs |
| Chtanova et al. (2004) J Immunol 173: 68; Chtanova et al. (2005) J Immunol 175:7837 | 16339519 | A_MF_2hEosinophils_U133A | A_MF_2hEosinophils_U133A | Eosinophils | Eos |
| Chtanova et al. (2004) J Immunol 173: 68; Chtanova et al. (2005) J Immunol 175:7837 | 16339519 | A_MF_ControlEosinophil | A_MF_ControlEosinophil | Eosinophils | Eos |
| Chtanova et al. (2004) J Immunol 173: 68; Chtanova et al. (2005) J Immunol 175:7837 | 16339519 | A_MF_ControlMASTCELL_U133A | A_MF_ControlMASTCELL_U133A | Mast cells unstimulated | MCs- |
| Chtanova et al. (2004) J Immunol 173: 68; Chtanova et al. (2005) J Immunol 175:7837 | 16339519 | A_MF_IgEMASTCELL_U133A | A_MF_IgEMASTCELL_U133A | Mast cells stimulated | MCs+ |
| Chtanova et al. (2004) J Immunol 173: 68; Chtanova et al. (2005) J Immunol 175:7837 | 16339519 | A_MF_neutrophils_U133A | A_MF_neutrophils_U133A | Neutrophils | PMNs |
| Chtanova et al. (2004) J Immunol 173: 68; Chtanova et al. (2005) J Immunol 175:7837 | 16339519 | A_TS_MSNeutroLPS_U133A | A_TS_MSNeutroLPS_U133A | Neutrophils | PMNs |
| Chtanova et al. (2004) J Immunol 173: 68; Chtanova et al. (2005) J Immunol 175:7837 | 16339519 | A_TS_PN_gdTcells_U133A | A_TS_PN_gdTcells_U133A | T cells gamma delta | γδ T cells |
| Chtanova et al. (2004) J Immunol 173: 68; Chtanova et al. (2005) J Immunol 175:7837 | 16339519 | A_TS_PN_gdTcellsREP_A | A_TS_PN_gdTcellsREP_A | T cells gamma delta | γδ T cells |
| GSE22886 | 19789058 | GSM565269 | CD8Tcell-N0-1 | T cells CD8 | CD8 T cells |
| GSE22886 | 19789058 | GSM565270 | CD8Tcell-N0-2 | T cells CD8 | CD8 T cells |
| GSE22886 | 19789058 | GSM565271 | CD8Tcell-N0-3 | T cells CD8 | CD8 T cells |
| GSE22886 | 19789058 | GSM565272 | CD8Tcell-N0-4 | T cells CD8 | CD8 T cells |
| GSE22886 | 19789058 | GSM565287 | MemoryTcell-RO-unactivated-1 | T cells CD4 memory RO unactivated | CD4 memory T cells- |
| GSE22886 | 19789058 | GSM565288 | MemoryTcell-RO-unactivated-2 | T cells CD4 memory RO unactivated | CD4 memory T cells- |
| GSE22886 | 19789058 | GSM565289 | MemoryTcell-RO-unactivated-3 | T cells CD4 memory RO unactivated | CD4 memory T cells- |
| GSE22886 | 19789058 | GSM565290 | MemoryTcell-RO-activated-1 | T cells CD4 memory RO activated | CD4 memory T cells+ |
| GSE22886 | 19789058 | GSM565291 | MemoryTcell-RO-activated-2 | T cells CD4 memory RO activated | CD4 memory T cells+ |
| GSE22886 | 19789058 | GSM565292 | MemoryTcell-RO-activated-3 | T cells CD4 memory RO activated | CD4 memory T cells+ |
| GSE22886 | 19789058 | GSM565293 | NKcell-control-1 | NK cells unstimulated | NK cells- |
| GSE22886 | 19789058 | GSM565294 | NKcell-control-2 | NK cells unstimulated | NK cells- |
| GSE22886 | 19789058 | GSM565295 | NKcell-control-3 | NK cells unstimulated | NK cells- |
| GSE22886 | 19789058 | GSM565296 | NKcell-control-4 | NK cells unstimulated | NK cells- |
| GSE22886 | 19789058 | GSM565297 | NKcell-IL2stimulated-1 | NK cells stimulated | NK cells+ |
| GSE22886 | 19789058 | GSM565298 | NKcell-IL2stimulated-2 | NK cells stimulated | NK cells+ |
| GSE22886 | 19789058 | GSM565299 | NKcell-IL2stimulated-3 | NK cells stimulated | NK cells+ |
| GSE22886 | 19789058 | GSM565300 | NKcell-IL2stimulated-4 | NK cells stimulated | NK cells+ |
| GSE22886 | 19789058 | GSM565301 | NKcell-IL2stimulated-5 | NK cells stimulated | NK cells+ |
| GSE22886 | 19789058 | GSM565302 | NKcell-IL15stimulated-1 | NK cells stimulated | NK cells+ |
| GSE22886 | 19789058 | GSM565303 | NKcell-IL15stimulated-2 | NK cells stimulated | NK cells+ |
| GSE22886 | 19789058 | GSM565304 | NKcell-IL15stimulated-3 | NK cells stimulated | NK cells+ |
| GSE22886 | 19789058 | GSM565305 | NKcell-IL15stimulated-4 | NK cells stimulated | NK cells+ |
| GSE22886 | 19789058 | GSM565306 | NKcell-IL15stimulated-5 | NK cells stimulated | NK cells+ |
| GSE22886 | 19789058 | GSM565307 | NKcell-IL15stimulated-6 | NK cells stimulated | NK cells+ |
| GSE22886 | 19789058 | GSM565308 | Bcell-naive-1 | B cells naive | Naive B cells |
| GSE22886 | 19789058 | GSM565309 | Bcell-naive-2 | B cells naive | Naive B cells |
| GSE22886 | 19789058 | GSM565310 | Bcell-naive-3 | B cells naive | Naive B cells |
| GSE22886 | 19789058 | GSM565311 | Bcell-naive-4 | B cells naive | Naive B cells |
| GSE22886 | 19789058 | GSM565312 | Bcell-naive-5 | B cells naive | Naive B cells |
| GSE22886 | 19789058 | GSM565313 | Bcell-naive-6 | B cells naive | Naive B cells |
| GSE22886 | 19789058 | GSM565314 | Bcell-naive-7 | B cells naive | Naive B cells |
| GSE22886 | 19789058 | GSM565315 | Bcell-Memory_IgG_IgA-1 | B cells memory | Memory B cells |
| GSE22886 | 19789058 | GSM565316 | Bcell-Memory_IgG_IgA-2 | B cells memory | Memory B cells |
| GSE22886 | 19789058 | GSM565317 | Bcell-Memory_IgG_IgA-3 | B cells memory | Memory B cells |
| GSE22886 | 19789058 | GSM565318 | Bcell-Memory_IgG_IgA-4 | B cells memory | Memory B cells |
| GSE22886 | 19789058 | GSM565319 | Bcell-Memory_IgM-1 | B cells memory | Memory B cells |
| GSE22886 | 19789058 | GSM565320 | Bcell-Memory_IgM-2 | B cells memory | Memory B cells |
| GSE22886 | 19789058 | GSM565321 | Bcell-Memory_IgM-3 | B cells memory | Memory B cells |
| GSE22886 | 19789058 | GSM565322 | Bcell-Memory_IgM-4 | B cells memory | Memory B cells |
| GSE22886 | 19789058 | GSM565323 | PlasmaCell-FromPBMC-1 | Plasma cells | PCs |
| GSE22886 | 19789058 | GSM565324 | PlasmaCell-FromPBMC-2 | Plasma cells | PCs |
| GSE22886 | 19789058 | GSM565325 | PlasmaCell-FromPBMC-3 | Plasma cells | PCs |
| GSE22886 | 19789058 | GSM565326 | PlasmaCell-FromBoneMarrow-1 | Plasma cells | PCs |
| GSE22886 | 19789058 | GSM565327 | PlasmaCell-FromBoneMarrow-2 | Plasma cells | PCs |
| GSE22886 | 19789058 | GSM565328 | PlasmaCell-FromBoneMarrow-3 | Plasma cells | PCs |
| GSE22886 | 19789058 | GSM565329 | PlasmaCell-FromBoneMarrow-4 | Plasma cells | PCs |

Fig. 16k

| Data set | PubMed ID | Sample ID | Sample type | Population | Abbreviated name |
|---|---|---|---|---|---|
| GSE22886 | 15789058 | GSM565330 | Monocyte-Day0-1 | Monocytes | Monos |
| GSE22886 | 15789058 | GSM565331 | Monocyte-Day0-2 | Monocytes | Monos |
| GSE22886 | 15789058 | GSM565332 | Monocyte-Day0-3 | Monocytes | Monos |
| GSE22886 | 15789058 | GSM565333 | Monocyte-Day0-4 | Monocytes | Monos |
| GSE22886 | 15789058 | GSM565334 | Monocyte-Day0-5 | Monocytes | Monos |
| GSE22886 | 15789058 | GSM565335 | Monocyte-Day0-6 | Monocytes | Monos |
| GSE22886 | 15789058 | GSM565336 | Monocyte-Day0-7 | Monocytes | Monos |
| GSE22886 | 15789058 | GSM565337 | Monocyte-Day0-8 | Monocytes | Monos |
| GSE22886 | 15789058 | GSM565338 | Monocyte-Day0-9 | Monocytes | Monos |
| GSE22886 | 15789058 | GSM565339 | Monocyte-Day0-10 | Monocytes | Monos |
| GSE22886 | 15789058 | GSM565340 | Monocyte-Day0-11 | Monocytes | Monos |
| GSE22886 | 15789058 | GSM565341 | Monocyte-Day0-12 | Monocytes | Monos |
| GSE22886 | 15789058 | GSM565354 | Monocyte-Day7-1 | Macrophages M0 | M0-MΦs |
| GSE22886 | 15789058 | GSM565355 | Monocyte-Day7-2 | Macrophages M0 | M0-MΦs |
| GSE22886 | 15789058 | GSM565356 | Monocyte-Day7-3 | Macrophages M0 | M0-MΦs |
| GSE22886 | 15789058 | GSM565357 | Monocyte-Day7-4 | Macrophages M0 | M0-MΦs |
| GSE22886 | 15789058 | GSM565358 | Monocyte-Day7-5 | Macrophages M0 | M0-MΦs |
| GSE22886 | 15789058 | GSM565359 | Monocyte-Day7-6 | Macrophages M0 | M0-MΦs |
| GSE22886 | 15789058 | GSM565360 | Monocyte-Day7-7 | Macrophages M0 | M0-MΦs |
| GSE22886 | 15789058 | GSM565361 | Monocyte-Day7-8 | Macrophages M0 | M0-MΦs |
| GSE22886 | 15789058 | GSM565362 | Monocyte-Day7-9 | Macrophages M0 | M0-MΦs |
| GSE22886 | 15789058 | GSM565363 | Monocyte-Day7-10 | Macrophages M0 | M0-MΦs |
| GSE22886 | 15789058 | GSM565364 | Monocyte-Day7-11 | Macrophages M0 | M0-MΦs |
| GSE22886 | 15789058 | GSM565365 | Monocyte-Day7-12 | Macrophages M0 | M0-MΦs |
| GSE22886 | 15789058 | GSM565366 | DendriticCell-Control-1 | Dendritic cells unstimulated | DCs- |
| GSE22886 | 15789058 | GSM565367 | DendriticCell-Control-2 | Dendritic cells unstimulated | DCs- |
| GSE22886 | 15789058 | GSM565368 | DendriticCell-Control-3 | Dendritic cells unstimulated | DCs- |
| GSE22886 | 15789058 | GSM565369 | DendriticCell-Control-4 | Dendritic cells unstimulated | DCs- |
| GSE22886 | 15789058 | GSM565370 | DendriticCell-Control-5 | Dendritic cells unstimulated | DCs- |
| GSE22886 | 15789058 | GSM565371 | DendriticCell-Control-6 | Dendritic cells unstimulated | DCs- |
| GSE22886 | 15789058 | GSM565372 | DendriticCell-LPSstimulated-1 | Dendritic cells stimulated | DCs+ |
| GSE22886 | 15789058 | GSM565373 | DendriticCell-LPSstimulated-2 | Dendritic cells stimulated | DCs+ |
| GSE22886 | 15789058 | GSM565374 | DendriticCell-LPSstimulated-3 | Dendritic cells stimulated | DCs+ |
| GSE22886 | 15789058 | GSM565375 | DendriticCell-LPSstimulated-4 | Dendritic cells stimulated | DCs+ |
| GSE22886 | 15789058 | GSM565376 | DendriticCell-LPSstimulated-5 | Dendritic cells stimulated | DCs+ |
| GSE22886 | 15789058 | GSM565377 | DendriticCell-LPSstimulated-6 | Dendritic cells stimulated | DCs+ |
| GSE22886 | 15789058 | GSM565378 | Neutrophil-Resting-1 | Neutrophils | PMNs |
| GSE22886 | 15789058 | GSM565379 | Neutrophil-Resting-2 | Neutrophils | PMNs |
| GSE22886 | 15789058 | GSM565380 | Neutrophil-Resting-3 | Neutrophils | PMNs |
| GSE22886 | 15789058 | GSM565381 | Neutrophil-Resting-4 | Neutrophils | PMNs |
| GSE22886 | 15789058 | GSM565382 | Neutrophil-Resting-5 | Neutrophils | PMNs |
| GSE7138 | 17244792 | GSM115055 | classical or M1 activated macrophag | Macrophages M1 | M1-MΦs |
| GSE7138 | 17244792 | GSM115056 | classical or M1 activated macrophag | Macrophages M1 | M1-MΦs |
| GSE7138 | 17244792 | GSM115057 | classical or M1 activated macrophag | Macrophages M1 | M1-MΦs |
| GSE7138 | 17244792 | GSM115058 | Alternative or M2 activated macroph | Macrophages M2 | M2-MΦs |
| GSE7138 | 17244792 | GSM115059 | Alternative or M2 activated macroph | Macrophages M2 | M2-MΦs |
| GSE7138 | 17244792 | GSM115060 | Alternative or M2 activated macroph | Macrophages M2 | M2-MΦs |
| E-MEXP-750 | 16791882 | CXCR5hiCOShi_U133A_1 | CXCR5hiCOShi_U133A_1 | T cells follicular helper | Tfh cells |
| E-MEXP-750 | 16791882 | CXCR5hiCOShi_U133A_2 | CXCR5hiCOShi_U133A_2 | T cells follicular helper | Tfh cells |
| E-MEXP-750 | 16791882 | CXCR5hiCOShi_U133A_3 | CXCR5hiCOShi_U133A_3 | T cells follicular helper | Tfh cells |
| E-MEXP-750 | 16791882 | TN_U133A_1 | TN_U133A_1 | T cells CD4 naive | CD4 naive T cells |
| E-MEXP-750 | 16791882 | TN_U133A_2 | TN_U133A_2 | T cells CD4 naive | CD4 naive T cells |
| E-MEXP-750 | 16791882 | TN_U133A_3 | TN_U133A_3 | T cells CD4 naive | CD4 naive T cells |
| GSE4527 | 16702978 | GSM101519 | Treg_1 | T cells regulatory (Tregs) | Tregs |
| GSE4527 | 16702978 | GSM101521 | Treg_2 | T cells regulatory (Tregs) | Tregs |

Fig. 17a

| Cell Identity / Data set | PubMed ID | Platforms (No. Studies) | No. Correct | Total Arrays | Percent Correct | In Fig. 1b |
|---|---|---|---|---|---|---|
| All populations (summed) | - | 4 (30) | 476 | 514 | 93% | |
| All populations (averaged) | - | 4 (30) | - | - | 91% | |
| B cells | | 3 (6) | 21 | 24 | 88% | |
| Chtanova et al. | 16339519 | HGU133A | 2 | 2 | 100% | |
| E-MEXP-2360 | 19846886 | HGU133Plus2 | 3 | 5 | 60% | |
| E-MEXP-384 (Lukk et al. 2010) | 21680796 | HGU133A | 3 | 3 | 100% | |
| E-TABM-145 (Lukk et al. 2010) | 19274049 | HGU133A | 1 | 2 | 50% | |
| GSE28490 | 22276136 | HGU133Plus2 | 5 | 5 | 100% | |
| HaemAtlas | 19228925 | HumanWG-6 v2.0 | 7 | 7 | 100% | |
| B cells naive | | 1 (1) | 5 | 5 | 100% | Y |
| E-MTAB-1771 | N/A | HGU133Plus2 | 5 | 5 | 100% | Y |
| B cells memory | | 1 (1) | 5 | 5 | 100% | Y |
| E-MEXP-2360 | 19846886 | HGU133Plus2 | 5 | 5 | 100% | Y |
| Dendritic cells stimulated | | 1 (1) | 3 | 8 | 38% | Y |
| Chtanova et al. | 16339519 | HGU133A | 3 | 8 | 38% | Y |
| Dendritic cells unstimulated | | 1 (1) | 3 | 4 | 75% | Y |
| Chtanova et al. | 16339519 | HGU133A | 3 | 4 | 75% | Y |
| Eosinophils | | 1 (1) | 5 | 5 | 100% | Y |
| GSE28490 | 22276136 | HGU133Plus2 | 4 | 4 | 100% | Y |
| GSE12837 | 19059999 | HGU133A | 1 | 1 | 100% | Y |
| Macrophages | | 1 (3) | 22 | 24 | 92% | |
| Chtanova et al. | 16339519 | HGU133A | 2 | 2 | 100% | |
| E-MEXP-360 (Lukk et al. 2010) | 16083882 | HGU133A | 4 | 4 | 100% | |
| GSE7138 (Lukk et al. 2010) | 17244792 | HGU133A | 16 | 18 | 89% | |
| Macrophages M0 | | 1 (1) | 5 | 5 | 100% | |
| GSE18686 | 20555352 | HumanHT-12 v3.0 | 5 | 5 | 100% | Y |
| Macrophages M2 | | 1 (1) | 14 | 15 | 93% | Y |
| GSE7568 | 18453574 | HGU133Plus2 | 14 | 15 | 93% | Y |
| Mast cells stimulated | | 1 (1) | 7 | 8 | 88% | Y |
| GSE19888 | 20190146 | HGU133A | 7 | 8 | 88% | Y |
| Mast cells unstimulated | | 1 (1) | 4 | 4 | 100% | Y |
| GSE19888 | 20190146 | HGU133A | 4 | 4 | 100% | Y |
| Monocytes | | 3 (7) | 36 | 43 | 84% | |
| E-MEXP-445 (Lukk et al. 2010) | 16849508 | HGU133A | 0 | 6 | 0% | Y |
| E-MEXP-583 (Lukk et al. 2010) | 17898786 | HGU133A | 4 | 5 | 80% | Y |
| E-TABM-145 (Lukk et al. 2010) | 19274049 | HGU133A | 1 | 1 | 100% | Y |
| GSE28490 | 22276136 | HGU133Plus2 | 10 | 10 | 100% | Y |
| GSE5580 (Lukk et al. 2010) | 17032758 | HGU133A | 12 | 12 | 100% | Y |
| GSE7138 (Lukk et al. 2010) | 17244792 | HGU133A | 2 | 2 | 100% | Y |
| HaemAtlas | 19228925 | HumanWG-6 v2.0 | 7 | 7 | 100% | Y |
| Neutrophils | | 2 (2) | 10 | 10 | 100% | |
| GSE28490 | 22276136 | HGU133Plus2 | 3 | 3 | 100% | Y |
| HaemAtlas | 19228925 | HumanWG-6 v2.0 | 7 | 7 | 100% | Y |

Fig. 17b

| Cell Identity / Data set | PubMed ID | Platforms (No. Studies) | No. Correct | Total Arrays | Percent Correct | In Fig. 1b |
|---|---|---|---|---|---|---|
| NK cells | | 2 (2) | 12 | 12 | 100% | |
| GSE28490 | 22276136 | HGU133Plus2 | 5 | 5 | 100% | |
| HaemAtlas | 19228925 | HumanWG-6 v2.0 | 7 | 7 | 100% | |
| NK cells unstimulated | | 1 (1) | 4 | 5 | 80% | Y |
| GSE12198 | 19383914 | HGU133Plus2 | 4 | 5 | 80% | Y |
| NK cells stimulated | | 1 (1) | 10 | 11 | 91% | Y |
| GSE12198 | 19383914 | HGU133Plus2 | 10 | 11 | 91% | Y |
| Plasma cells | | 2 (6) | 149 | 154 | 97% | Y |
| E-MEXP-2360 | 19846886 | HGU133Plus2 | 10 | 10 | 100% | Y |
| GSE2113 (Lukk et al. 2010) | 15735737 | HGU133A | 7 | 9 | 78% | |
| GSE6365 (Lukk et al. 2010) | 17229636 | HGU133A | 41 | 42 | 98% | |
| GSE6401 (Lukk et al. 2010) | 17367409 | HGU133A | 38 | 38 | 100% | |
| GSE6477 (Lukk et al. 2010) | 19996089 | HGU133A | 52 | 54 | 96% | |
| GSE6691 (Lukk et al. 2010) | 17252022 | HGU133A | 1 | 1 | 100% | |
| T cells | | 1 (7) | 64 | 67 | 96% | |
| Chtanova et al. | 16339519 | HGU133A | 7 | 8 | 88% | |
| E-MEXP-549 (Lukk et al. 2010) | 16584535 | HGU133A | 17 | 17 | 100% | |
| E-MEXP-76 | 15498038 | HGU133A | 15 | 17 | 88% | |
| GSE5580 (Lukk et al. 2010) | 17032758 | HGU133A | 14 | 14 | 100% | |
| GSE5720 (Lukk et al. 2010) | 20053763 | HGU133A | 1 | 1 | 100% | |
| GSE6740 (Lukk et al. 2010) | 17251300 | HGU133A | 4 | 4 | 100% | |
| E-MEXP-750 | 16791882 | HGU133A | 6 | 6 | 100% | |
| T cells CD4 | | 3 (6) | 34 | 38 | 89% | |
| E-TABM-145 (Lukk et al. 2010) | 19274049 | HGU133A | 0 | 2 | 0% | |
| GSE28490 | 22276136 | HGU133Plus2 | 4 | 5 | 80% | |
| GSE473 (Lukk et al. 2010) | 19216740 | HGU133A | 3 | 3 | 100% | |
| GSE6740 (Lukk et al. 2010) | 17251300 | HGU133A | 14 | 15 | 93% | |
| HaemAtlas | 19228925 | HumanWG-6 v2.0 | 7 | 7 | 100% | |
| E-MEXP-750 | 16791882 | HGU133A | 6 | 6 | 100% | |
| T cells CD8 | | 3 (4) | 29 | 29 | 100% | Y |
| E-TABM-145 (Lukk et al. 2010) | 19274049 | HGU133A | 2 | 2 | 100% | Y |
| GSE28490 | 22276136 | HGU133Plus2 | 5 | 5 | 100% | Y |
| GSE6740 (Lukk et al. 2010) | 17251300 | HGU133A | 15 | 15 | 100% | Y |
| HaemAtlas | 19228925 | HumanWG-6 v2.0 | 7 | 7 | 100% | Y |
| T cells follicular helper | | 1 (1) | 6 | 6 | 100% | Y |
| Chtanova et al. | 15210760 | HGU133A | 6 | 6 | 100% | Y |
| T cells gamma delta | | 1 (1) | 8 | 12 | 67% | Y |
| GSE27291 | 21968660 | HGU133Plus2 | 8 | 12 | 67% | Y |
| T cells memory | | 2 (2) | 16 | 16 | 100% | Y |
| GSE11057 | 19568420 | HGU133Plus2 | 9 | 9 | 100% | Y |
| Chtanova et al. | 16339519 | HGU133A | 4 | 4 | 100% | Y |
| E-MEXP-750 | 16791882 | HGU133A | 3 | 3 | 100% | Y |
| T cells naive | | 1 (1) | 4 | 4 | 100% | Y |
| GSE11057 | 19568420 | HGU133Plus2 | 4 | 4 | 100% | Y |

Fig. 18

| Method | Input | Output | Method | Robust to unknown content/noise [a] | Robust to multicollinearity [b] | P-value for deconvolution of cell fractions? | Single samples independently processed? | Reference |
|---|---|---|---|---|---|---|---|---|
| CIBERSORT | Reference profiles | Fractions | nu-SVR | Y | Y | Y | Y | Current work |
| RLR | Reference profiles | Fractions | Robust regression | N | N | N | Y | Current work |
| QP | Reference profiles | Fractions | Quadratic prog. | N | N | N | Y | Gong et al. (2011) |
| LLSR | Reference profiles | Fractions | Least squares | N | N | N | Y | Abbas et al. (2009) |
| PERT | Reference profiles | Fractions/GEPs | Maximum likelihood | N | N | N | N | Qiao et al. (2012) |
| DSA | Marker genes | Fractions/GEPs | Quadratic prog. | N | N | N | N | Zhong et al. (2013) |
| PSEA | Marker genes | Fractions/GEPs | Least squares | N | N | N | N | Kuhn et al. (2011) |
| MMAD | Marker genes | Fractions/GEPs | Maximum likelihood | N | N | N | N | Liebner et al. (2013) |
| csSAM | Fractions | GEPs | Least squares | - | - | - | N | Shen-Orr et al. (2010) |

Note: All methods shown require prior knowledge of marker genes, signature GEPs, or cell fractions, and take an arbitrary number of cell types as input. For details, see Methods.

[a] Shown in this work (e.g., Figs. 6-8)
[b] Shown in this work (Fig. 9). Also, see Methods.

Fig. 19a

Correlation Coefficient (R) for Bulk Tissues

| Related figures | Signature matrix | Bulk tissue[a] | Unknown content? | R statistic[b] | CIBERSORT | LLSR | QP | RLR | PERT | DSA | MMAD | Dataset description |
|---|---|---|---|---|---|---|---|---|---|---|---|---|
| Fig. 2a,b; Fig. 6 | Abbas | Simulated tumors | Yes | Median | 0.86 | 0.81 | 0.19 | 0.86 | 0.21 | 0.20 | 0.86 | Added noise/tumor (Abbas et al.; added colon cancer cell line) |
| Fig. 2c; Fig. 7 | Abbas | Simulated tumors | Yes | Median | 0.83 | 0.16 | 0.16 | 0.20 | 0.21 | 0.19 | 0.20 | Spike 1 (Abbas et al.; added colon cancer cell line) |
| Fig. 8 | LM22 | Simulated solid tiss | Yes | Median | 0.86 | 0.86 | 0.41 | 0.64 | 0.46 | | | Spike 2 (22 leukocyte types; added noise) |
| Fig. 9a | Pseudo-cells | Simulated solid tiss | Yes | Mean | 0.94 | 0.78 | 0.76 | 0.77 | | | | Collinearity 1 (add 2^N(0.5) noise to sig matrix) |
| Fig. 9b | Pseudo-cells | Simulated solid tiss | Yes | Mean | 0.95 | 0.25 | 0.24 | 0.29 | | | | Collinearity 2 (add 2^N(0.7.5) noise to sig matrix) |
| Fig. 9c | Pseudo-cells | Simulated solid tiss | Yes | Mean | 0.70 | 0.20 | 0.17 | 0.21 | | | | Collinearity 3 (add 2^N(0.10) noise to mixture) |
| Fig. 9d | Pseudo-cells | Simulated solid tiss | Yes | Mean | 0.86 | 0.89 | 0.89 | 0.86 | | | | Collinearity 4 (5% unknown) |
| Fig. 9e | Pseudo-cells | Simulated solid tiss | Yes | Mean | 0.86 | 0.76 | 0.77 | 0.86 | | | | Collinearity 5 (25% unknown) |
| Fig. 9f | Pseudo-cells | Simulated solid tiss | Yes | Mean | 0.72 | 0.54 | 0.55 | 0.46 | | | | Collinearity 6 (50% unknown) |
| Fig. 2e; Fig. 10b | LM22 (11 types) | Primary melanoma | Yes | Median | 0.86 | 0.73 | 0.86 | 0.70 | 0.74 | | | Robustness to immune content (primary melanoma) |
| Fig. 2e; Fig. 10b | LM22 (11 types) | Blood mixed w/ bre | Yes | Median | 0.86 | 0.86 | 0.87 | 0.87 | 0.92 | | | Robustness to immune content (blood vs. breast) |
| Fig. 2g | LM22 (11 types) | FL tumors | Yes | Direct | 0.86 | 0.89 | 0.92 | 0.96 | 0.86 | | | FL flow - global (all cells) |
| Fig. 2g | LM22 (11 types) | FL tumors | Yes | Direct | 0.71 | 0.23 | 0.13 | 0.26 | 0.43 | | | FL flow - CD4 T cells |
| Fig. 2g | LM22 (11 types) | FL tumors | Yes | Direct | 0.86 | 0.86 | 0.86 | 0.76 | 0.25 | | | FL flow - CD8 T cells |
| Fig. 2g | LM22 (11 types) | FL tumors | Yes | Direct | 0.83 | 0.86 | 0.86 | 0.39 | 0.93 | | | FL flow - B cells |
| Fig. 2h | LM22 (11 types) | Normal lung tissues | Yes | Direct | 0.87 | 0.86 | 0.92 | 0.97 | | | | Normal lung (flow vs. independent microarray exps) |
| Fig. 2i | LM22 | DLBCL tumors | Yes | Direct | 0.86 | 0.76 | 0.74 | 0.74 | 0.86 | | | FFPE vs Frozen DLBCL |

| | | | | Median | 0.86 | 0.24 | 0.52 | 0.68 | 0.43 | 0.20 | 0.44 | All |

Fig. 19b

RMSE for Bulk Tissues

| Related figures | Signature matrix | Bulk tissue[a] | Unknown content? | RMSE statistic[b] | CIBERSORT | LLSR | QP | RLR | PERT | DSA | MMAD | Dataset description |
|---|---|---|---|---|---|---|---|---|---|---|---|---|
| Fig. 2a,b; Fig. 6 | Abbas | Simulated tumors | Yes | Median | 0.076 | 0.250 | 0.253 | 0.190 | 0.230 | 0.184 | 0.161 | Added noise/tumor (Abbas et al.; added colon cancer cell line) |
| Fig. 2c; Fig. 7 | Abbas | Simulated tumors | Yes | Median | 0.019 | 0.211 | 0.214 | 0.171 | 0.146 | 0.175 | 0.585 | Spike 1 (Abbas et al.; added colon cancer cell line) |
| Fig. 8 | LM22 | Simulated solid tiss | Yes | Median | 0.014 | 0.036 | 0.041 | 0.025 | 0.029 | | | Spike 2 (22 leukocyte types; added noise) |
| Fig. 2e; Fig. 10b | LM22 (11 types) | Primary melanoma | Yes | Median | 0.087 | 0.352 | 0.468 | 0.086 | 0.072 | | | Robustness to immune content (primary melanoma) |
| Fig. 2e; Fig. 10b | LM22 (11 types) | Blood mixed w/ bre | Yes | Median | 0.024 | 0.035 | 0.048 | 0.034 | 0.029 | | | Robustness to immune content (blood vs. breast) |
| Fig. 2g | LM22 (11 types) | FL tumors | Yes | Direct | 0.088 | 0.161 | 0.131 | 0.192 | 0.254 | | | FL flow – global (all cells) |
| Fig. 2g | LM22 (11 types) | FL tumors | Yes | Direct | 0.086 | 0.186 | 0.164 | 0.122 | 0.268 | | | FL flow – CD4 T cells |
| Fig. 2g | LM22 (11 types) | FL tumors | Yes | Direct | 0.048 | 0.039 | 0.042 | 0.015 | 0.256 | | | FL flow – CD8 T cells |
| Fig. 2g | LM22 (11 types) | FL tumors | Yes | Direct | 0.116 | 0.204 | 0.152 | 0.126 | 0.557 | | | FL flow – B cells |
| Fig. 2h | LM22 (11 types) | Normal lung tissues | Yes | Direct | 0.035 | 0.160 | 0.076 | 0.055 | 0.060 | | | Normal lung (flow vs. independent microarray exps) |
| Fig. 2i | LM22 | DLBCL tumors | Yes | Direct | 0.047 | 0.050 | 0.078 | 0.053 | 0.034 | | | FFPE vs Frozen DLBCL |
| | | | | Median | 0.048 | 0.161 | 0.148 | 0.086 | 0.146 | 0.230 | 0.374 | All |

Fig. 19c

Correlation Coefficient (R) for Idealized Mixtures

| Related figures | Signature matrix | Tissue | Unknown content? | R statistic[a] | CIBERSORT | LSF | Q | RLR | PERT | DSA | MMAD | Dataset description |
|---|---|---|---|---|---|---|---|---|---|---|---|---|
| Fig. 1d | LM22 (3 types) | Whole blood | No | Direct | 0.86 | 0.78 | 0.90 | 0.89 | | | | Whole blood - global (GSE20300) (mixture and BM joint quantile-normalized) |
| Fig. 1d | LM22 (3 types) | Whole blood | No | Direct | | | 0.82 | 0.66 | 0.82 | | | Whole blood - Lymphocytes (GSE20300) (mixture and BM joint quantile-normalized) |
| Fig. 1d | LM22 (3 types) | Whole blood | No | Direct | 0.81 | 0.82 | | 0.75 | | | | Whole blood - Monocytes (GSE20300) (mixture and BM joint quantile-normalized) |
| Fig. 1d | LM22 (3 types) | Whole blood | No | Direct | | | | 0.82 | 0.62 | | | Whole blood - Neutrophils (GSE20300) (mixture and BM joint quantile-normalized) |
| " | LM22 (3 types) | Whole blood | No | Direct | 0.79 | 0.60 | | | 0.59 | | | Whole blood - global (GSE20300) |
| " | LM22 (3 types) | Whole blood | No | Direct | | | 0.82 | 0.79 | | | | Whole blood - Lymphocytes (GSE20300) |
| " | LM22 (3 types) | Whole blood | No | Direct | 0.70 | 0.64 | | 0.71 | | | | Whole blood - Monocytes (GSE20300) |
| " | LM22 (3 types) | Whole blood | No | Direct | | | 0.83 | 0.81 | | | 0.92 | Whole blood - Neutrophils (GSE20300) |
| Fig. 5a | Blood cell lines | In vitro mixture | No | Direct | 0.92 | 0.89 | | | | | | Abbas et al. - global (GSE11103) |
| Fig. 5a | Blood cell lines | In vitro mixture | No | Direct | 1.00 | 1.00 | 1.00 | 1.00 | 1.00 | 1.00 | 1.00 | Abbas et al. - Jurkat (GSE11103) |
| Fig. 5a | Blood cell lines | In vitro mixture | No | Direct | 1.00 | 1.00 | 1.00 | 1.00 | 1.00 | 1.00 | 0.99 | Abbas et al. - IM-9 (GSE11103) |
| Fig. 5a | Blood cell lines | In vitro mixture | No | Direct | 1.00 | 1.00 | | 1.00 | 1.00 | 1.00 | 0.99 | Abbas et al. - Raji (GSE11103) |
| Fig. 5a | Blood cell lines | In vitro mixture | No | Direct | 0.98 | 0.98 | | 0.98 | 1.00 | 0.98 | 0.98 | Abbas et al. - THP-1 (GSE11103) |
| Fig. 5b | Neural populations | In vitro mixture | No | Direct | 0.96 | 0.96 | 0.96 | | 0.96 | 0.96 | | Kuhn et al. - global (GSE19380) |
| Fig. 5b | Neural populations | In vitro mixture | No | Direct | 0.96 | 0.96 | 0.96 | | 0.95 | 0.95 | | Kuhn et al. - Neuronal (GSE19380) |
| Fig. 5b | Neural populations | In vitro mixture | No | Direct | | 0.97 | 0.97 | | | | | Kuhn et al. - Astrocyte (GSE19380) |
| Fig. 5b | Neural populations | In vitro mixture | No | Direct | 1.00 | 1.00 | 1.00 | 1.00 | 1.00 | 1.00 | 1.00 | Kuhn et al. - Oligodendrocyte (GSE19380) |
| Fig. 5b | Neural populations | In vitro mixture | No | Direct | 1.00 | 1.00 | 1.00 | | 0.99 | | | Kuhn et al. - Microglia (GSE19380) |

| | | | | | | | | | | | | |
|---|---|---|---|---|---|---|---|---|---|---|---|---|
| | | | | Median | 0.86 | 0.78 | 0.86 | 0.80 | | | | Whole blood only |
| | | | | Median | | 0.98 | 0.99 | | 0.98 | 0.98 | | In vitro mixtures only |

Fig. 19d

RMSE for Idealized Mixtures

| Related figures | Signature matrix | Tissue | Unknown content? | RMSE statistic* | CIBERSORT | LLSR | QP | RLR | PERT | DSA | MMAD | Dataset description |
|---|---|---|---|---|---|---|---|---|---|---|---|---|
| Fig. 1d | LM22 (3 types) | Whole blood | No | Direct | | 0.165 | | 0.122 | | | | Whole blood - global (GSE203300) (mixtures and BM joint quantile-normalized) |
| Fig. 1d | LM22 (3 types) | Whole blood | No | Direct | | 0.200 | 0.126 | 0.118 | | | | Whole blood - Lymphocytes (GSE203300) (mixtures and BM joint quantile-normalized) |
| Fig. 1d | LM22 (3 types) | Whole blood | No | Direct | 0.063 | | 0.067 | 0.075 | | | | Whole blood - Monocytes (GSE203300) (mixtures and BM joint quantile-normalized) |
| Fig. 1d | LM22 (3 types) | Whole blood | No | Direct | | 0.190 | | 0.164 | | | | Whole blood - Neutrophils (GSE203300) (mixtures and BM joint quantile-normalized) |
| | LM22 (3 types) | Whole blood | No | Direct | | 0.216 | | | 0.217 | | | Whole blood - global (GSE203300) |
| | LM22 (3 types) | Whole blood | No | Direct | | | 0.147 | 0.220 | 0.203 | | | Whole blood - Lymphocytes (GSE203300) |
| | LM22 (3 types) | Whole blood | No | Direct | 0.193 | | 0.086 | 0.101 | | | | Whole blood - Monocytes (GSE203300) |
| | LM22 (3 types) | Whole blood | No | Direct | 0.218 | 0.253 | 0.141 | | 0.276 | | | Whole blood - Neutrophils (GSE203900) |
| Fig. 5a | Blood cell lines | In vitro mixture | No | Direct | 0.068 | 0.068 | 0.068 | | | | 0.083 | Abbas et al. - global (GSE11103) |
| Fig. 5a | Blood cell lines | In vitro mixture | No | Direct | 0.025 | | | 0.028 | 0.022 | 0.025 | | Abbas et al. - Jurkat (GSE11103) |
| Fig. 5a | Blood cell lines | In vitro mixture | No | Direct | 0.076 | 0.111 | 0.111 | 0.084 | 0.044 | 0.066 | 0.087 | Abbas et al. - IM-9 (GSE11103) |
| Fig. 5a | Blood cell lines | In vitro mixture | No | Direct | 0.031 | 0.022 | 0.022 | | 0.050 | 0.026 | | Abbas et al. - Raji (GSE11103) |
| Fig. 5a | Blood cell lines | In vitro mixture | No | Direct | 0.062 | 0.072 | 0.072 | | | 0.066 | | Abbas et al. - THP-1 (GSE11103) |
| Fig. 5b | Neural populations | In vitro mixture | No | Direct | 0.045 | 0.050 | 0.049 | | | 0.054 | | Kuhn et al. - global (GSE19380) |
| Fig. 5b | Neural populations | In vitro mixture | No | Direct | 0.056 | 0.061 | 0.059 | | 0.070 | 0.067 | | Kuhn et al. - Neuronal (GSE19380) |
| Fig. 5b | Neural populations | In vitro mixture | No | Direct | 0.061 | | | | 0.084 | 0.073 | | Kuhn et al. - Astrocyte (GSE19380) |
| Fig. 5b | Neural populations | In vitro mixture | No | Direct | 0.034 | | | 0.025 | 0.027 | 0.030 | | Kuhn et al. - Oligodendrocyte (GSE19380) |
| Fig. 5b | Neural populations | In vitro mixture | No | Direct | | 0.010 | 0.010 | | 0.016 | | | Kuhn et al. - Microglia (GSE19380) |

| | | | | Median | 0.126 | 0.199 | | 0.143 | | | | Whole blood only |
| | | | | Median | 0.050 | 0.056 | 0.054 | | 0.057 | 0.052 | | In vitro mixtures only |

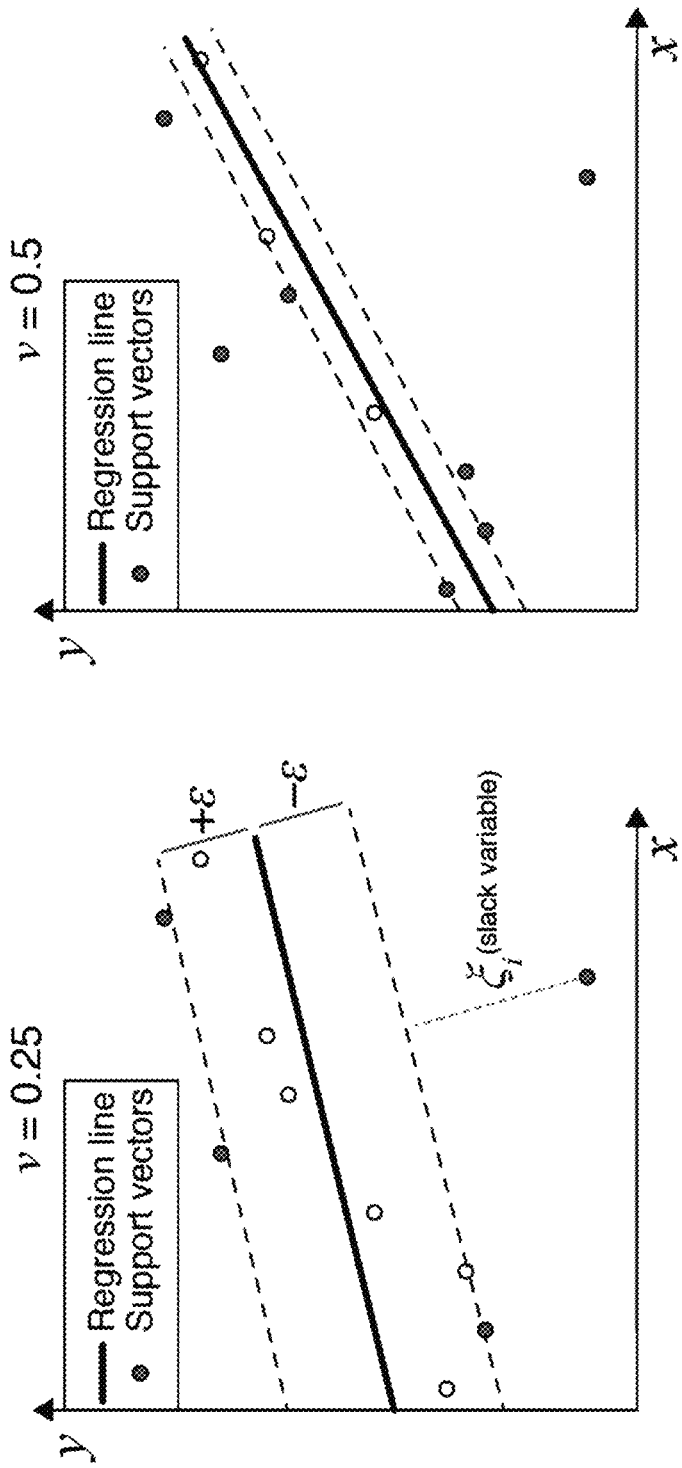

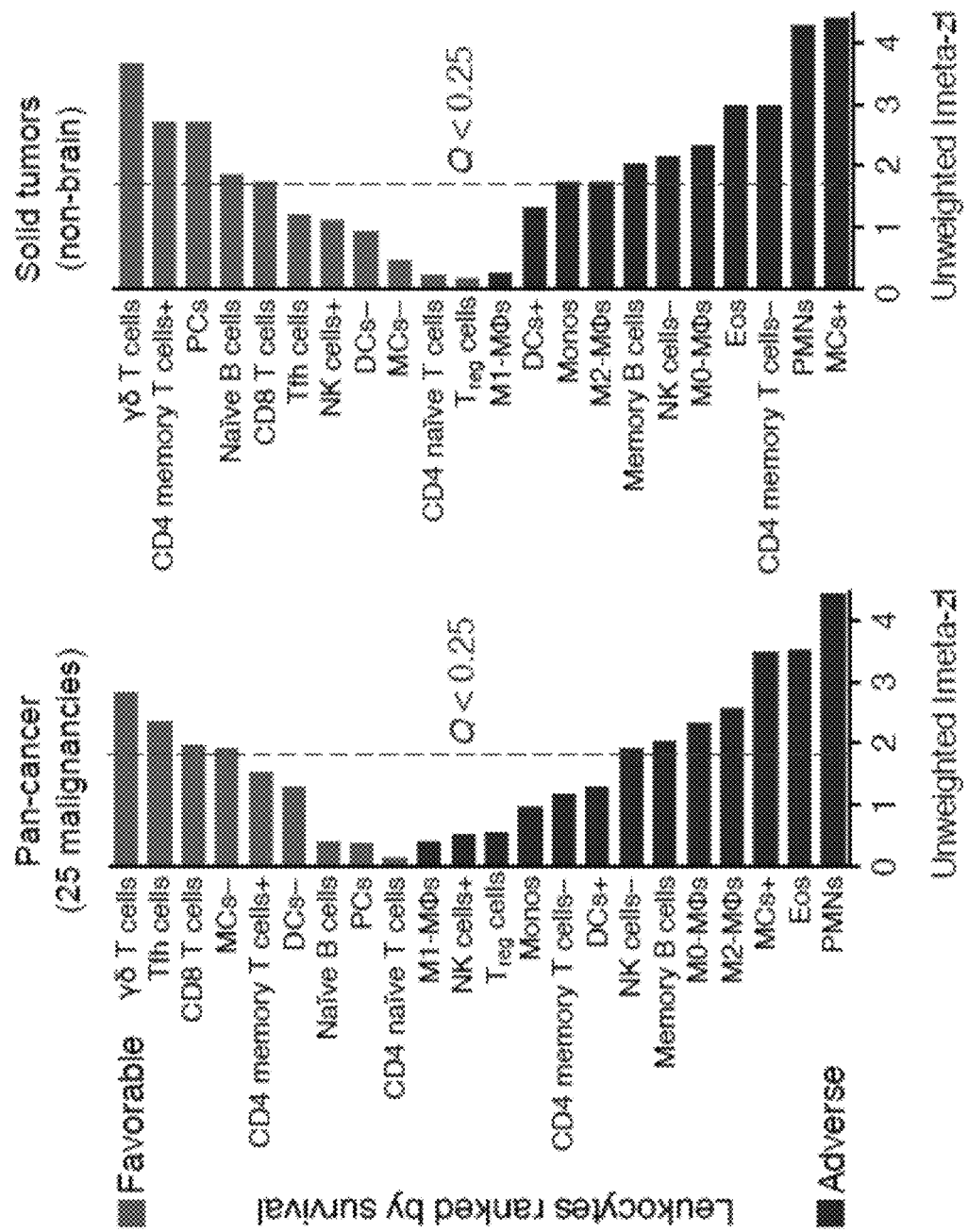

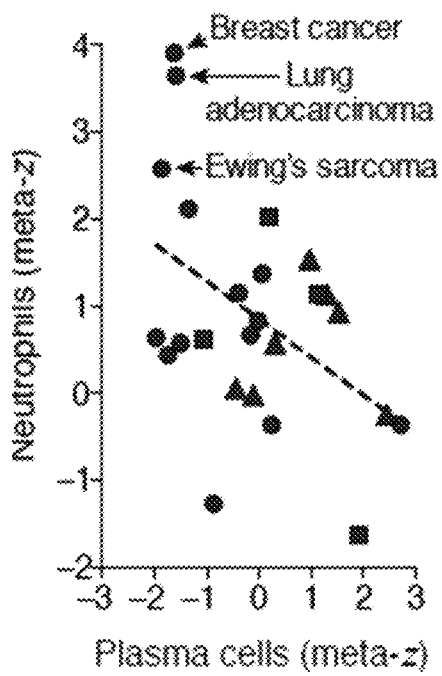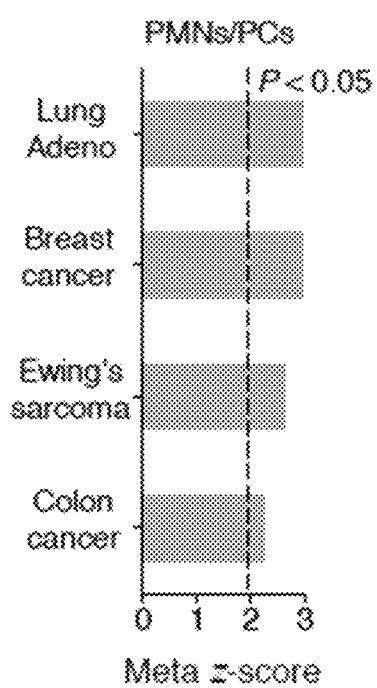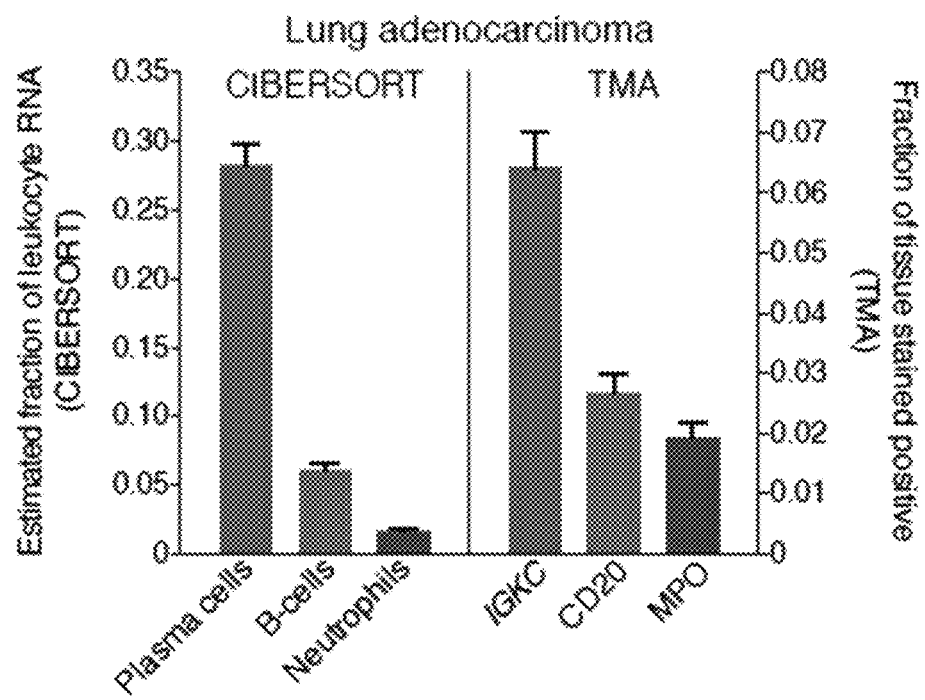
Fig. 24a
Fig. 24b
Fig. 24c

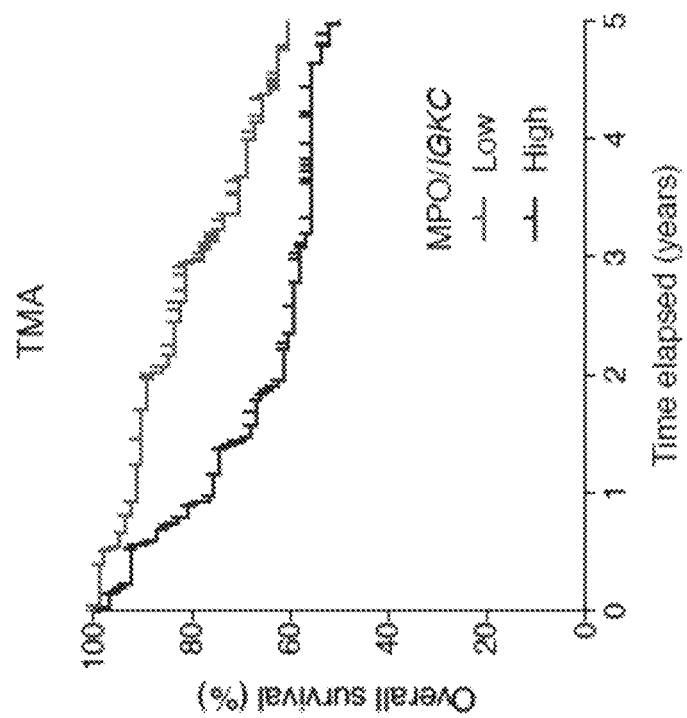
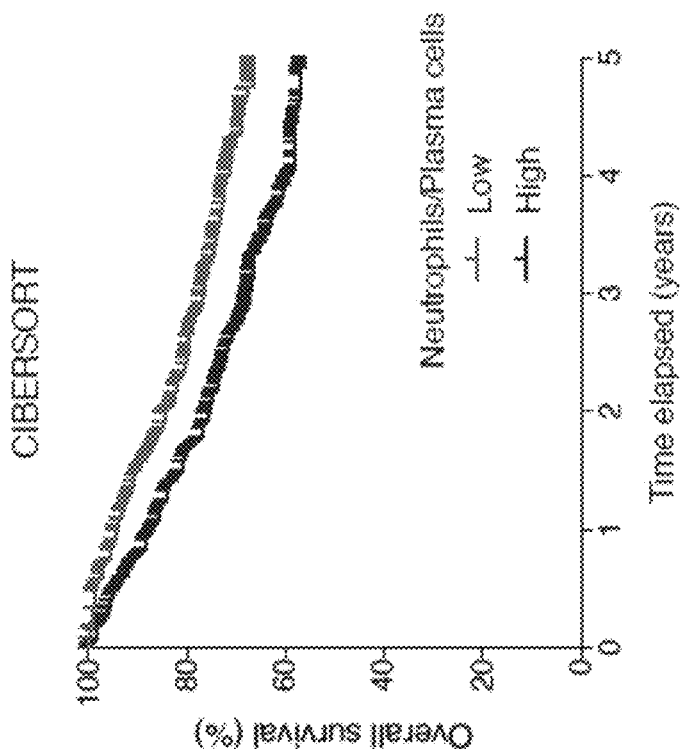

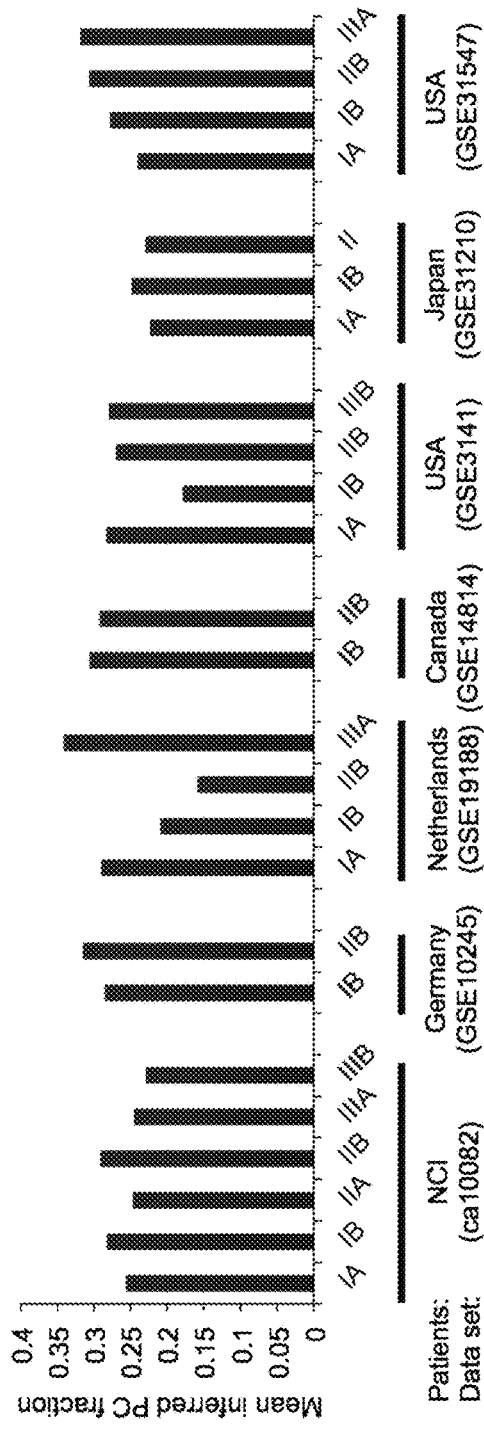
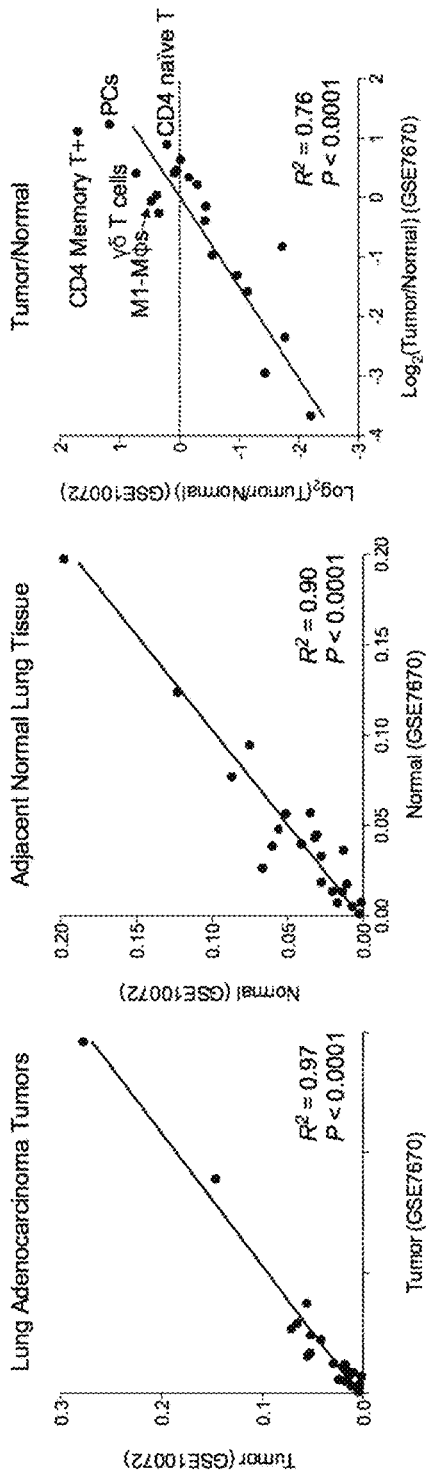
Fig. 27a
Fig. 27b

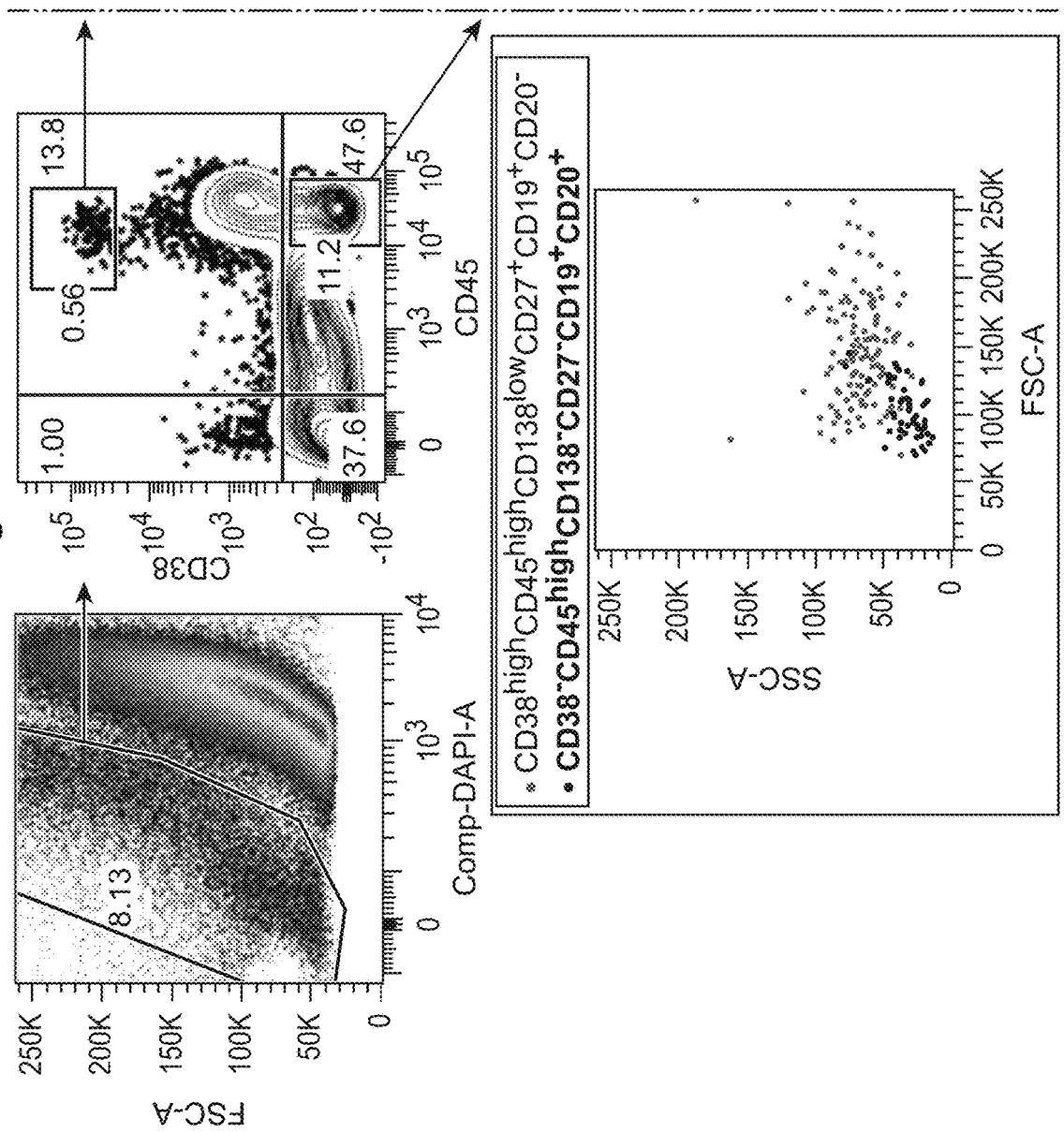

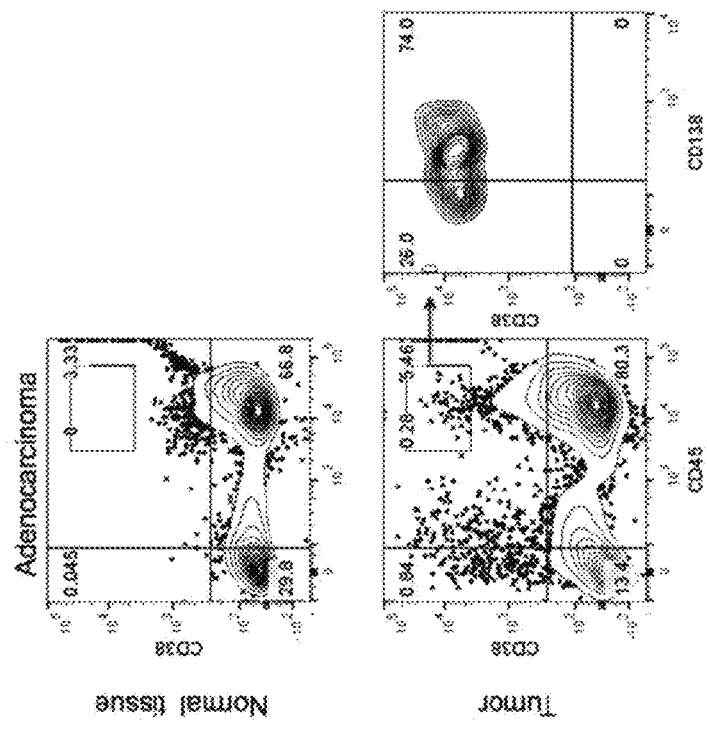
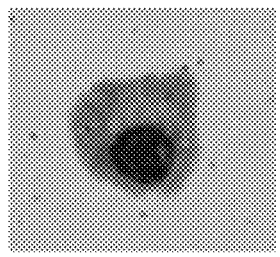
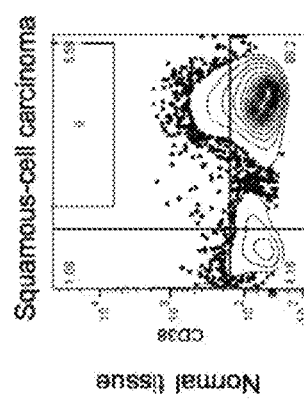
Fig. 27f
Fig. 27g
Fig. 27h

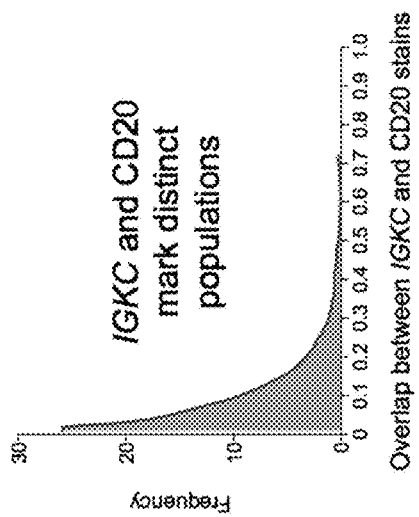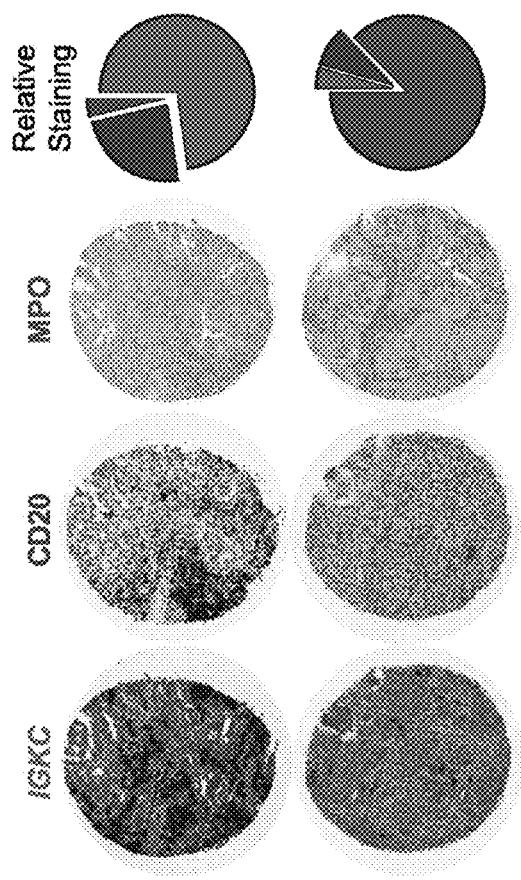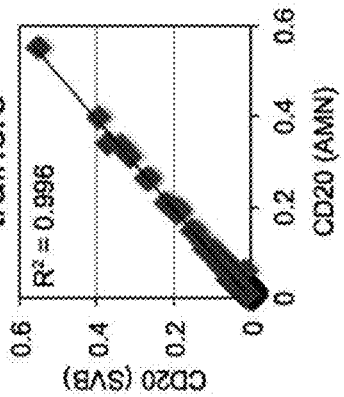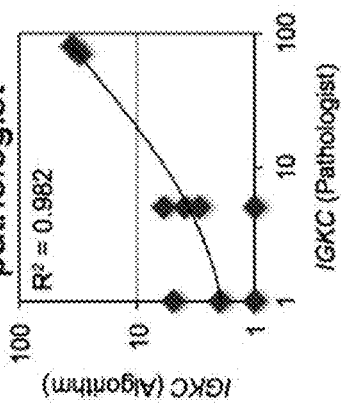

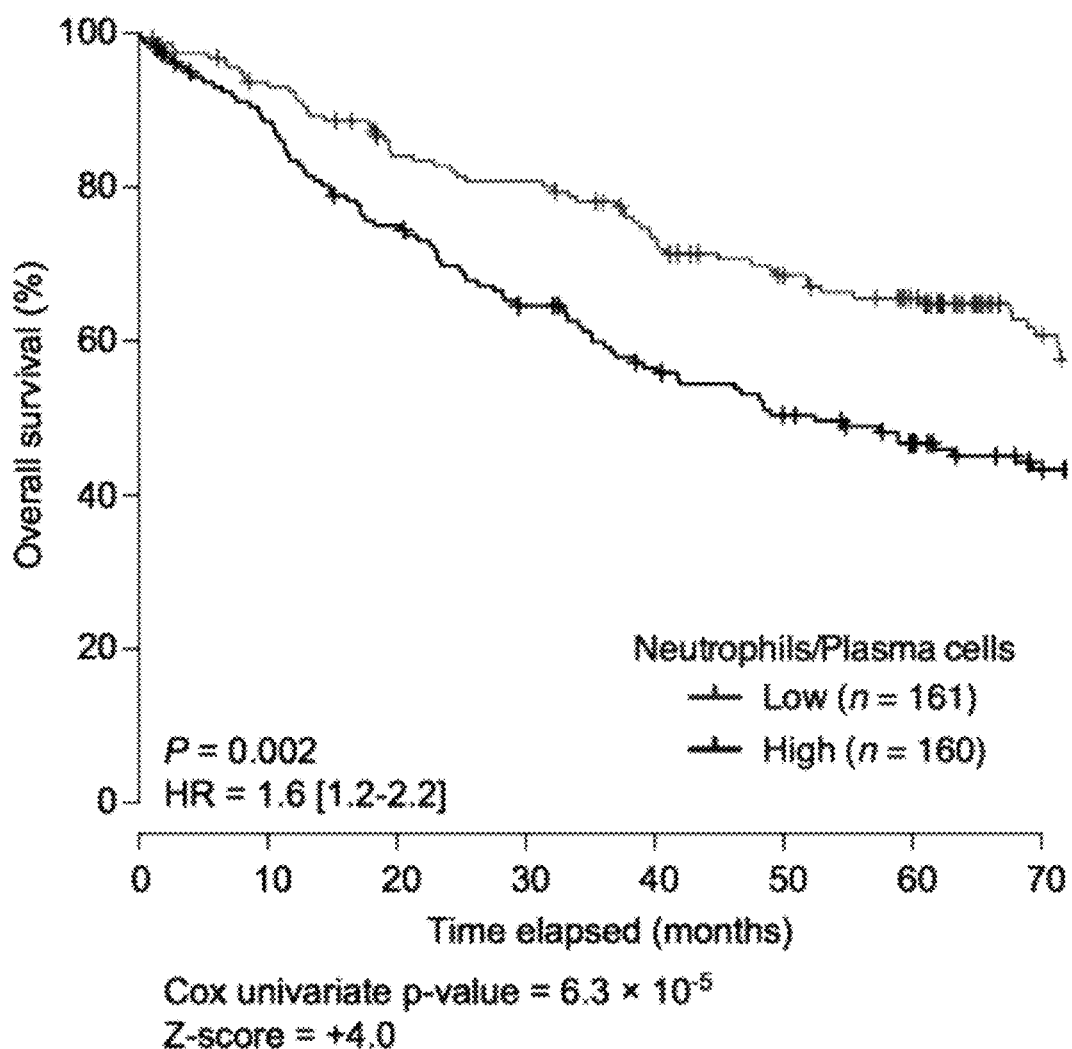

```
                        SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
ctgttgtgtg cctgctgaat                                                   20

<210> SEQ ID NO 2
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 2
ctaatacgac tcactatagg gttaaagcca aggaggagga g                           41
```

METHODS AND SYSTEMS FOR DETERMINING PROPORTIONS OF DISTINCT CELL SUBSETS

CROSS-REFERENCE TO RELATED APPLICATIONS

This application is a continuation of U.S. patent application Ser. No. 15/004,611, filed Jan. 22, 2016, issued as U.S. Pat. No. 10,167,514, which claims the benefit of U.S. Provisional Patent Application No. 62/106,601, filed Jan. 22, 2015, which application is incorporated herein by reference in its entirety.

GOVERNMENT RIGHTS

This invention was made with government support under contract W81XWH-12-1-0498 awarded by the Department of Defense and under contract CA009302 awarded by the National Institutes of Health. The government has certain rights in the invention.

BACKGROUND

Changes in cell composition underlie diverse physiological states of metazoans and their complex tissues. For example, in malignant tumors, levels of infiltrating immune cells are associated with tumor growth, cancer progression and patient outcome. Common methods for studying cell heterogeneity, such as immunohistochemistry and flow cytometry, rely on a limited repertoire of phenotypic markers, and tissue disaggregation prior to flow cytometry can lead to lost or damaged cells, altering results.

Recently, computational methods were reported for predicting fractions of multiple cell types in gene expression profiles (GEPs). While such methods perform accurately on mixtures with well-defined composition (e.g., blood), they are considerably less effective for mixtures with unknown content and noise (e.g., solid tumors), and for discriminating closely related cell types (e.g., naïve vs. memory B cells). Moreover, the absence of statistical significance tests in previous approaches renders their results difficult to interpret.

SUMMARY

Methods of deconvolving a feature profile of a physical system are provided herein. The present method may include: optimizing a regression between a) a feature profile of a first plurality of distinct components and b) a reference matrix of feature signatures for a second plurality of distinct components, wherein the feature profile is modeled as a linear combination of the reference matrix, and wherein the optimizing includes solving a set of regression coefficients of the regression, wherein the solution minimizes 1) a linear loss function and 2) an $L_2$-norm penalty function; and estimating the fractional representation of one or more distinct components among the second plurality of distinct components present in the sample based on the set of regression coefficients.

A method of the present disclosure may include: i) obtaining a physical sample containing a first plurality of distinct components; ii) generating a feature profile m from the sample, wherein the feature profile includes combinations of features associated with the first plurality of distinct components; iii) optimizing a regression between m and a reference matrix B of feature signatures, each feature signature being representative of a distinct component among a second plurality of distinct components, wherein m is modeled as a linear combination of B, wherein the optimizing includes solving for f containing a set of regression coefficients of the regression, wherein the solution minimizes: a linear loss function; and an $L_2$-norm penalty function; and iv) estimating the fractional representation of one or more distinct components of the second plurality of distinct components in the sample based on the set of regression coefficients.

In any embodiment, the solving for f may include selecting a subset of features in B among a plurality of different subsets of feature signatures of B to minimize the linear loss function.

In any embodiment, the linear loss function may be a linear ε-insensitive loss function.

In any embodiment, the optimizing may include using support vector regression (SVR). In some embodiments, the support vector regression is ε-SVR. In some embodiments, the support vector regression is v(nu)-SVR. In some embodiments, the method further includes iterating the method using different values of v to generate different solutions for f for each different value of v. In some embodiments, the method further includes identifying a solution that has the lowest error between: a) the feature profile m; and b) the product of f and the reference matrix B, among the different solutions for f. In some embodiments, the lowest error is obtained using a Pearson product-moment correlation coefficient, Spearman rank correlation, root mean squared error (RMSE), Euclidean distance, or mean absolute deviation (MAD).

In any embodiment, the method may further include determining a significance value for the estimation of the relative proportions of cell subsets by: a) generating a random feature profile m* comprising features randomly selected from a parent feature profile, wherein the parent feature profile comprises the feature profile and wherein m and m* have the same Euclidean norm; b) optimizing a regression between m* and the reference matrix B, wherein m* is modeled as a linear combination of B, wherein the optimizing comprises solving for f* comprising a set of regression coefficients of the regression, wherein the solution minimizes: a linear loss function; and an $L_2$-norm penalty function; c) calculating the product of f* and the reference matrix B to generate a reconstituted feature profile; d) determining a difference measurement between the random feature profile and the reconstituted feature profile; and e) determining a significance value based on a distribution of difference measurements determined from i iterations of steps a)-d), wherein i is a number greater than 1. In some embodiments, the difference measurement is the Pearson product-moment correlation coefficient, Spearman rank correlation, root mean squared error (RMSE), Euclidean distance, or mean absolute deviation (MAD). In some embodiments, the significance value is the p-value. In some embodiments, i is between 10 and 1000.

In any embodiment, the sample may include at least one distinct component represented in the feature signature at 10% or less of the total amount of the second plurality of distinct components present in the sample.

In any embodiment, distinct components represented in the feature signature may be present in the sample at 50% or less of the total amount of distinct components in the sample.

In any embodiment the reference matrix B may contain at least one distinct feature that is present in the feature profile of two or more distinct components of the second plurality of distinct components.

In any embodiment, the reference matrix B may be a subset or superset of an initial reference matrix of feature signatures comprising a number of features that is different from the number of features in B, and wherein the number of features in B provides for a condition number that is lower than the initial reference matrix.

In any embodiment, the method may further include calculating the amount of all the distinct components of the second plurality of distinct components present in the physical sample relative to all the distinct components of the first plurality of distinct components by dividing: the median value of all features associated with the distinct components of the second plurality of distinct components, with the median value of all features in the sample.

In any embodiment, the sample may be a biological sample. In some embodiments, the first plurality of distinct components are distinct cell subsets. In some embodiments, the cell subsets comprise brain cell subsets. In some embodiments, the brain cell subsets comprise subsets of at least one of neuronal cells, astrocytes, oligodendrocytes, and microglia. In some embodiments, the cell subsets comprise subsets of at least one of stromal cells, stem cells, neural cells, and progenitor cells. In some embodiments, the cell subsets comprise tumor cell subsets. In some embodiments, the cell subsets comprise leukocyte subsets. In some embodiments, the cell subsets comprise subsets of tumor infiltrating leukocytes. In some embodiments, the cell subsets comprise subsets of lymphocytes. In some embodiments, the leukocyte subsets comprise two or more cell types selected from the group consisting of: naïve B cells, memory B cells, Plasma cells, CD8T cells, naïve CD4 T cells, CD4 memory RO unactivated T cells, CD4 memory RO activated T cells, follicular helper T cells, regulatory T cells, gamma delta T cells, unstimulated NK cells, stimulated NK cells, Monocytes, Macrophages M0, Macrophages M1, Macrophages M2, unstimulated Dendritic cells, stimulated Dendritic cells, unstimulated Mast cells, stimulated Mast cells, Eosinophils, and Neutrophils. In some embodiments, the cell subsets comprise subsets of cells at different cell cycle stages. In some embodiments, the subsets of cells at different cell cycle stages comprise one or more subsets of cells at interphase, mitotic phase or cytokinesis. In some embodiments, the subsets of cells at different cell cycle stages comprise one of more subsets of cells at prophase, metaphase, anaphase, or telophase. In some embodiments, the subsets of cells at different cell cycle stages comprise one of more subsets of cells at $G_0$, $G_1$, $G_2$, or S phase. In some embodiments, the first plurality of distinct components are distinct cellular signaling pathways, gene regulatory pathways, or metabolic pathways. In some embodiments, the distinct cellular signaling pathways comprise cytokine signaling, death factor signaling, growth factor signaling, survival factor signaling, hormone signaling, Wnt signaling, Hedgehog signaling, Notch signaling, extracellular matrix signaling, insulin signaling, calcium signaling, G-protein coupled receptor signaling, neurotransmitter signaling, and combinations thereof. In some embodiments, the distinct metabolic pathways comprise glycolysis, gluconeogenesis, citric acid cycle, fermentation, urea cycle, fatty acid metabolism, pyrimidine biosynthesis, glutamate amino acid group synthesis, porphyrin metabolism, aspartate amino acid group synthesis, aromatic amino acid synthesis, histidine metabolism, branched amino acid synthesis, pentose phosphate pathway, purine biosynthesis, glucoronate metabolism, inositol metabolism, cellulose metabolism, sucrose metabolism, starch and glycogen metabolism, and combinations thereof. In some embodiments, the feature profile comprises a gene expression profile, protein-protein interaction profile, protein phosphorylation profile, cellular electrical activity profile, chromatin modification profile, chromosome binding profile, enzymatic activity profile, metabolite profile or combinations thereof. In some embodiments, the feature profile comprises a gene expression profile representing the RNA transcriptome of cells in the biological sample. In some embodiments, the biological sample is an archived tissue sample. In some embodiments, the biological sample is a blood sample. In some embodiments, the biological sample is derived from a solid tissue sample. In some embodiments, the solid tissue sample is a tumor sample. In some embodiments, the solid tissue sample is a formalin-fixed, paraffin embedded (FFPE) sample. In some embodiments, the biological sample is a purified sample. In some embodiments, the biological sample is a leukocyte-enriched sample. In some embodiments, the method further includes obtaining the sample from an individual.

In any embodiment, the first plurality of distinct components may be distinct chemical compounds. In some embodiments, the distinct chemical compounds comprise organic compounds, inorganic compounds, toxins, microorganism, metabolites, allergens, and combinations thereof. In some embodiments, the feature profile comprises nuclear magnetic resonance (NMR) spectra, electromagnetic radiation absorbance and/or emission spectra, circular dichroism spectra, Raman spectra, mass spectra, chromatograms, and combinations thereof. In some embodiments, the sample is a biological sample, an environmental sample or a food stuff sample. In some embodiments, the sample is an environmental sample, and wherein the environmental sample is an air sample, water sample or a soil sample. In some embodiments, the sample is an environmental sample, and the environmental sample is obtained from a river, ocean, lake, rain, snow, sewage, sewage processing runoff, agricultural runoff, industrial runoff, tap water, drinking water, exhaust system, land fill, urban development site or farm land.

Also provided herein is a computer-implemented method for deconvolving a feature profile of a physical system, including: obtaining a first feature profile m of a combination of a first plurality of distinct components of a physical system; and computationally processing the first feature profile m, wherein the computational processing includes: i) optimizing a regression between m and a reference matrix B of feature signatures for a second plurality of distinct components of the physical system, wherein m is modeled as a linear combination of B, wherein the optimizing comprises solving for f comprising a set of regression coefficients of the regression, wherein the solution minimizes: a linear loss function; and an $L_2$-norm penalty function; and iii) estimating the fractional representation of one or more distinct components among the second plurality of distinct components present in the physical system based on the set of regression coefficients. In some embodiments, the first feature profile m comprises data representing electricity usage, telecommunication usage, or traffic patterns. In some embodiments, the method further includes collecting the data to generate the first feature profile m.

In any embodiment, the first feature profile m may be generated from a physical sample comprising a first plurality of distinct components.

In any embodiment, the physical sample may be a biological sample, an environmental sample, or a food stuff sample.

Also provided herein is a non-transitory computer readable storage medium storing one or more programs, the one or more programs comprising instructions that, when executed by one or more processors of a computer system, causes the one or more processors to perform at least part of an embodiment of a method of deconvolving a feature profile of a sample, as described herein.

Also provided herein is non-transitory computer readable storage medium storing one or more programs, the one or more programs comprising instructions that, when executed by one or more processors of a computer system, causes the one or more processors to perform an embodiment of a computer-implemented method of deconvolving a feature profile of a physical system, as described herein.

Also provided herein is a system comprising one or more processors; and a memory storing one or more programs, the one or more programs comprising instructions that, when executed by one or more processors of a computer system, causes the one or more processors to perform at least part of an embodiment of a method of deconvolving a feature profile of a sample, as described herein.

Also provided herein is a system comprising one or more processors; and a memory storing one or more programs, the one or more programs comprising instructions that, when executed by one or more processors of a computer system, causes the one or more processors to perform an embodiment of a computer-implemented method of deconvolving a feature profile of a physical system, as described herein.

Also provided herein is a method of evaluating a disease in an individual, comprising: i) obtaining a biological sample from an individual having or suspected of having a disease; ii) estimating the fractional representation of one or more distinct components among a plurality of distinct components present in the sample by performing a method according to an embodiment of a method of deconvolving a feature profile of a sample, as described herein; and iii) determining a prognosis and/or diagnosis for the disease based on a comparison between the estimated fractional representation of the one or more distinct components in the sample and a reference fractional representation of the one or more distinct components in one or more reference samples, wherein the reference samples are derived from a cohort of individuals having the disease and wherein the one or more distinct components are diagnostic and/or prognostic of the disease. In some embodimenets, the method further includes providing a report in physical or electronic form, wherein the report indicates the prognosis and/or diagnosis determined for the individual.

Also provided herein is a method of evaluating a predictive, prognostic and/or diagnostic value of a clinical sample feature, comprising: i) obtaining a biological sample from a cohort of individuals having a disease; ii) estimating a fractional representation of one or more distinct components among a plurality of distinct components present in the sample by performing a method according to an embodiment of a method of deconvolving a feature profile of a sample, as described herein; iii) determining a predictive, prognostic and/or diagnostic value associated with a distinct component in the biological sample for the disease based on a correlation between the fractional representation of one or more distinct components and a clinical outcome of the disease in the cohort of individuals. In some embodiments, a therapy for the disease has been administered to the individuals in the cohort.

Also provided herein is a method of predicting a clinical outcome of a disease therapy, comprising: i) estimating a fractional representation of one or more distinct components among a plurality of distinct components present in a sample obtained from an individual who has received a therapy for a disease, by performing a method according to an embodiment of a method of deconvolving a feature profile of a sample, as described herein; and ii) predicting the clinical outcome of the therapy based on a comparison between the estimated fractional representation of the one or more distinct components in the sample and a predetermined association of the one or more distinct components with clinical outcomes for the therapy. In some embodiments, the association of the one or more distinct components with clinical outcomes for the therapy is determined by a method according to an embodiment of a method of evaluating a predictive, prognostic and/or diagnostic value of a clinical sample feature, as described herein. In some embodiments, the method further includes providing a report in physical or electronic form, wherein the report indicates the predicted clinical outcome of the therapy for the individual. In some embodiments, the report further comprises a recommended future course of action for administering a therapy to the individual for the disease, based on the predicted clinical outcome of the therapy.

Also provided herein are methods of estimating the relative proportions of cell subsets in a biological sample by computationally processing a feature profile of the biological sample are provided herein. Computational processing includes applying support vector regression to a feature profile of the biological sample, using a reference matrix of cell subset feature signatures, to estimate the relative proportions of cell subsets in the biological sample. Each of the cell subset feature signatures may correspond to a different cell subset. The method may further comprise determining a significance value for the identification of the plurality of cell subsets. Systems and computer readable media for performing the subject methods are also provided.

BRIEF DESCRIPTION OF THE FIGURES

Certain aspects of the following detailed description are best understood when read in conjunction with the accompanying drawings. It is emphasized that, according to common practice, the various features of the drawings are not to scale. On the contrary, the dimensions of the various features are arbitrarily expanded or reduced for clarity. Included in the drawings are the following figures:

(FIG. 1a) Schematic of the approach. (FIGS. 1b-1c) Application of a leukocyte signature matrix (i.e., LM22) to deconvolution of (FIG. 1b) 208 arrays of distinct purified or enriched leukocyte subsets (FIG. 17), and (FIG. 1c) 3,061 diverse human transcriptomes, split into non-cell lines and cell lines. Sensitivity (Sn) and specificity (Sp) in c are defined in relation to positive and negative groups, described in Methods. AUC, area under the curve. (FIG. 1d) CIBERSORT analysis of whole blood samples for lymphocytes, monocytes, and neutrophils compared to corresponding proportions measured by Coulter counter[11]. CIBERSORT fraction in FIG. 1b denotes the relative fraction assigned to each leukocyte subset by CIBERSORT. Resting and activated subsets in FIG. 1b are indicated by '+' and '-', respectively.

(FIGS. 2a-2c) CIBERSORT accuracy for leukocyte subset resolution in simulated tissues, in relation to (FIG. 2a) performance across added tumor content (x-axis) and noise (y-axis), (FIG. 2b) deviation of mixtures in FIG. 2a from their original, unmodified values, and (FIG. 2c) detection limits of a given cell type as a function of increasing tumor content (n=5 random mixtures for each data point). (FIG. 2d) Comparison of six GEP deconvolution methods with CIBERSORT, with respect to the analyses shown in FIGS. 2a-2c (FIGS. 7, 8). (FIG. 2e) Analysis of in vitro mixtures of whole blood added to breast tissue. Left: Reported blood proportions are consistent with gene expression data (LM22 normalized immune index; Methods). Right: Stability of leukocyte deconvolution across methods. (FIG. 2f) CIBERSORT consistency across independent studies within and across cancer types (for leukocyte abbreviations, see FIGS. 16j-16k). (FIGS. 2g-2i) CIBERSORT performance compared between (FIG. 2g) paired frozen and FFPE DLBCL samples, and compared to flow cytometry analysis of (FIG. 2h) normal lung tissues and (i) follicular lymphoma tumors. Asterisks in i indicate potential outliers from the same patient. Surface markers used for quantitation in FIG. 2h and FIG. 2i are indicated in parentheses. Results in FIGS. 2e-2i were obtained using LM22 and then collapsed into 11 major leukocyte types before analysis (FIGS. 16a-16i). Values in FIG. 2c and FIG. 2h are presented as medians±95% confidence intervals.

FIGS. 3a-3d: Deep deconvolution and enumeration of individual cell subsets in 41 human subjects. (FIGS. 3a-3c) Direct comparison between CIBERSORT and flow cytometry with respect to: (FIG. 3a) eight immune subsets in PBMCs from 20 subjects, (FIG. 3b) FOXP3+ Tregs in PBMCs from another set of 7 subjects, and (FIG. 3c) three immune subsets, including malignant B cells, in tumor biopsies from 14 subjects with FL. (FIG. 3d) Comparison of five expression-based deconvolution methods on the datasets analyzed in FIGS. 3a-3c. The shaded gray area denotes deconvolved cell types that significantly correlated with flow cytometry (P<0.05). Scatterplots for all methods are provided in FIGS. 13a-13b, 14. In three instances, correlation coefficients could not be determined; these were assigned a value of zero for inclusion in this panel (FIGS. 19a-19d; FIGS. 13a-13b). Data are presented as means±standard deviations. All data, including RMSE values, are provided in FIGS. 19a-19d.

FIGS. 4a-4c: LM22 signature matrix and comparison to Abbas et al. (FIG. 4a) Heat map of the LM22 signature matrix (FIGS. 16a-16i) depicting the relative expression of each gene across 22 leukocyte subsets. Gene expression levels were unit variance normalized, and cell subsets and genes were clustered hierarchically using Euclidean distance (higher expression, red; lower expression, blue). (FIG. 4b) Overlap between LM22 and a previously published signature matrix (Abbas et al., 2009)[5] with respect to genes, cell subsets, and expression arrays used. For gene overlap between Abbas et al. and LM22, we considered all Affymetrix probe sets as 'genes', including those not resolvable to HUGO gene symbols (n=36). For LM22 details, see FIGS. 16a-16k. (FIG. 4c) All-versus-all heat map of correlation coefficients (Pearson) comparing the reference profiles of each cell subset in LM22 (genes were normalized as described in Methods; same as FIGS. 16a-16i).

FIGS. 5a-5b: Validation of LM22 by analysis of purified leukocytes. (FIG. 5a) Fractions of each LM22 cell subset called by CIBERSORT in validation arrays containing purified/enriched leukocytes profiled in LM22 (related to FIG. 1b; also see FIGS. 17a-17b). Results for arrays of a given cell subset are summarized as median fractions. Cell subset abbreviations in the color key are defined in FIGS. 16j-16k. (FIG. 5b) Left: B and T lymphocytes were flow-sorted from five human tonsils to mean purity levels exceeding 95% and 98%, respectively, and then profiled by microarray. Right: The fractional representations of these B/T cells, along with any remaining leukocyte content, as inferred by CIBERSORT.

FIGS. 6a-6c: Resolution of well-defined mixtures with CIBERSORT. Analysis of CIBERSORT performance using different signature matrices (top) applied to different mixtures (bottom). Top: Cell population reference expression signatures for (FIG. 6a) purified blood cancer cell line expression profiles in GSE11103[5], (FIG. 6b) neural gene expression profiles in GSE19380[6], and (FIG. 6c) LM22 (FIGS. 16a-16k). Bottom: Comparison of known and inferred fractions for defined mixtures of (FIG. 6a) blood cancer cell lines (GSE11103[5]) and (FIG. 6b) neural cell types (GSE19380[6]). (FIG. 6c) CIBERSORT analysis of pre- and post-Rituximab therapy PBMC samples, including one paired sample, from four Non-Hodgkin's lymphoma patients using LM22 (pooled into 11 leukocyte types for clarity; see FIGS. 16a-16k).

(FIG. 7a) Performance landscape of each method with respect to added tumor content (x-axis) and non-log linear noise (y-axis) (see Methods for details). (FIG. 7b) Accuracy of each method, evaluated as a function of the deviation of each mixture from its original, unmodified values (represented on the x-axis as 1−R). Performance with respect to known cell type proportions in FIG. 7a is presented as Pearson's correlation coefficient, with a floor of zero. To illustrate estimation bias, the differences between known and predicted cell type proportions (represented as percentages) are presented as root mean squared error (RMSE) in FIG. 7b, with a ceiling of 40.

(FIG. 9a) Same as FIG. 8, except here, detection limit was assessed using defined inputs of naïve B-cells added to simulated mixtures of the remaining 21 cell types from LM22 (FIGS. 16a-16k). The impact of unknown content on detection limit was evaluated by adding simulated GEPs created by randomly permuting naïve B-cell genes. Data are presented as medians (n=4 mixtures)±95% confidence intervals. (FIG. 9b) Same as FIG. 9a, but for all cell types in LM22. To prevent higher magnitude spike-ins from driving the correlation, we summarized performance using the non-parametric Spearman rank correlation, and compared known and predicted fractions over all spike-ins and levels of unknown content tested. Considering these results in aggregate, CIBERSORT significantly outperformed other methods tested (P<0.0001; paired two-sided Wilcoxon signed rank test; n=22 cell subsets). Of note, CIBERSORT also outperformed other methods in relation to linear fit, as measured by Pearson correlation. For further details, see Methods.

FIGS. 10a-10e: Analysis of feature (gene) selection in defined mixtures. (FIG. 10a) Results from applying CIBERSORT to a spike series, in which the LM22 reference profile for CD8 T cells was spiked into the corresponding reference profile for resting mast cells (MCs-) in even increments (n=21). (Of note, both cell types have highly distinct expression vectors in LM22; see FIG. 4c.) (FIG. 10b) Comparison between genes selected by support vector regression (SVR) to deconvolve 100% resting mast cells, but not CD8 T cells, and vice versa. For each unique subset of genes, expression levels in the LM22 signature matrix are further compared between resting mast cells and CD8 T cells. A paired and unpaired two-sided Wilcoxon signed rank test was used for within group and between group comparisons, respectively. Data are presented as medians±interquartile range. While genes uniquely selected for the 100% CD8 T cell sample are significantly more expressed in CD8 T cells than resting mast cells, the magnitude is small. Moreover, the opposite scenario is not observed for resting mast cell genes in the 100% resting mast cell sample, suggesting SVR gene selection is not strongly correlated with the presence or absence of a particular cell subset in the mixture. (FIG. 10c) Comparison between gene expression levels in LM22 and the frequency each gene was selected, if at all, by SVR from the set of 19 mixtures with >0% CD8 T cells and >0% resting mast cells (see panel FIG. 10a). Top: Comparison with expression levels of (left) CD8 T cells or (right) resting mast cells. Bottom: Comparison with mean expression levels of (left) CD8 T cells and resting mast cells or (right) all cell subsets in LM22. Regardless of spike-in composition, the highest correlation between expression and gene selection frequency was observed when considering all cell types in LM22.

(FIGS. 11a-11d) The effect of multicollinearity on deconvolution performance is shown for mixtures with unknown content (FIG. 11a-FIG. 11c) or noise added to the signature matrix (FIG. 11d). Each panel is organized as follows: Top: The mean cross-correlation coefficient (left y-axis) and corresponding mean condition number kappa[5] (right y-axis) of signature matrix GEPs over a broad range of multicollinearity values (x-axis; Methods), Mean cross correlation indicates the average value of an all-versus-all correlation comparison (Pearson) of signature matrix reference profiles, whereas kappa is a measure of signature matrix stability (Methods). Both metrics capture multicollinearity (or the degree of similarity among reference profiles) in the signature matrix. Bottom left: The relative performance of four deconvolution methods on simulated mixtures, comparing known and predicted cellular fractions (y-axis). Results from 20 levels of multicollinearity are shown ordered by increasing multicollinearity (left to right). Each level of multicollinearity was simulated 10 times, and summarized values are presented as means s.e.m. Bottom right: Summarization of the performance of each method as a box plot, with interquartile range contained in the box and minimum and maximum points denoted by whiskers. Group comparisons between CIBERSORT and other methods were performed using a paired two-sided Wilcoxon signed rank test. All signature matrices and mixture vectors were unit variance normalized prior to analysis. For additional details, see Methods.

(FIG. 12a) Results are shown for the 22 leukocyte subsets resolved in each tumor, related to FIG. 2g. Data points (circles) are colored as in FIG. 2g and indicate cell type. Deconvolution results for sample IDs 11 and 14 were not significantly correlated between FFPE and frozen conditions (NS). (FIG. 12b) Scatter plots for representative cell types across all 18 tumors.

FIGS. 13a-13b: Comparison of deconvolution methods for enumeration of 9 leukocyte subsets in PBMCs (related to FIGS. 3a, 3b). (FIG. 13a) Scatter plots comparing flow cytometry with 5 deconvolution methods for the enumeration of 8 leukocyte subsets in 20 PBMC samples. (FIG. 13b) Same as FIG. 13a but for Tregs profiled in a separate cohort of 7 PBMC samples. Of 10 total phenotypic subsets analyzed (Methods), the 9 subsets shown here were deconvolved by at least 1 method with a correlation coefficient of at least 0.5. Detailed performance metrics for all 10 subsets (including gamma delta T cells) are provided in FIGS. 19a-19d.

Figure 16A:
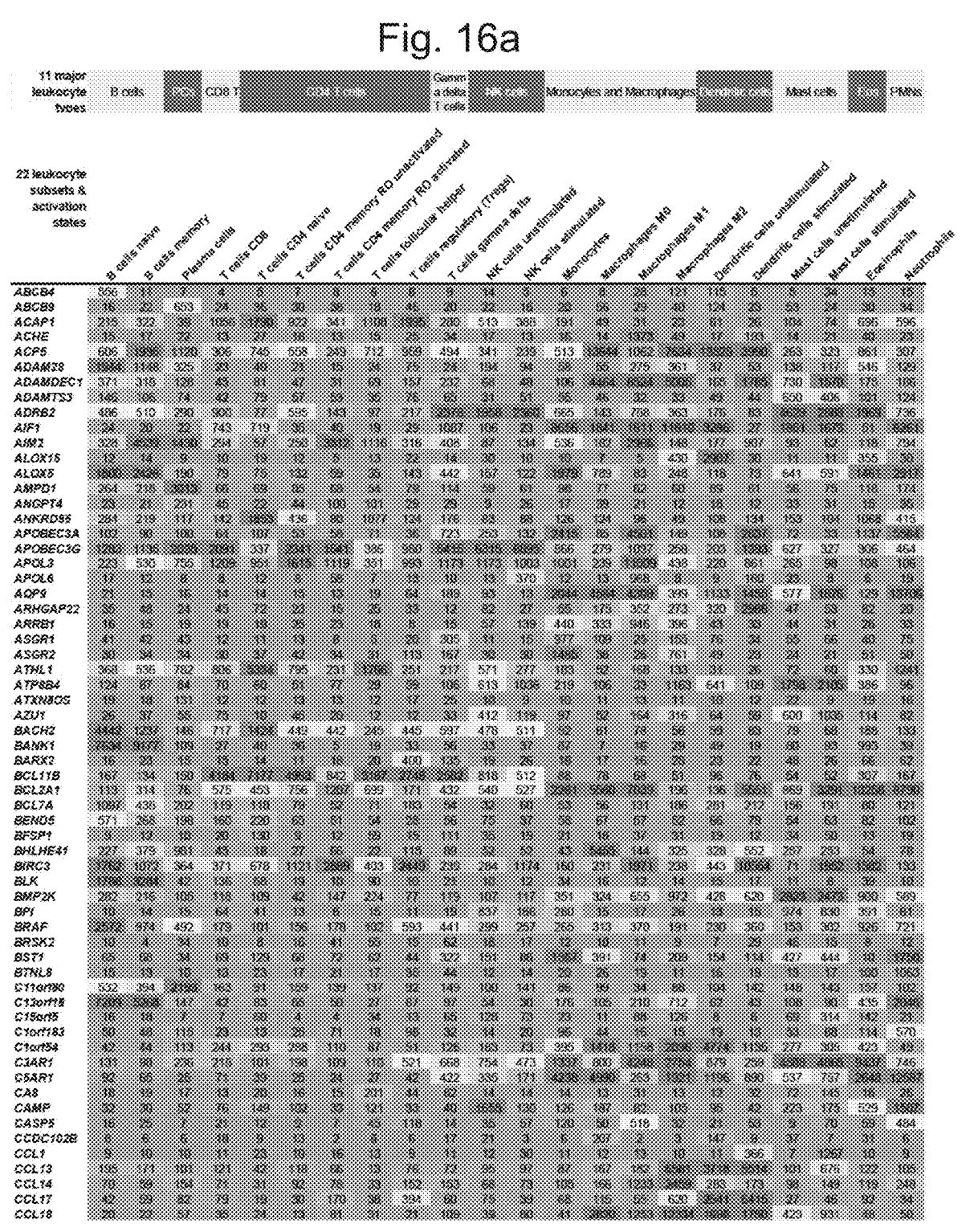
Figure 16B:
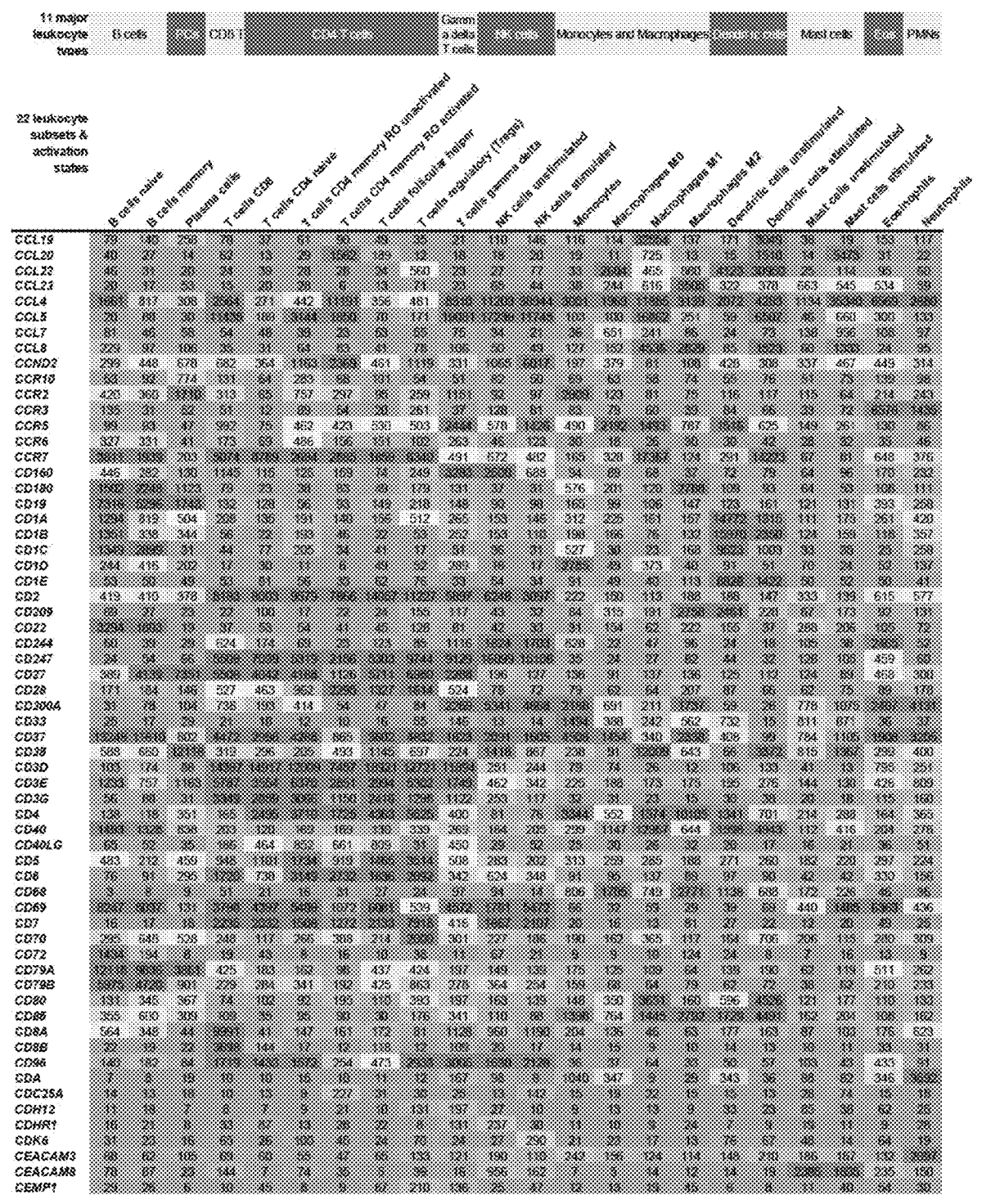
Figure 16C:
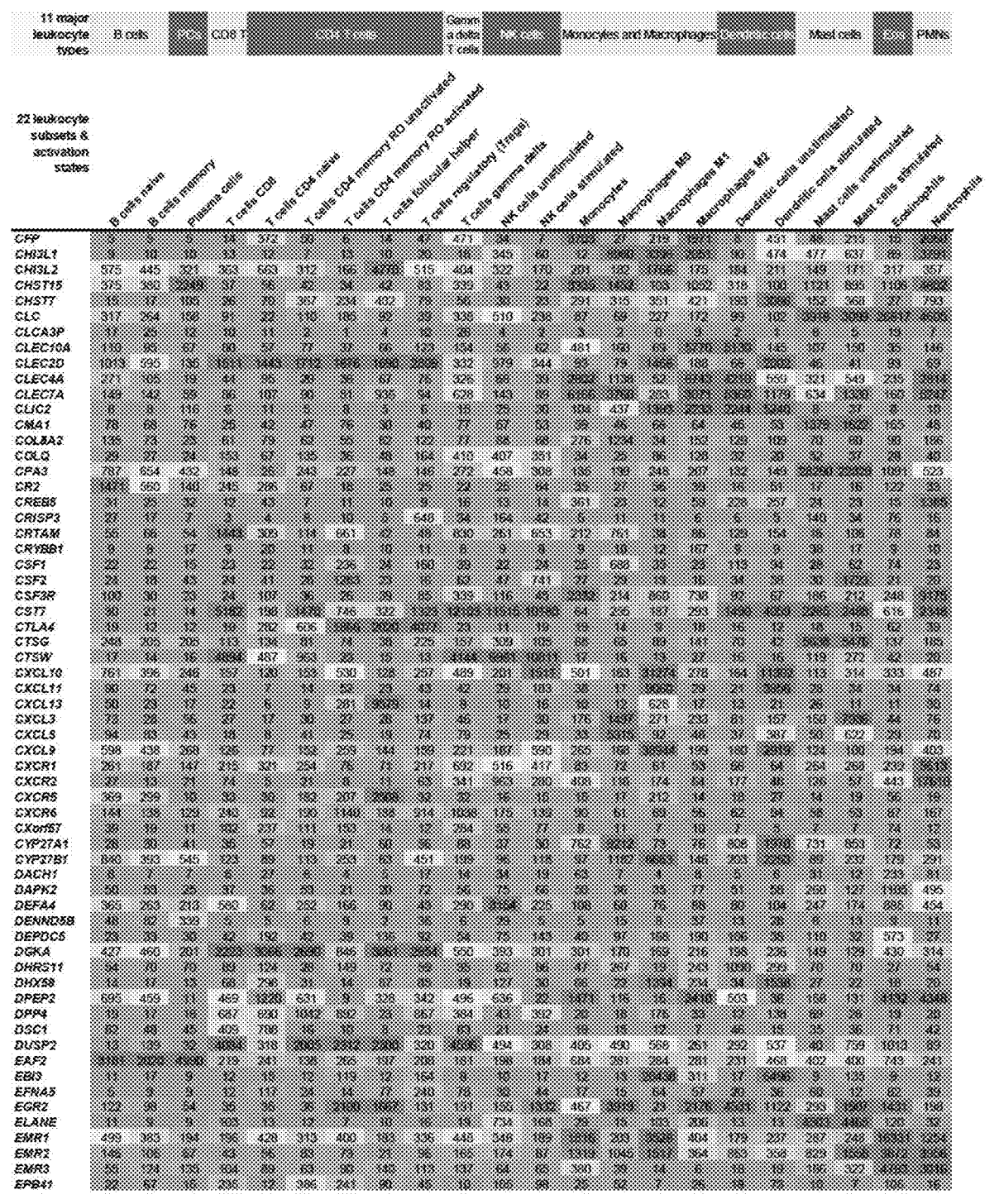
Figure 16D:
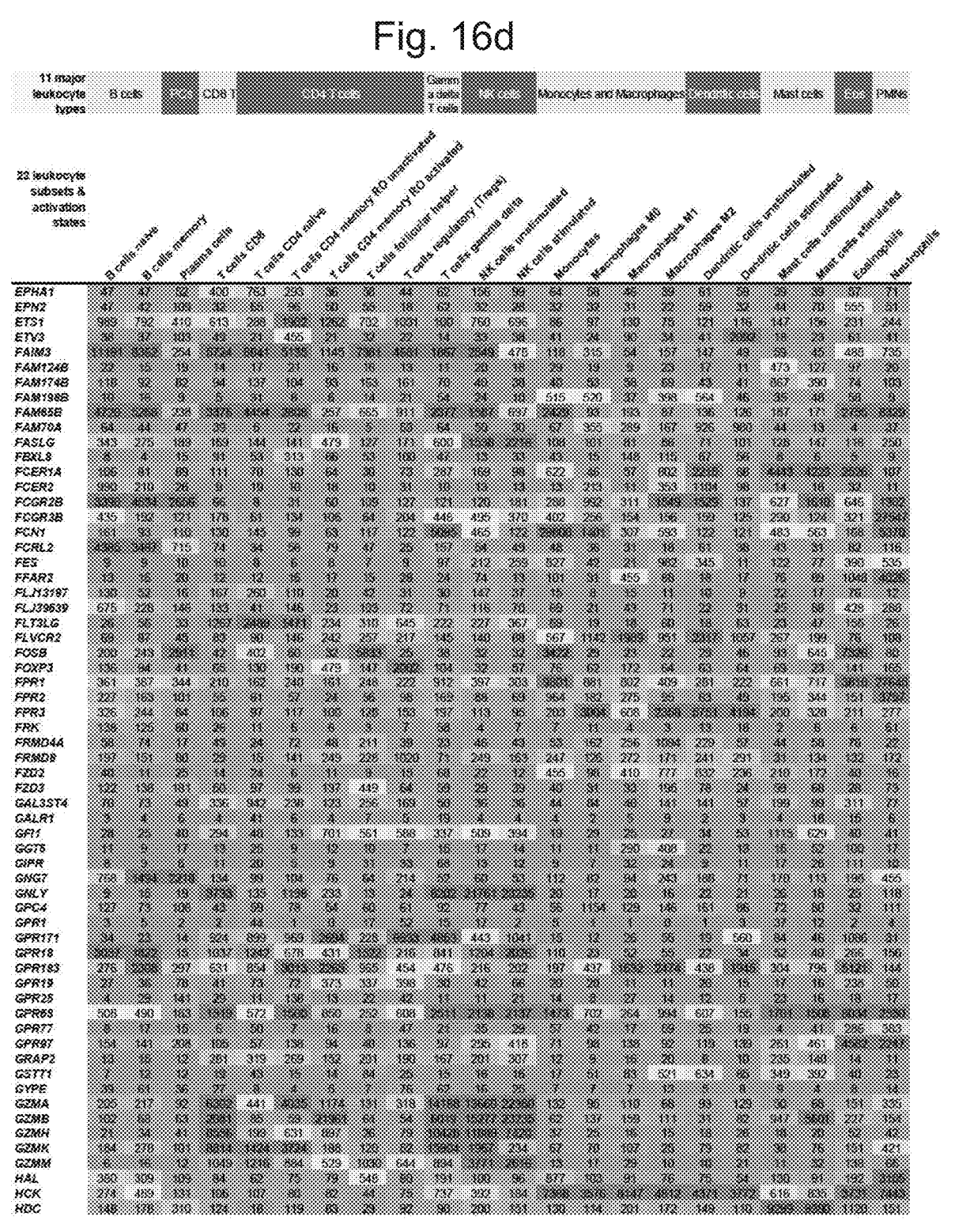
Figure 16E:
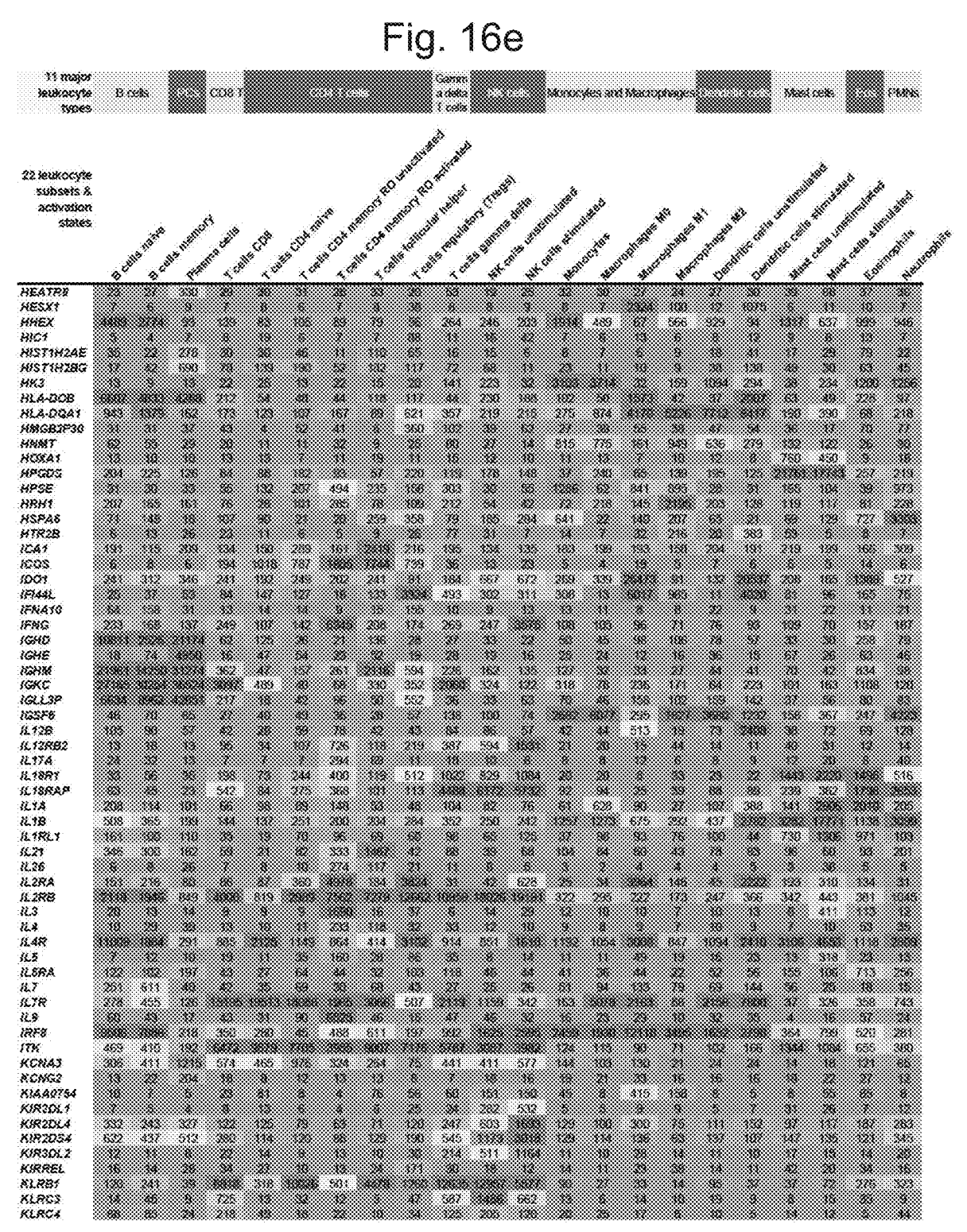
Figure 16F:
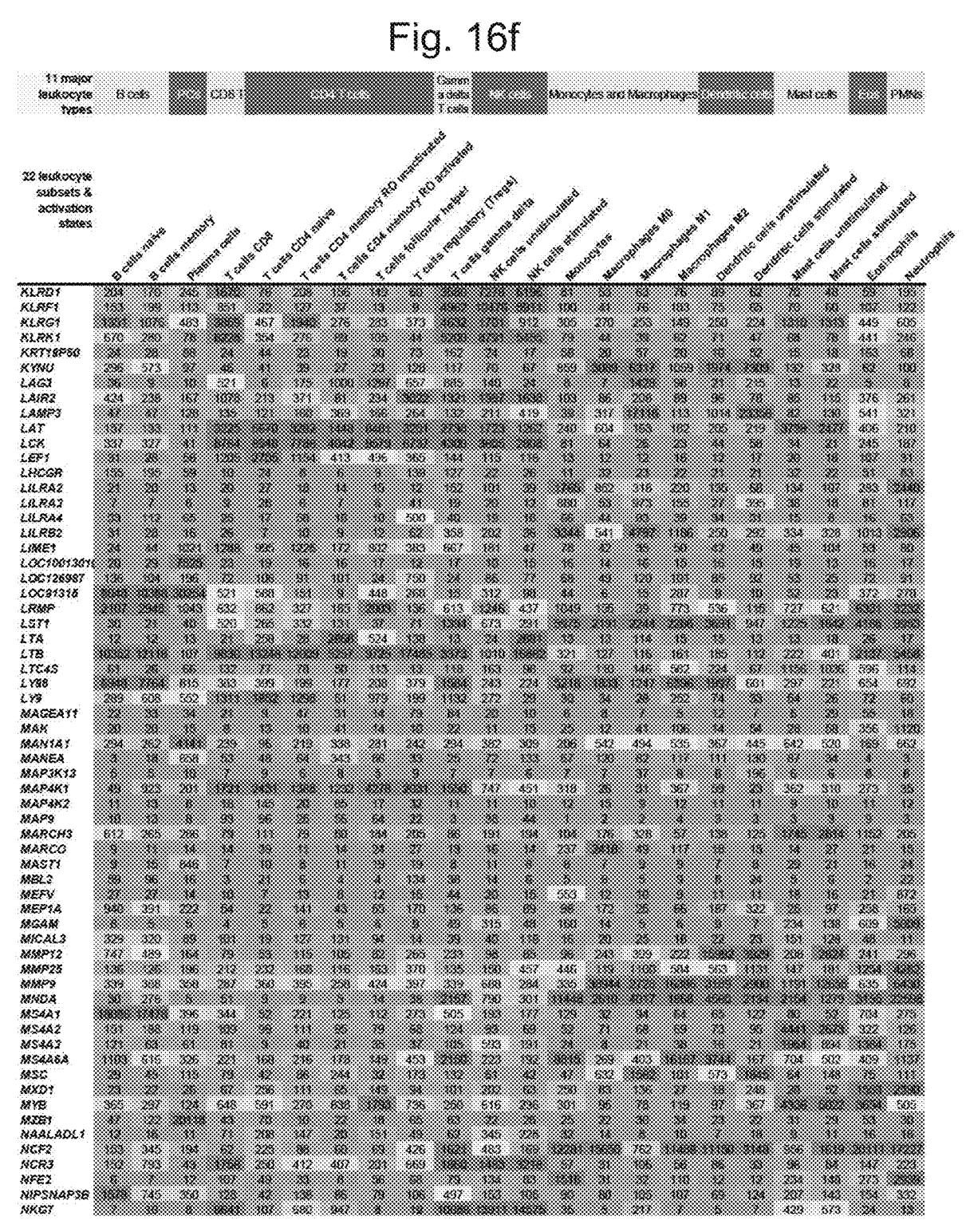
Figure 16G:
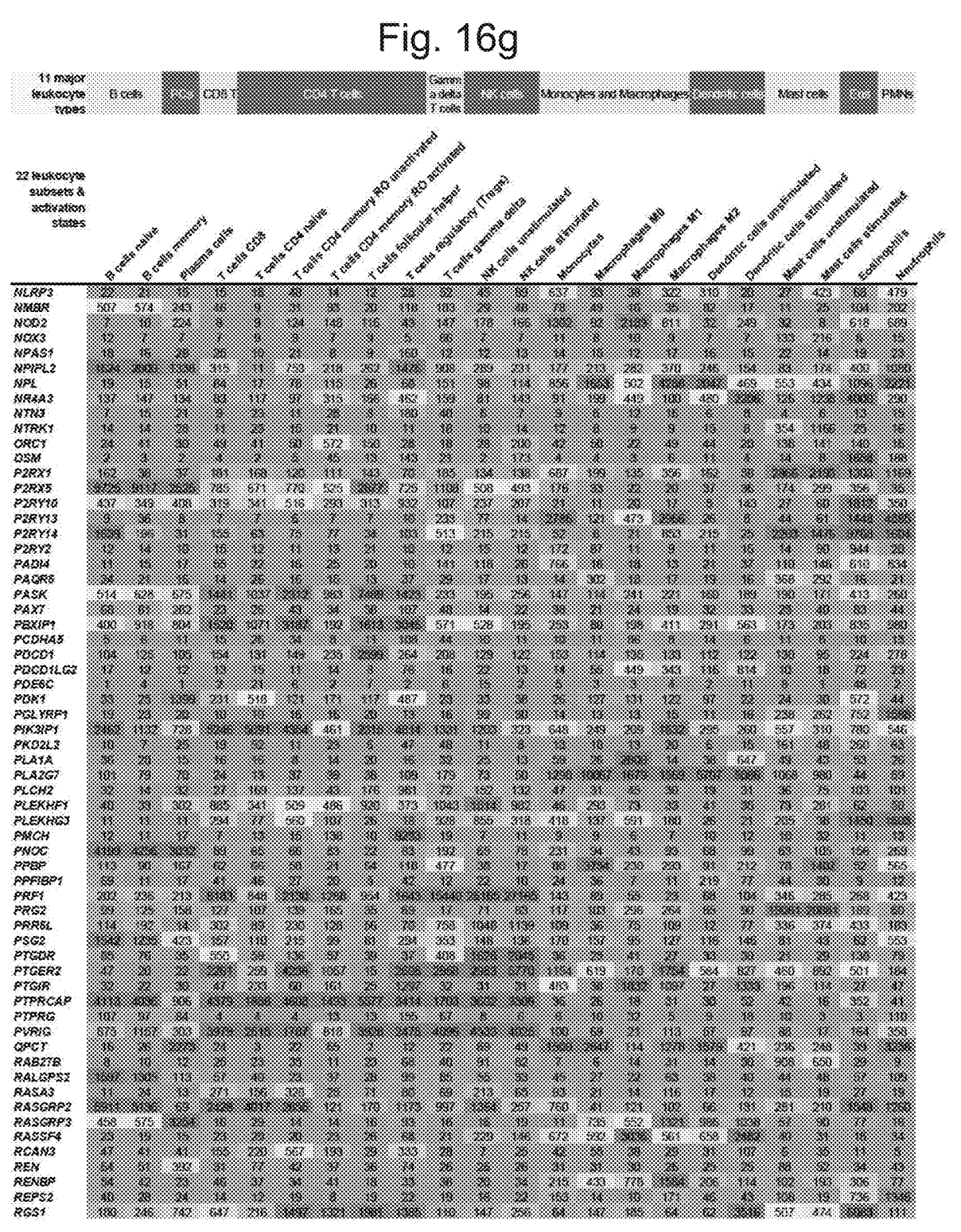
Figure 16H:
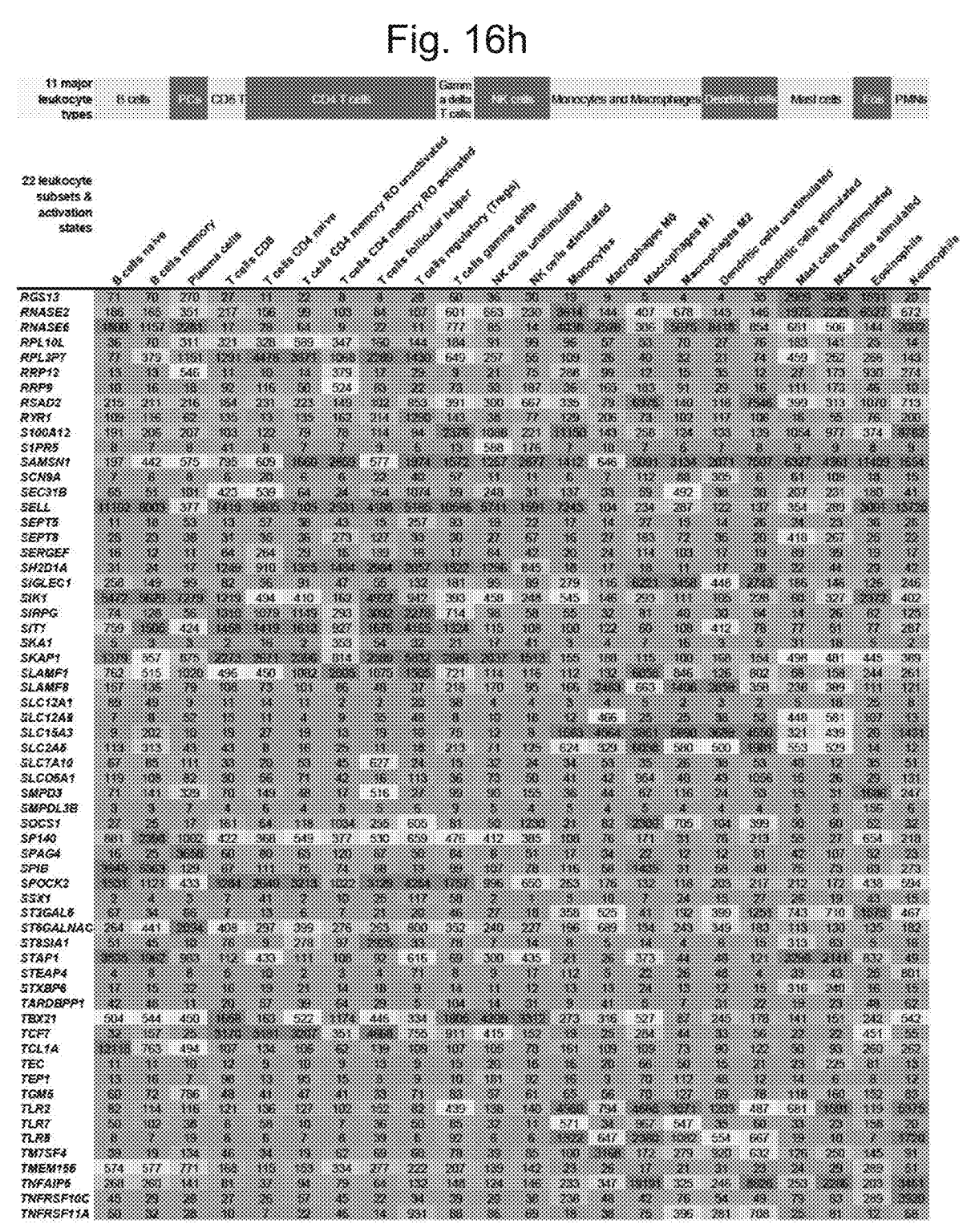
Figure 16I:
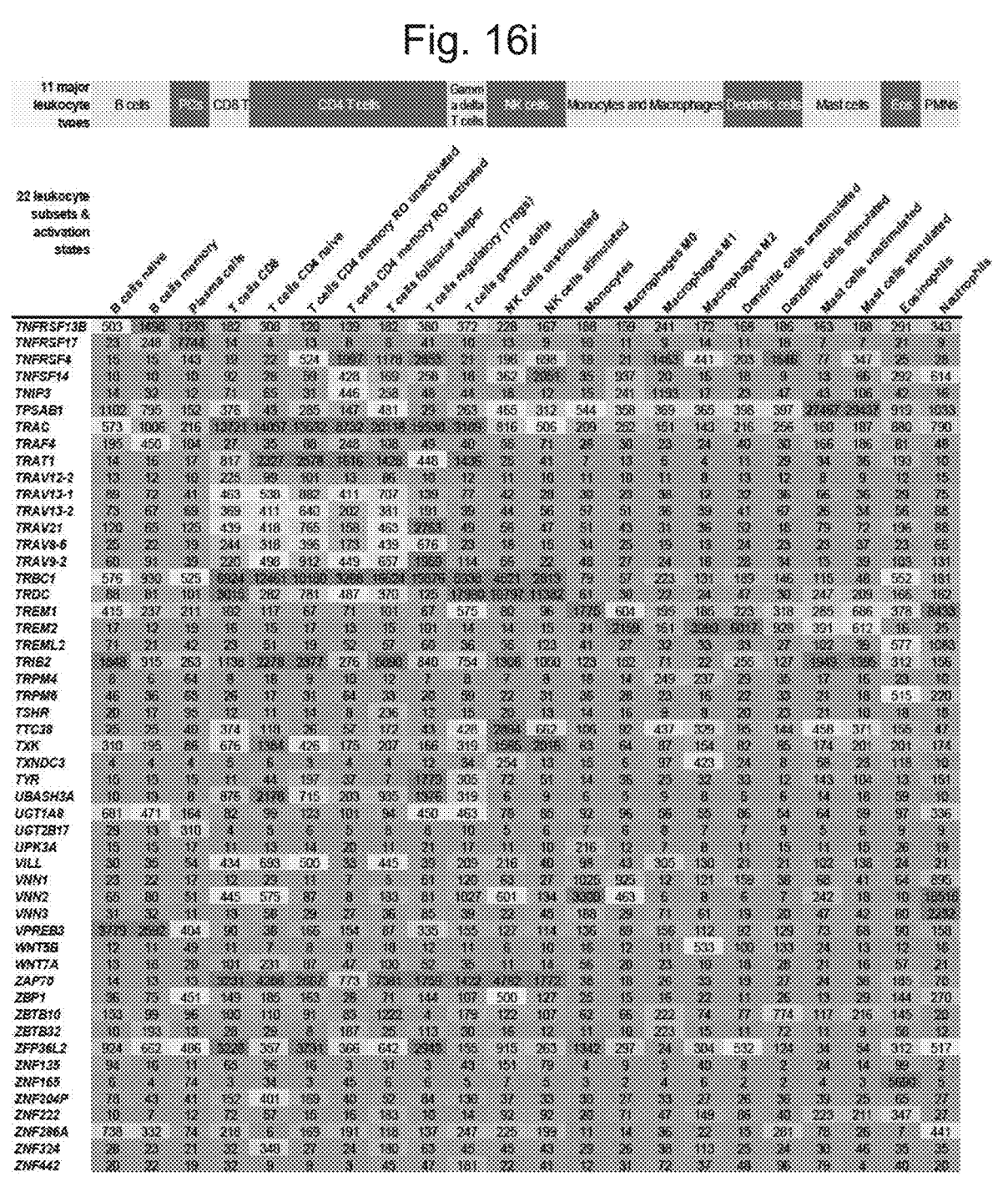

FIGS. 16a-16k: Leukocyte signature matrix (LM22). Shown are the normalized expression levels (Affymetrix intensity) of gene signatures that distinguish 22 immune cell types from each other and other cell types (FIGS. 16a-16i). As described in Methods, genes were filtered against other normal and cancer cell types to enhance their specificity. Source data are provided in the neighboring sheet (Samples). Leukocyte abbreviations found throughout the accompanying manuscript are provided in FIGS. 16j and 16k.

FIGS. 17a-17b: Validation of LM22 on external datasets of purified hematopoietic populations. CIBERSORT was applied to external data sets that contained purified samples to estimate fractions of the cell types included in its signature matrix in each sample. The type of cell type with the highest fraction predicted by CIBERSORT was compared to the known purified cell type, and counted as correct if these matched.

FIG. 18: Feature comparison of GEP deconvolution methods. All methods shown require prior knowledge of marker genes, signature GEPs, or cell fractions, and take an arbitrary number of cell types as input. For details, see Methods. "a" denotes whether shown in this work (e.g., FIGS. 6a-6c, 7a-7b, and 8). "b" denotes shown in this work (FIGS. 9a-9b, Methods).

FIGS. 19a-19d: Performance of each algorithm on idealized mixtures. Cells are colored according to the relative performance on each analysis. For correlation coefficient, red=highest, blue=lowest. For RMSE, blue=highest, red=lowest. LM22 was collapsed into 3 major leukocyte types (lymphocytes, monocytes, and neutrophils) to compare to ground truth mixture proportions (GSE20300). "a" Denotes whether the statistic was derived from a single experiment (i.e., Direct) or aggregated using median. FIG. 19a provides a Correlation Coefficient (R) for bulk tissues.

FIG. 19b provides a RMSE for bulk tissues. FIG. 19c provides a Correlation Coefficient (R) for Idealized Mixtures. FIG. 19d provides a RMSE for Idealized Mixtures.

FIG. 21 is a collection of graphs showing an illustrative example of support vector regression.

FIGS. 23a-23d are a collection of graphs showing inferred leukocyte frequencies and prognostic associations in 25 human cancers, according to embodiments of the present disclosure.

FIGS. 24a-24e are a collection of graphs showing the ratio of infiltrating PMNs to plasma cells is prognostic in diverse solid tumors, according to embodiments of the present disclosure.

FIGS. 27a-27h are a collection of graphs and images showing plasma cell levels in non-small cell lung cancer and adjacent normal tissues, according to embodiments of the present disclosure.

FIGS. 28a-28e are a collection of graphs and images showing assessment of tissue microarray (TMA) markers and staining quantification, and prognostic significance of inferred polymorphonuclear (PMN)/plasm cell (PC) levels in held-out expression datasets, according to embodiments of the present disclosure.

DEFINITIONS

Figure 1A:
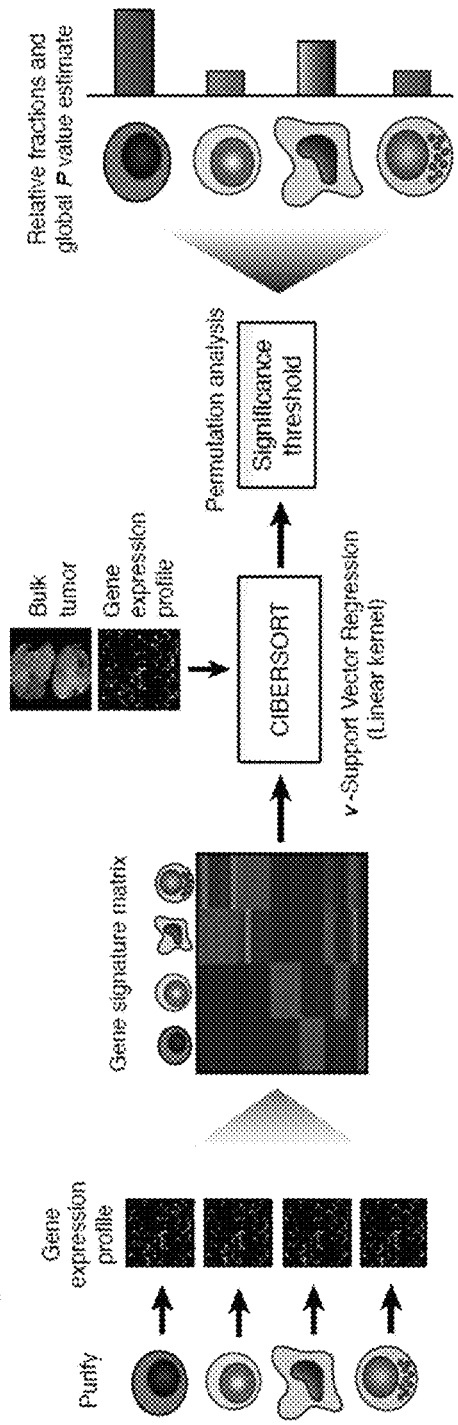
FIGS. 1a-1d: Overview of CIBERSORT and application to leukocyte deconvolution.

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Still, certain terms are defined below for the sake of clarity and ease of reference.

A "plurality" contains at least 2 members. In certain cases, a plurality may have at least 10, at least 100, at least 1000, at least 10,000, at least 100,000, at least $10^6$, at least $10^7$, at least $10^8$ or at least $10^9$ or more members.

A "physical system" as used herein, may refer to any collection of elements (molecules, cells, tissues, organisms, electrical circuits, devices, appliances, computers, vehicles, buildings, etc.), where the elements are functionally related, directly or indirectly, to each other (e.g., the presence, position or activity of one element of the system directly or indirectly affects the presence, position or activity of another element in the system). In some cases, the physical system is a physical sample.

"Physical sample" as used herein, may refer to any collection of matter (e.g., in liquid, solid of gaseous form) that can be physically isolated as a coherent unit from an environment from which the collection is obtained. The term "biological sample" as used herein refers to any physical sample (e.g., in solid or liquid form) that is either obtained from an organism, or contains an organism, or a portion thereof (e.g., tissue sample, biopsies, cell samples of an organism). The biological sample may be obtained from cell culture or from an organism. The biological sample may be purified through the removal of one or more components of the biological sample.

"Distinct component" as used herein, may refer to any form of matter (e.g., molecule, compound, protein, nucleic acid, cell, etc.), or a collection thereof, that is categorized into a group based on one or more empirically determined properties and/or functional relationships. Each distinct component may have one or more members that share one or more empirically determined properties and/or functional relationships among.

The term "cell subset" as used herein refers to any group of cells in a biological sample whose presence is characterized by one or more features, such as gene expression on the RNA level, protein expression, genomic mutations, biomarkers, and so forth. A cell subset may be, for example, a cell type or cell sub-type.

The term "estimated relative proportions of cell subsets" or "vector of relative proportions of cell subsets" as used herein refers to the relative proportion of each of the cell subsets (e.g., as estimated by embodiments of the subject methods). As such, the relative proportions of each cell subset may be understood as a vector (with each cell subset being a different dimension of said vector). As used herein, "relative proportion of a cell subset" refers to the proportion (e.g., abundance) of the cell subset to another cell subset, to other cell subset, or to all cell subsets whose relative proportions are being estimated.

The term "feature" as used herein refers to any empirically determined property of a physical sample or a physical system (e.g., a physical sample, a biological sample, etc.). In some cases, the abundance (i.e., value) of a feature may be indicative of the abundance of a distinct component in the sample or the physical system (e.g., indicative of the abundance of one or more cell subsets in a biological sample). In some cases, features include gene expression on the mRNA, protein expression, specific genotypes, biomarkers, or a combination thereof.

"Feature profile" as used herein, may refer to a set of measured values for a collection of features in a physical sample (e.g., a biological sample) or in a physical system. Where the physical sample or physical system contains a plurality of distinct components, the measured value for any given feature may be a combination (e.g., sum, such as a linear sum) of the contribution of each distinct component to the feature, according to the amount of each distinct component present. The feature profile may be represented by a vector m whose elements correspond to the measured values of each of the features.

The term "feature profile of a biological sample" as used herein refers to the measured values of a collection of features of the biological sample. Examples of sample feature profiles include a "gene expression profile" or "GEP" (e.g., as obtained by microarray analysis), a protein expression profile, a genotype profile (e.g., of a sample having heterogeneous tumor cells), a biomarker profile (e.g., of free biomarkers in the sample or biomarkers on/in cells of the sample), and so forth.

"Feature signature" as used herein, may refer to a feature profile that is characteristic of (or representative of) a substantially pure or highly enriched collection of members of a distinct component. A group of feature signatures for a plurality of distinct elements may be represented by a matrix B. One distinct element in the matrix may or may not have the same set of features in the feature signature than another distinct element.

The term "cell subset reference profile" or "cell subset feature profile" as used herein refers to the feature profile (e.g., values of features) associated with a specific cell subset.

Reference profiles may be obtained by measuring features of purified or enriched cell subsets. In some cases, the term "reference matrix of cell subset feature signatures" as used herein refers to a matrix of expected feature values for multiple cell subsets. Some reference profiles exhibit "multicollinearity", a phenomenon in which reference profiles of different cell subsets are highly correlated, which can prevent reliable deconvolution.

The term "deconvolution" as used herein refers to the process of identifying (i.e., estimating) the relative proportions of cell subsets in a mixture of cell subsets.

"Fractional representation", "relative proportion", and "contribution" are used interchangeably to refer to the portion of the measured value of a feature that is attributable to a distinct component relative to the total value of the feature attributable to all the distinct components included in a reference matrix of feature signatures.

The term "subset" as used herein refers to a matrix or vector (e.g., a feature profile) obtained by reducing one or more dimensions (e.g., number of features) of an initial matrix of vector (e.g., an initial feature profile). "Superset" as used herein, may refer to a matrix or vector obtained by increasing one or more dimensions of an initial matrix or vector. A "parent matrix" or "parent vector" may refer to a superset of the matrix or vector (i.e, "child" matrix or vector). In some cases, a parent feature profile differs from a feature profile of which the parent is a superset by having more features.

The term "reconstituted feature profile" or "deconvolution result" refers to a feature profile calculated based on estimated relative proportions (or fractional representation) of distinct components (e.g., cell subsets) and a known reference matrix. Specifically, a reconstituted feature profile may be calculated from the product of the estimated relative proportions of distinct components, e.g., cell subsets (or "vector of relative proportions of cell subsets") and a reference matrix.

The term "support vector regression" or "SVR" as used herein refers to an instance of support vector machine (SVM), a class of optimization methods for binary classification problems, in which a hyperplane is discovered that maximally separates both classes. The support vectors are a subset of the input data that determine hyperplane boundaries. Unlike standard SVM, SVR fits a hyperplane bound to the input data points, thus performing a regression, and does so within a margin of error $\varepsilon$, and a unique linear error penalty (i.e., an $\varepsilon$-insensitive loss function), rendering it relatively robust to outliers and overfitting. Two major types of SVR are "nu-support vector regression" (or "v-SVR") and "epsilon-support vector regression" (or $\varepsilon$-SVR). In v-SVR, the v parameter conveniently controls both the upper bound of training errors $\varepsilon$ and the sparsity of support vectors.

The term "Cell-type Identification By Estimating Relative Subsets Of RNA Transcripts" or "CIBERSORT" as used herein refers to a nu-SVR method of estimating the relative proportions of each cell type of interest based on an input matrix of reference gene expression signatures.

The term "Monte Carlo sampling" as used herein refers to repeated random sampling to obtain a distribution over an unknown probabilistic entity.

The term "significance value" as used herein refers to the probability of obtaining a result assuming that the null hypothesis is true. In certain embodiments, the null hypothesis is that no cell subsets in the signature matrix are represented in a given feature profile of the biological sample. In certain aspects, the significance value may be a "p-value", which as used herein is the probability of obtaining a test statistic result at least as extreme or as close to the one that was actually observed, assuming that the null hypothesis is true.

As used herein, the term "difference measurement" refers to any measurement of the relationship (e.g., difference, correlation, deviation, etc.) between two values or vectors.

The term "error" as used herein refers to the deviation of a calculated value or values from an expected value or values. The term "root-mean square error" or "RMSE" refers to the amount by which the values predicted by an estimator differ from the quantities being estimated. The RMSE of an estimator with respect to an estimated parameter is defined as the square root of the mean square error.

The term "correlation coefficient" as used herein refers to a measure of linear fit. A "Pearson product-moment correlation coefficient" or "Pearson's R" is a measure of the strength and direction of the linear relationship between two variables and is defined as the covariance of the variables divided by the product of their standard deviations.

The term "RNA transcriptome" as used herein refers to the aggregate RNA expression levels of cells in a biological sample.

The term "leukocytes" or "white blood cell" as used herein refers to any immune cell, including monocytes, neutrophils, eosinophils, basophils, and lymphocytes. The term "lymphocytes" as used herein refer to cells commonly found in lymph, and include natural killer cells (NK cells), T-cells, and B-cells. It will be appreciated by one of skill in the art that the above listed immune cell types can be divided into further subsets.

The term "tumor infiltrating leukocytes" as used herein refers to leukocytes that are present in a solid tumor.

The term "blood sample" as used herein refers to any sample prepared from blood, such as plasma, blood cells isolated from blood, and so forth.

The term "solid tissue sample" as used herein refers to a sample obtained from solid tissue, such as a lymph node, harvested organ, biopsy (e.g., tumor biopsy), and so forth. The sample itself may be reconstituted and suspended.

The term "archived tissue sample" as used herein refers to a tissue sample that has undergone long-term storage.

The term "purified sample" as used herein refers to any sample in which one or more cell subsets are enriched. A sample may be purified by the removal or isolation of cells based on characteristics such as size, protein expression, and so forth.

DETAILED DESCRIPTION

As summarized above, the present disclosure includes a method of deconvolving a feature profile of a sample or physical system. The physical sample or physical system may include a mix of multiple components (i.e. a heterogeneous physical sample or heterogeneous physical system), where the relative proportion of individual components to the mix is unknown. The disclosed methods provide a way to estimate the relative contribution of different components to the total collection of components, or at least to a collection of components of interest, as described herein, in a physical sample or physical system by measuring multiple features of the physical system and using a signature profile of the collection of components of interest to deconvolve the measured features. The present method models the measured features as a linear combination of the signature profile, even if the measured features may include contributions from components that are not represented in the signature profile. The deconvolution is achieved by optimizing a regression between the measured features and the signature profile, where the optimization leads to the minimization of 1) a linear loss function and 2) an $L_2$-norm penalty function. The solution obtained by the optimization includes a vector of regression coefficients, which may be used to derive the fractional representation of a distinct component of the signature matrix among all the distinct components of the signature matrix in the feature profile. The present method also includes calculating the amount of a distinct component represented in the signature matrix relative to all distinct components, regardless of their presence or absence in the signature matrix, as described herein.

In some embodiments, the present method of estimating the relative proportions of cell subsets in a biological sample includes computationally processing a feature profile of the biological sample by applying support vector regression to a feature profile of the biological sample, using a reference matrix of cell subset feature signatures, to estimate the relative proportions of cell subsets in the biological sample. Each of the cell subset feature signatures may correspond to a different cell subset. The method may further comprise determining a significance value for the identification of the plurality of cell subsets. Systems and computer readable media for performing the subject methods are also provided.

Prior to further describing methods, systems and computer readable medium of the present disclosure, a description of physical samples (e.g., biological samples), physical systems, distinct components (e.g., cell subsets), features, and related concepts are provided below.

Physical Samples and Physical Systems

The present disclosure includes a method for deconvolving a feature profile of a physical system (e.g., a heterogeneous physical system). The physical system of interest may include any physical system, where multiple components are present within a physical system and contribute (e.g. contribute in a manner that can be approximated by a linear model) to a feature profile of the physical system. The physical system may or may not include a component of interest. The physical system may include any number of components. In some cases, the physical system includes 5 or more, e.g., 10 or more, 20 or more, including 100 or more, e.g., $10^3$ or more, $10^4$ or more (such as 15,000; 20,000 or 25,000 or more), distinct (i.e., different) components, that differ from each other in terms an empirically determined property.

In some cases, the physical system is a physical sample containing a plurality of distinct components, as descried further below. In some embodiments, the physical system is a collection of cells in vivo or ex vivo (e.g., a collection of cells in a tissue sample), a collection of tissues in an organism, a collection of organisms in an ecosystem or a society, etc. In some embodiments, the physical system is a collection of electrical circuits in a device, a collection of devices in a room, a collection of computers on a network, a collection of appliances in a building, a collection of buildings in a city or portion thereof, a collection vehicles on a road or highway system, etc.

In the present disclosure, a physical sample may be any suitable sample that contains a mix of distinct components, where multiple distinct components contribute (e.g., contribute in a manner that can be approximated by a linear model) to a feature profile of the physical sample. In some embodiments, the physical sample is a biological sample, as described further below. In some cases, the physical sample is an environmental sample, such as an air sample, water sample, or a soil sample. The environmental sample may be obtained from any suitable source, such as, without limitation, a river, ocean, lake, rain, snow, reservoir, sewage, sewage processing runoff, agricultural runoff, industrial runoff, tap water, drinking water, exhaust system (e.g., industrial exhaust, vehicular exhaust, etc.), compost, land fill, urban development site or farm land. In some cases, the physical sample is a food stuff sample, i.e., material that is suitable for, or being prepared for consumption by an animal, e.g., human, dog, cat, bird, fish, etc. In some cases, the physical sample is a synthetic chemical mix, e.g., commercially sold chemical mixes, such as fertilizer, coatings (e.g., paint, lacquer, etc.), drugs, detergent, etc.

Biological Samples

In some embodiments, the biological sample may be obtained in vitro from a cell culture or from an organism. In certain aspects, the organism may be an animal, such as a primate (e.g., human), rodent (e.g., mouse, rat, hamster, guinea pig), rabbit, or any other suitable animal. A biological sample collected from an organism may be a tissue samples such blood, solid tissue from brain, lymph node, thymus, bone marrow, spleen, skeletal muscle, heart, colon, stomach, small intestine, kidney, liver, lung, and so forth. A tissue sample may be obtained by harvesting an organ or by performing a biopsy as known in the art. In certain aspects, the biological sample is a blood sample, such as whole blood, plasma or cells obtained from blood.

In certain aspects, the biological sample may be a tumor biopsy. A biopsy refers to any tissue sample containing cancer cells that is obtained (e.g., by excision, needle aspiration, etc.) from a subject. The biopsy may be in the form of a cell suspension, thin section (e.g., a tissue section mounted on a slide), or any other suitable form.

In certain aspects, the biological sample may be a cell dispersion or suspension in a solution. The solution may be a balanced salt solution, e.g., normal saline, PBS, Hank's balanced salt solution, etc., conveniently supplemented with fetal calf serum, human platelet lysate or other factors, in conjunction with an acceptable buffer at low concentration, such as from 5-25 mM. Convenient buffers include HEPES, phosphate buffers, lactate buffers, etc. The separated cells may be collected in any appropriate medium that maintains the viability of the cells. Various media are commercially available and may be used according to the nature of the cells, including dMEM, HBSS, dPBS, RPMI, Iscove's medium, etc., frequently supplemented with fetal calf serum or human platelet lysate. In other aspects, the biopsy may be a tissue section. For example, the biopsy may be a thin tissue section mounted on a microscopy slide. The biological sample of any of the above embodiments may be fixed and/or permeabilized as known to one of skill in the art.

The sample may be a whole sample, e.g., in crude form. Alternatively, the sample may be fractionated prior to analysis, e.g., by density gradient centrifugation, panning, magnetic bead sorting, fluorescence activated cell sorting (FACS), etc., to enrich for one or more cell types of interest.

In some cases, the biological sample is a cell-free sample, e.g., a cell or tissue homogenate. In some cases, the biological sample comprises a single cell.

In certain aspects, the subject methods include obtaining a sample, e.g., biological sample (e.g., as discussed above) prior to estimating the relative proportions of cell subsets in the biological sample.

Distinct Components

The distinct components of the physical sample of physical system according to the present disclosure may be any distinct components that contribute to the feature profile of the physical sample of physical system. In some cases, the distinct components are distinct cell subsets, as described further below.

In some embodiments, the distinct components include distinct subsets of cells at different cell cycle stages. A subset of cells may include cells in any suitable cell cycle stage, including, but not limited to, interphase, mitotic phase or cytokinesis. In some embodiments, cells in a subset of cells are at prophase, metaphase, anaphase, or telophase. In some cases, the cells in a subset of cells is quiescent ($G_0$ phase), at the $G_1$ checkpoint ($G_1$ phase), replicated DNA but before mitosis ($G_2$ phase), or undergoing DNA replication (S phase).

In some embodiments, the distinct components include different functional pathways within one or more cells. Functional pathways of interest include, without limitation, cellular signaling pathways, gene regulatory pathways, or metabolic pathways. Thus, in some embodiments, the method of the present disclosure may be a method estimating the relative activity of different signaling or metabolic pathways in a cell, a collection of cells, a tissue, etc., by measuring multiple features of the signaling or metabolic pathways (e.g., measuring activation state of proteins in a signaling pathway; measuring expression level of genes in a gene regulatory network; measuring the level of a metabolite in a metabolic pathway, etc.). The cellular signaling pathways of interest include any suitable signaling pathway, such as, without limitation, cytokine signaling, death factor signaling, growth factor signaling, survival factor signaling, hormone signaling, Wnt signaling, Hedgehog signaling, Notch signaling, extracellular matrix signaling, insulin signaling, calcium signaling, G-protein coupled receptor signaling, neurotransmitter signaling, and combinations thereof. The metabolic pathway may include any suitable metabolic pathway, such as, without limitation, glycolysis, gluconeogenesis, citric acid cycle, fermentation, urea cycle, fatty acid metabolism, pyrimidine biosynthesis, glutamate amino acid group synthesis, porphyrin metabolism, aspartate amino acid group synthesis, aromatic amino acid synthesis, histidine metabolism, branched amino acid synthesis, pentose phosphate pathway, purine biosynthesis, glucoronate metabolism, inositol metabolism, cellulose metabolism, sucrose metabolism, starch and glycogen metabolism, and combinations thereof.

In some embodiments, the distinct components include distinct chemical compounds. The distinct components may include any suitable chemical compounds that contribute to the feature profile. Suitable chemical compounds include, without limitation, organic compounds, inorganic compounds (e.g., salts, metals, ions, etc.), toxins, microorganism (e.g., bacteria, viruses, fungi, protists, etc.), metabolites, allergens, etc.

Cell Subsets

In some embodiments, a cell subset may be any group of cells in a biological sample whose presence is characterized by one or more features (such as gene expression on the RNA level, protein expression, genomic mutations, biomarkers, and so forth). A cell subset may be, for example, a cell type or cell sub-type.

In certain aspects, one or more cell subsets may be leukocytes (i.e., white blood cells or WBCs). Potential leukocyte cell subsets include monocytes, dendritic cells, neutrophils, eosinophils, basophils, and lymphocytes. These leukocyte subsets can be further subdivided, for example, lymphocyte cell subsets include natural killer cells (NK cells), T-cells (e.g., CD8 T cells, CD4 naïve T cells, CD4 memory RO unactivated T cells, CD4 memory RO activated T cells, follicular helper T cells, regulatory T cells, and so forth) and B-cells (naïve B cells, memory B cells, Plasma cells). Immune cells subsets may be further separated based on activation (or stimulation) state.

In certain aspects, leukocytes may be from an individual with a leukocyte disorder, such as a blood cancer, an autoimmune disease, mycleodysplastic syndrome, and so forth. Examples of a blood disease include Acute lymphoblastic leukemia (ALL), Acute myelogenous leukemia (AML), Chronic lymphocytic leukemia (CLL), Chronic myelogenous leukemia (CML), Acute monocytic leukemia (AMoL), Hodgkin's lymphoma, Non-Hodgkin's lymphoma, and myeloma. Examples of autoimmune disease include alopecia areata, autoimmune hemolytic anemia, autoimmune hepatitis, dermatomyositis, diabetes (type 1), glomerulonephritis, Graves' disease, Guillain-Barré syndrome, idiopathic thrombocytopenic purpura, myasthenia gravis, some forms of myocarditis, multiple sclerosis, pemphigus/pemphigoid, pernicious anemia, polyarteritis nodosa, polymyositis, primary biliary cirrhosis, psoriasis, rheumatoid arthritis, scleroderma/systemic sclerosis, Sjögren's syndrome, and systemic lupus erythematosus.

In certain aspects, one or more cell subsets may include tumor infiltrating leukocytes. Tumor infiltrating leukocytes may be in mixture with cancer cells in the biological sample, or may be enriched by any methods described above or known in the art.

In certain aspects, one or more cell subsets may include cancer cells, such as blood cancer, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, and brain cancer.

Cell subsets of interest also include brain cells, including neuronal cells, astrocytes, oligodendrocytes, and microglia, and progenitor cells thereof. Other cell subsets of interest include stem cells, pluripotent stem cells, and progenitor cells of any biological tissue, including blood, solid tissue from brain, lymph node, thymus, bone marrow, spleen, skeletal muscle, heart, colon, stomach, small intestine, kidney, liver, lung, and so forth.

Features

Features of interest include any characteristic of a physical sample, e.g., a biological sample, or a physical system that may be indicative of the presence of one or more distinct components, e.g., cell subsets. In certain aspects, the abundance (i.e., value) of a feature may be indicative of the abundance of one or more distinct components, e.g., cell subsets. Features may be aggregate features of the sample, e.g., biological sample, such as total amounts of mRNA, protein, specific genotypes, biomarkers, and so forth.

Features such as gene expression and/or cell genotype may be of interest. For example, cell types and/or states may be differentiated by gene expression. In another example, cancer cells may be differentiated based on genetic heterogeneity resulting from mutation. Such features may be measured by any means known in the art, including PCR methods (e.g., quantitative PCR of cDNA synthesized from RNA), RNA-Seq, DNA-seq, DNA microarray, tiling array, NanoString® nCounter®, northern blot, serial analysis of gene expression (SAGE) and so forth. Features such as protein expression may be measured by any means known in the art, including western blot, protein microarray, ELISA, other immunoassays, mass spectrometry, and so forth.

In some embodiments, the feature profile includes suitable, measured properties of distinct chemical compounds, obtained by any suitable method. In some cases, the features include nuclear magnetic resonance (NMR) (such as $^1$H, $^{13}$C, $^2$H, $^6$Li, $^{10}$B, $^{11}$B, $^{14}$N, $^{15}$N, $^{17}$O, $^{19}$F, $^{23}$Na, $^{29}$Si, $^{31}$P, $^{35}$Cl, $^{113}$Cd, $^{129}$Xe, or $^{195}$Pt NMR) spectra, electromagnetic radiation (e.g., ultrviolet, visible, infrared radiation) absorbance and/or emission spectra, circular dichroism spectra, Raman spectra, mass spectra, and chromatograms (e.g., from affinity chromatography, liquid chromatography, size-exclusion chromatography, etc.).

Features (such as cell-free biomarkers) may be measured by any means known in the art, including western blot, ELISA, mass spectrometry, chromatography (e.g., thin layer chromatography, gas chromatography, liquid chromatography, and so forth). For example, a feature may be the intensity of a peak observed on a chromatograph or a mass spectrum.

In certain aspects, the method may include obtaining feature measurements from a physical sample, e.g., a biological sample, or a physical system. In other aspects, the method may include obtaining feature measurements from a database, such as, without limitation, a publically available DNA microarray database, RNA-seq database, and/or a DNA-seq database, or any other suitable database of feature measurements.

Reference profiles of feature signatures may be obtained by measuring features of purified or enriched distinct components, e.g., distinct cell subsets. For example, a cell subset may be purified by density gradient centrifugation, panning, magnetic bead sorting, fluorescence activated cell sorting (FACS), etc., as described above. Alternatively, a cell subset may be cultured in vitro, e.g., through stimulation and/or differentiation of precursor cells. After isolation of a cell subset, features of the cell subset may be measured (e.g., as described above or as known to one of skill in the art). In certain aspects, gene expression of a cell subset may be measured (e.g., by DNA microarray analysis) to obtain a gene expression profile (GEP) of the cell subset.

In some cases, feature signatures for a distinct component that is a signaling pathway is obtained by measuring the features in a functional cell-free system that includes components of the signaling pathway, by selectively activating the signaling pathway pharmacologically or inducibly in a cellular environment, etc. In some cases, feature signatures for a distinct component that is a chemical compound is obtained by measuring the features in substantially pure or enriched sample of the chemical compound.

In certain aspects, a signature matrix includes levels of specific mRNA, protein, genotypes, and/or biomarkers for any of the cell subsets described above. Signature matrices are often termed 'base or basis matrices' in prior studies, and can be obtained, for example by differential expression analysis of purified or enriched cell populations. Gene signature matrices can be made more robust by minimizing an inherent matrix property called the condition number, which measures the stability of the linear system to input variation or noise. In certain aspects, signature matrix stability may be measured via the 2-norm condition number, calculated with the kappa function, e.g., in R.

Some reference profiles in the same signature matrix may exhibit "multicollinearity", a phenomenon in which reference profiles of multiple distinct components, e.g., cell types, are highly correlated. Multicollinearity may prevent deconvolution, or reduce confidence in deconvolution of the relative amounts of distinct components, e.g., cell subsets, in a physical sample, e.g., biological sample, as could be reported by a significance value in the subject methods. The severity of multicollinearity between two reference profiles in a signature matrix of the subject invention as measured by the variance inflation factor (VIF), may be 1 or greater, e.g., 2 or more, 5 or more, 10 or more, 15 or more, including 20 or more, and in some cases may be 50 or less, e.g., 40 or less, 30 or less, 20 or less, 15 or less, including 10 or less.

In some cases, the reference matrix has a 2-norm condition number of 1 or more, e.g., 2 or more, 5 or more, 8 or more, 10 or more, 15 or more, 20 or more, 50 or more, 100 or more, 500 or more, including 1,000 or more, and in some embodiments has a 2-norm condition number of $10^4$ or less, e.g., $10^3$ or less, 500 or less, 250 or less, 200 or less, 150 or less, 100 or less, 50 or less, 30 or less, 20 or less, 15 or less, 8 or less, including 5 or less. In some embodiments, the reference matrix has a 2-norm condition number in the range of 1 to 5, e.g., 5 to 8, 8 to 10, 8 to 15, 10 to 15, 15 to 20, 20 to 30, 20 to 50, 50 to 100, 100 to 150, 100 to 200, 100 to 250, 100 to 500, 500 to 1,000, including 1,000 to 10,000.

The condition number of a reference matrix may be adjusted using any suitable method. In some cases, the condition number of an initial reference matrix is reduced by adding or removing one or more features from the matrix, thereby generating a superset or subset of the initial reference matrix that has a lower condition number. This process may be iterated until a sufficiently low condition number for the final reference matrix is obtained.

In certain aspects, the reference matrix may include at least one feature (e. g. gene), e.g., at least 2, at least 3, at least 5, at least 10, at least 20, at least 50, including at least 100 features that are associated with (e.g., expressed by) two or more, e.g., 5 or more, 10 or more, including 15 or more of the distinct components (e.g., cell subsets), and in some cases, by 20 or fewer, e.g., 15 or fewer, 12 or fewer, 10 or fewer, including 8 or fewer of the distinct components. In some cases, the reference matrix may include at least one feature (e.g., gene), e.g., at least 2, at least 3, at least 5, at least 10, at least 20, at least 50, including at least 100 features that are associated with (e.g., expressed by) 2 to 20, e.g., 2 to 15, 2 to 12, including 5 to 10 distinct components (e.g., cell subsets). In some cases, the reference matrix may include 10,000 or fewer, e.g., 5,000 or fewer, 1,000 or fewer, 500 or fewer, 200 or fewer, including 100 or fewer features (e.g., genes) that are associated with (e.g., expressed by) a plurality of distinct components (e.g., cell subsets).

In certain aspects, candidate features for inclusion in the signature matrix may be filtered. In certain embodiments, features with low values and/or variance may be filtered from the signature matrix. For example, features with values and/or variance that is in the lower 90%, lower 80%, lower 75%, lower 50%, or lower 25% as compared to other candidate features may be filtered out. In another example, features with values and/or variance that is higher than 90%, 80%, 75%, 50%, or 25% as compared other candidate features may be included in the signature matrix. In some embodiments, features enriched in distinct components that are not represented in the signature matrix are not included in the signature matrix. In some embodiments, features having a value higher than a threshold value in distinct components that are not represented in the signature matrix are not included in the signature matrix.

Features that are more predictive for distinct components, e.g., cell subsets, of interest may be included in the signature matrix. For example, the method may comprise calculating an enrichment score (ES) for a given feature in a given distinct component, e.g., cell subset, or physical sample/physical system based on the sum of linear model coefficients from all pairwise comparisons of that feature with other distinct components, e.g., cell subsets, or physical samples/physical systems. In certain aspects, features may be selected for inclusion in the signature matrix based on fold change in the value of the feature for a distinct component, e.g., cell subset, as compared to other distinct components, e.g., cell subsets. For example, features that are 2 fold or higher, 5 fold or higher, 10 fold or higher, or 20 fold or higher in one distinct component, e.g., cell subset, than any other distinct component, e.g., cell subset, may be selected to be included in the signature matrix. Conversely, features may be excluded from the signature matrix to reduce multicollinearity.

In certain aspects, the subject methods include isolating one or more distinct components e.g., cell subsets, and measuring features of the one or more distinct components e.g., cell subsets to obtain a signature matrix. For example, cells in a first biological sample may be separated into separate cell subsets by FACS. Separate cell subsets may be analyzed by DNA microarray to obtain a gene expression profile (GEP) for each of the separate cell subsets. The GEP for each cell subset may then be compiled to generate a signature matrix with values for expression of a number of genes for each of the cell subsets (e.g., as seen in FIG. 16).

Examples of sample feature profiles include a "gene expression profile" or "GEP" (e.g., as obtained by microarray analysis), a protein expression profile, a genotype profile (e.g., of a sample having heterogeneous tumor cells), a biomarker profile (e.g., of free biomarkers in the sample or biomarkers on/in cells of the sample), or a combination thereof. A feature profile of a sample may be obtained as described above (e.g., features may be measured directly from a biological sample or the feature profile may be obtained from a database, such as a publically available DNA microarray database). As discussed above, a biological sample may include any cell type. In certain embodiments, the feature profile of a sample may be a benchmarking data set.

The present method may provide for a sensitive method of estimating the fractional representation of a distinct component in a physical sample or physical system, where the distinct component is present at a low fraction. In some embodiments, the physical sample or physical system includes at least one distinct component represented in the feature signature at a concentration of 10% or less, e.g., 8.0% or less, 6.0% or less, 4.0% or less, 2.0% or less, including 1.0% or less, and in some cases at a concentration of 0.01% or more, e.g., 0.05% or more, 0.1% or more, 0.5% or more, including 1.0% or more, of the total amount of the second plurality of distinct components present in the sample. In some embodiments, the physical sample or physical system includes at least one distinct component represented in the feature signature at a concentration in the range of 0.01% to 10%, e.g., 0.05% to 8.0%, 0.1% to 6.0%, 0.1% to 4.0%, including 0.1% to 2.0%, of the total amount of the second plurality of distinct components present in the sample.

The present method may provide for robustly estimating the fractional representation of a distinct component in a physical sample or physical system in the presence of distinct components that are not represented in the signature matrix. In some embodiments, distinct components represented in the feature signature are present in the sample at 50% or less, e.g., 45% or less, 40% or less, 35% or less, 30% or less, 25% or less, 20% or less, 10% or less, including 5% or less, and in some cases, 1% or more, e.g., 5% or more, 10% or more, 20% or more, 30% or more, 35% or more, including 40% or more of the total amount of distinct components in the sample. In some embodiments, distinct components represented in the feature signature are present in the sample in the range of 1 to 50%, e.g., 5 to 50%, 10 to 50%, including 20 to 45%.

In certain aspects, a biological sample may include cells that are not represented by the signature matrix. For example, 5% or more, 10% or more, 25% or more, 50% or more, 75% or more, 5% to 50%, 5% or less, 10% or less, 25% or less, or 50% or less of the cells in the biological sample may not be represented by cell subsets in the signature matrix.

Alternatively or in addition, a biological sample may include cell subsets represented by the signature matrix that are present in low amounts, such as 10% or less, 5% or less, 2% or less, 1% or less, 0.5% or less, 0.25% or less, 0.1% or less, between 0.1% and 10%, between 0.25% and 2%, and so forth.

Methods of Deconvolving a Feature Profile

In general terms, a method of the present disclosure may include obtaining a physical sample, e.g., a biological sample, that includes a collection of distinct components. A feature profile m is generated from the physical sample, e.g., by measuring values for a plurality of features. The feature profile m is deconvolved by regressing m and a reference matrix B that contains feature signatures for distinct components of interest with a linear function and optimizing the regression such that the solution minimizes: 1) a linear loss function and 2) an $L_2$-norm penalty function. The deconvolution solves for f, which is a vector containing the regression coefficients. The fractional representations of a distinct component in the reference matrix among all the distinct components that are represented in the reference matrix in the feature profile are estimated based on the regression coefficients in f.

In general terms, a linear loss function penalizes data points according to their distance to a regression hyperplane, or to a fixed distance ε from the hyperplane in the case of an ε-insensitive linear loss function. Thus in some embodiments, the linear loss function is a linear ε-insensitive loss function. An $L_2$ norm penalty function penalizes model complexity and minimizes the variance in the weights assigned to highly correlated predictors (e.g., distinct components in the reference matrix).

In some cases, estimating the fractional representations of distinct components present in the physical sample includes setting negative regression coefficients in f to zero, and normalizing the remaining non-zero regression coefficients to sum to 1.

Also provided herein is a computer-implemented method for deconvolving a feature profile of a physical system. The computer-implemented method may include obtaining a feature profile m of a collection of distinct components in a physical system, and computationally processing the feature profile using a reference matrix B of feature signatures and regression with a linear model relating m to B, to solve for f, as described above. In particular, the solution is obtained when the optimization of the regression minimizes: 1) a linear loss function and 2) an $L_2$-norm penalty function. The regression coefficients in f is then used to derive an estimate of the fractional representation of a distinct component represented in the reference matrix among all the distinct components that are represented in the reference matrix in the feature profile.

In some embodiments, the optimization is done using a suitable algorithm, e.g., using a general purpose computer programmed with a suitable algorithm. Any suitable optimization algorithm that minimizes a linear loss function and an $L_2$-norm penalty function may be used. In some cases, the optimization is done using support vector regression (SVR). In some embodiments, the SVR is ε-SVR or v(nu)-SVR.

Also provided herein are methods of estimating the relative proportions of cell subsets in a biological sample by computationally processing a feature profile of the biological sample are provided herein. Computational processing includes applying support vector regression to a feature profile of the biological sample, using a reference matrix of cell subset feature signatures, to estimate the relative proportions of cell subsets in the biological sample. As described above, each of the cell subset feature signatures corresponds to a different cell subset. The biological sample, cell subsets, feature profile of the biological sample, reference matrix of cell subset feature signatures (i.e., signature matrix), and methods of obtaining them, are described in the above sections.

Support vector regression, or "SVR", is an instance of support vector machine (SVM), a class of optimization methods for binary classification problems in which a hyperplane is discovered that maximally separates both classes. The support vectors are a subset of the input data that determine hyperplane boundaries. Unlike standard SVM, SVR fits a hyperplane to the input data points, thus performing a regression, and does so within a margin of error ε, and a unique linear error penalty (i.e., an ε-insensitive loss function), rendering it relatively robust to outliers and overfitting. SVR is robust to noise and unknown content by (i) enforcing a sparse, compact solution to the regression via feature selection (e.g., selection of distinct components in a reference matrix), and (ii) by minimizing a linear error model (i.e., ε-insensitive loss function) that outperforms other common loss functions (e.g., squared error used in LLSR) in noisy samples. In certain aspects, support vector regression may be performed in non-log linear space.

Unlike previous methods, SVR performs a feature selection, in which distinct components, e.g., genes, from the signature matrix are adaptively selected to deconvolve a given mixture, i.e. a feature profile. In certain aspects, support vector regression may only use a portion of the feature profile of the biological sample and reference matrix of distinct component, e.g., cell subset, feature signatures to estimate the relative proportions of distinct components, e.g., cell subsets, in the physical sample, e.g., biological sample, or physical system. For example, support vector regression may use 80% or less, e.g., 60% or less, 50% or less, 25% or less, 10% or less, 5% or less, including 1% or less of the features present in the feature profile of the physical sample, e.g., biological sample, or physical system, and the reference matrix to estimate the relative proportions of distinct components, e.g., cell subsets, in the physical sample, e.g., biological sample, or physical system.

Two major types of SVR are "nu-support vector regression" (or "v-SVR"), which is described by Scholkopf et al. (Neural Comput. 12, 1207-1245 (2000)), and "epsilon-support vector regression" (or ε-SVR), which is described by Drucker et al. (MIT Press, Vol. 9. (1997)). In certain aspects, the SVR may be ε-SVR.

Alternatively, the SVR may be v-SVR. In v-SVR, the v parameter conveniently controls both the upper bound of training errors ε and the sparsity of support vectors. v-SVR may be applied with a linear kernel to solve for (estimate) the relative proportions of distinct components e.g., cell subsets, in the physical sample, e.g., biological sample, or physical system. In certain aspects, the method includes iterating through different values of nu (v) to obtain different results (different estimates of the relative proportions of distinct components e.g., cell subsets, in the physical sample, e.g., biological sample, or physical system). The method may include iterating through 2 or more, 3 or more, 4 or more, 5 or more, 10 or more, or 20 or more values of nu. The value of nu can be between 0 and 1. For example, the method may comprise iterating through nu values of 0.25, 0.5, and 0.75. The method may further include selecting the result obtained which has the lowest error between the feature profile of the physical sample, e.g., biological sample, or physical system and the product of the result and the reference matrix of cell subset feature signatures. In certain aspects, the lowest error is the lowest root-mean square error (RMSE). The RMSE may be calculated as the square root of the mean square error between the feature profile of the physical sample, e.g., biological sample, or physical system and the product of the result and the reference matrix of the distinct components e.g., cell subset, feature signatures. In some cases, the lowest error is obtained by using a Pearson product-moment correlation coefficient, Spearman rank correlation, Euclidean distance, or mean absolute deviation (MAD), or any other suitable measure of error.

The number of features in the signature matrix should be equal to or greater than the number of distinct components, e.g., cell subsets, in the signature matrix. In certain aspects the number of features may be substantially more than the number of distinct components, e.g., cell subsets, and the system may therefore be overdetermined. For example, the number of features in the signature matrix may be 2 times or more, 3 times or more, 5 times or more, 10 times or more, 20 times or more, 50 times or more, or 100 times or more than the number of distinct components, e.g., cell subsets, in the signature matrix.

In certain aspects, the step of applying support vector regression to estimate the relative proportions of cell subsets includes enforcing a non-negativity constraint. For example, following support vector regression any cell subsets that would be estimated to be at a negative abundance or proportion (below zero) may be set to zero.

The proportion of distinct components, e.g., cell subsets, may be a relative proportion of distinct components, e.g., cell subsets. As such, after applying support vector regression and optionally enforcing a non-negativity constraint, the calculated abundance (e.g., coefficient) of each distinct component, e.g., cell subset, may be normalized to sum to 1, in order to obtain a relative abundance of each distinct components, e.g., cell subset.

To decrease running time and promote better overall performance, the feature profile of the physical sample, e.g., biological sample or the physical system, and/or the reference matrix of distinct components, e.g., cell subset, feature signatures may be normalized to zero mean and unit variance prior to running CIBERSORT, or otherwise transformed to reduce runtime.

The method may further comprise determining a significance value for the identification and estimation of the relative proportions of the distinct components, e.g., cell subsets. In certain embodiments, an empirically defined global p-value for the deconvolution may be determined using Monte Carlo sampling. The significance value may indicate the likelihood of the null hypothesis that no distinct components, e.g., cell types, in the signature matrix are present in a given feature profile of a physical sample, e.g., biological sample or physical system.

As described in the Experimental section, the product of the signature matrix (denoted by B) and the vector consisting of the unknown fractions of each distinct components, e.g., cell type, (denoted by f) model the feature profile of the physical sample, e.g., biological sample or physical system (m) as shown by the formula: $m = f \times B$.

In certain aspects, the method further includes determining a significance value for the estimation of the relative proportions of distinct components, e.g., cell subsets, by: a) generating a random feature profile m* containing features randomly selected from a parent feature profile, wherein the parent feature profile comprises the feature profile and wherein m and m* have the same Euclidean norm (i.e., $|m|=|m^*|$); b) optimizing a regression between m* and the reference matrix B, wherein m* is modeled as a linear combination of B, wherein the optimizing comprises solving for f* comprising a set of regression coefficients of the regression, wherein the solution minimizes: a linear loss function; and an $L_2$-norm penalty function; c) calculating the product of f* and the reference matrix B to generate a reconstituted feature profile; d) determining a difference measurement between the random feature profile m* and the reconstituted feature profile; and e) determining a significance value based on a distribution of the difference measurements determined from i iterations of steps a)-d), wherein i is a number greater than 1.

In certain aspects, the difference measure of step d) may be a correlation coefficient, such as the Pearson product-moment correlation coefficient. Alternatively, another difference metric may be used instead of the Pearson product-moment correlation coefficient. Examples of other distance metrics include RMSE, goodness of fit metrics, standard deviation, Spearman rank correlation, Euclidean distance, or mean absolute deviation (MAD), and so forth.

The parent feature profile may be any suitable feature profile that is larger (i.e., has more distinct element In certain aspects, the significance value of step e) may be the p-value. The distribution in step e) may be a null distribution.

The number of iterations i may be any suitable integer, and may be 2 or more, 5 or more, 10 or more, 25 or more, 50 or more, 100 or more, 200 or more, 500 or more, 1,000 or more, 10,000 or more, and in some cases may be 10,000 or less, e.g., 1,000 or less, 800 or less, 600 or less, including 500 or less. In some cases, i may be between 2 and 10,000, between 10 and 1,000, between 50 and 500, including between 200 and 600, and so forth.

In certain aspects, the method may include screening candidate reference matrixes and/or feature profiles to identify those that provide a low significance value.

The feature profile may be any suitable feature profile, as described above, depending on the physical sample or physical system of interest. In certain aspects, the feature profile of the biological sample may be a gene expression profile (GEP), e.g., as described in embodiments of the above sections. The gene expression profile may represent the RNA transcriptome of cells in the biological sample.

The distinct components may be any suitable distinct components, as described above. In some cases, the distinct components are distinct cell subsets. The cell subsets (e.g., of the signature matrix and/or whose relative abundance is estimated by SVR) may be any of the cell subsets described in the above sections. In certain aspects the cell subsets may include brain cell subsets. For example, the cell subsets may include one or more of neuronal cells, astrocytes, oligodendrocytes, and microglia. In certain aspects, the cell subsets may include one or more of stromal cells, stem cells, neural cells, and progenitor cells. In certain aspects, the cell subsets may include tumor cells, such as blood cancer, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, and/or brain cancer cells.

In certain aspects, the cell subsets comprise leukocytes, e.g., as described in the above sections. The leukocytes may be tumor infiltrating leukocytes (e.g., in mixture with cancer cells or purified from cancer cells). Leukocyte cell subsets may comprise lymphocytes, such as one or more of naïve B cells and memory B cells, and such as one or more of CD8 T cells, CD4 naïve T cells, CD4 memory RO unactivated T cells, CD4 memory RO activated T cells, follicular helper T cells, and regulatory T cells. In certain aspects, leukocyte cell subsets may include one or more of a B cell, plasma cell, CD8 T cell, CD4 T cell, gamma delta T cell, NK cell, monocyte, macrophage, dendritic cell, mast cell, eosinophil, and neutrophil cell subset.

In certain aspects, the cell subsets may include two or more, 5 or more, 10 or more, or 15 or more, or all of the following cell subsets: naïve B cells, memory B cells, Plasma cells, CD8T cells, naïve CD4 T cells, CD4 memory RO unactivated T cells, CD4 memory RO activated T cells, follicular helper T cells, regulatory T cells, gamma delta T cells, unstimulated NK cells, stimulated NK cells, Monocytes, Macrophages M0, Macrophages M1, Macrophages M2, unstimulated Dendritic cells, stimulated Dendritic cells, unstimulated Mast cells, stimulated Mast cells, Eosinophils, and Neutrophils.

As described above, the physical sample, e.g., biological sample, may be any of a number of physical sample, e.g., biological samples. In certain aspects the biological sample is an archived tissue sample, a blood sample, a solid tissue sample, a tumor sample, a purified sample, a leukocyte-enriched sample, or a combination thereof.

The present method may provide for an accurate estimate of the relative proportions of distinct components contributing to a feature profile. In some cases, estimates obtained by the present method may have a statistically significant R value (e.g., Pearson product-moment correlation coefficient) of 0.50 or more, e.g., 0.60 or more, 0.70 or more, 0.80 or more, 0.85 or more, 0.90 or more, 0.95 or more, 0.97 or more, including 0.99 or more, and in some cases may have a statistically significant R value of 0.99 or less, e.g., 0.98 or less, 0.96 or less, 0.94 or less, 0.92 or less, 0.90 or less, including 0.85 or less, when compared against an independently determined estimate of the relative proportions of distinct components. In some cases, estimates obtained by the present method may have a statistically significant R value in the range of 0.50-0.99, e.g., 0.60 to 0.98, 0.70 to 0.96, including 0.80 to 0.94, when compared against an independently determined estimate of the relative proportions of distinct components. The independently determined estimate of the relative proportions of distinct components may be any suitable independent estimate. In some case the independent estimate is a known amount of distinct components added to a sample. In some cases, the independent estimate is an estimate obtained from flow cytometry (e.g., fluorescence-activated cell sorting (FACS)) analysis.

Computer Systems and Computer Readable Storage Medium

Figure 20:
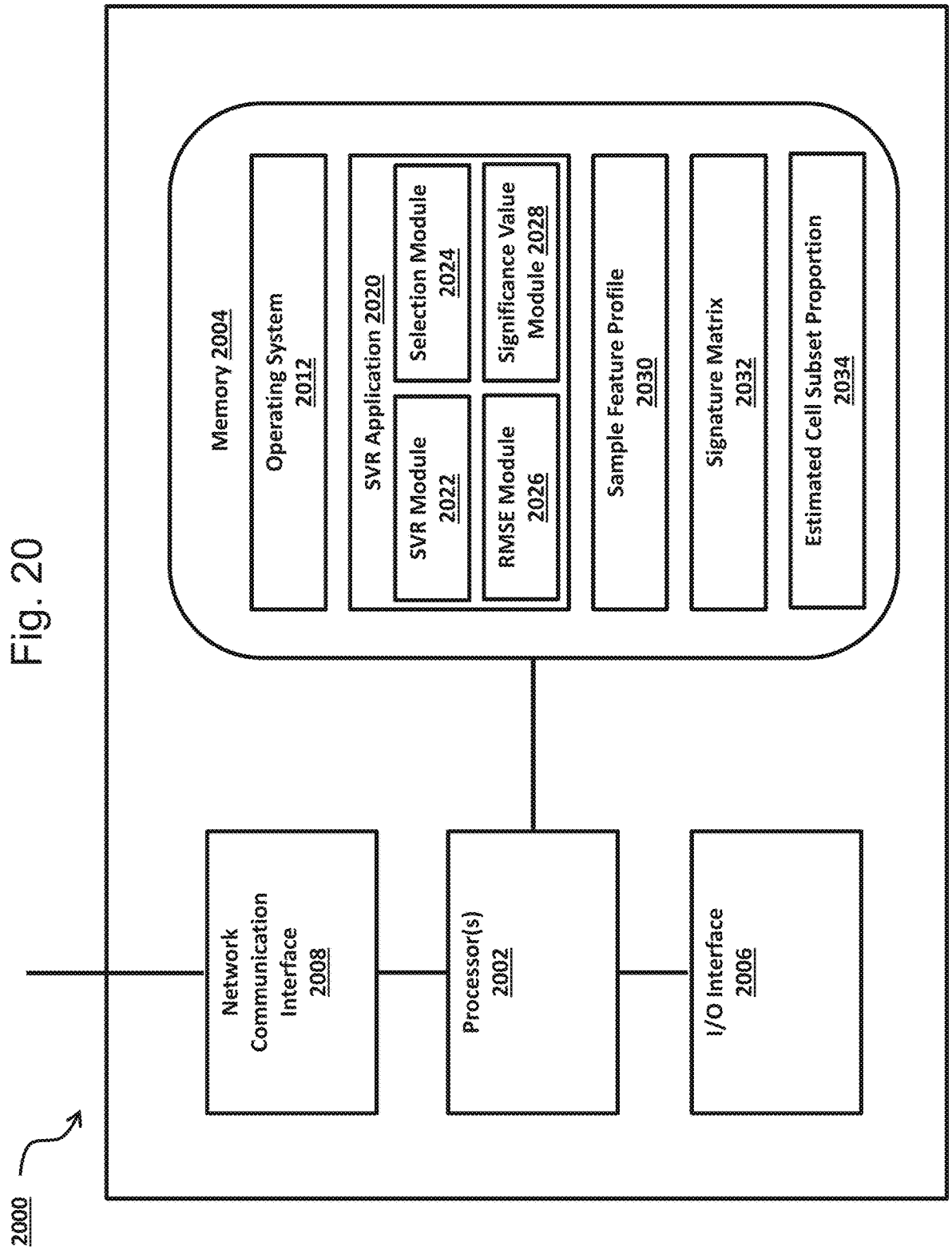
FIG. 20: Schematic diagram of a system of the subject invention, according to one embodiment. The system includes a memory having a support vector regression application configured to perform the subject methods.

FIG. 20 is a block diagram of a computer system 2000 in accordance with certain embodiments.

As shown in FIG. 20, the system 2000 includes one or more processing units (also called herein "processors") 2002, memory 2004 (i.e., a computer readable storage medium), an input/output (I/O) interface 2006, and a network communications interface 2008. These components communicate with one another over one or more communication buses or signal lines. In some embodiments, the memory 2004, or the computer readable storage media of memory 2004, stores an operating system 2012, programs, modules, instructions, and stored data. The one or more processors 2002 are coupled to the memory 2004 and operable to execute these programs, modules, and instructions, and read/write from/to the stored data.

In some embodiments, the processing units 2002 include one or more microprocessors, such as a single core or multi-core microprocessor. In some embodiments, the processing units 2002 include one or more general purpose processors. In some embodiments, the processing units 2002 include one or more special purpose processors.

In some embodiments, the memory 2004 includes high-speed random access memory, such as DRAM, SRAM, DDR RAM or other random access solid state memory devices. In some embodiments the memory 2004 includes non-volatile memory, such as one or more magnetic disk storage devices, optical disk storage devices, flash memory devices, or other non-volatile solid state storage devices. In some embodiments, the memory 2004 includes one or more storage devices remotely located from the processing units 2002. The memory 2004, or alternately the non-volatile memory device(s) within the memory 2004, includes a computer readable storage medium. In some embodiments, the memory 2004 includes a non-transitory computer readable storage medium.

In some embodiments, the I/O interface 2006 is coupled to one or more input/output devices, such as one or more displays, keyboards, touch-sensitive surfaces (such as a track pad or a touch-sensitive surface of the touch-sensitive display), speakers, and microphones. The I/O interface 2006 may be configured to receive user inputs (e.g., voice input, keyboard inputs, etc.) from a user and process them accordingly. The I/O interface 2006 may also be configured to present outputs (e.g., sounds, images, text, etc.) to the user according to various program instructions implemented on the system 2000.

In some embodiments, the network communications interface 2008 includes wired communication port(s) and/or wireless transmission and reception circuitry. The wired communication port(s) receive and send communication signals via one or more wired interfaces, e.g., Ethernet, Universal Serial Bus (USB), FIREWIRE, etc. The wireless circuitry receives and sends RF signals and/or optical signals from/to communications networks and other communications devices. The wireless communications may use any of a plurality of communications standards, protocols and technologies, such as GSM, EDGE, CDMA, TDMA, Bluetooth, Wi-Fi, VoIP, Wi-MAX, or any other suitable communication protocol. The network communications interface 2008 enables communication between the system 2000 with networks, such as the Internet, an intranet and/or a wireless network, such as a cellular telephone network, a wireless local area network (LAN) and/or a metropolitan area network (MAN), and other devices. Network communications interface 2008 is configured to facilitate communications between the system 2000 and other devices over a network.

In some aspects, the computer 2000 may be a personal device (e.g., laptop, desktop, workplace computer, portable device, etc.). A computer 2000 that is a personal device may not need to be connected to a network.

In some aspects, the computer 2000 is a server or a collection of servers, and may not need an I/O interface. For example, the computer 2000 may be a server, and a deconvolution program of the present disclosure, e.g., the SVR Application, 2020 may be accessed by a user through a website.

In some embodiments, the operating system 2012 (e.g., LINUX, UNIX, OS X, WINDOWS, or an embedded operating system) includes various software components and/or drivers for controlling and managing general system tasks (e.g., memory management, storage device control, power management, etc.) and facilitates communications between various hardware, firmware, and software components.

It should be noted that the system 2000 is only one example, and that the system 2000 may have more or fewer components than shown, may combine two or more components, or may have a different configuration or arrangement of the components. The various components shown in FIG. 20 may be implemented in hardware, software, firmware, including one or more signal processing and/or application specific integrated circuits, or a combination of thereof.

In FIG. 20, the deconvolution program, e.g., support vector regression (SVR) application, 2020 includes one or more programs stored in the memory 2004, and comprises instructions to perform methods according to one or more embodiments of the above methods section. The deconvolution program, e.g., SVR application, 2020 may include any of the following exemplary modules or a subset or a superset thereof.

In some cases, a deconvolution module, e.g., SVR Module 2022, may be configured to apply support vector regression, or any other regression algorithm that minimizes a linear loss function; and an $L_2$-norm penalty function, to a feature profile of the physical sample, e.g., biological sample, or physical system, using a reference matrix of distinct component, e.g., cell subset, feature signatures, to estimate the relative proportions of distinct component, e.g., cell subsets, in the physical sample, e.g., biological sample, or physical system, according to an embodiment described in the above methods section.

A Selection Module 2024 may be configured to select (or filter) features to include in the signature matrix and/or select feature profile(s), according to any of the embodiments described in the above methods section.

A RMSE Module 2026 may be configured to determine the result with the lowest error over different values of nu, according to any of the embodiments described in the above methods section.

A Significance Value Module 2028 may be configured to determine a significance value for the estimation of the relative proportions of cell subsets by selecting a subset of the feature profile by a) generating a random feature profile m* containing features randomly selected from a parent feature profile, wherein the parent feature profile comprises the feature profile and wherein m and m* have the same Euclidean norm; b) optimizing a regression between m* and the reference matrix B, wherein m* is modeled as a linear combination of B, wherein the optimizing comprises solving for f* comprising a set of regression coefficients of the regression, wherein the solution minimizes: a linear loss function; and an $L_2$-norm penalty function; c) calculating the product of f* and the reference matrix B to generate a reconstituted feature profile; d) determining a difference measurement between the random feature profile m* and the reconstituted feature profile; and e) determining a significance value based on a distribution of the difference measurements determined from i iterations of steps a)-d), wherein i is a number greater than 1. The Significance Value Module 2028 may employ the deconvolution module, e.g., SVR module, in step b). The Significance Value Module 2028 may further be configured to perform any of the other embodiments described in the above methods section.

The deconvolution program, e.g., SVR Application, 2020 may further include additional modules to perform any of the other embodiments described in the above methods section. In certain aspects, the deconvolution program, e.g., SVR Application, 2020 may be stored in a portable computer readable storage medium separate from the computer 2000.

In some embodiments, the memory 2004 stores a feature profile 2030 of any of the embodiments of the above methods section. In some embodiments, the memory 2004 stores a signature matrix 2032 of any of the embodiments of the above methods section. In some embodiments, the memory 2004 stores estimated cell subset proportions 2034 of any of the embodiments of the above methods section.

The methods described herein are performed by the computer system 2000. In some embodiments, the computer system 2000 is a distributed computer system. For example, the computer system 2000 includes a first set of one or more processors located remotely from a second set of one or more processors. In some embodiments, the computer system 2000 includes a web server configured to provide a web interface. In some embodiments, the web interface is configured to receive data. In some embodiments, the web interface is configured to display results.

In certain aspects, the deconvolution program, e.g., SVR Application, 2020 may be configurable by a user. For example, a the deconvolution program, e.g., SVR Application, 2020 may include a user interface module (not shown) configured to enable a user to determine one or more settings, such as the feature profile 2030 and/or signature matrix 2032 to apply the deconvolution algorithm, e.g., SVR, to the values for nu, criteria by which features are selected by the selection module 2024, the number of iterations to be run by the significance value module 2028, or any other settings that would allow for one or more embodiments described in the above methods section.

Utility

Further aspects of the present disclosure include methods and systems to accurately enumerate cell subsets in a biological sample based on a feature profile of the biological sample. Feature profiles include gene expression profiles, protein expression profiles, tumor genotype profiles, and biomarker profiles. The subject systems and methods represent an advance over other cell subset deconvolution methods for the analysis of mixed biological material, with potential applications including immune monitoring and novel biomarker and therapeutic target discovery.

Figure 1C:
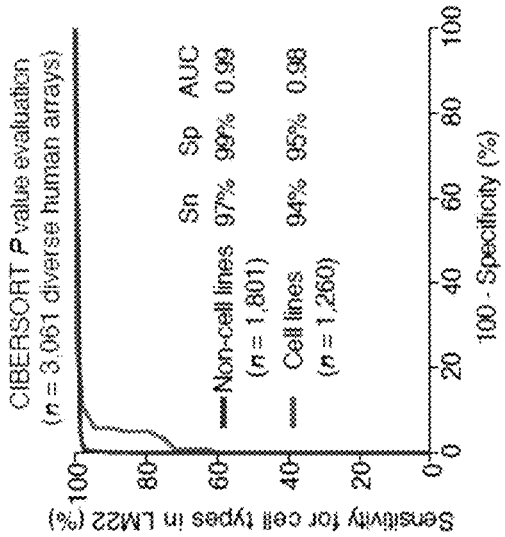
Figure 1B:
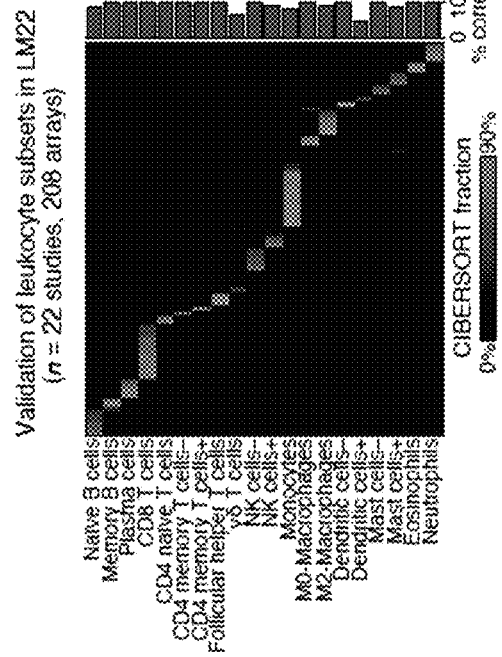
Figure 15:
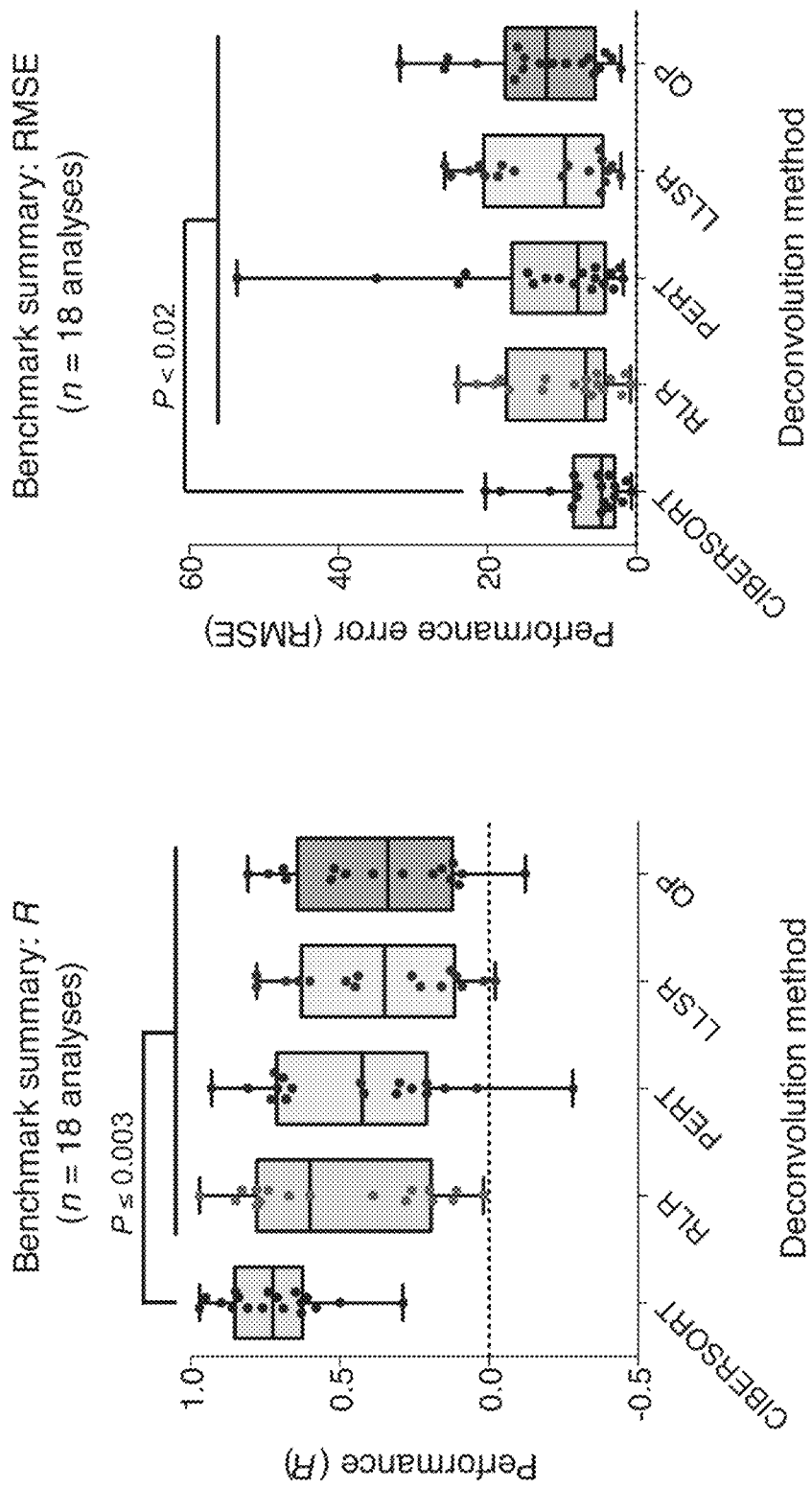
FIG. 15: Summary of benchmarking results for five deconvolution methods applied to complex mixtures. Using two measures of performance (R and RMSE), CIBERSORT significantly outperformed other gene expression-based methods (paired two-sided Wilcoxon signed rank test), and generally performed better than all other methods on complex mixtures (FIG. 2d). Raw data are provided in "Complex Mixtures" in FIGS. 19a-19d. For details of deconvolution methods, see FIG. 18 and Methods.

In some cases, the subject methods accurately resolves relative fractions of diverse cell subsets in GEPs from complex tissues, and provides a measure of statistical confidence for each result. The subject methods exhibit significantly improved accuracy for the analysis of mixtures with (i) noise or unknown content and (ii) closely related cell types (FIG. 15). Moreover, when applied with statistical filtration, the subject methods allow for highly sensitive and specific discrimination of cellular subsets (FIG. 1b,c).

In certain aspects, a method of characterizing cell composition of complex tissues from their gene expression profiles is provided. When applied to enumeration of hematopoietic subsets in RNA mixtures from fresh, frozen, and fixed tissues, including solid tumors, the subject methods outperformed other methods with respect to noise, unknown mixture content, and closely related cell types. The subject systems and methods should enable large-scale analysis of RNA specimens for cellular biomarkers and therapeutic targets. A method to accurately enumerate cell subsets in RNA mixtures from whole tissues could therefore facilitate new insights into disease-associated cellular variation.

In some embodiments the subject methods provide a way to analyze cellular heterogeneity in microarray or RNA-Seq data derived from fresh, frozen, and fixed clinical specimens, thereby complementing methods that require living cells as input.

The present methods and systems find used in a variety of application where estimating the distribution of multiple distinct components within a system is desired. In some cases, the present methods and systems are used for environmental monitoring, food quality and safety inspection, electrical usage monitoring, traffic congestion monitoring, consumer product safety, etc., where deconvolving a feature profile of a physical sample or physical system may provide the contribution of individual components to a complex mixture of many components.

The present methods and systems may also find use in evaluating a disease in an individual, evaluating the predictive, prognostic and/or diagnostic value of a clinical sample feature in a disease, and/or predicting a clinical outcome of a disease therapy, based on an association between the relative proportion of one or more distinct components in a sample from an individual with the disease, as determined by a method of the present disclosure, with clinical outcomes.

Thus, provided herein is a method that includes obtaining a biological sample from an individual having a disease, and estimating a fractional representation of one or more distinct components among a plurality of distinct components present in the sample by performing a method of deconvolving a feature profile, as described herein. The estimated fractional representation of one or more distinct components may be used to determine its value for prognosing and/or diagnosing the disease and/or predicting a response to therapy based on the correlation of the estimated fractional representation of the distinct component and a clinical outcome of the disease. Thus, the present methods provide new biomarkers for prognosis or diagnosis of a disease, and/or for predicting the outcome of a therapy for a disease. A clinical outcome of a therapy for a disease may then be predicted based on the new biomarkers.

"Predicting," as used herein, refers to the process of establishing that a specific event will, or is likely to, occur, or an outcome will be, or is likely to be, achieved, prior to the event or outcome taking place. In some cases, predicting an outcome to therapy is done before the therapy is administered to the patient.

The disease may be any suitable disease, such as, without limitation, cancer, diabetes, inflammatory disease, autoinflammatory disease, infectious disease, neurological disease (e.g., Alzheimer's disease, Parkinson's disease, multiple sclerosis, dementia, depression, psychosis, etc.), metabolic disease, cardiovascular disease, muscular dystrophy, Huntington's disease, etc.

In some cases, the disease is a cancer, which may be any suitable cancer, such as, but not limited to, human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom macroglobulinemia, follicular lymphoma and heavy chain disease.

The individual may be any suitable patient. In some cases the patient has been diagnosed with a disease. In some cases, the patient has received a therapy for the disease. In some embodiments, the sample is obtained from a cohort of individuals who have the same or similar disease, where the cohort may include 1 or more, e.g., 2 or more, 3 or more, 5 or more, 10 or more, 20 or more, 50 or more, 100 or more, 200 or more, including 400 or more individuals.

The therapy may be any suitable therapy. In some cases, the therapy includes administering a pharmaceutical composition to the individual, where the pharmaceutical composition may include naturally derived and/or synthetic drugs, e.g., small molecule drugs, antibiotics, antibodies, vaccines, etc. In some cases, the therapy is immunotherapy.

A method of the present disclosure may also include generating a physical/tangible report and or and electronic report indicating the results of the diagnosis, prognosis, and/or predicted response to a treatment. The report may be provided in any suitable format, such as, but not limited to, paper, a non-transient computer readable medium (e.g., compact disc, universal serial bus drive, etc.), electronic mail, etc. In some embodiments, the report contains one or more recommended courses of action (e.g., whether to continue or stop a therapy, which therapy to administer, etc.) for a medical personnel (e.g., physician, nurse, pharmacist, etc.) and/or the individual.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

In order to further illustrate the present invention, the following specific examples are given with the understanding that they are being offered to illustrate the present invention and should not be construed in any way as limiting its scope.

EXPERIMENTAL

Example 1: Robust Enumeration of Cell Subsets from Expression Profiles of Complex Tissues CIBERSORT uses an input matrix of reference gene expression signatures to estimate the relative proportions of each cell type of interest. However, cell type-specific expression patterns are not required for every gene (Methods). To deconvolve the mixture, a novel application of linear support vector regression (SVR) was employed, a machine learning approach highly robust to noise[9]. Unlike a number of other methods, SVR performs a feature selection, in which genes from the signature matrix are adaptively selected to deconvolve a given mixture. An empirically defined global P value for the deconvolution is then determined (FIG. 1a, Methods).

Figure 4A:
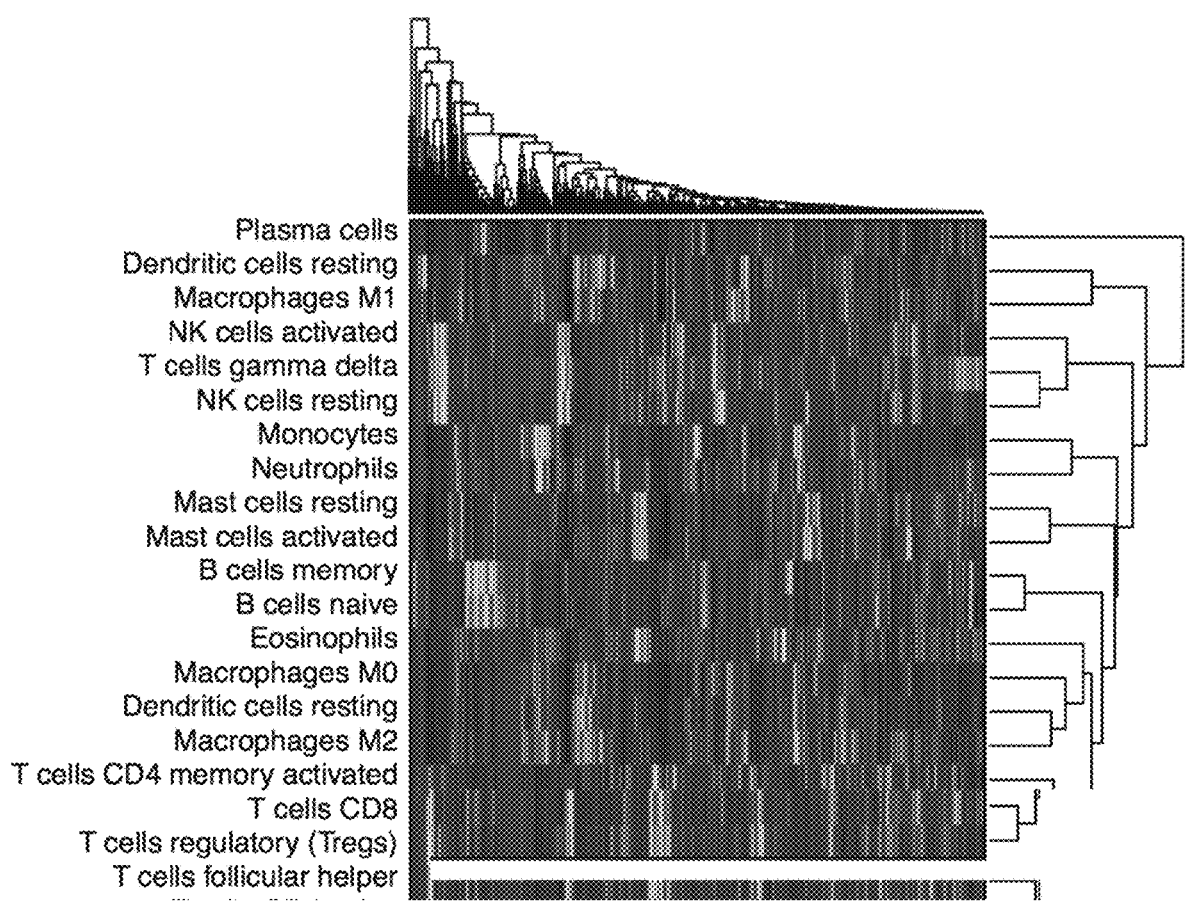
Figure 4C:
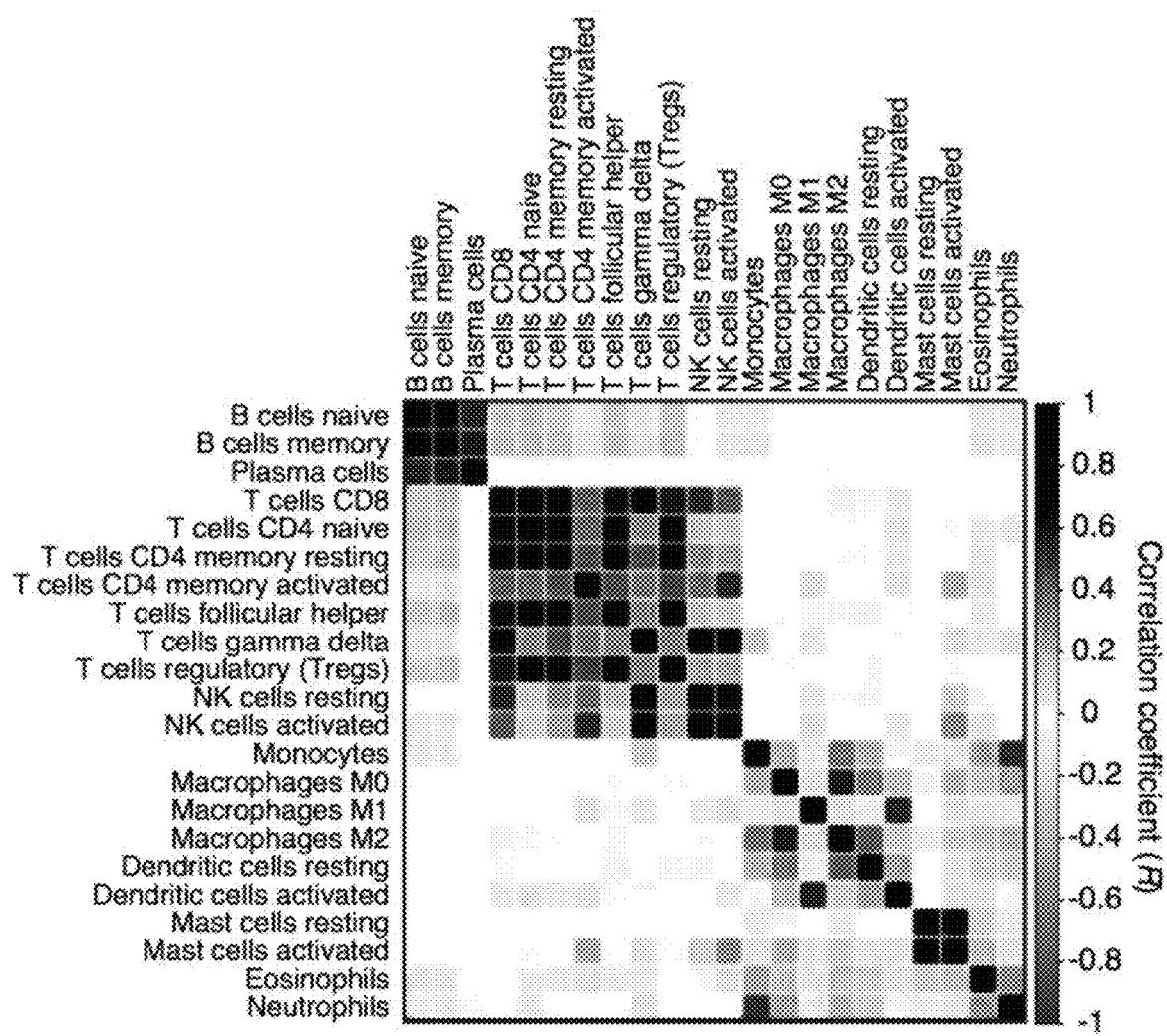
Figure 5B:
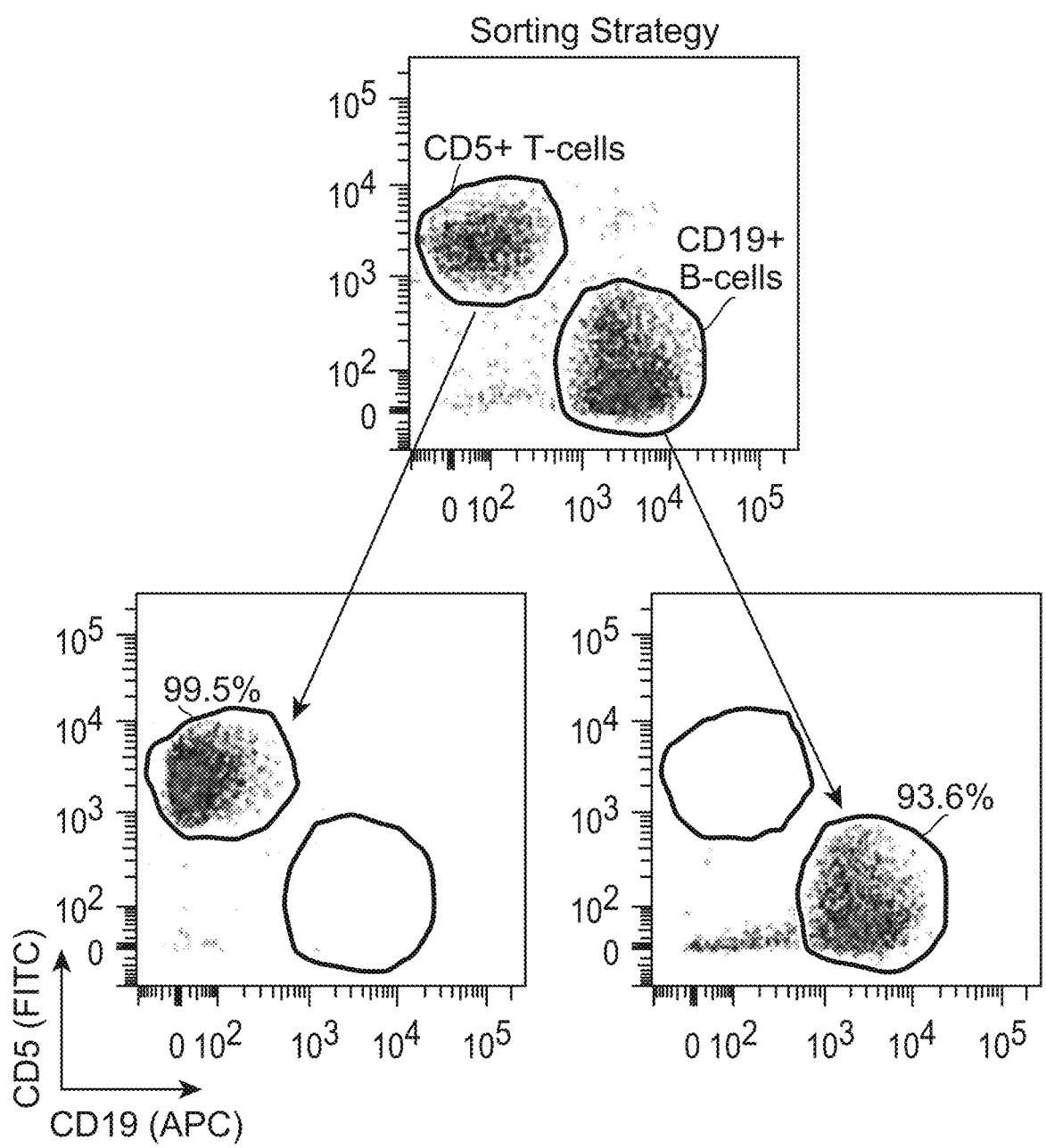

As an initial application, the feasibility of leukocyte deconvolution from bulk tumors, and therefore designed and validated a leukocyte signature matrix, was determined. Termed LM22, this signature matrix consists of 547 genes that accurately distinguish 22 mature human hematopoietic populations and activation states, including seven T cell types, naïve and memory B cells, plasma cells, NK cells, and myeloid subsets (FIG. 16, FIG. 4, Methods). Cell subsets can be further grouped into 11 major leukocyte types based on shared lineage in the hematopoietic hierarchy (FIG. 16). Using CIBERSORT, LM22 was first validated against additional datasets profiling variably purified leukocyte subsets, confirming the cell type specificities of integrated genes and correctly classifying 93% of datasets into distinct cell phenotypes (FIG. 1b, FIG. 5a, FIG. 17). As further validation, CIBERSORT produced results consistent with the high purity of T and B cells that were flow-sorted from five human tonsils (FIG. 5b).

To evaluate the CIBERSORT empirical P value metric for sensitivity and specificity, LM22 was applied to deconvolve 3,061 human transcriptomes[10]. Monte Carlo based random gene samplings was employed to generate "null" mixtures (Methods), then scored expression profiles from known hematopoietic and non-hematopoietic cell sources as "positive" and "negative" samples using CIBERSORT. This distinction was considered separately for variably purified primary tissue specimens (n=1,801 total, positive=1,425, negative=376) and transformed cell lines (n=1,260 total, positive=118, negative=1,142). In both groups, at an empirical P value threshold of ~0.01, CIBERSORT achieved ≥94% sensitivity and ≥95% specificity for distinguishing positive from negative samples (AUC≥0.98; FIG. 1c). Of note, results were similar using an independently derived leukocyte signature matrix[4] instead of LM22 (data not shown), supporting the generality of the approach.

Figure 1D:
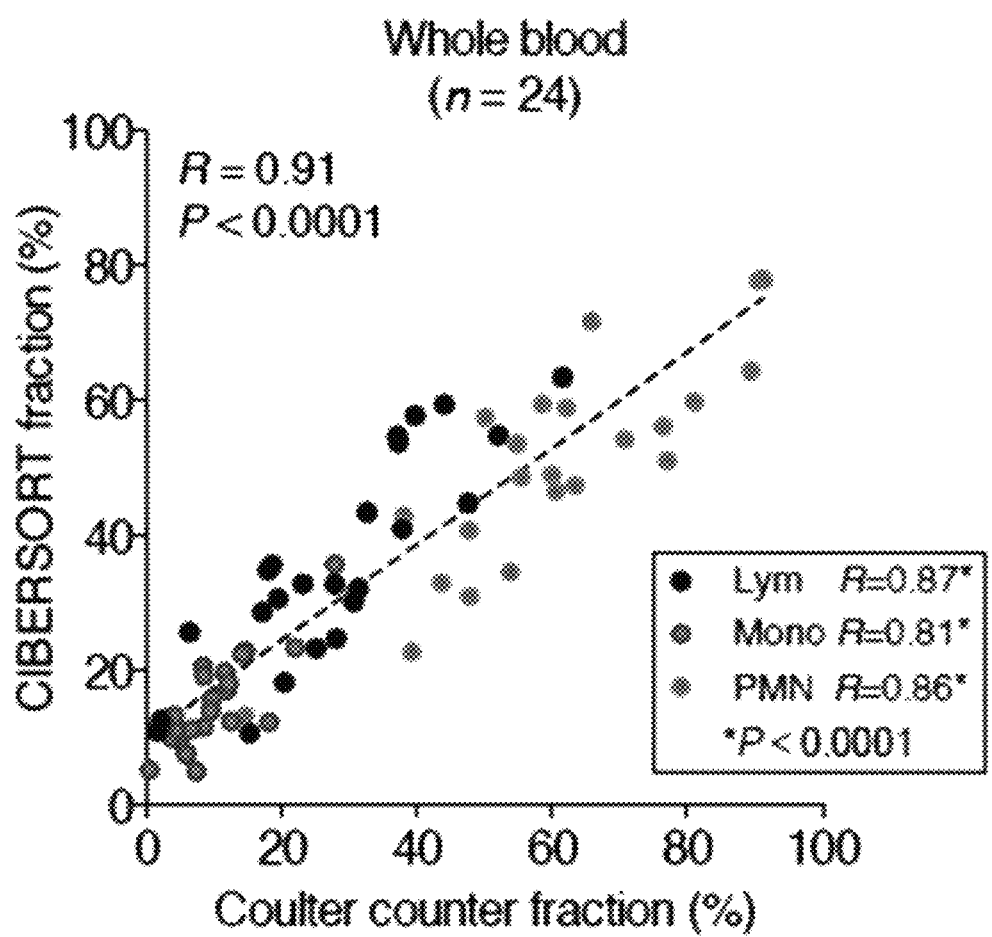

CIBERSORT was next benchmarked on idealized mixtures with well-defined composition, in which the majority of the mixture can be accounted for by highly distinct (uncorrelated) reference profiles of purified cell types, and the contribution from unknown cell content and noise is minimal[4,11,12]. CIBERSORT results were compared with six GEP deconvolution methods—four that take reference expression profiles as input: PERT[6], quadratic programming (QP)[5], linear least squares regression (LLSR)[4], and robust linear regression (RLR); and two that take genes uniquely expressed in a given cell type as input (i.e., marker genes): MMAD[7] and DSA[8] (FIG. 18). To the best of our knowledge, it is noted that RLR was first applied to GEP deconvolution in this work. CIBERSORT, like other methods, achieved accurate results on idealized mixtures, whether for in vitro mixtures of blood cancer cell lines[4] and neural cell types[12] (FIG. 6a,b), or whole blood[11] (FIG. 1d) (FIG. 19). Consequently, it was asked whether CIBERSORT might be useful for immune monitoring with LM22, and profiled peripheral blood in patients immediately before and after receiving rituximab monotherapy for Non-Hodgkin's lymphoma. CIBERSORT analysis of post-treatment peripheral blood mononuclear cells (PBMCs) with LM22 revealed a selective depletion of B cells targeted by rituximab in four patients (FIG. 6c), suggesting utility for immune monitoring during immunotherapy, especially when specimens cannot be immediately processed.

CIBERSORT's technical performance against other methods was then compared on mixtures with unknown content, employing commonly used benchmark datasets consisting of four admixed blood cancer cell lines[4], each with highly distinct reference profiles (Methods). By combining these mixtures with a colon cancer cell line, human solid tumors was simulated with varying leukocyte infiltration (1% to 100%). The addition of non-log linear noise was also tested to simulate sample handling, stochastic gene expression variation, and platform-to-platform differences. While this simulation framework does not fully reflect biological admixtures of solid tumors, it provided a reasonable model in which immune content and added noise could be finely tuned and tested. Moreover, the performance of each method is unlikely to significantly improve in more complicated mixtures.

Figure 2A:
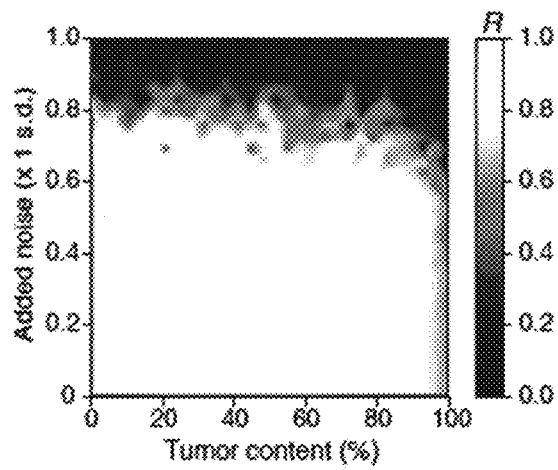
FIGS. 2a-2i: Performance assessment on diverse RNA mixtures from complex tissues.
Figure 2B:
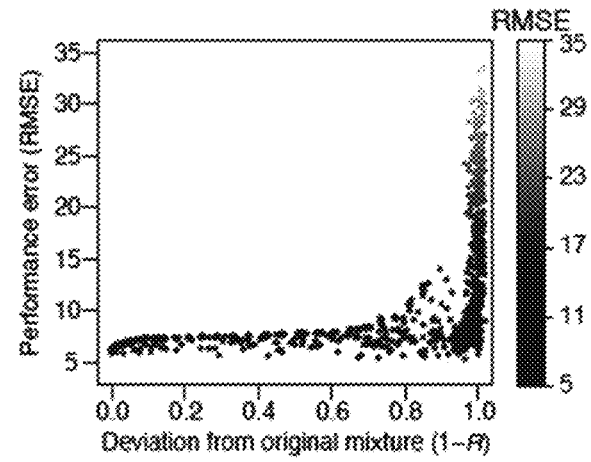

Nearly all methods degraded in performance as a function of signal loss (FIG. 7, FIG. 19), showing highly reduced accuracy below 50% immune content. Only CIBERSORT accurately resolved known mixture proportions over nearly the entire range of tumor content (up to ~95%) and noise (up to ~70%) (FIG. 2a), exhibiting strong performance on mixtures that diverged considerably from their original compositions (Pearson's R as low as ~0.05; FIG. 2b). Furthermore, since many solid tumor types are composed of fewer than 50% infiltrating immune cells[13], the parameter range in which CIBERSORT outperformed other methods is highly relevant for bulk tumor analysis.

Figure 2C:
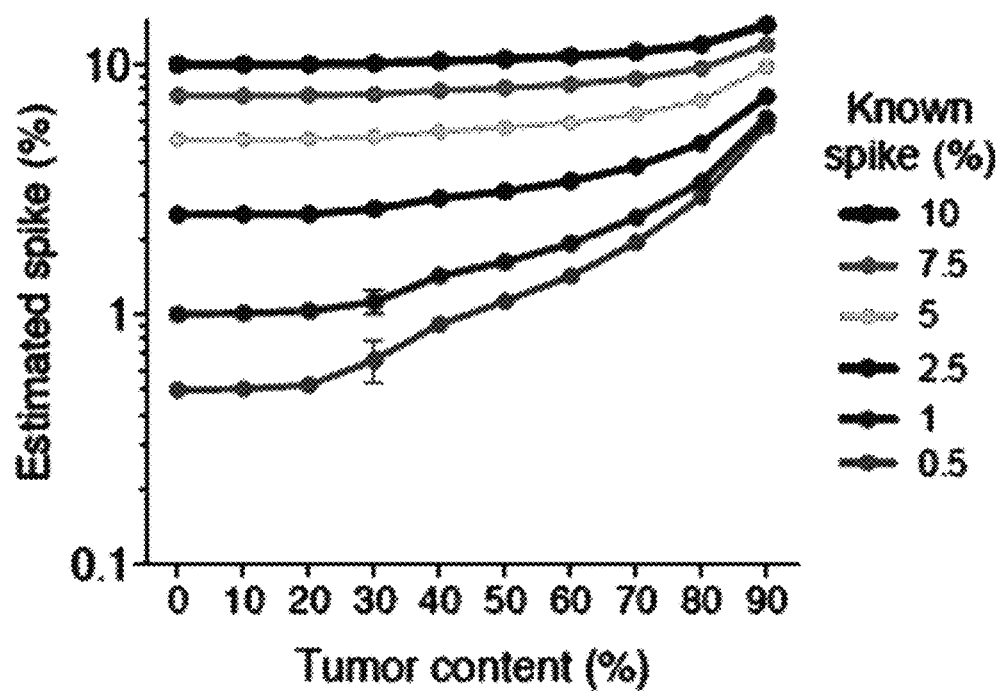
Figure 2D:
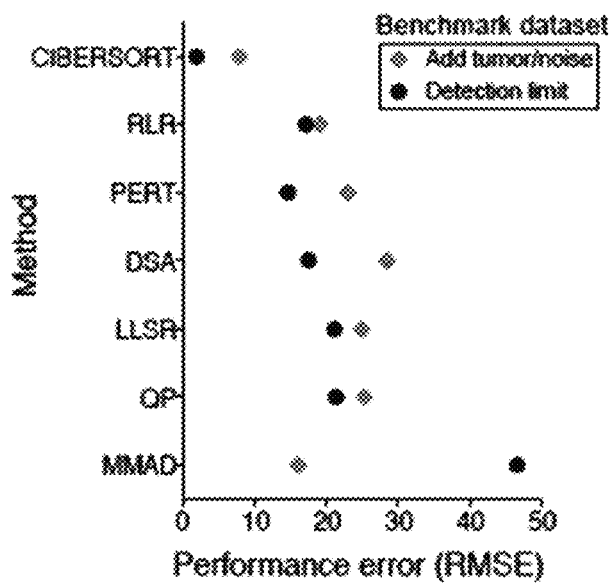
Figure 7A:
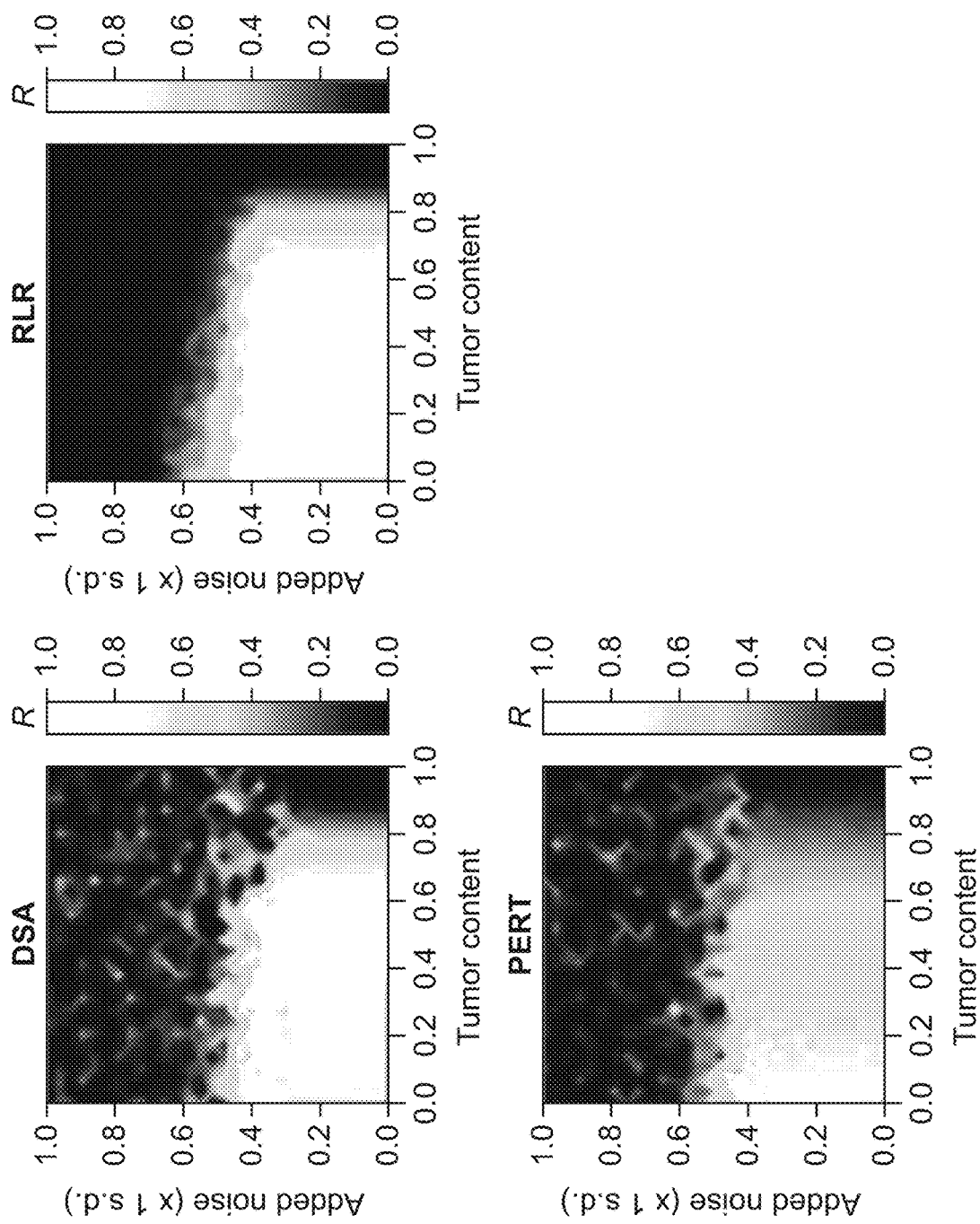
FIGS. 7a-7b: Comparative analysis of deconvolution methods on simulated tumors with added noise (related to FIGS. 2a, 2b).
Figure 7B:
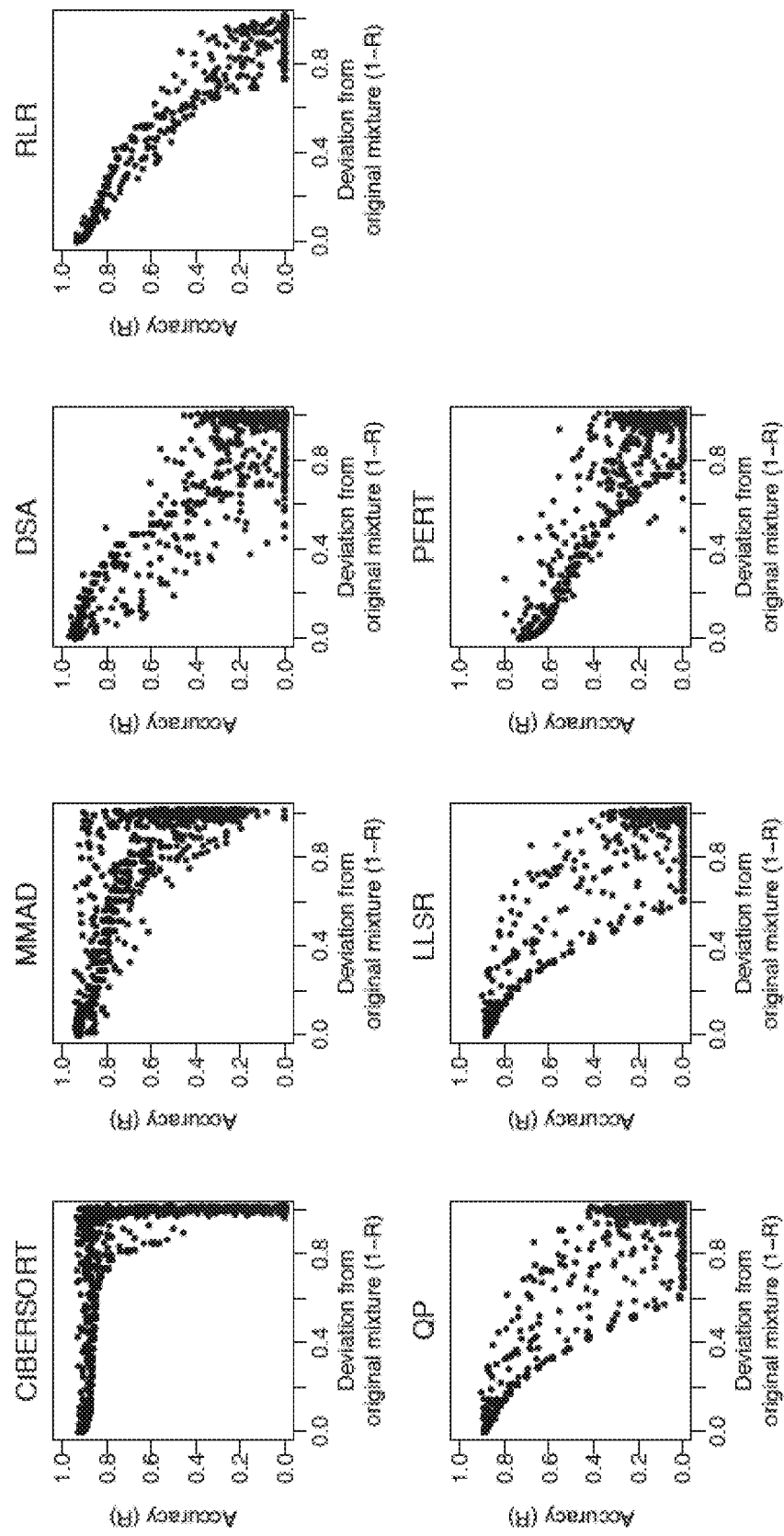
Figure 8:
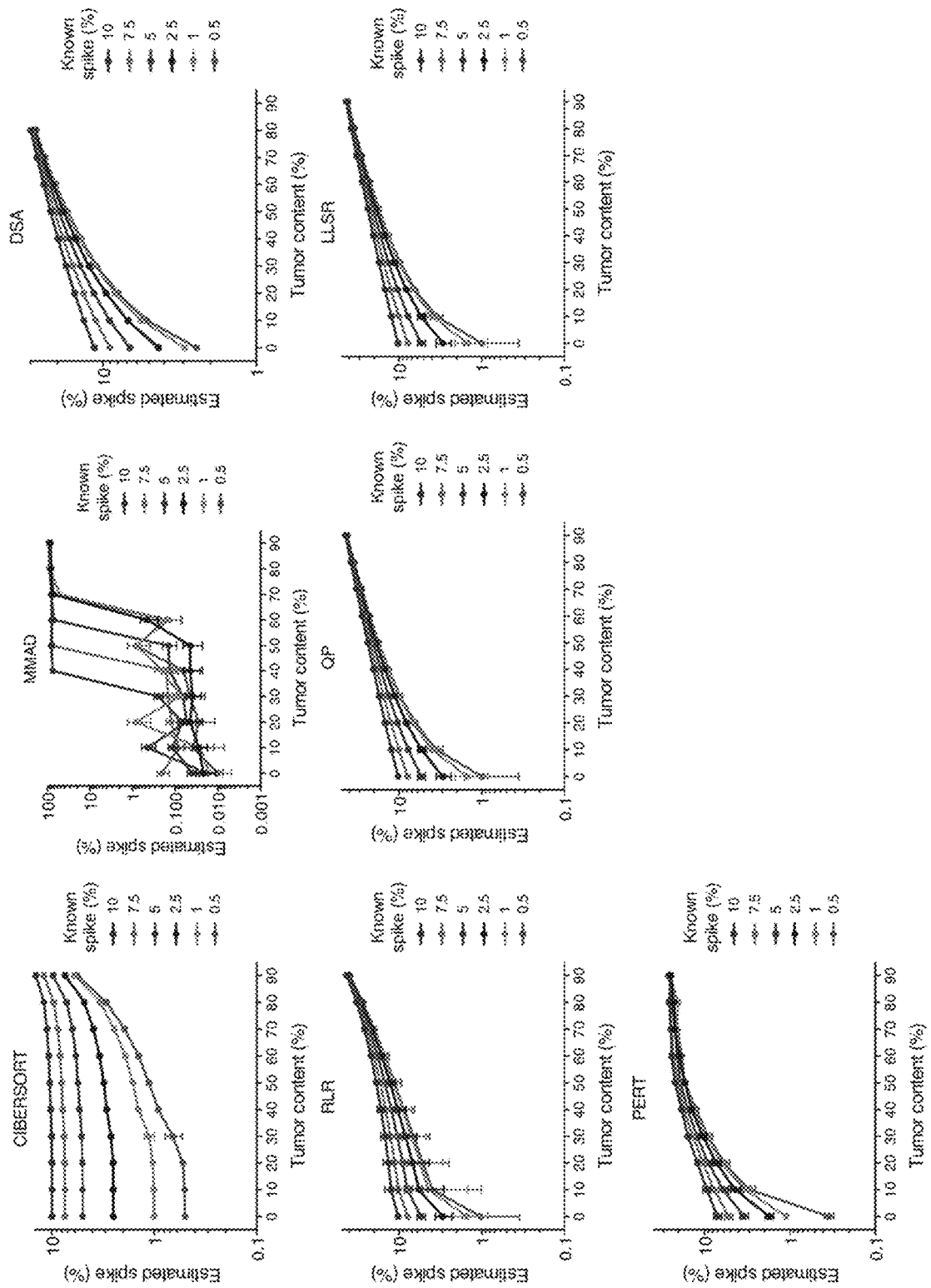
FIG. 8: Comparison of deconvolution methods with respect to detection limit in simulated mixtures with unknown content (related to FIGS. 2c, 2d). Each color represents a defined input concentration for a given cell type (here, Jurkat), and each line represents its concentration as predicted by GEP deconvolution. Known Jurkat concentrations were measured across a range of added tumor content in five simulated mixtures of four blood cell lines, with different concentrations of a colon cancer line (see Methods). Data are presented as medians (n=5 mixtures)±95% confidence intervals.
Figure 9A:
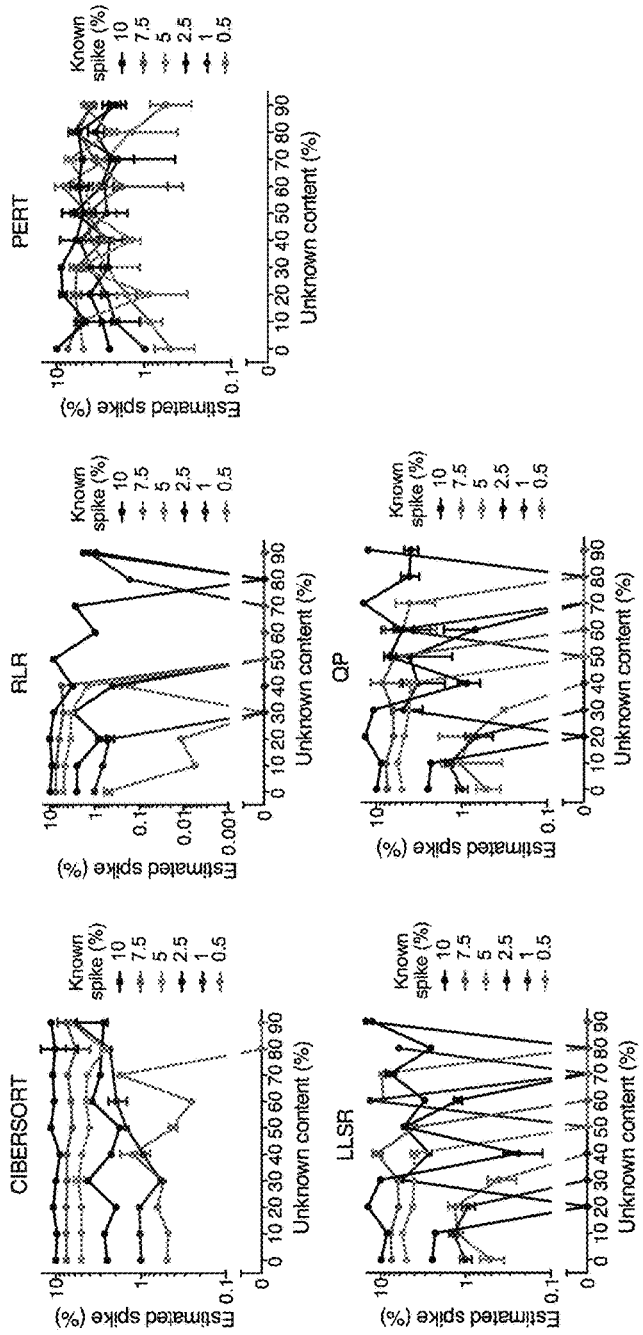
FIGS. 9a-9b: Analysis of detection limit for each cell subset in LM22.

To assess the detection limit of each method for rare cell types in bulk tissues, a second synthetic dataset of the same cell lines was created, but with one blood cell line spiked into random mixtures of the other three blood subsets. CIBERSORT detected cellular fractions down to 0.5% in mixtures containing up to 50% tumor content, and down to 1% in mixtures with over 50% tumor content (FIG. 2c). While all methods overestimated spike-ins with higher tumor content, the effect was least pronounced for CIBERSORT (FIG. 8). Overestimation was less common in a separate analysis, in which each cell type in LM22 was spiked into random combinations of the remaining 21 immune subsets over a range of unknown content (FIG. 9). Overall, CIBERSORT consistently outperformed other methods, substantially in some cases (FIG. 2d, FIGS. 7-9, and FIG. 19).

An aspect of CIBERSORT is the context-dependent analysis of signature matrix genes, known as feature selection. This procedure increases CIBERSORT's tolerance to noise[14]; however, if feature selection were influenced by the identities of cell subsets in the mixture, then the absence of one cell type might impact enumeration of closely related cell types. To test this, a simple spike series of two uncorrelated reference profiles from LM22 (mast cells and CD8 T cells) was used to determine whether selected features (i.e., genes) correlate with defined mixture composition (FIG. 10a). Unexpectedly, no such relationship was found (FIG. 10b,c), suggesting that marker genes for a cell type present in the signature matrix but absent from the mixture are not necessarily discarded; rather, they are likely useful to CIBERSORT by bounding the regression (e.g., CD8A was chosen regardless of whether CD8 T cells were present, likely informing their absence; Methods).

Therefore, CIBERSORT's discriminatory ability on cell types was investigated with highly correlated reference profiles (e.g., naïve vs. memory B cells). Such profiles exhibit multicollinearity, a phenomenon whereby proportions of similar cell types cannot be reliably determined[15]. Previous approaches avoid this issue by requiring marker genes with cell type-specific expression[7,8,12], or by using highly distinct gene expression signatures[4,5], therefore limiting the possible cellular repertoire for deconvolution. CIBERSORT was compared with other methods by deconvolving synthetic mixtures of 10 increasingly correlated simulated cell types. It was found that CIBERSORT performed most accurately, whether in the presence of unknown content or added noise (FIG. 11), demonstrating potential for deep deconvolution[3] of many cell subsets in diverse tissues.

Figure 2E:
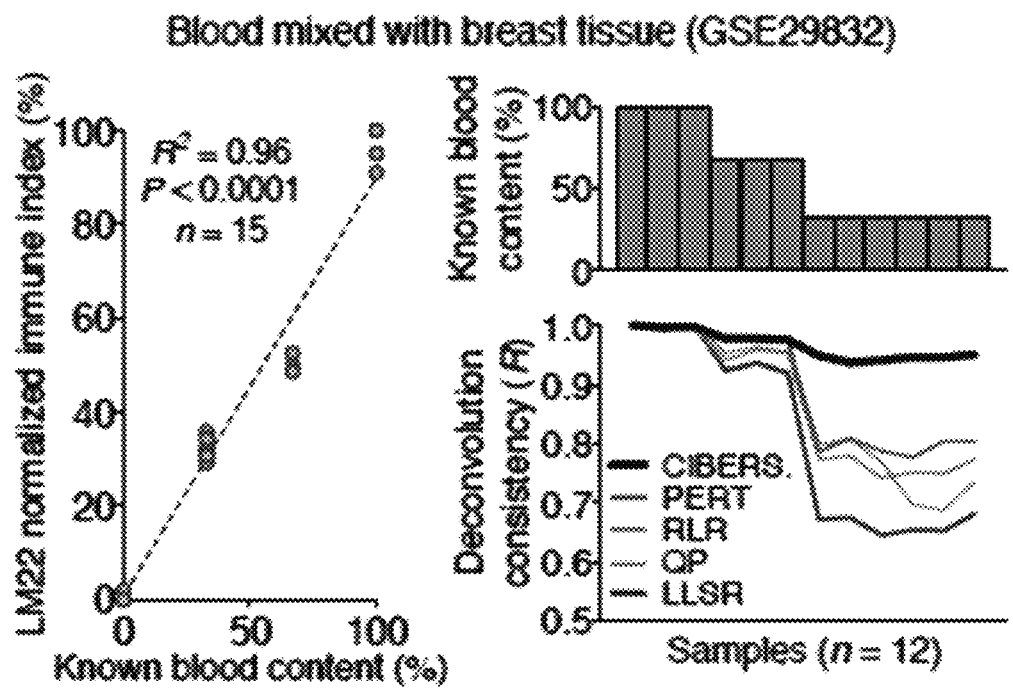
Figure 2F:
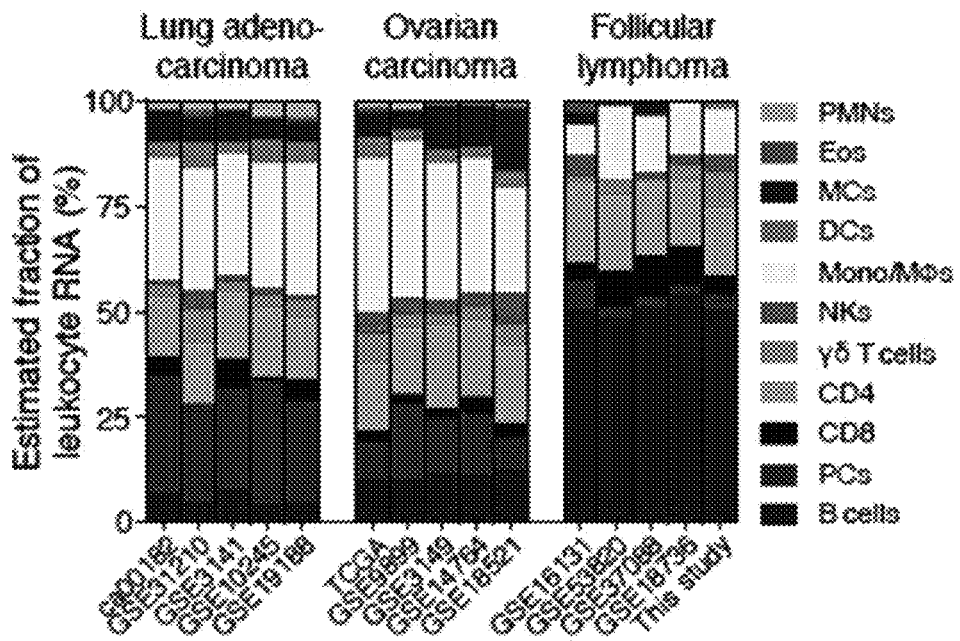

Having benchmarked CIBERSORT on simulated mixtures, in vitro and in vivo mixtures of solid tissues, including bulk tumors, were tested. LM22 was used for all subsequent analyses and therefore restricted our comparative assessments to expression-based methods (i.e., RLR, PERT, QP, LLSR). First, the stability of leukocyte deconvolution in defined mixtures of whole blood spiked into breast tissue was tested[5]. After verifying relative spike-in proportions by comparison with immune-related gene expression (FIG. 2e, left), CIBERSORT was found to be significantly more consistent than other methods (P<0.02; n=9 samples with <100% blood; paired two-sided Wilcoxon signed rank test; FIG. 2e, right; FIG. 19). Separately, across independent studies, leukocyte fractions enumerated by CIBERSORT were more similar within a cancer type than across cancers (FIG. 2f). These results indicate that unknown content and lab-specific factors only marginally impact CIBERSORT performance.

Figure 2G:
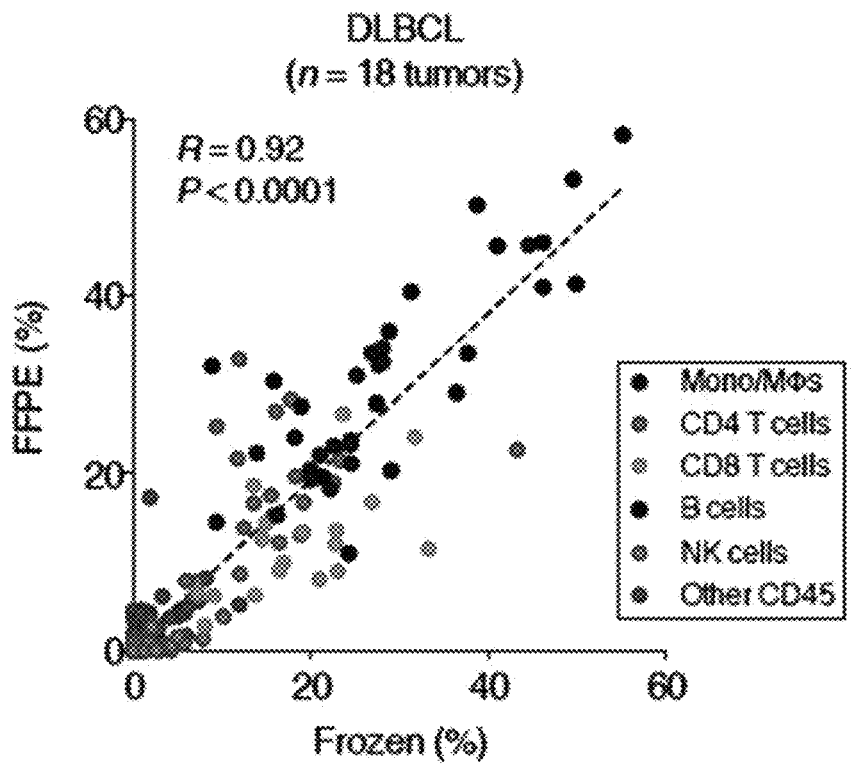
Figure 12A:
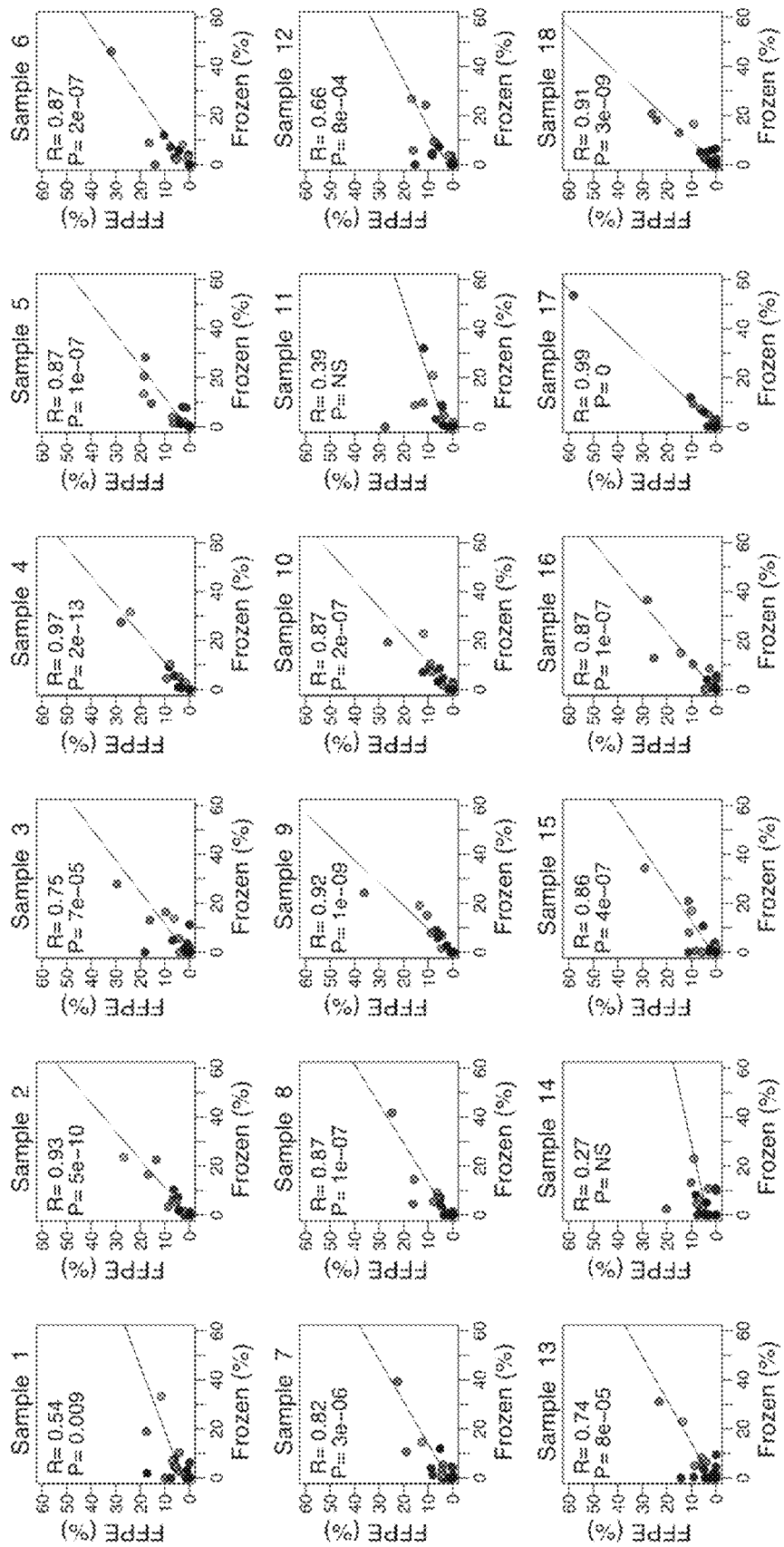
FIGS. 12a-12b: Comparison of leukocyte deconvolution results between frozen and FFPE samples in 18 individual DLBCL tumors (GSE18377[7]).
Figure 12B:
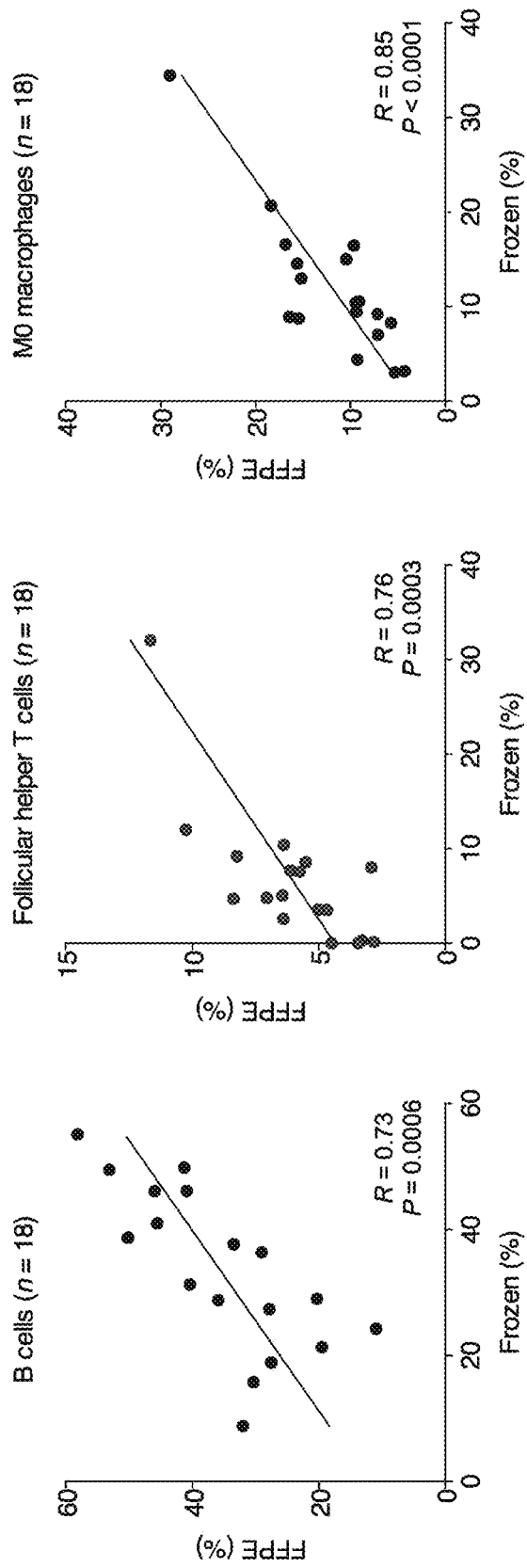

It was next asked whether CIBERSORT could be applied to formalin-fixed, paraffin embedded (FFPE) samples, routinely generated in clinical laboratories for long-term storage. Using publicly available GEPs consisting of matching FFPE and frozen DLBCL tumors (n=18), it was found that leukocyte fractions estimated by CIBERSORT were significantly correlated across all tumors (FIG. 2g) and were more concordant than other methods (FIG. 19). Indeed, CIBERSORT results were also significantly correlated in 16 of 18 individual tumors (P<0.05; FIG. 12a) and in specific cell subsets (FIG. 12b), implying potential utility for large-scale analysis of cellular composition in FFPE specimens.

To evaluate CIBERSORT against ground truth measurements of leukocyte content in solid tissues, flow cytometry was used to enumerate immune subsets in two tissue types: lung specimens obtained during surgical resection of early stage non-small cell lung carcinomas (NSCLCs), and disaggregated lymph node biopsies from follicular lymphoma (FL) patients. Whether applied to (i) independent microarray studies of normal lung tissues or (ii) GEPs from 14 paired bulk FL samples, results were significantly correlated with corresponding flow cytometry measurements (P≤0.005, FIGS. 2h and 2i, respectively) and in both tissue types, more closely reflected experimental values than previous methods (FIG. 19).

To assess performance on individual cell subsets, flow cytometry was used to enumerate nearly 50% of the phenotypic repertoire of LM22 (10 of 22 cell subsets), and evaluated CIBERSORT's capability for deep deconvolution in primary human samples, including blood and tumor biopsies. Blood samples from 27 adult subjects were profiled for 10 distinct cell phenotypes captured in LM22 among PBMCs (20 subjects were profiled for 9 cell types, and 7 profiled for FOXP3+ Tregs; see Flow Cytometry method section). Of these 10 phenotypes, half are highly collinear in LM22 (e.g., naïve and memory B cells; FIG. 4c) and half have low frequencies (<5%) in PBMCs (naïve and memory B cells, activated memory CD4 T cells, gamma delta T cells, and Tregs). Despite the diversity of phenotypes analyzed, 90% of distinct leukocyte subsets were significantly correlated between CIBERSORT and flow cytometry (P≤0.02; FIG. 3a), including 4 of 5 subsets with median fractions below 5% (e.g., Tregs; FIG. 3b). Only gamma delta T cells were not significant (albeit positively correlated; R=0.29), possibly due to technical issues with flow cytometry or the use of a suboptimal reference profile (FIG. 5a). Separately, levels of CD4/CD8 T cells and malignant B cells in tumor biopsies from 14 FL patients were examine and profiled by flow cytometry and microarray (i.e., FIG. 2i). The proportions of all three subsets estimated by CIBERSORT were significantly correlated with flow cytometry (P≤0.02; FIG. 3c).

Figure 13A:
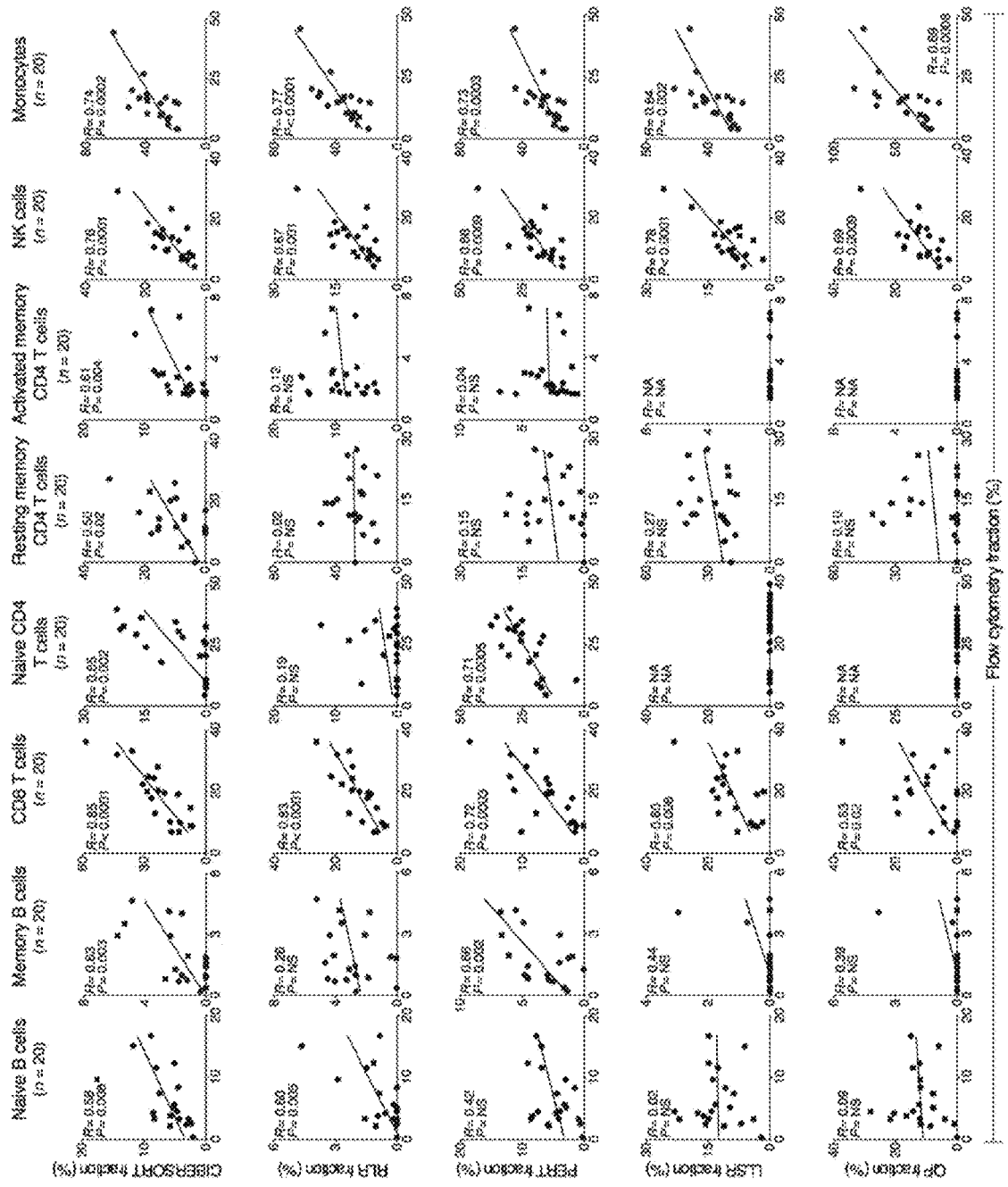
Figure 14:
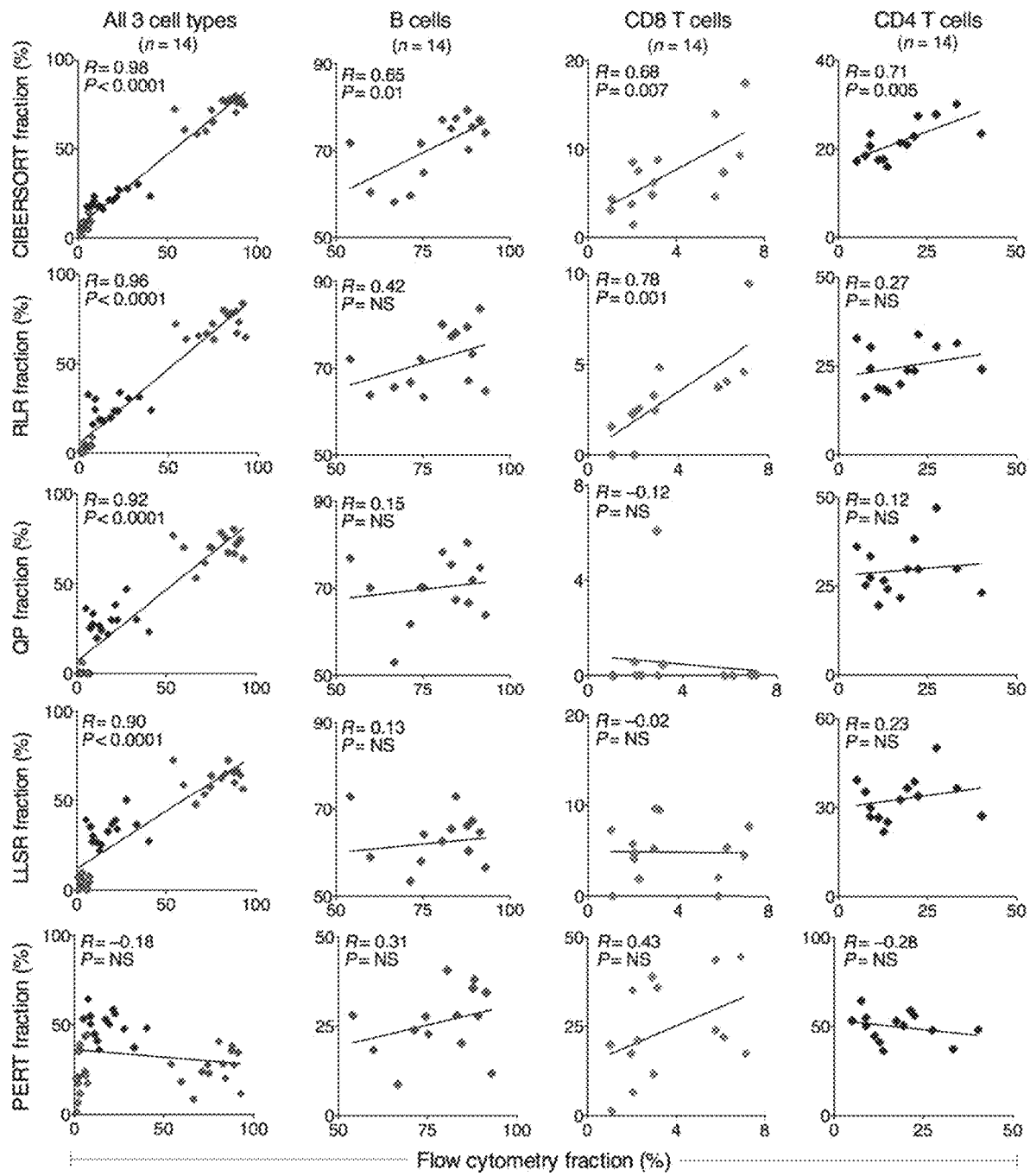
FIG. 14: Comparison of deconvolution methods for enumeration of 3 leukocyte subsets in FL tumor biopsies (related to FIGS. 2i, 3c). Scatter plots comparing flow cytometry with 5 deconvolution methods for the enumeration of 3 leukocyte subsets, including malignant B cells, in disaggregated FL lymph node biopsies. For RMSE values of individual cell subsets, see FIGS. 19a-19d.

When applied to the same datasets, other expression-based methods were generally less accurate, and none yielded significant correlations for >50% of analyzed phenotypes (FIG. 3d, FIGS. 13-14, FIG. 19). Moreover, certain subsets were prone to complete "drop out" when enumerated by other methods, likely owing to multicollinearity (e.g., naïve CD4 T cell levels estimated by QP and LLSR in PBMCs; FIG. 3d, FIGS. 13-14). Furthermore, in the context of FL tumor biopsies, significant correlations were only achievable by other methods when considering all three phenotypes together, not for individual subsets (except for CD8 T cells inferred by RLR; FIG. 14). Potential reasons for these performance differences are discussed in Methods. Collectively, these results further demonstrate the advantages of CIBERSORT for deep deconvolution and enumeration of cell subsets in tissues with complex compositions.

Experimental Methods

The following methods were used for Example 1.

Patient Samples

All patient samples in this study were reviewed and approved by the Stanford Institutional Review Board in accordance with the Declaration of Helsinki. For FIG. 5b, tonsils were collected as part of routine tonsillectomy procedures at Lucile Packard Children's Hospital at Stanford University with informed consent for research use, and then mechanically disaggregated before cell suspensions were cryopreserved. For "patient 1" shown in FIG. 6c, peripheral blood mononuclear cells (PBMCs) were isolated from specimens taken before and immediately following 4 weekly doses of infusional rituximab (375 mg m−2) monotherapy for extranodal marginal zone lymphoma (EMZL) in a subject without measurable circulating disease. For patients 2 and 3 in FIG. 6c, PBMCs were respectively isolated from specimens taken immediately following 4 cycles and 6 cycles of RCHOP immunochemotherapy for treatment of DLBCL. For patient 4 in FIG. 6c, PBMCs were isolated from a subject following 4 cycles of Rituximab for treatment of FL; this subject had ~2% circulating lymphoma cells at diagnosis, which were undetectable by CIBERSORT and flow cytometry following 4 Rituximab infusions. For FIG. 2h, adjacent normal lung tissue specimens were obtained during surgical resection of early stage non-small cell lung tumors. For FIG. 2i and FIG. 3c, surgical tissue biopsies were obtained from untreated FL patients enrolled in a Phase III clinical trial (NCT00017290[17]). For FIG. 3a and FIG. 3b, PBMCs were obtained from 20 and 7 adult subjects, respectively. The former comprised adults of varying ages receiving influenza immunization (NCT01827462), and the latter was comprised of "patient 4" in FIGS. 6c and 6 healthy subjects (see Flow Cytometry methods section).

Flow Cytometry

All panels are detailed below, with antibody clones indicated in brackets (all reagents were obtained from BD Biosciences). Panels related to FIG. 3a were configured using lyophilized reagent plates (Lyoplates, BD Biosciences, San Diego, CA), with the exception of reagents in parentheses, which were added as liquid antibodies.

| FIG. | Tissue | Panel | n | FITC | PE | PerCP-Cy5.5 | PE-Cy7 | APC | APC-H7 |
|---|---|---|---|---|---|---|---|---|---|
| 5b | Tonsils | T/B cell | 5 | CD5 [L17F12] | — | — | — | CD19 [HIB19] | — |
| 2h | Normal lung tissue | Leukocyte | 11 | CD4 [OKT4] | CD14 [HCD14] | CD19 [HIB19] | CD56 [HCD56] | CD8 [SK1] | — |
| 2i, 3c | FL lymph nodes | T/B cell | 14 | CD8 [SK1] | — | — | — | — | — |
| 3a | PBMCs 1 | T cell | 20 | (CD85j) [GHI/75] | (CD28) [L293] | CD4 [SK3] | CD45RA [HI100] | CD27 [L128] | CD8 [SK1] |
| 3a | PBMCs 1 | Activated T cell | 20 | (TCRgd) [11F2] | (PD-1) [EH12.1] | CD4 [SK3] | CD38 [HB7] | HLA-DR [L243] | CD8 [SK1] |

| | | | | | | | | | |
|---|---|---|---|---|---|---|---|---|---|
| 3a | PBMCs 1 | B cell | 20 | IgD [IA6-2] | CD24 [ML5] | CD19 [SJ25C1] | CD38 [HB7] | CD27 [L128] | CD20 [2H7] |
| 3a | PBMCs 1 | CXCR3+ | 20 | CD16 + 56 [3G8/NCAM16.2] | CXCR3 [1C6/CXCR3] | CD4 [SK3] | CD33 [P67.6] | CD19 [SJ25C1] | CD8 [SK1] |
| 3b | PBMCs 2 | Treg | 7 | — | CD4 [SK3] | — | — | — | — |

| | FIG. | Tissue | Panel | V450 | A700 | Pac-Blue | APC-Cy7 | Alexa-647 |
|---|---|---|---|---|---|---|---|---|
| | 5b | Tonsils | T/B cell | — | — | — | — | — |
| | 2h | Normal lung tissue | Leukocyte | — | CD45 [HI30] | — | — | — |
| | 2i, 3c | FL lymph nodes | T/B cell | — | — | CD4 [RPA-T4] | CD20 [L27] | — |
| | 3a | PBMCs 1 | T cell | CD3 [UCHT1] | — | — | — | — |
| | 3a | PBMCs 1 | Activated T cell | CD3 [UCHT1] | — | — | — | — |
| | 3a | PBMCs 1 | B cell | CD3 [UCHT1] | — | — | — | — |
| | 3a | PBMCs 1 | CXCR3+ | CD3 [UCHT1] | — | — | — | — |
| | 3b | PBMCs 2 | Treg | — | — | CD3 [UCHT1] | — | FOXP3 [236A/E7] |

For FIG. 5b, tonsil-derived cell suspensions were thawed, washed, counted, and subsequently stained with monoclonal antibodies (above table) to label B cells (CD19+) and T cells (CD5+), without stimulation. Each population was sorted using a FACSAria II instrument (BD Biosciences) to >95% purity for subsequent expression profiling.

Figure 2H:
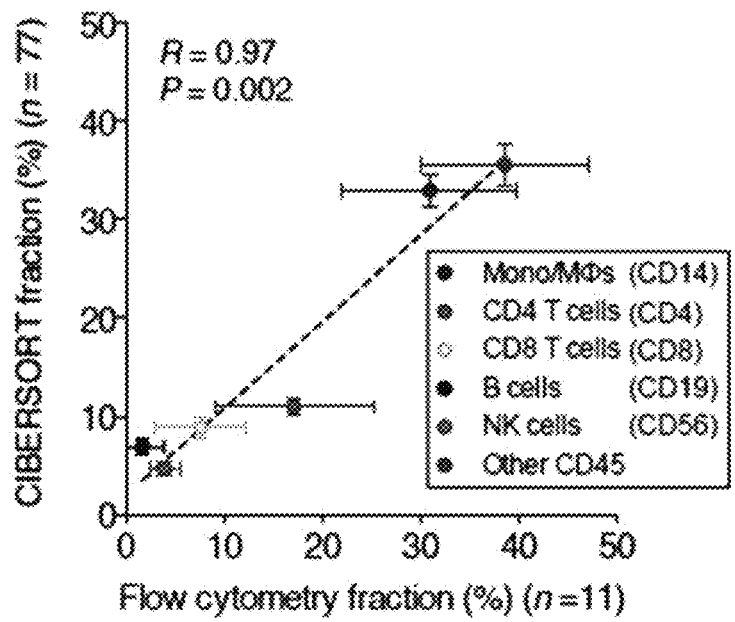

For FIG. 2h, fresh normal lung tissue samples were cut into small pieces and dissociated into single cell suspensions by 45 min of Collagenase I (STEMCELL Technologies) digestion. Dissociated single cells were suspended at 1×10$^7$ per mL in staining buffer (HBSS with 2% heat-inactivated calf serum). After 10 min of blocking with 10 μg/μL rat IgG, the cells were stained for at least 10 min with the antibodies indicated in the above table. After washing, stained cells were re-suspended in staining buffer with 1 μg/mL DAPI, and the following populations were enumerated using a FACSAria II instrument (BD Biosciences): total leukocytes (CD45+), monocytes (CD14+), CD8 T cells (CD8+), CD4 T cells (CD4+), NK cells (CD56+), and B cells (CD19+).

Figure 2I:
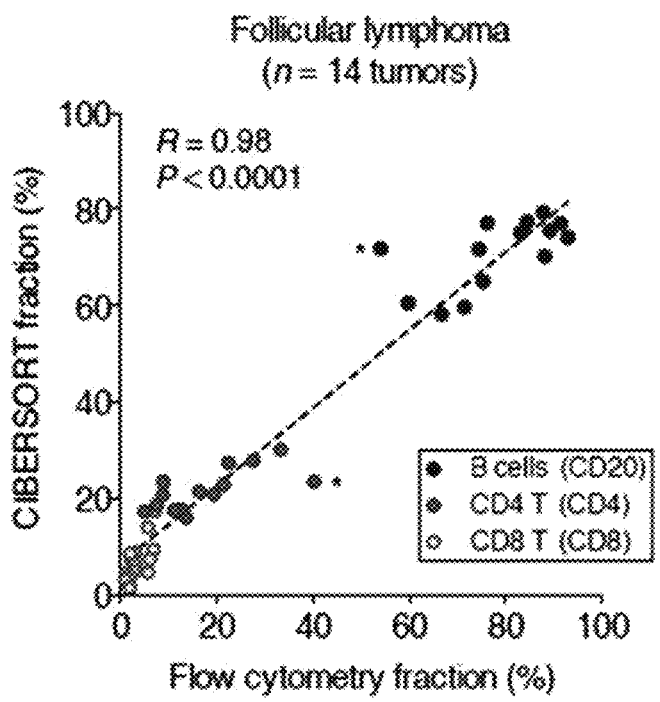
Figure 3A:
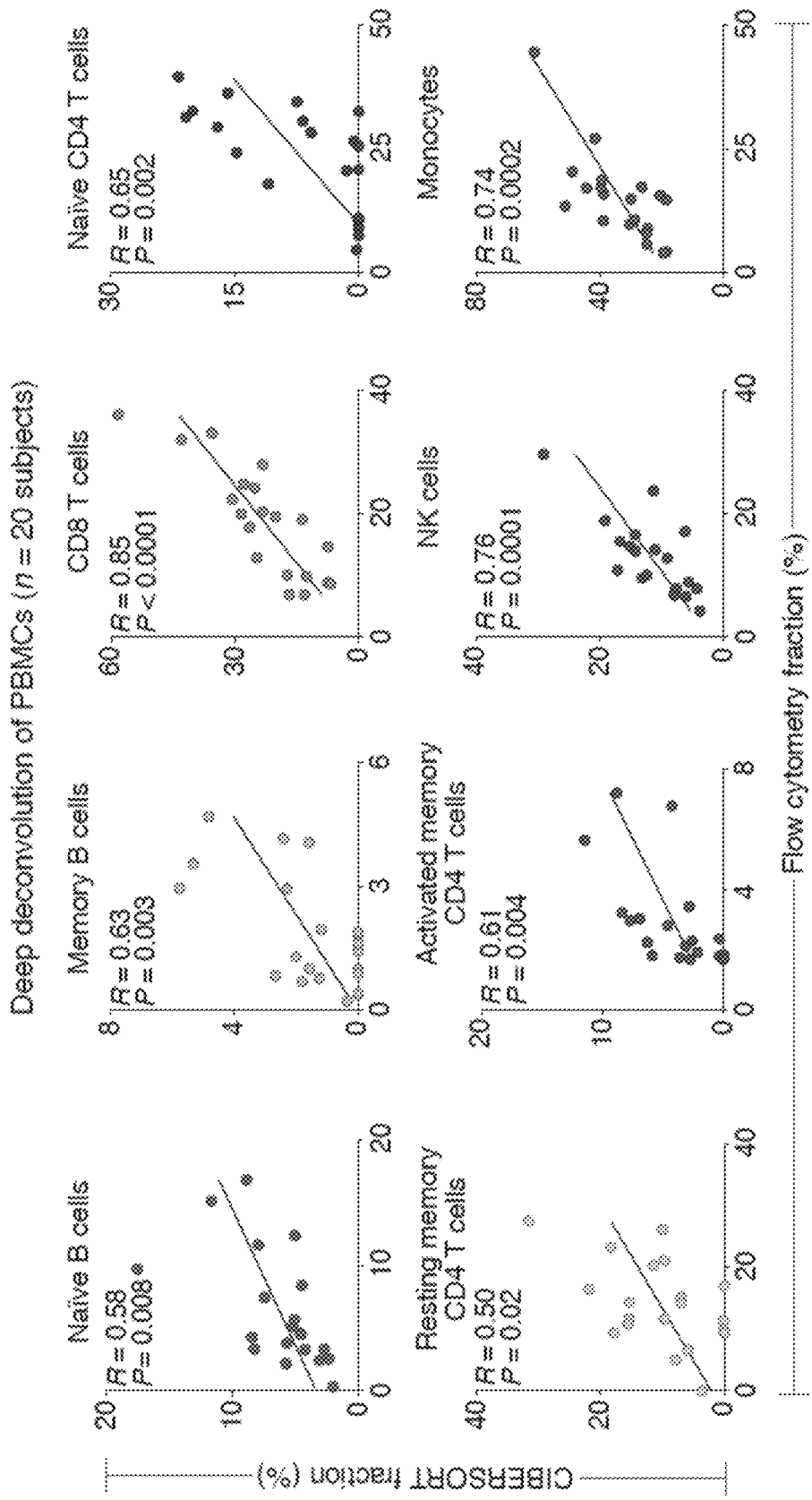

For FIGS. 2i and 3c (and FIG. 14), diagnostic FL tumor cell suspensions were stained with monoclonal antibodies (above table) to label CD4 T cells (CD4+), CD8 T cells (CD8+), and B cells (CD20+). Stained cells were detected on a FACSCalibur or an LSR II 3-laser cytometer (BD Biosciences).

For FIG. 3a (and FIG. 13a), flow cytometry phenotyping was performed on PBMCs from healthy adults using lyophilized reagent plates (Lyoplates, BD Biosciences). The plates were configured with staining cocktails shown in the above table to enumerate the following cell subsets: naïve B cells (CD3−CD19+CD20+CD24−CD38+), memory B cells (CD3−CD19+CD20+CD24+CD38−), CD8 T cells (CD3+CD8+), naïve CD4 T cells (CD3+CD4+CD45RA+CD27+), memory CD4 T cells (CD3+CD4+CD45RA−), gamma delta T cells (TCRgd+), NK cells (CXCR3+CD16+CD56+), and monocytes (identified by size via forward- and side-scatter properties). Staining was performed according to the published protocol for Lyoplates on an LSRII flow cytometer (BD Biosciences)[1]. Reagents in parentheses in the above table were added as liquid antibodies, and were not part of the Lyoplate per se.

Characteristic changes in gene expression accompany the phenotypic transition from naïve (CDR45RA+CD45RO−) to memory (CD45RO+CDR45RA−) T cells. Two such genes were profiled in the activated T cell panel (above table): HLA-DR, a canonical T cell activation marker primarily expressed on memory CD4 T cells (as opposed to naïve subsets), and CD38, another known activation marker predominantly expressed on naïve CD4 T cells[3,4]. While the activation T cell panel did not include CD45RA or CD45RO, previous findings were confirmed by analyzing data from a separate study (data not shown), in which PBMCs were profiled using a panel that included αCD3, αCD4, αCD45RA, αHLA-DR and αCD38. Among CD3+ CD4+ cells in 6 healthy subjects, a strong correlation between total HLA-DR+ cells and HLA-DR+CD45RA− (activated memory) cells was confirmed (R=0.97, P=0.001; RMSE=0.7%). Conversely, total HLA-DR−CD38+ counts were significantly correlated with HLA-DR−CD38+ CD45RA+(naïve) cells (R=0.87; P=0.001; RMSE=11.9%), suggesting that the CD3+CD4+HLA-DR+ phenotype represents a reasonable surrogate for activated memory CD4 T cells in healthy adult PBMCs. Therefore, to compare flow cytometry data with activated and resting memory CD4 subsets (from LM22) in this study, counts of CD3+CD4+ HLA-DR+ cells were used to estimate levels of activated memory CD4 T cells, and subtracted these values from total memory CD4 T cells (CD3+CD4+CD45RA−) to estimate resting memory CD4 T cells.

Finally, for the enumeration of regulatory T cells (Tregs) in FIG. 3b (and FIG. 13b), peripheral blood was obtained from 6 healthy adult males by venipuncture into K2EDTA vacutainers (BD Biosciences) and processed immediately. Whole blood was diluted two-fold with PBS and mononuclear cells (PBMCs) isolated using Ficoll-Paque Plus (GE Healthcare). PBMCs were washed twice with PBS, counted, and 1×10$^6$ cells per individual, along with 1×10$^6$ cells from viably preserved PBMCs obtained from patient 4 in FIG. 6c, were stained with αCD3, and αCD4 (see table above). Cells were washed in PBS, resuspended in Fix/Perm Buffer (eBiosciences), and incubated on ice for 20 min. Cells were washed twice in Perm/Wash Buffer (eBiosciences), and stained with αFOXP3. Cells were washed once in Perm/Wash Buffer and data collected using an LSRFortessa flow cytometer (BD Biosciences). Tregs were defined as CD3+ CD4+FOXP3+ non-doublet cells, and enumerated as a fraction of all intact PBMCs.

Gene Expression Profiling

Nucleic acids were extracted from tonsil specimens (FIG. 5b) and PBMCs (patients 1 to 3 in FIG. 6c) using AllPrep DNA/RNA Mini kits (Qiagen). For FL specimens (FIG. 2i, FIG. 3c), total RNA and genomic DNA were prepared and stored using TRIzol and RNeasy Midi Kits (Qiagen, Valencia, CA). Sufficient nucleic acid was confirmed for 80% of archival FL specimens after quality control assessment of a subset of these patients. Total RNA from FL samples was linearly amplified (3' IVT Express, Affymetrix) prior to microarray hybridization. For all above samples, total cellular RNA (at least 300 ng) was assessed for yield (NanoDrop 2000, Thermo Scientific), and quality (2100 Bioanalyzer, Agilent), and cRNA was hybridized to HGU133 Plus 2.0 microarrays (Affymetrix) according to the manufacturer's protocol.

Two additional cohorts of PBMCs were analyzed in this study (FIG. 3a,b). For the first cohort (n=20 subjects; FIG. 3a), PBMCs (~1×106 viable cells per mL) were collected in 1 mL TRIzol (Invitrogen) and stored at −80° C. until use. Total RNA was isolated according to the TRIzol protocol (Invitrogen). Total RNA yield was assessed using the Thermo Scientific NanoDrop 1000 micro-volume spectrophotometer (absorbance at 260 nm and the ratio of 260/280 and 260/230). RNA integrity was assessed using a Bioanalyzer NANO Lab-on-a-Chip instrument (Agilent). Biotinylated, amplified antisense complementary RNA (cRNA) targets were prepared from 200 to 250 ng of total RNA using the Illumina RNA amplification kit (Applied Biosystems/Ambion), and 750 ng of labeled cRNA was hybridized overnight to Human HT-12 V4 BeadChip arrays (Illumina). The arrays were then washed, blocked, stained and scanned on an Illumina BeadStation 500 following the manufacturer's protocols. BeadStudio/GenomeStudio software version 1.9.0 (Illumina) was used to generate signal intensity values from the scans. For the second cohort (FIG. 3b), PBMCs (1.4×106 to 4.0×106 cells per mL) from 6 healthy male adults were isolated and prepared, as described in the Flow Cytometry methods section, and then frozen at −80° C. until use. Total cellular RNA (≥300 ng) was isolated from these 6 subjects along with viably preserved PBMCs from patient 4 (FIG. 6c) using RNeasy Mini Kit (Qiagen) and assessed for yield (NanoDrop 2000, Thermo Scientific), and quality (2100 Bioanalyzer, Agilent). Total RNA was linearly amplified (3' IVT Express, Affymetrix) cRNA was hybridized to HGU133A microarrays (Affymetrix) according to the manufacturer's protocol.

CIBERSORT: Method

A new approach for Cell Type Identification By Estimating Relative Samples Of RNA Transcripts (CIBERSORT) is proposed. This strategy is based on a novel application of nu-support vector regression (v-SVR)[9], a machine-learning method that outperformed other approaches in benchmarking experiments (FIG. 15, FIG. 19). SVR is an instance of support vector machine (SVM), a class of optimization methods for binary classification problems, in which a hyperplane is discovered that maximally separates both classes. The support vectors are a subset of the input data that determine hyperplane boundaries. Unlike standard SVM, SVR fits a hyperplane to the input data points, thus performing a regression (FIG. 21). All data points within ε (termed the 'ε-tube') are ignored (open circles in FIG. 21, left panel), whereas all data points lying outside of the ε-tube are evaluated according to a linear ε-insensitive loss function. These outlier data points, referred to as 'support vectors' (filled circles in FIG. 21), define the boundaries of the ε-tube and are sufficient to completely specify the linear regression function. In this way, support vectors can provide a sparse solution to the regression in which overfitting is minimized (a type of feature selection). Notably, support vectors represent genes selected from the signature matrix in this work.

FIG. 21. A simple two-dimensional dataset analyzed with linear v-SVR, with results shown for two values of v (note that both panels show the same data points). As detailed in the Methods, linear SVR identifies a hyperplane (which, in this two-dimensional example, is a line) that fits as many data points as possible (given its objective function[10]) within a constant distance, ε (open circles). Data points lying outside of this 'ε-tube' are termed 'support vectors' (red circles), and are penalized according to their distance from the ε-tube by linear slack variables ($\xi_i$). Importantly, the support vectors alone are sufficient to completely specify the linear function, and provide a sparse solution to the regression that reduces the chance of overfitting. In v-SVR, the v parameter determines both the lower bound of support vectors and upper bound of training errors. As such, higher values of v result in a smaller ε-tube and a greater number of support vectors (right panel). For CIBERSORT, the support vectors represent genes selected from the signature matrix for analysis of a given mixture sample, and the orientation of the regression hyperplane determines the estimated cell type proportions in the mixture.

The primal objective of SVR is to minimize both a loss function and penalty function given a defined set of constraints. The former measures the error associated with fitting the data whereas the latter determines model complexity. More specifically, SVR solves an optimization problem that minimizes the following two quantities: (1) a linear ε-insensitive loss function, which outperforms other common loss functions (e.g., squared error used in LLSR) in noisy samples, and (2) an $L_2$-norm penalty function (the same as that used in ridge regression), which penalizes model complexity while minimizing the variance in the weights assigned to highly correlated predictors (e.g., closely related cell types), thereby combating multicollinearity (e.g., FIGS. 11a-11d, FIG. 3d).

Two major types of SVR have been described, ε-SVR and v-SVR, however v-SVR was applied in CIBERSORT since the v parameter conveniently controls both the upper bound of training errors ε and the sparsity of support vectors[9]. Higher values of v yield narrower ε-tubes and consequently, more support vectors (FIG. 21). For CIBERSORT, v-SVR is applied with a linear kernel to solve for f, and the best result from three values of v={0.25, 0.5, 0.75} is saved, where best is defined as the lowest root mean squared error RMSEmin between m and the deconvolution result, f×B. The current implementation of CIBERSORT executes v-SVR using the 'svm' function in the R package, 'e1071'. Regression coefficients are extracted with the following R command:

coef<-t(model$coefs) %*% model$SV

Negative SVR regression coefficients are subsequently set to zero (as done for LLSR), and the remaining regression coefficients are normalized to sum to 1, yielding a final vector of cell type fractions, f (notably, f denotes relative, not absolute fractions of each cell type from B in m). To decrease running time and promote better overall performance, both B and m are each normalized to zero mean and unit variance prior to running CIBERSORT. As previously suggested for other linear deconvolution methods, CIBERSORT works best on expression values in non-log linear space[19].

Taken together, linear v-SVR as implemented by CIBERSORT, uniquely addresses key outstanding issues of gene expression deconvolution, including (1) robustness to noise and overfitting owing to both a linear loss function and feature selection of genes from the signature matrix, and (2) tolerance to multicollinearity via utilization of the $L_2$-norm penalty function. Moreover, CIBERSORT does not require cell type-specific expression patterns for every gene, allowing the construction of signature matrices with more cell types and phenotypic states than other methods (FIGS. 22a-22e).

FIGS. 22a-22e. (FIG. 22a) Heat map of signature matrix 1 (SM1), which contains only cell type specific marker genes. (FIG. 22b) Heat map of signature matrix 2 (SM2), which contains only non-cell type specific marker genes. (FIG. 22c) CIBERSORT and DSA deconvolution performance on ten mixtures created using SM1. (FIGS. 22d, 22e) Deconvolution performance on ten mixtures created using SM2: (FIG. 22d) CIBERSORT and RLR, (e) QP, LLSR, and PERT. For details, see Online Methods. Statistical concordance between known and observed cell type proportions was determined by linear regression (dashed lines) and Pearson correlation (R).

P-value estimation. In contrast to previous methods, CIBERSORT also produced an empirical P value for the deconvolution using Monte Carlo sampling. This approach allowed CIBERSORT to test the null hypothesis that no cell types in the signature matrix (e.g., LM22) were present in a given GEP mixture, m. For this purpose, the Pearson product-moment correlation R calculated between m and f×B was used as the test statistic, though other distance metrics could be used. In order to derive an empirical P value, CIBERSORT first derived a null distribution R*. Because the signature matrix B contained only a small subset of genes g compared to the whole transcriptome, g expression values were randomly drawn from the parent GEP of m to create a random mixture $m^*_i$, such that $|m|=|m^*_i|$. CIBERSORT was then run on $m^*_i$ to produce a vector of estimated cellular fractions, $f^*_i$. CIBERSORT determined the correlation coefficient $R^*_i$ between the random mixture $m^*_i$ and the reconstituted mixture, $f^*_i \times B$. This process was repeated for I iterations (=500 in this work) to produce R*.

CIBERSORT Running Time

Using 3 threads to simultaneously process three values of v (=0.25, 0.5, and 0.75; see above), and a 2.3 GHz Intel Core i7 CPU with 8 GB RAM, CIBERSORT runtime was clocked with LM22 at approximately 1.7 sec per mixture sample after an empirical P value was calculated. The latter depends on the number of permutations selected, and for 100×, would take ~170 sec, or an additional 2.75 min.

CIBERSORT Implementation

CIBERSORT was developed in Java and R with a simple command-line interface for processing gene expression data representing a mixture of different cell types, along with a signature genes file that enumerates the genes that define the signature expression profile for each cell type. Given these data, the tool generates the fractional representations of each cell type present in the mixture and returns it to the website to be rendered as a heat map table and stacked bar plot representations. The application can also produce custom signature gene files when provided with gene expression profiles of reference cell populations and a class comparison table for those populations.

The back end website for CIBERSORT was built in PHP. The interactive user interface is powered by the jQuery JavaScript library and various open source libraries (including phpMailer, idiorm, blueimp jQuery-File-Upload, DataTables, phpExcel and mPDF), with the graphical user interface of the website powered by Twitter Bootstrap 2.3.2. The site runs on an Apache server on a virtual machine and stores user and job data in a MySQL database. Of note, the user has complete control over their data and can delete them at will.

GEP Deconvolution Methods

LLSR, QP, RLR and DSA were run in R using stats (lm function), quadprog, MASS (rlm function, 100 maximum iterations), and DSA[8] packages, respectively. Negative coefficients from LLSR were set to zero to approximate the approach used by Abbas et al.[4], and QP was run with non-negativity and sum to 1 constraints used by Gong et al[5,16]. MMAD and PERT were run in Matlab using author-supplied code[6,7] (PERT was converted from Octave using the Matlab converter, oct2ml). Of note, PERT was assessed using the same signature gene matrices used for the other expression-based methods. MMAD was evaluated using marker genes only, as this approach yielded superior results when compared to expression-based deconvolution (FIG. 3C vs. FIG. 3A in Liebner et al.[7]). However, cell-specific marker genes could not be determined for all cell types in LM22, and therefore, MMAD and DSA were not run on datasets where LM22 was applied. All methods were run in non-log linear space.

Microarray Datasets and Preprocessing

Samples profiled on Illumina or Agilent platforms in FIG. 1b (and FIG. 17) were downloaded as normalized matrices from public repositories (either NCBI, EBI, or literature; referenced in FIG. 17), and probes were converted to HUGO gene symbols using chipset definition files available from the NCBI gene expression omnibus (GEO). Human transcriptome data from FIG. 1c were downloaded as RMA-normalized arrays (E-MTAB-62, EBI ArrayExpress). All other Affymetrix arrays (including those analyzed in FIG. 1b and those generated in this work) were obtained as CEL files, MAS5 normalized using the affy package in Bioconductor, mapped to NCBI Entrez gene identifiers using a custom chip definition file (Brainarray version 16; brainarray(dot)mbni(dot)med(dot)umich(dot)edu/Brainarray/), and converted to HUGO gene symbols. The Illumina BeadChip arrays analyzed in FIG. 3a were normalized with limma v3.20.8 (Bioconductor) using normexp background correction with negative controls (neqc function). For non-Affymetrix platforms, probes mapping to >1 gene were collapsed at the gene-level according to the probe with highest mean expression across all samples. All microarray studies were quantile normalized prior to analysis. For normal lung tissues in FIG. 2h, GEO datasets, GSE7670 and GSE10072, were analyzed and for paired frozen and FFPE samples of DLBCL tumors in FIG. 2g, GSE18377 was analyzed.

LM22 Signature Matrix

GEP data from the public domain for 22 leukocyte subsets profiled on the HGU133A platform were obtained (FIG. 16). Probesets were preprocessed as described above. Significantly differentially expressed genes between each population and all other populations were identified using a two-sided unequal variance t-test. Genes with a q-value<0.3 (false discovery rate[21]) were considered significant.

For each leukocyte subset, significant genes were ordered by decreasing fold change compared to other cell subsets, and the top G marker genes from each cell subset were combined into a signature matrix $B^G$. G was iterated from 50 to 200 across all subsets, and retained the signature matrix with the lowest condition number (condition number=11.4; G=102; n=547 distinct genes (FIGS. 16a-16k). Of note, the condition number of this signature matrix is higher than others (below) due to concordance among related cell types and activation states of a given cell type.

To prevent genes expressed on non-hematopoietic cell types from confounding deconvolution results, two gene filtration strategies were used. First, genes with enriched expression in non-hematopoietic cells or tissues were identified using the Gene Enrichment Profiler, an online compendium of diverse cells and tissues profiled on HGU133A (xavierlab2(dot)mgh(dot)harvard(dot)edu/EnrichmentProfiler/)[22]. Gene Enrichment Profiler calculates an enrichment score (ES) for a given gene in a given cell/tissue type based on the sum of linear model coefficients from all pairwise comparisons of that gene with other samples. For each gene and cell/tissue type with ES>0, the fraction of non-hematopoietic cell/tissue samples in the Gene Enrichment Profiler database was determined, and excluded genes from the signature matrix with a non-hematopoietic fraction >0.05. As a second filtration step, all genes from further analysis with a mean $\log_2$ expression level ≥7 in all non-hematopoietic cancer cell lines profiled in the Cancer Cell Line Encyclopedia (CCLE) were omitted (pre-normalized gene expression data were extracted from CCLE_Expression_Entrez_2012-09-29(dot)txt, downloaded from the Broad Institute). This signature matrix was termed "LM22".

To validate the gene signatures used to distinguish each leukocyte subset in LM22, CIBERSORT was applied to a variety of external datasets, each containing one purified population also present in the signature matrix. GEPs from three microarray platforms were tested, Affymetrix HGU133A and HGU133 Plus 2.0, and the Illumina Human-6 v2 Expression BeadChip. Affymetrix platforms were normalized and processed the same as described for signature matrix GEPs. The BeadChip dataset was downloaded as a processed normalized matrix from ArrayExpress (E-TABM-633), and for genes mapped to more than one probe, the probe associated with highest expression across all samples was further analyzed. For each sample, the population with the highest CIBERSORT-inferred fraction was compared to the known cell type to assess CIBERSORT accuracy (FIG. 17).

For the analysis presented in FIG. 1c, arrays were grouped into 1,801 primary human specimens, consisting of 1,425 "positive" samples containing at least 1 mature hematopoietic subset in LM22 and 376 "negative" samples containing incompletely differentiated non-hematopoietic specimens, normal brain tissue (which typically contains microglia, but generally not cell types in LM22), and hematopoietic stem cells and progenitors (not in LM22). Arrays were separately grouped into 1,260 transformed cell lines, divided into 118 "positive" hematopoietic samples and 1,142 "negative" samples, the latter consisting of both non-hematopoietic samples and K562 erythromyeloblastoid cell lines, which are hematopoietic in origin but highly distinct from subsets present in LM22. Poorly annotated arrays were excluded from this analysis. While significance filtering was not applied in comparing CIBERSORT to other methods, a P value cutoff (≤0.005; see FIG. 1c) was imposed for deconvolution of bulk tumors in FIG. 2f.

Other Signature Matrices

In addition to LM22 (above), custom signature matrices were designed for the mixtures of human hematopoietic cell lines and neural populations shown in FIG. 6a,b. In both cases, previously normalized series matrix datasets (GSE11103 and GSE19380) were downloaded from GEO and quantile normalized. Signature matrices were subsequently constructed using the same condition number minimization algorithm described for LM22 (above), omitting non-hematopoietic gene filtration and validation steps. The final signature matrices for GSE11103 and GSE19380 were comprised of 584 probe sets (condition number=1.86) and 280 probe sets (condition number=1.8), respectively. To compare CIBERSORT performance with marker gene-based methods (as in FIG. 19), marker genes from each signature matrix were defined by selecting all genes with at least 5-fold higher expression in one cell type compared to the others (as in ref 7).

Statistical Analysis

Concordance between known and predicted cell type proportions was determined in most cases by Pearson correlation coefficient (R) and Root Mean Squared Error (RMSE) to measure linear fit and estimation bias, respectively. Importantly, the latter was calculated on cell type proportions represented as percentages. Group comparisons were determined using a two-sided Wilcoxon signed rank test, paired or unpaired as appropriate. All results with P<0.05 were considered significant. Statistical analyses were performed with R, GraphPad Prism v6.0d, or customized code.

Analysis of Simulated Tumors With Added Noise

CIBERSORT was benchmarked against six GEP deconvolution methods (RLR and five others[4-8]) by comparing their results on mixtures with different levels of unknown content (i.e., tumor) and noise. To facilitate a fair comparison, previously defined in vitro mixtures (n=12) of four blood cell lines (GSE11103), each of which is highly distinct and readily deconvolved were used (FIG. 6a). To evaluate expression-based methods, a signature matrix with nearly 600 distinguishing genes (described above and applied in FIG. 6a) was used, whereas for marker-based deconvolution, marker genes as described above (n=500 genes) were selected. To simulate tumors with infiltrating leukocytes, we combined the cell line mixtures with defined inputs of a GEP from a colon cancer cell line (HCT116), calculated as the mean of two replicate arrays (GSM269529 and GSM269530; GSE10650). Both GSE11003 and GSE10650 datasets were MASS and quantile normalized together prior to analysis. To introduce noise, values randomly sampled from the following distribution, $2^\wedge N(0, f\times\sigma)$, where f ranged from 0 to 1 (i.e., y-axis in FIG. 2a and FIG. 7a), and σ was the global standard deviation across the original mixtures represented in log 2 space (=11.6) were added. Since GSE11103 consists of four distinct mixtures with three replicates each, the performance of each algorithm was measured over the entire set of 12 mixtures (R and RMSE; FIG. 7, FIG. 19). Moreover, this was independently iterated over tumor content (0% to <100%) and noise (f, 0 to 1) in 30 regularly spaced intervals, such that together, 900 sets of mixtures were analyzed.

Analysis of Cell Type-Specific Marker Genes.

Figure 22A:
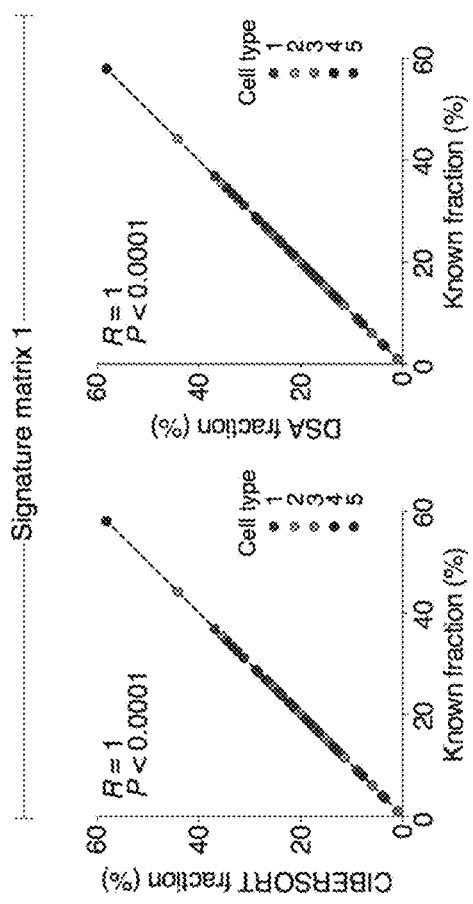
FIGS. 22a-22e are a collection of graphs and tables showing the impact of marker genes on deconvolution, according to embodiments of the present disclosure.
Figure 22C:
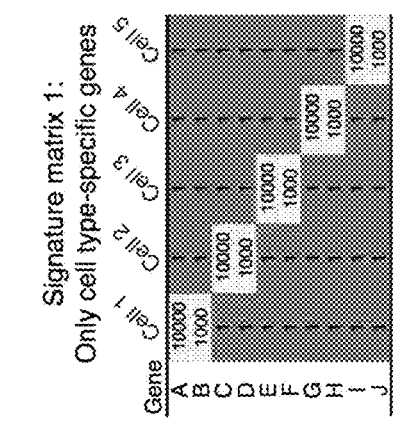
Figure 22B:
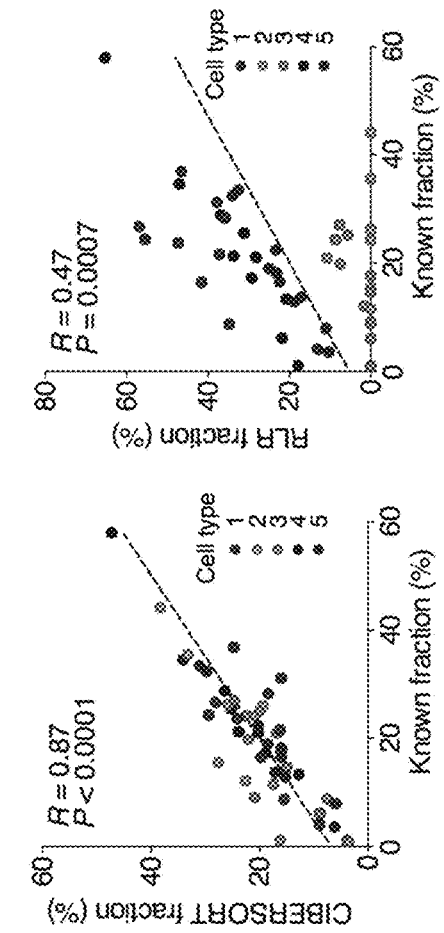
Figure 22D:
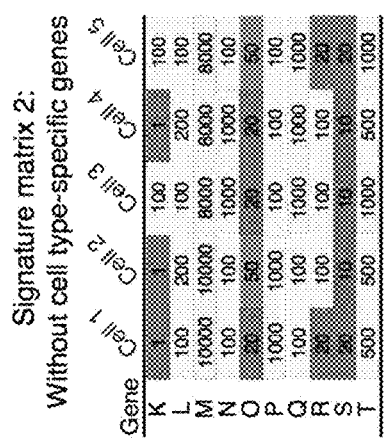
Figure 22E:
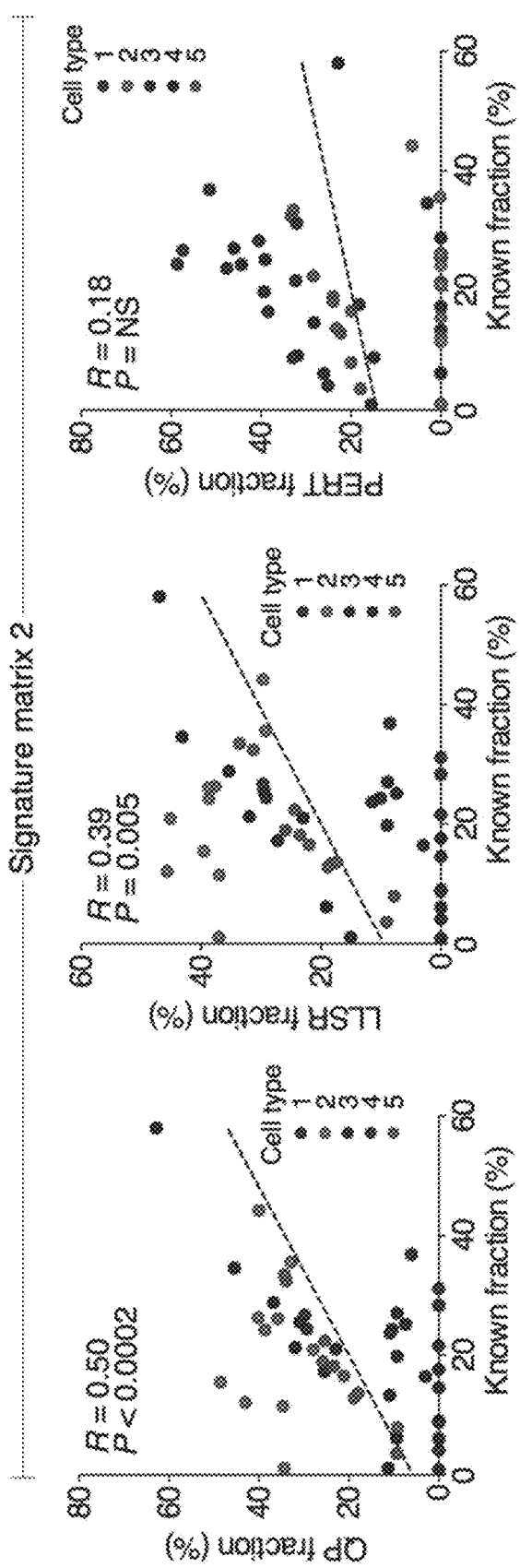

Cell type-specific marker genes may be difficult if not impossible to ascertain between closely related cell types. As such, whether marker genes expressed by >1 cell type in the signature matrix could still be useful to CIBERSORT was tested, provided that each reference profile in the signature matrix remains unique. Two artificial signature matrices (containing ten genes and five cell types each) representing opposite extremes were created: one containing only cell type specific genes (called SM1; FIG. 22a) and the other without any cell type specific genes (called SM2; FIG. 22b). Of note, unlike signature matrices derived from real expression data, SM1 and SM2 are fully defined and therefore ideally suited for this analysis. Moreover, reference profiles in SM2 are highly inter-correlated, as might be expected for subsets without unique marker genes. Random mixing proportions were generated according to a uniform distribution, and combined the cell types in each signature matrix to create ten mixtures. Low-level noise was then added by randomly shuffling genes in one of the mixtures and combining 5% of the resulting vector with 95% of each of the ten mixtures. CIBERSORT and DSA were compared using SM1 (FIG. 22c), and CIBERSORT, RLR, QP, LLSR, and PERT were compared using SM2 (FIGS. 22d, 22e). While CIBERSORT performed identically to DSA on SM1, it was substantially more accurate than other methods on SM2, closely approximating its performance on SM1 (FIGS. 22d, 22e). This analysis demonstrates CIBERSORT's softer dependency on cell type specific signature matrix genes, an important requirement for deep deconvolution.

Analysis of Cell Subset Detection Limit

Figure 9B:
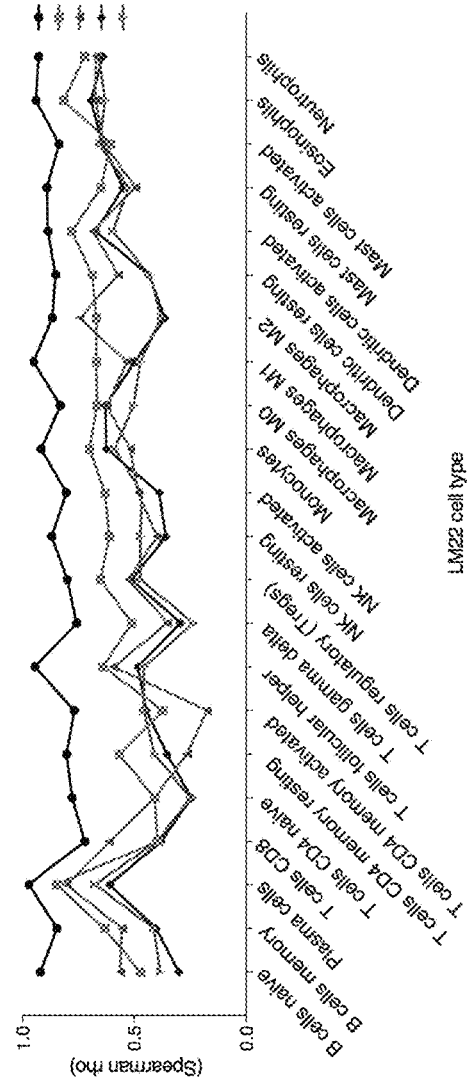
Figure 11A:
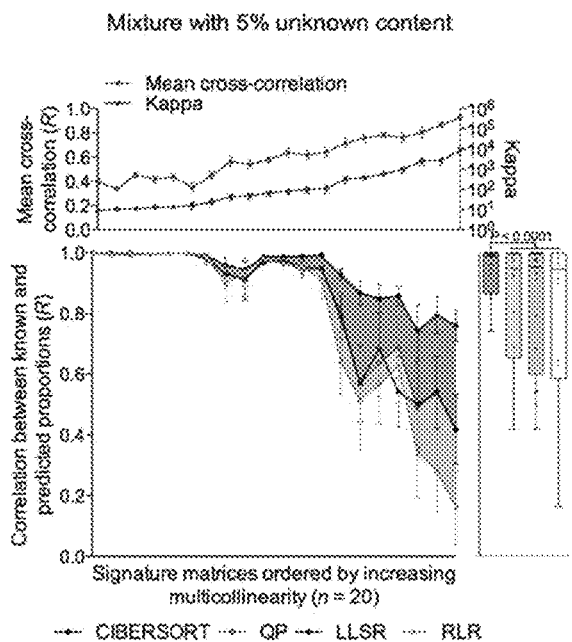
FIGS. 11a-11d: Impact of multicollinearity on signature-matrix based methods.
Figure 11B:
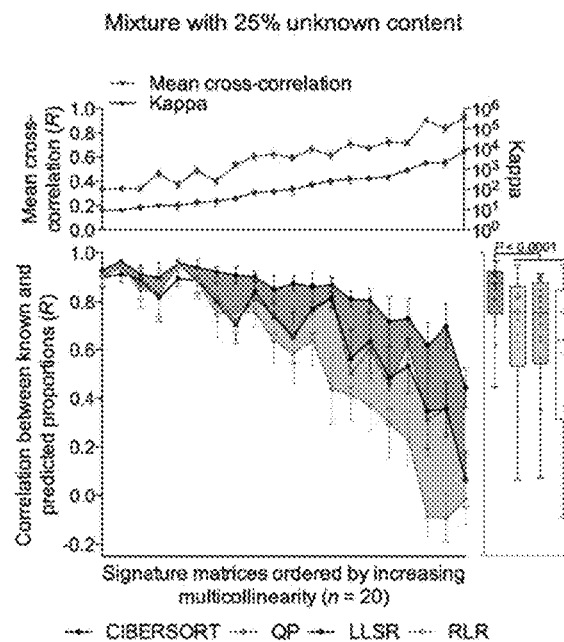
Figure 11C:
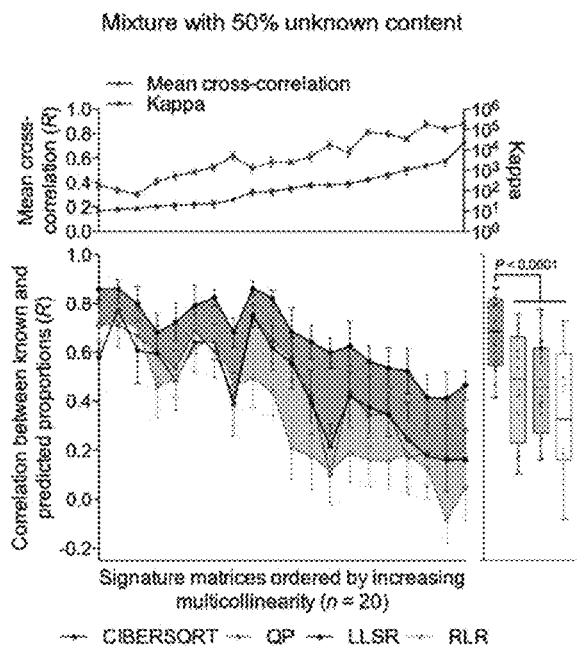
Figure 11D:
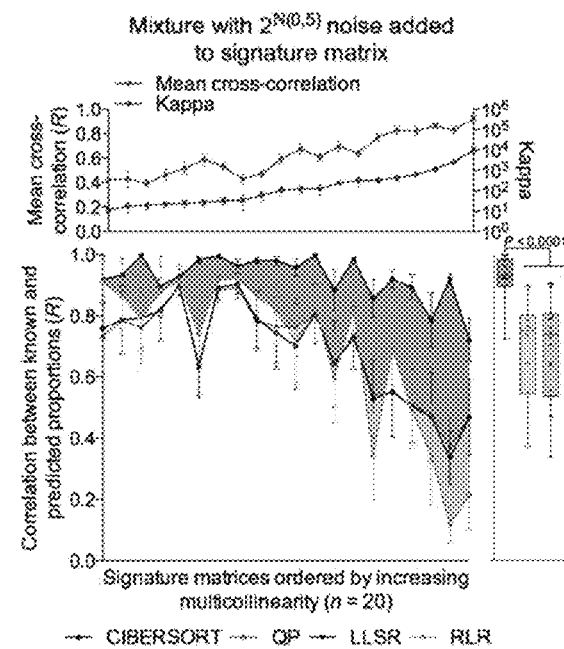

Two in silico experiments were performed to assess the detection limits of different deconvolution algorithms. In the first experiment (FIG. 8), the same cell line GEPs described above was used to compare CIBERSORT and RLR with five other GEP deconvolution methods[4-8]. The detection limit was evaluated using Jurkat cells (spike-in concentrations of 0.5%, 1%, 2.5%, 5%, 7.5%, and 10%), whose reference GEP (median of three replicates in GSE11103) was added into randomly created background mixtures of the other three blood cell lines. Five mixtures were created for each spike-in concentration. Predicted Jurkat fractions were assessed in the presence of differential tumor content, which was simulated by adding HCT116 (described above) in ten even increments, from 0% to 90%. Of note, the same marker/signature genes described was also used for simulated tumors (above). In a second experiment (FIG. 9a), CIBERSORT was compared with QP[5], LLSR[4], PERT[6], and RLR. Naïve B cell GEPs from the leukocyte signature matrix were spiked into four random background mixtures of the remaining 21 leukocyte subsets in the signature matrix. The same background mixtures were used for each spike-in. The addition of unknown content was also tested by adding defined proportions (0 to 90%) of randomly permuted expression values from a naïve B cell reference transcriptome (median expression profile from samples used to build LM22, FIG. 16). This analysis was then repeated for each of the remaining leukocyte subsets in LM22 (FIG. 9b).

Analysis of Multicollinearity

CIBERSORT wasss compared with three signature gene expression-based deconvolution methods, QP[5], LLSR[4], and RLR (this work), for the impact of multicollinearity (i.e., the degree of inter-sample correlation in the signature matrix) on mixtures with unknown components (i.e., parts of mixture unaccounted for in the signature matrix), and noise added to either B or m. Random signature matrices were created from 41 naïve B cell signature genes (derived from GSE22886[23]) by randomly selecting and permuting P gene expression values from the original non-random set of 41 genes, thus maintaining realistic gene expression distributions (n=10 populations). The number of genes P was used to control multicollinearity within the signature matrix (higher P=less collinear, and vice versa), and for each P, 10 random signature matrices were generated. Simulated mixtures were created by randomly apportioning populations from the signature matrix. To simulate unknown content (FIG. 11a-c), three concentrations (5%, 25%, and 50%) of 10 additional cell populations were randomly combined and added to each mixture. Non-log linear noise was additively introduced into simulated mixtures (FIG. 11d) by randomly sampling from $2^{\wedge}N(0, j)$ (the exponent denotes a normal distribution with mean of zero and standard deviation j). Under all conditions tested, CIBERSORT outperformed the other three methods.

Analysis of Deconvolution Consistency

LM22 was applied to a publicly available dataset (GSE29832) to measure stability of deconvolution results over defined levels of blood admixed with breast tissue. To confirm reported fractions of blood admixed with breast tissue, these proportions were compared with an LM22 normalized immune index, defined for each sample as the median gene expression value of all genes in LM22 (FIG. 16) divided by the median expression level of the transcriptome, and normalized into the range of known leukocyte content across the datasets (FIG. 2e, left). As a consistency metric, deconvolution results were compared for each sample with results from the sample with highest immune purity (FIG. 2e, right).

REFERENCES

1. Hanahan, D. & Weinberg, R. A. Cell 144, 646-674 (2011).
2. Coussens, L. M., Zitvogel, L. & Palucka, A. K. Science 339, 286-291 (2013).
3. Shen-Orr, S. S. & Gaujoux, R. Curr. Opin. Immunol. 25, 571-578 (2013).
4. Abbas, A. R., Wolslegel, K., Seshasayee, D., Modrusan, Z. & Clark, H. F. PLoS One 4, e6098 (2009).
5. Gong, T. et al. PLoS One 6, e27156 (2011).
6. Qiao, W. et al. PLoS Comput. Biol. 8, e1002838 (2012).
7. Liebner, D. A., Huang, K. & Parvin, J. D. Bioinformatics (2013).
8. Zhong, Y., Wan, Y.-W., Pang, K., Chow, L. & Liu, Z. BMC Bioinformatics 14, 89 (2013).
9. Schölkopf, B., Smola, A. J., Williamson, R. C. & Bartlett, P. L. Neural Comput. 12, 1207-1245 (2000).
10. Lukk, M. et al. Nat. Biotechnol. 28, 322-324 (2010).
11. Shen-Orr, S. S. et al. Nat. Methods 7, 287-289 (2010).
12. Kuhn, A., Thu, D., Waldvogel, H. J., Faull, R. L. M. & Luthi-Carter, R. Nat. Methods 8, 945-947 (2011).
13. Yoshihara, K. et al. Nat. Commun. 4, 2612 (2013).
14. Cherkassky, V. & Ma, Y. Neural Netw. 17, 113-126 (2004).
15. Farrar, D. E. & Glauber, R. R. Rev. Econ. Stat. 49, 92-107 (1967).
16. Gong, T. & Szustakowski, J. D. Bioinformatics 29, 1083-1085 (2013).
17. Levy, R. et al. J. Clin. Oncol. 32, 1797-1803 (2014).
18. Lu, P., Nakorchevskiy, A. & Marcotte, E. M. Proc. Natl. Acad. Sci. U.S.A 100, 10370-10375 (2003).
19. Zhong, Y. & Liu, Z. Nat. Methods 9, 8-9 (2012).
20. Drucker, H., Burges, C. J. C., Kaufman, L., Smola, A. & Vapnik, V. Support Vector Regression Machines, Vol. 9. (MIT Press, 1997).
21. Storey, J. D. & Tibshirani, R. Proc. Natl. Acad. Sci. U.S.A 100, 9440-9445 (2003).
22. Benita, Y. et al. Blood 115, 5376-5384 (2010).
23. Abbas, A. R. et al. Genes Immun. 6, 319-331 (2005).

Example 2: Leukocyte Frequencies and Prognostic Associations Inferred in 25 Human Cancers Using CIBERSORT Materials and Methods The following materials and methods were used for Examples 2 and 3.

PREdiction of Clinical Outcomes From Genomic Profiles (PRECOG) Assembly and Quality Control.

To identify cancer gene expression datasets with corresponding patient outcome data, the NCBI Gene Expression Omnibus (GEO), EBI ArrayExpress, NCI caArray, and Stanford Microarray Database were queried for the terms, survival, prognosis, prognostic, or outcome. Perl scripts were implemented to download processed and raw data, and associated annotation. For data within NCBI, the array platform was determined from the SOFT format file, and the corresponding annotation file was retrieved from GEO. From these, the Probe ID, Genbank accession, HUGO gene symbol and gene description were extracted based on the internal headers of the SOFT annotation file. The desired fields were specified manually if this automated procedure failed. For older platforms, such as cDNA microarrays, where annotations had not been recently updated, the probe sequences were re-mapped to HUGO gene symbols via the Genbank or Refseq accession number through the NCBI Entrez gene identifier. In cases without available accessions, but with the DNA sequence of the probe, the mapping was performed using BLAT to compare probes to a Refseq reference and look for unique highest-scoring hits.

Scripts were written to extract sample annotation information from GEO SOFT format files and parse them into tables. Since the contents of annotation fields are not semantically enforced, sample data can be contained in various fields, including Sample_title, Sample_characteristics, Sample_description, and Sample_source. Moreover, not all fields are specified for every sample. To parse this information into tabular format, the correct variable name (column header) was estimated by searching for common substrings across samples. In some cases, a dataset clearly had survival information, but was not deposited with the genomic data. In such cases, supplementary information of corresponding literature was first searched for the missing information. Failing this, corresponding and first authors were contacted, of which roughly half supplied the requested data.

All tabulations of clinical annotations were further checked and manually curated. This process included verification of results in selected studies by direct comparison of Kaplan-Meier plots and time scales with those in the corresponding primary publications, as well as consistency of prognostic genes across studies. Separately, errors due to technical issues or the curation process were estimated by comparing annotated gender to the ratio of RPS4Y 1 to XIST (male:female) expression levels after microarray normalization, as detailed below. Furthermore, identical samples present in more than one dataset were identified using MD5 checksums for Affymetrix data, and by cross-correlation analysis of expression vectors, and redundant samples were accordingly eliminated.

The following gene expression normalization strategy was applied to allow unification of data from diverse microarray platforms within PRECOG. For Affymetrix GeneChip data, raw CEL files were obtained when possible, and were normalized with the MAS5 algorithm (affy package v. 1.26 of Bioconductor v. 1.8 in R 2.15.1), using a custom CDF (Chip Definition File) for probeset summarization, which updates and maps array oligonucleotides to Entrez gene identifiers (brainarray(dot)mbni(dot)med(dot)umich(dot)edu/Brainarray/). Each dataset, regardless of platform, was quantile normalized separately. Moreover, each gene was $\log_e$ transformed if not already in log space, and was then unit mean/variance standardized across samples within a given dataset. While alternative microarray normalization methods have been proposed (e.g., RMA, gcRMA, fRMA, SCAN-UPC), for survival analysis no significant benefit was observed in comparing Affymetrix data normalized as described above to alternate normalization strategies. TCGA RNA-seq and clinical data were downloaded from the TCGA Data Coordinating Center using TCGA-assembler. The gene-level RNA-seq data were pre-processed using TCGA-assembler's ProcessRNASeqData function. RNA-seq and clinical data were matched via the patient barcode provided by TCGA.

For each study, the association of each probe on an array platform with survival outcomes was assessed via Cox proportional hazards regression using the coxph function of the R survival package (v. 2.37). Cox coefficients, hazard ratios with 95% confidence intervals, P values, and z-scores were obtained for each array probe. For datasets that had not been processed with Custom CDF, which yields a unique per-gene expression value, survival z-scores for probes were collapsed to the gene level by averaging z-scores of probes that matched to the same HUGO gene symbol. Z-scores for each gene were summarized across all datasets in each malignancy using Liptak's weighted meta-z test, with weights set to the square roots of sample sizes. To identify genes with cancer-wide prognostic significance, and avoid bias due to cancers with different sample sizes, weighted meta-z-scores were further combined into a single global meta-z-score for each gene using Stouffer's method (unweighted).

Validation of z Statistics in PRECOG.

Using lung adenocarcinoma as a test case, the relationship between the weighted meta-z-score metric and standard z-scores were assessed, the latter of which were derived from a merged expression matrix consisting of GEPs from lung adenocarcinoma studies in PRECOG. For this purpose, datasets that had at least 40 stage I samples were selected. To mitigate batch effects, each gene in each dataset were standardized such that it had unit mean and variance across stage I samples. Sample annotations were manually reviewed to ensure that staging corresponded to American Joint Committee on Cancer (AJCC) version 6 (2002), based on TNM (Tumor-Nodes-Metastasis) information. Many datasets pre-dated version 7 of AJCC, and did not contain the required detail for annotating to that standard. These refinements and standardizations permitted merging of samples from different datasets comprising different array platforms and different distributions of tumor stage across the cohort. In all, lung adenocarcinoma GEPs from n=1,106 patients were compared, and weighted meta-z scores were found to be significantly correlated with merged z-scores (Spearman's R=0.9, P<$2.2 \times 10^{-16}$). Similar results were observed when comparing the meta- and merged-z statistics for a compendium of 5 AML studies, thus validating the use of the meta-z statistic. Of note, while batch-correction procedures were applied to merge expression datasets prior to calculating cross-study z-scores, these steps were not necessary with the meta-z metric, as z-scores from individual studies were directly integrated. This suggests that the meta-z approach effectively overcomes batch differences across datasets.

The influence of batch effects within individual datasets were further evaluated using Combat (Johnson, W. E., Li, C. & Rabinovic, A. Adjusting batch effects in microarray expression data using empirical Bayes methods. *Biostatistics* 8, 118-127 (2007)). Applied to microarray processing dates in four AML studies, only a modest effect on prognostic z-scores was observed, as pre- and post-batch-corrected data were all highly correlated (R≥0.92, P<$2.2 \times 10^{-16}$). To test whether batch correction of samples profiled by different study sites would improve data quality, pre- and post-batch-corrected expression data from the NCI director's challenge lung adenocarcinoma dataset (ca00182) were compared with a control dataset consisting of prognostic meta-z scores from a pooled set of all remaining 19 lung adenocarcinoma studies in PRECOG. Little difference in performance was observed for the most prognostic genes, with changes primarily affecting genes whose association with survival outcomes was subtle.

PRECOG False Discovery Rate.

While z-scores and meta-z scores were analyzed in this work, Q values for global unweighted meta-z and weighted cancer-specific meta-z-scores were estimated using the False Discovery Rate (FDR) method of Storey and Tibshirani (Storey, J. D. & Tibshirani, R. Statistical significance for genomewide studies. *Proc. Natl. Acad. Sci. U.S.A.* 100, 9440-9445 (2003)), and are available for all analyzed z-score matrices online (precog(dot)stanford(dot)edu). Notably, of 23,288 HUGO gene symbols in PRECOG, 4,385 (19%) have a global meta-z significant at Q<0.05 (|meta-z|>2.6), and 2,986 (13%) are significant at a Q<0.01 (|meta-z|>3.22).

Blinding and Sample Selection Criteria.

No blinding was used in this work. Duplicate and non-diagnostic (relapse) samples were excluded from analysis.

Inferring TAL Levels in Bulk Tumor GEPs.

The samples profiled within PRECOG primarily represent bulk diagnostic pre-therapy tumor specimens, which often contain a variety of cell types, including diverse TALs. Given the enrichment of lymphocyte markers in favorably prognostic genes across PRECOG, a method to systematically "unmix" or deconvolve bulk tumor GEPs in PRECOG may reveal new insights into tumor immunobiology. A new approach for Cell Type Identification By Estimating Relative Subsets Of RNA Transcripts (CIBERSORT), a machine-learning method that outperformed other approaches in benchmarking experiments, was recently developed. CIBERSORT produces an empirical P value for the deconvolution using Monte Carlo sampling. Like other linear deconvolution methods, CIBERSORT only operates on expression values in non-log linear space.

TAL Heterogeneity and Prognostic Associations.

CIBERSORT was applied to all normalized PRECOG GEPs from Affymetrix HGU133 platforms (57 studies and 25 cancers). In all, 5,782 tumor GEPs were successfully deconvolved (CIBERSORT P<0.005). For each dataset, estimated mRNA fractions of each leukocyte subset were related to survival using univariate Cox regression. Weighted meta-z scores were determined using the same approach described for PRECOG in order to build an immune-centric version of PRECOG (iPRECOG, FIG. 26a), and unweighted global meta-z scores were used to summarize pan-cancer leukocyte associations in FIG. 23c.

Immune-PRECOG False Discovery Rate.

To differentiate real from stochastic variation in inferred leukocyte prognostic associations, P values and meta-z scores were first compared in immune-PRECOG (FIG. 26b), as any deviation from a standard normal distribution must be considered when drawing statistical conclusions. 1000 null meta-z matrices were generated by (1) shuffling the cell type fractions inferred for each dataset, and (2) computing z-scores and corresponding meta-z scores to capture relationships to overall survival. A tight correspondence between the distribution of null meta-z scores and a standard normal distribution was found (FIG. 26b). Having validated the normality of the meta-z score, FIG. 26a was then filtered using a range of statistical significance thresholds, and at each cutoff, compared observed versus expected fractions for all leukocyte prognostic associations (FIG. 26c). At a two-sided P value threshold of 0.05 (|z|>1.96), nearly three times more prognostic associations than would be expected by random chance was found; at P<0.01, there was a five-fold enrichment, which continued to increase with lower P value cutoffs (FIG. 26c).

Separately, a similar analysis was performed on the global meta-z scores shown in FIG. 23c. Here, the null meta-z scores from FIG. 26c was integrated into null global meta-z scores and recomputed the analysis shown for pan-cancer leukocyte prognostic associations (plotted as the fraction of leukocyte subsets retained at different significance thresholds; FIG. 26d). Taken together, these results explicitly quantify significant versus stochastic variation in leukocyte prognostic associations at different statistical cutoffs, and allow others to tune the nominal statistical threshold to achieve a desired false discovery rate.

Relative PMN Levels Versus Necrotic Tissue Content.

Relative RNA fractions of PMNs inferred by CIBERSORT were not correlated with annotated necrotic content in lung squamous cell carcinoma (TCGA; $R^2$=0.01; P=NS) or melanoma (microarray dataset GSE8401[76]; $R^2$~0; P=NS).

Flow Cytometry Versus CIBERSORT.

Figure 23A:
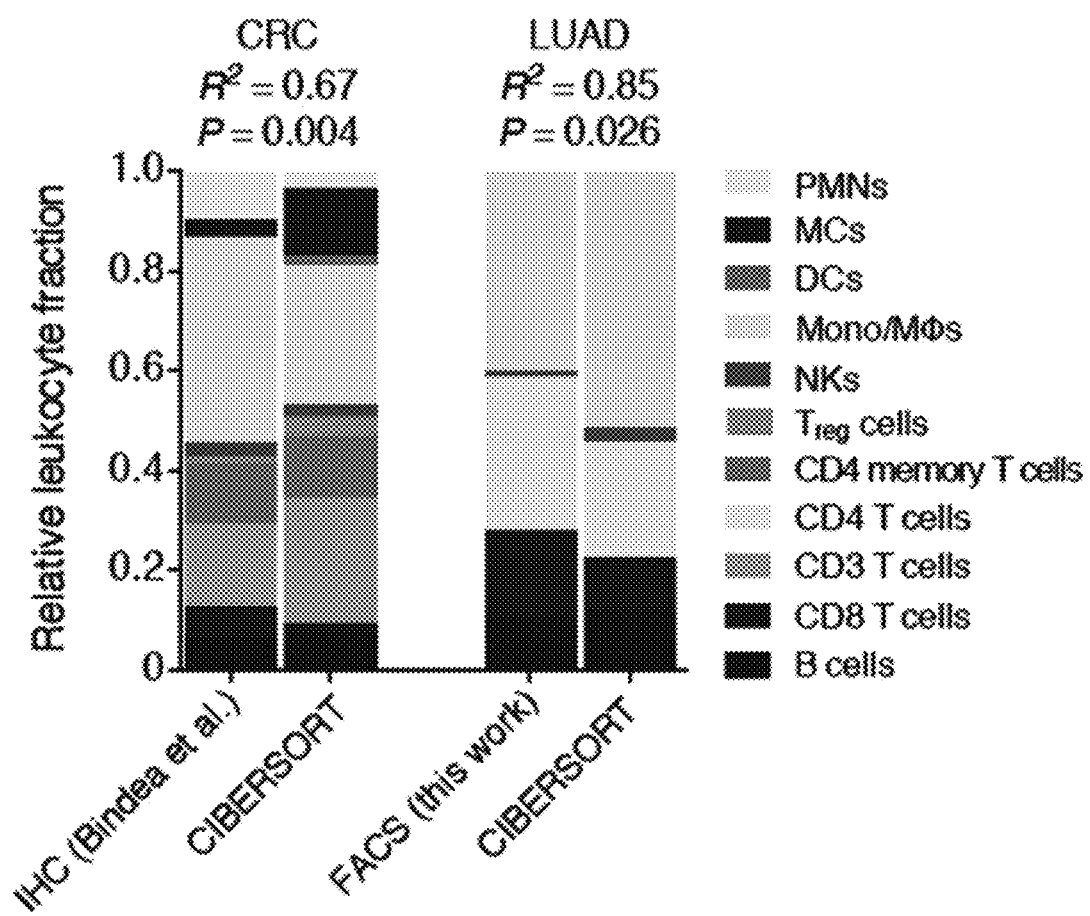

Flow cytometry analysis of non-small cell lung cancer tumor (n=13) specimens was performed as described below, and median fractions of $CD4^+$, $CD8^+$, $CD19^+$, $CD56^+$, and $CD14^+$ populations were normalized by overall $CD45^+$ content (FIG. 23a). For comparison with CIBERSORT, leukocyte signature matrix populations were grouped into the same cluster of differentiation categories: $CD14^+$, monocytes, macrophages, and dendritic cells; $CD4^+$, all T cell subsets except CD8 and γδ T cells; $CD8^+$, CD8 T cells; $CD19^+$, naïve and memory B-cells, $CD56^+$, resting and activated NK cells. Median CIBERSORT-inferred fractions for lung adenocarcinoma GEPs, shown in FIG. 23a, were determined from two publicly available microarray datasets, GSE7670[77] and GSE10072[78].

Patient Samples.

All aspects of this study were approved by the Stanford Institutional Review Board in accordance with the Declaration of Helsinki guidelines for the ethical conduct of research, and all patients involved provided informed consent. For FIG. 23a, fresh human lung tumor samples were obtained from Stanford Tissue Bank. For tissue microarray analyses (FIGS. 24c, 24e, 27c-27h), patient samples were retrieved from the surgical pathology archives at the Stanford Department of Pathology and linked to a clinical database using the Cancer Center Database and STRIDE Database tools from Stanford.

Human Lung Dissociation and Flow Cytometry.

Fresh human lung tumor samples were cut into small pieces and dissociated into single cell suspensions by 45 minutes of Collagenase I (STEMCELL Technologies) digestion. Dissociated single cells were suspended at $1 \times 10^7$ per mL in staining buffer (HBSS with 2% heat-inactivated calf serum). After 10 minutes of blocking with 10 μg μl$^{-1}$ rat IgG, the cells were stained for at least 10 minutes with the antibodies listed below. After washing, stained cells were re-suspended in staining buffer with μg/ml DAPI, analyzed, and sorted with a FACS Aria II cell sorter (BD Biosciences). Antibodies used for experiments related to FIG. 23a: CD45-A700, CD14-PE, CD8-APC, CD4-FITC, CD56-PE-cy7, and CD19-PerCP-cy5.5. Antibodies used for enumeration of plasmacytic cells: CD45-PE-cy7, CD20-PerCP-cy5.5, CD138-PE, CD38-APC, CD19-A700, and CD27-FITC. All antibodies were obtained from BioLegend.

Tissue Microarray (TMA) Cohort.

Patients with lung cancer were reviewed to identify those who had surgically treated disease and paraffin embedded samples from 1995 through June, 2010 for inclusion. Patients with recurrent or metastatic disease samples only were excluded. Medical charts were reviewed to clinically annotate the tumor specimens with demographic, operative procedures, imaging data, and follow-up. Pathology reports were reviewed to confirm specimen type, site, pathology, stage, histology, invasion status and operative procedure. Treated samples (neoadjuvant therapy) were excluded, resulting in a final analysis cohort of 187 pre-treated lung adenocarcinoma tumor specimens with follow-up data.

TMA Cohort Follow-up.

Recurrence was defined by imaging or biopsy and patients with advanced disease or who did not have at least 6 months of follow-up were censored for further analyses. The National Death Index (NDI) was used to define vital status through Oct. 30, 2010. Patients not dead were assumed to be alive except for those who had left the country or were from other countries (who were censored) since the NDI relies on a social security number for vital status assessment. Synchronous tumors resected over time were eligible for prognostic assessment in patients with two primaries.

TMA Construction.

The Stanford Lung Cancer TMA was developed from surgical specimens that contained viable tumor from duplicate slides that were reviewed by a board-certified pathologist. The pathologist was not blinded to sample identity. The area of highest tumor content was marked for coring blocks corresponding to the slides. 2 mm cores were used to build the tissue microarray. These cores were aligned by histology and stage and negative controls were taken from the West Lab and included a variety of benign and malignant tissues (65 cores) that included normal non-lung tissue (12 cores), abnormal non-lung tissue (13 cores), placental markers (23 cores) and normal lung (17 cores). Normal lung consisted of a specimen adjacent, but distinct, from tumor over the years 1995 through 2010 to assess the variability of staining by year. OligoDT analysis was performed on the finished array to assess the architecture of selected cores and adequacy of tissue content prior to target IHC analysis. A co-registered Hematoxylin & Eosin (H&E) slide was used as well to verify tumor location for cases where this was unclear on initial inspection.

TMA Immunohistochemistry.

MPO (DAKO) and CD20 (clone L26, DAKO) immunohistochemistry performed on 4 mm sections using the Ventana BenchMark XT automated immunostaining platform (Ventana Medical Systems/Roche, Tucson, AZ).

TMA RNA In Situ Hybridization.

The RNA in situ hybridization probe for IGKC was designed against chr2: 88,937,790-88,938,290 (hg18) using primer 5'-CTG TTG TGT GCC TGC TGA AT-3' (SEQ ID NO:1) and the T7 promoter-tagged primer 5'-CTA ATA CGA CTC ACT ATA GGG TTA AAG CCA AGG AGG AGG AG-3' (SEQ ID NO:2). RNA in situ hybridizations were performed on TA369, as described previously.

TMA Microscopy.

All slides were scanned at 20× on an Ariol imaging analysis system (originally built by Applied Imaging).

TMA Staining Quantification and Analysis.

To facilitate consistency and reproducibility in quantitating TMA staining patterns, the performance of GemIdent, a supervised in silico image segmentation system, was evaluated. As an initial exercise, GemIdent was trained on a single lung adenocarcinoma specimen to recognize both IGKC stains and non-tissue background (white space). GemIdent was then applied to 10 TMA specimens to generate separate image masks of both IGKC localization and non-tissue background (i.e., "empty space"). A custom Perl script was used to process each image mask and quantify the staining area of IGKC for each specimen (by first removing non-tissue white space to calculate the surface area of each tissue). To test the utility of this approach, a board-certified pathologist (RBW) scored IGKC for the same 10 specimens. The pathologist had no knowledge of the results from automated staining, but was not blinded to sample identity. Both assessments were highly correlated ($R^2=0.98$; FIG. 28c). In a separate exercise, two independent operators trained GemIdent on distinct CD20-stained specimens. CD20-stained fractions were then quantified across the entire TMA (n=187 lung adenocarcinomas) and results were processed as described above. The concordance between independent operators was very high ($R^2\sim1$; FIG. 28d). These data support the utility of GemIdent coupled with image post-processing for automated scoring of TMA specimens. This approach was applied to quantitatively score IGKC, CD20, and MPO for all lung adenocarcinoma TMA specimens (e.g., see FIG. 28a).

Comparison Between TALs and Circulating Leukocytes.

Among patients with available perioperative circulating leukocyte (lymphocyte and PMN) counts, the sample closest to the date of procedure (DOP), within −120 to +28 days, were analyzed, where precedence was given to preoperative samples (total n=48 lung adenocarcinoma patients). No relationships were found between circulating leukocyte (CL) levels and TALs quantified on the TMA. Moreover, while the ratio of MPO to IGKC levels remained significantly prognostic within this patient subset (P=0.02), CL levels had no significant relationship to survival.

Results

Leukocyte Composition in Bulk Tumors

Infiltration of tumors by specific leukocyte cell subsets such as $CD8^+$ and $CD45RO^+$ memory T-lymphocytes has been largely linked with favorable outcomes in different cancers, while others such as regulatory T-cells and macrophages can confer good or poor prognosis depending on context. To systematically and comprehensively map compositional differences in TALs and their relationships to survival, a new machine-learning framework for Cell-type Identification By Estimating Relative Subsets Of known RNA Transcripts (or CIBERSORT) was applied. CIBERSORT outperforms previous deconvolution methods with respect to noise, unknown mixture content, and closely related cell types, in statistically estimating relative proportions of cell subsets from expression profiles of complex tissues (e.g., bulk tumors). As input, purified expression profiles for 22 distinct leukocyte subsets, and defined "barcodes" of gene expression signatures that robustly distinguish these cell types without requiring cell type-specific marker genes were used. At a |meta-z score|>3.3 (corresponding to two-sided P<0.001), 28% of these barcode genes (152 of 547) are individually significant in PRECOG, out of 2,851 total pan-cancer prognostic genes at the same significance threshold. This was higher than expected by random chance (P<0.001, Chi-squared test). Whether directly or indirectly compared against flow cytometry and immunohistochemistry, CIBERSORT exhibited robust performance on solid tumors, accurately estimating relative fractions of leukocyte subsets in colorectal cancer and lung adenocarcinoma (FIG. 23a), and follicular lymphoma.

Figure 23B:
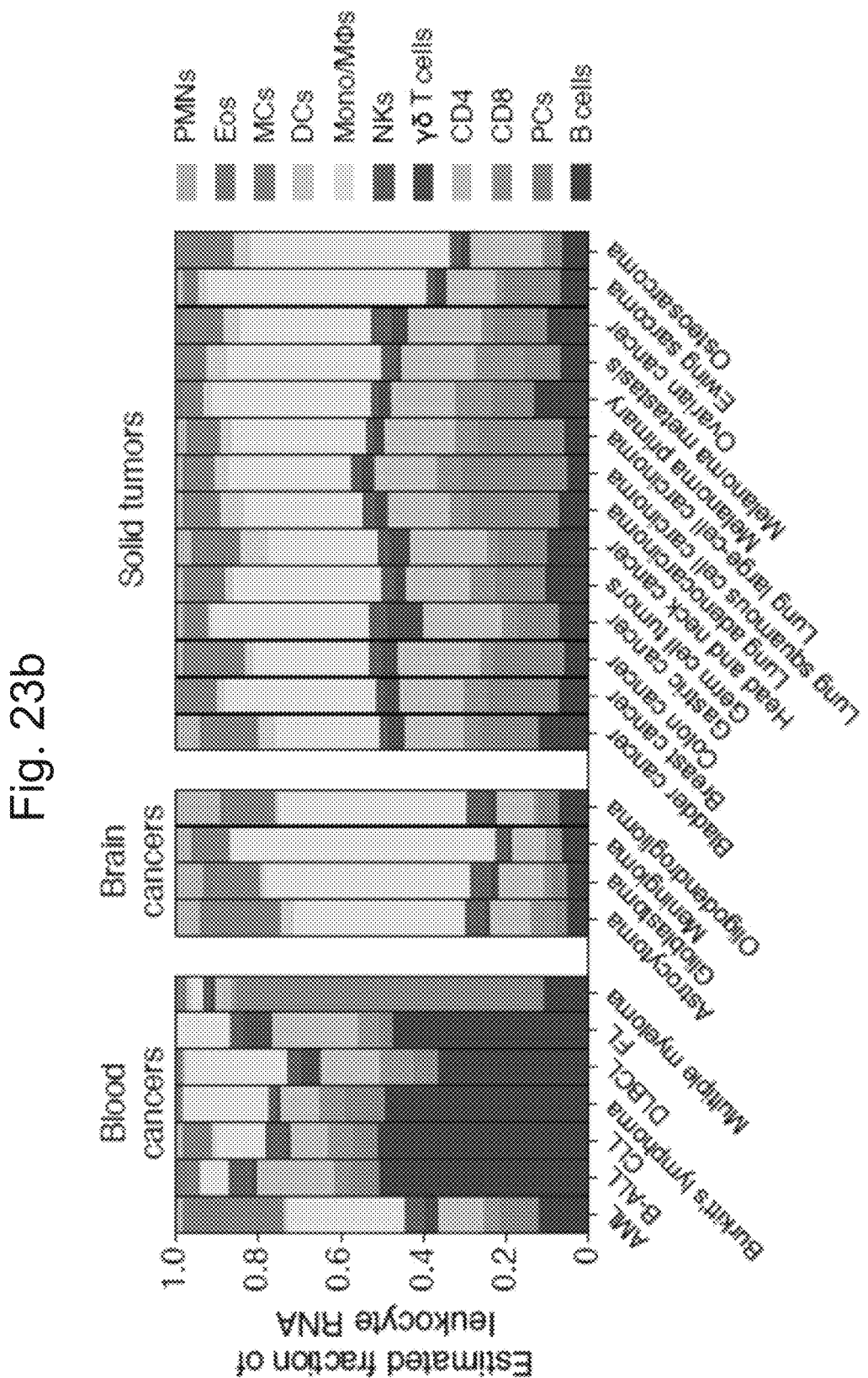
Figure 25A:
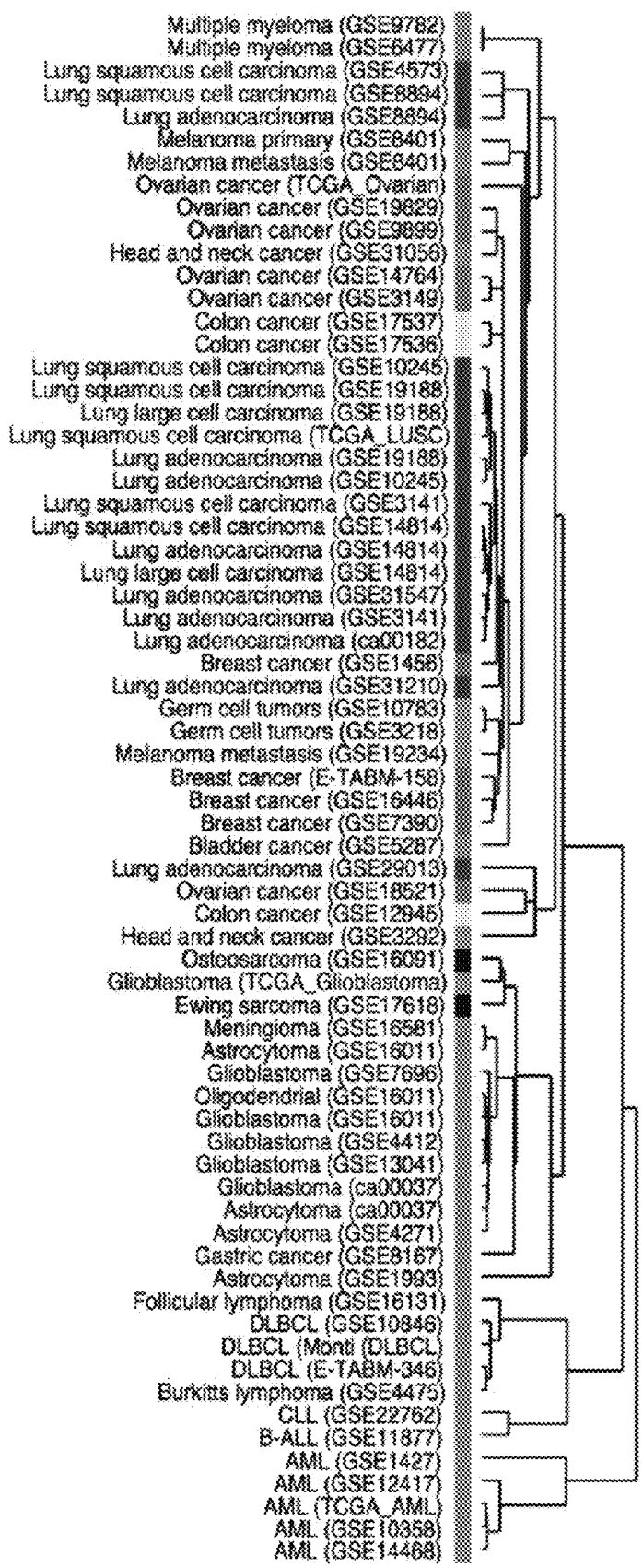
FIGS. 25a-25c are a collection of graphs showing correlation analyses of estimated leukocyte fractions across cancer types and datasets, according to embodiments of the present disclosure.

Applied to PRECOG, CIBERSORT revealed striking differences in relative leukocyte composition between hematopoietic neoplasms, brain cancers, and non-brain solid tumors (FIG. 23b). Variation in TAL content was also consistent and reproducible across independent studies of the same cancer type, including solid tumors (FIG. 25a). Of note, while the majority of tumors profiled within PRECOG were unpurified and uncontrolled with respect to tumor content, CIBERSORT correctly inferred high fractions of plasma cells in multiple myeloma-enriched specimens (FIG. 23b). Furthermore, as expected, B-cell signatures were found to predominate in B-cell malignancies (FIG. 23b), suggesting that CIBERSORT has general utility for discerning cell of origin in diverse cancers.

Figure 23D:
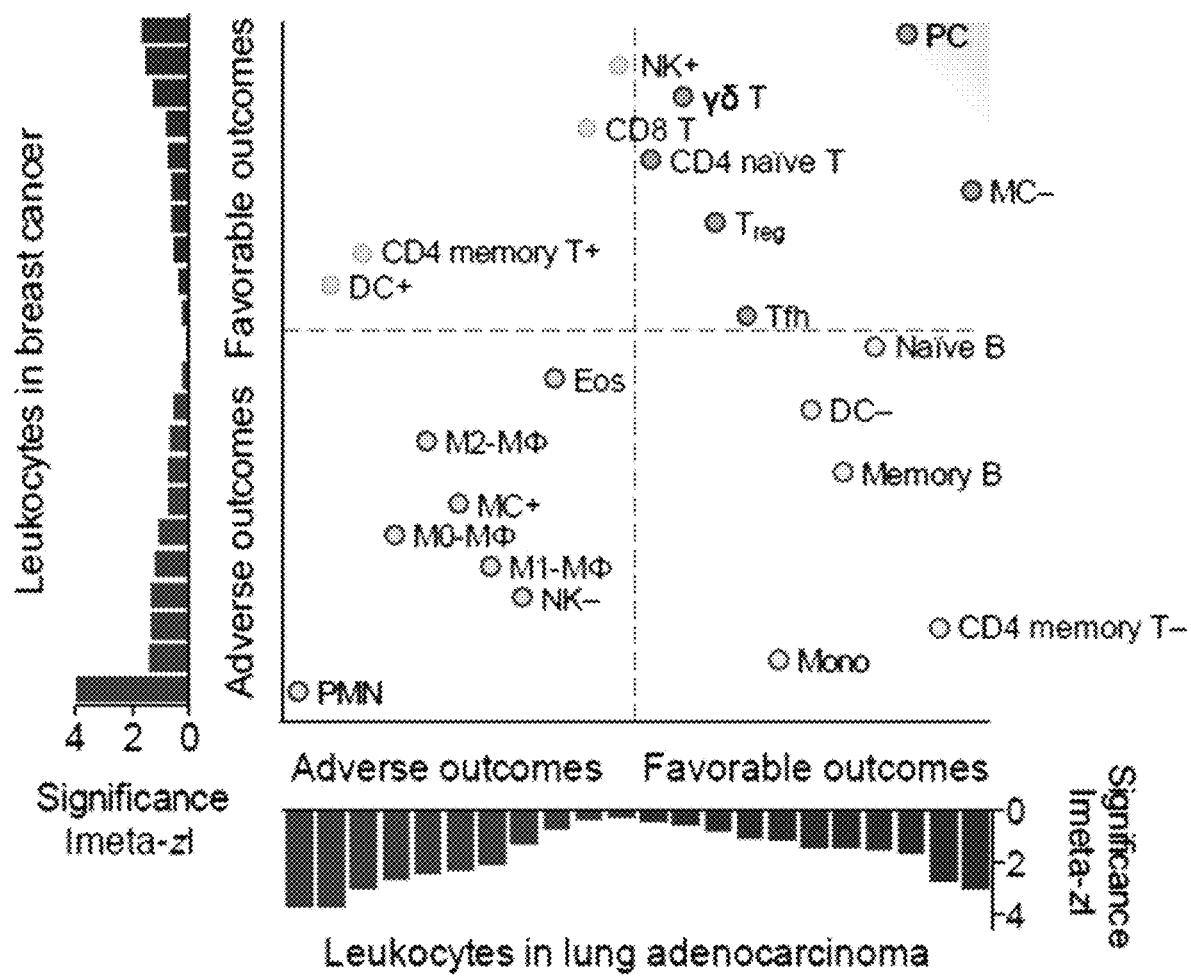

FIGS. 23a-23d: Inferred leukocyte frequencies and prognostic associations in 25 human cancers. (FIG. 23a) Relative leukocyte fractions enumerated in solid tumors by CIBERSORT versus immunohistochemistry (IHC) or flow cytometry (FACS) on independent samples. CRC, colorectal cancer; LUAD, lung adenocarcinoma. To approximate ground truth proportions in CRC biopsies, levels were inferred by averaging previously reported leukocyte counts from the tumor center and invasive margin of 107 patients. Baseline leukocyte fractions in LUAD biopsies were enumerated by FACS (n=13 tumors; data represented as medians; details in Methods). CIBERSORT results are represented as mean leukocyte fractions for the corresponding histologies. (FIG. 23b) Estimated mRNA fractions of 22 leukocyte subsets across 25 cancers (Affymetrix platforms only; see Methods), pooled into 11 immune populations here for clarity. (FIG. 23c) Global prognostic associations for 22 leukocyte types across 25 cancers (n=5,782 tumors; left) and 14 solid non-brain tumors (n=3,238 tumors; right), ranked by unweighted meta-z score, with a false discovery rate (FDR) threshold of 25% indicated for each plot. For individual cancers, see FIG. 26a. (FIG. 23d) Concordance and differences in TAL prognostic associations between breast cancers and lung adenocarcinoma (for FDRs, see FIG. 26c). Resting and activated subsets in FIGS. 23c, 23d are indicated by − and +, respectively.

Figure 25B:
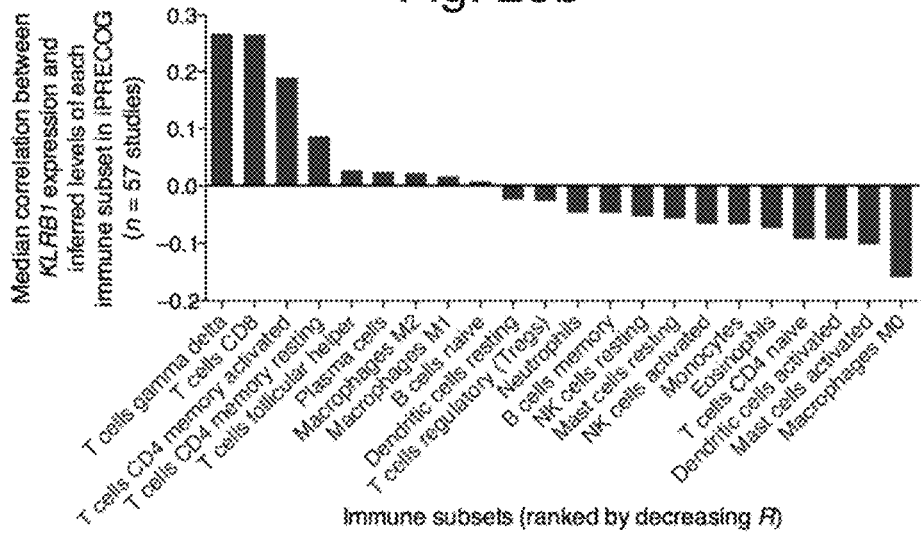
Figure 25C:
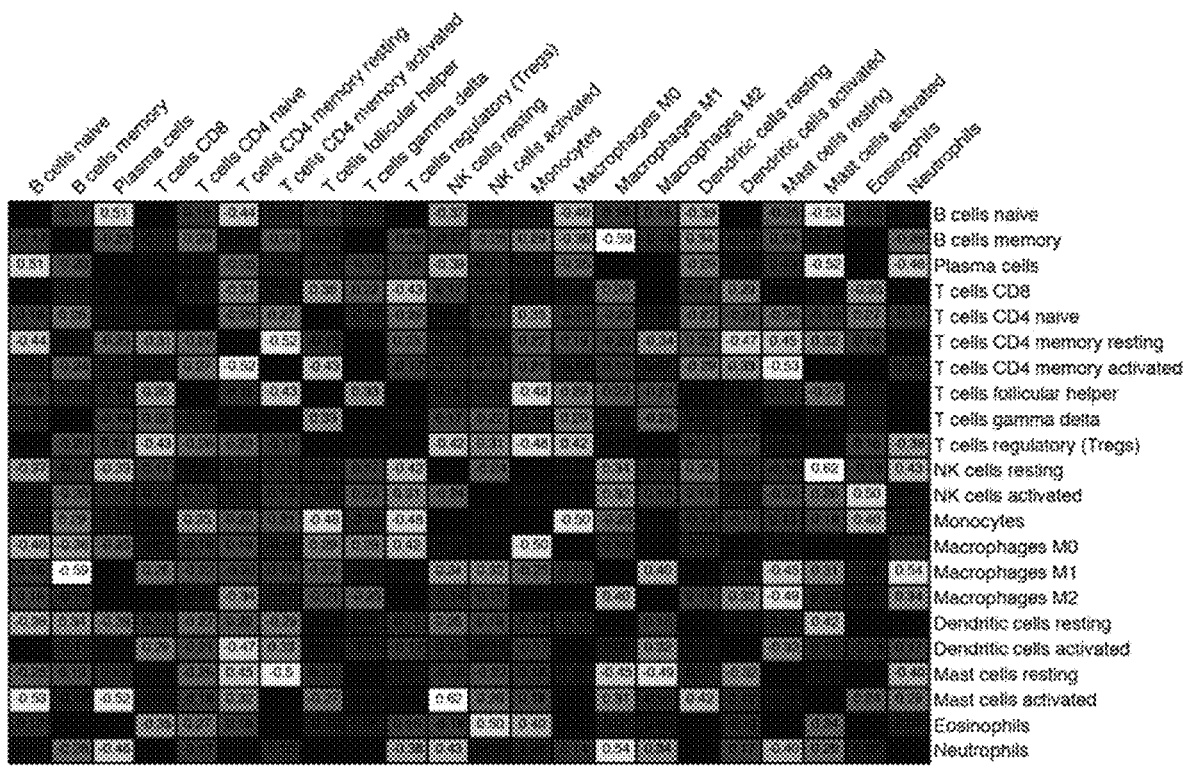

FIGS. 25a-25c: Correlation analyses of estimated leukocyte fractions across cancer types and datasets. (FIG. 25a) Dendrogram showing results of centroid hierarchical clustering applied to leukocyte composition vectors (n=22 subsets per dataset). Centered correlation was used as the distance metric. Clustering of cancers of the same type from independent studies illustrates the reproducibility of CIBERSORT's estimation of relative immune infiltration levels. (FIG. 25b) Pearson correlation coefficients between KLRB1 expression and inferred levels of each immune subset across all 57 studies analyzed in immune PRECOG. Data are presented as medians. (FIG. 25c) Cross-correlation analysis of leukocyte prognostic associations across cancers. All pairwise Pearson correlations between the meta-z scores of immune populations in immune PRECOG (FIG. 26a), illustrated as a heat map.

Prognostic Associations of TALs

Figure 26A:
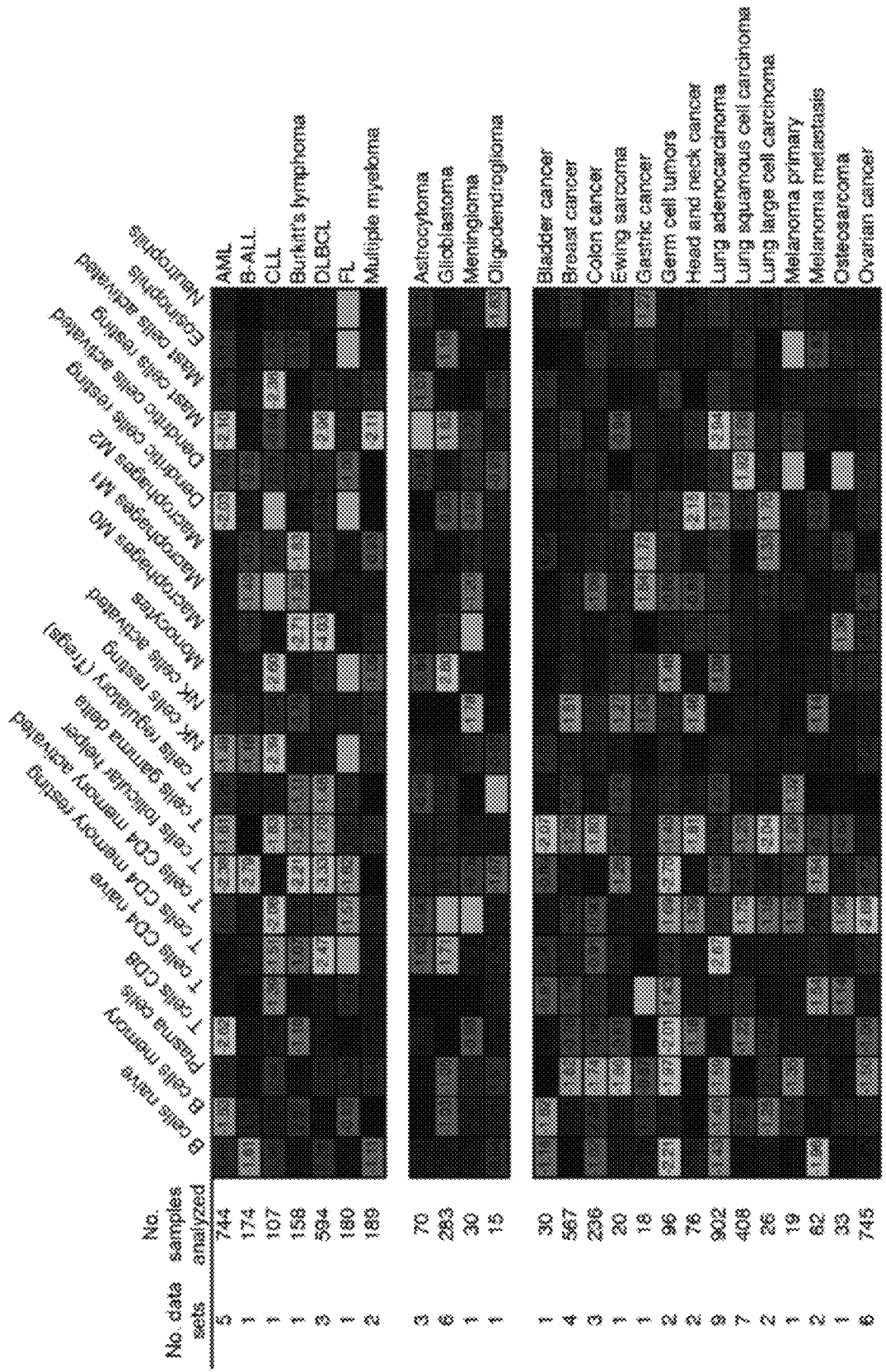
FIGS. 26a-26d are a collection of graphs showing prognostic associations between 22 leukocyte subsets and 25 cancer histologies, according to embodiments of the present disclosure.
Figure 26B:
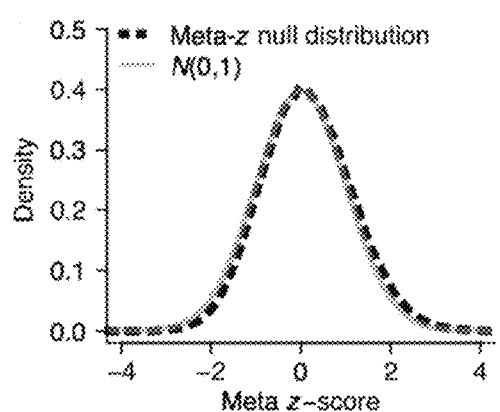
Figure 26C:
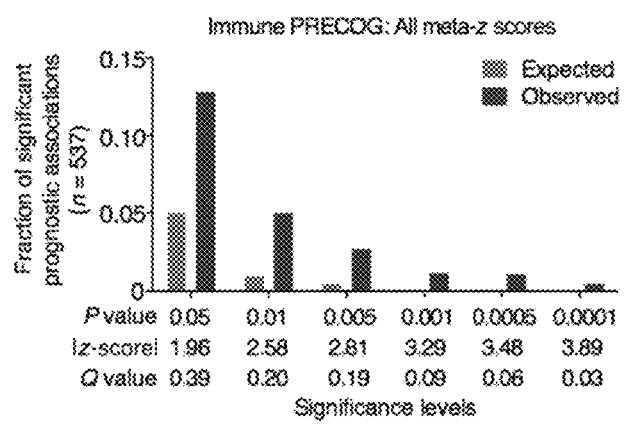
Figure 26D:
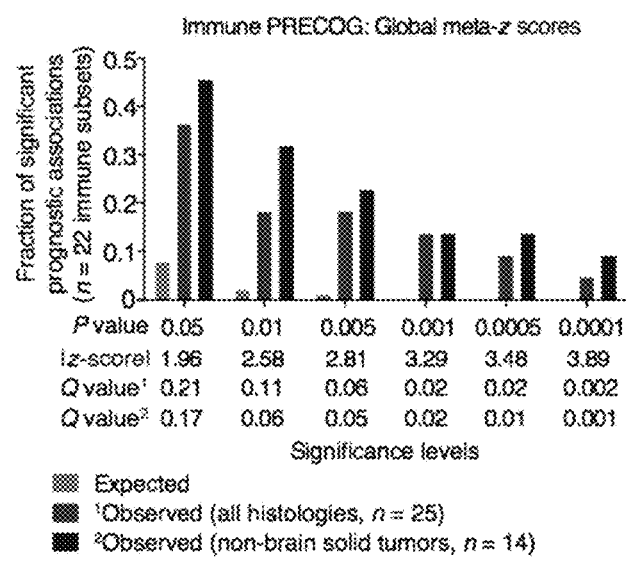

To complement the gene-centric survival analysis, a global map of prognostic associations for 22 immune populations across human malignancies was assembled (FIG. 26a). Considerable variation between cell subsets and cancer-specific outcomes was observed, and many of these associations are statistically significant (FIGS. 26b-26d). Pooling cancers yielded significant global leukocyte prognostic patterns, in which higher levels of estimated T-cell fractions were found to generally correlate with superior survival while increasing levels of myeloid populations primarily correlated with poorer survival. Intra-tumoral γδ cell[37,38] and polymorphonuclear (PMN)[39,40] signatures emerged as the most significant favorable and adverse cancer-wide prognostic populations, respectively (FIG. 23c, left). Moreover, when inferred leukocyte fractions were compared with KLRB1 expression across cancers, γδ T-cell and CD8 T-cell signatures were most highly correlated (FIG. 25b), suggesting a link to the prognostic significance of this gene. No relationship between estimated PMN levels was found in datasets with annotated necrotic tissue content (Methods), suggesting that intra-tumoral PMNs are not simply a correlate of tissue necrosis. Furthermore, consistent with previous reports, signatures of tumor-associated M2 macrophages were found to predict worse outcomes than pro-inflammatory M1 macrophages, and anti-CD3/anti-CD28-costimulated, but not resting, CD45RO$^+$ memory helper T-cells were correlated with superior outcomes.

FIGS. 26a-26d: Prognostic associations between 22 leukocyte subsets and 25 cancer histologies. (FIG. 26a) Heat map depicting relationships between hematopoietic subsets and survival, represented as a meta z-score matrix. Red cells denote adverse outcomes and green cells denote favorable outcomes. (FIG. 26b) False discovery rates of leukocyte prognostic associations. Comparison of null distribution of z-scores obtained from shuffling cell type fractions in immune-PRECOG (dashed black line) to a standard normal distribution shows high concordance. (FIG. 26c) Expected versus observed fractions of statistically significant associations between cell type proportions and outcome obtained by filtering results in FIG. 26a at various z-score cutoffs. P values and estimated FDRs are shown for each z-score value. The more stringent the cutoff, the higher the ratio of observed to expected significant associations (3-fold at P<0.05, 5-fold at P<0.01), indicating that immune-PRECOG captures statistically robust associations. (FIG. 26d) Similarly to FIG. 26b, but applied to global meta-z scores obtained from combining the individual cancer meta-z-scores across 25 cancer histologies or non-brain solid tumors (related to FIG. 23c). Details for FIG. 26b-26d are provided in Methods.

Prognostic TALs in Solid Tumors

By comparing leukocyte survival signatures in breast and lung cancer—two of the most highly profiled cancers in PRECOG—two populations were identified, PMNs and plasma cells (PCs), with unexpectedly strong yet reciprocal relationships to survival (FIG. 23d). PC signatures are significant predictors of favorable survival across solid tumors in general (FIG. 23c, right), and were the most inversely correlated prognostic population to PMNs (FIG. 24a) when assessed globally in a cross-correlation analysis between human cancers (FIG. 25c). Estimated PC levels were not correlated with tumor stage (FIG. 27a). Since PC signatures were found to be higher in tumors than in adjacent normal tissues (FIG. 27b), the prognostic value of tumor infiltrating PCs is unlikely a proxy for general immunological health, supporting a role for antigen-driven processes required for their clonal expansion and emergent humoral immune responses. Furthermore, a simple ratio of estimated PMN to PC levels was found to be significantly prognostic in diverse solid tumors (FIG. 24b).

FIG. 24: Ratio of infiltrating PMNs to plasma cells is prognostic in diverse solid tumors. (FIG. 24a) Prognostic associations between inferred PMN and plasma cell (PC) frequencies are significantly inversely correlated across the cancer landscape (Pearson R=−0.46, P=0.02). Each point represents an individual cancer: triangles, blood cancers; squares, brain cancers; circles, remaining cancers. (FIG.

24b) Meta-z scores depict the prognostic significance of combining PMN and PC levels into a ratiometric index, for diverse solid tumors (FIG. 24c) Comparison between CIBERSORT and tissue microarray analysis for PC, B-cell, and PMN frequencies in lung adenocarcinoma, using IGKC, CD20, and MPO, respectively, as surrogate markers for TMA (n=187 specimens). Lung adenocarcinoma arrays from publicly available datasets (GSE7670 and GSE10072) were analyzed with CIBERSORT (n=85 tumors). (d,e) Kaplan-Meier Plots depict patients stratified by (FIG. 24d) the median level of PMN to PC fractions inferred in lung adenocarcinoma microarray studies (P=0.0005, log-rank test; n=453 high and 453 low patients) and (FIG. 24e) the median level of MPO/IGKC stained positive in lung adenocarcinoma tissue sections (P=0.028, log-rank test; n=94 high and 93 low patients). Hazard ratios were 1.5 (1.2-1.9, 95% CI) for FIGS. 24d and 1.7 (1.1-2.6, 95% CI) for FIG. 24e. Inferred PMN to PC levels were also significantly prognostic in continuous models assessed by univariate Cox regression in FIG. 24d (P=0.003, Z=2.98) and e (P=0.0005, Z=3.46). Data in c are presented as means±s.e.m. All patients were right censored after 5 years in FIG. 24d and FIG. 24e.

FIGS. 27a-27h: Plasma cell levels in non-small cell lung cancer and adjacent normal tissues. (FIG. 27a) Relative RNA fractions of plasma cells inferred by CIBERSORT are independent of lung adenocarcinoma stage. (FIG. 27b) Relative fractions of 22 leukocyte subsets, as inferred by CIBERSORT, are compared between two independent microarray datasets (GSE7670 and GSE10072) containing both lung adenocarcinoma tumor and adjacent normal specimens. (FIGS. 27c, 27d) Representative H&E stains of lung adenocarcinoma tissue specimens. Stained lung adenocarcinoma tumor sections showing cells (indicated by arrows) that morphologically resemble (FIG. 27c) plasma cells and (FIG. 27d) neutrophils. (FIG. 27e-27h) Flow cytometric analysis and morphological assessment of plasmacytic cells in lung cancer. (FIG. 27e) Gating strategy for enrichment of $CD38^{high}/CD45^{high}/CD138^{low}/CD27^+/CD19^+/CD20^-$ cells from a lung adenocarcinoma tumor. As expected for plasmacytic cells, $CD38^{high}/CD45^{high}/CD138^{low}/CD27^+/CD19^+/CD20^-$ cells are larger than $CD38^-/CD45^{high}/CD138^-/CD27^+/CD19^+/CD20^+$ cells (B-cells) by forward and side scattering. (FIG. 27f) Using the gating strategy described in e, plasmacytic cells were sorted from a fresh lung adenocarcinoma tumor and isolated for microscopy by cytospinning. A representative cell with morphological features characteristic of plasmacytic cells is shown (100× oil objective lens). Representative flow cytometry results showing a considerable increase in plasmacytic cells in lung squamous cell carcinoma (FIG. 27g) and lung adenocarcinoma (FIG. 27h) tumors as compared to normal adjacent tissues.

Figure 27C:
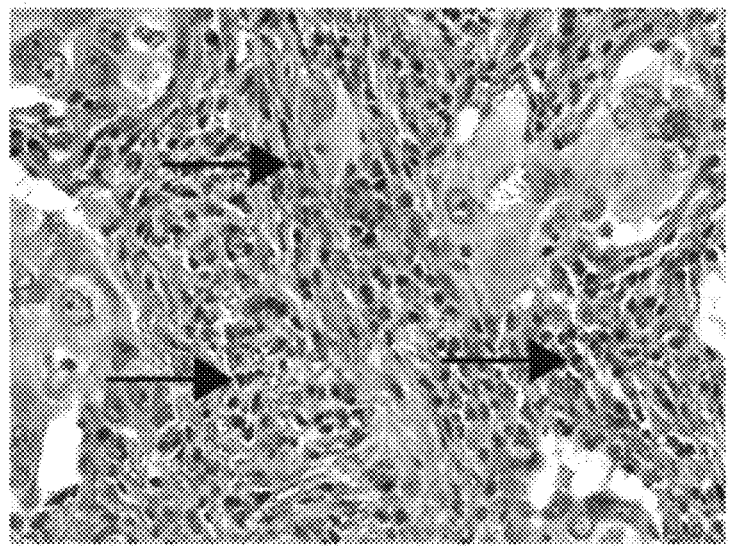
Figure 27D:
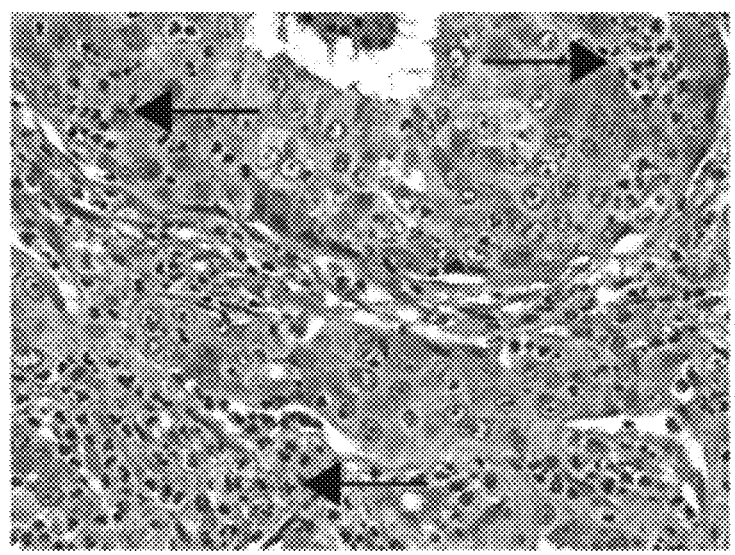
Figure 27E:
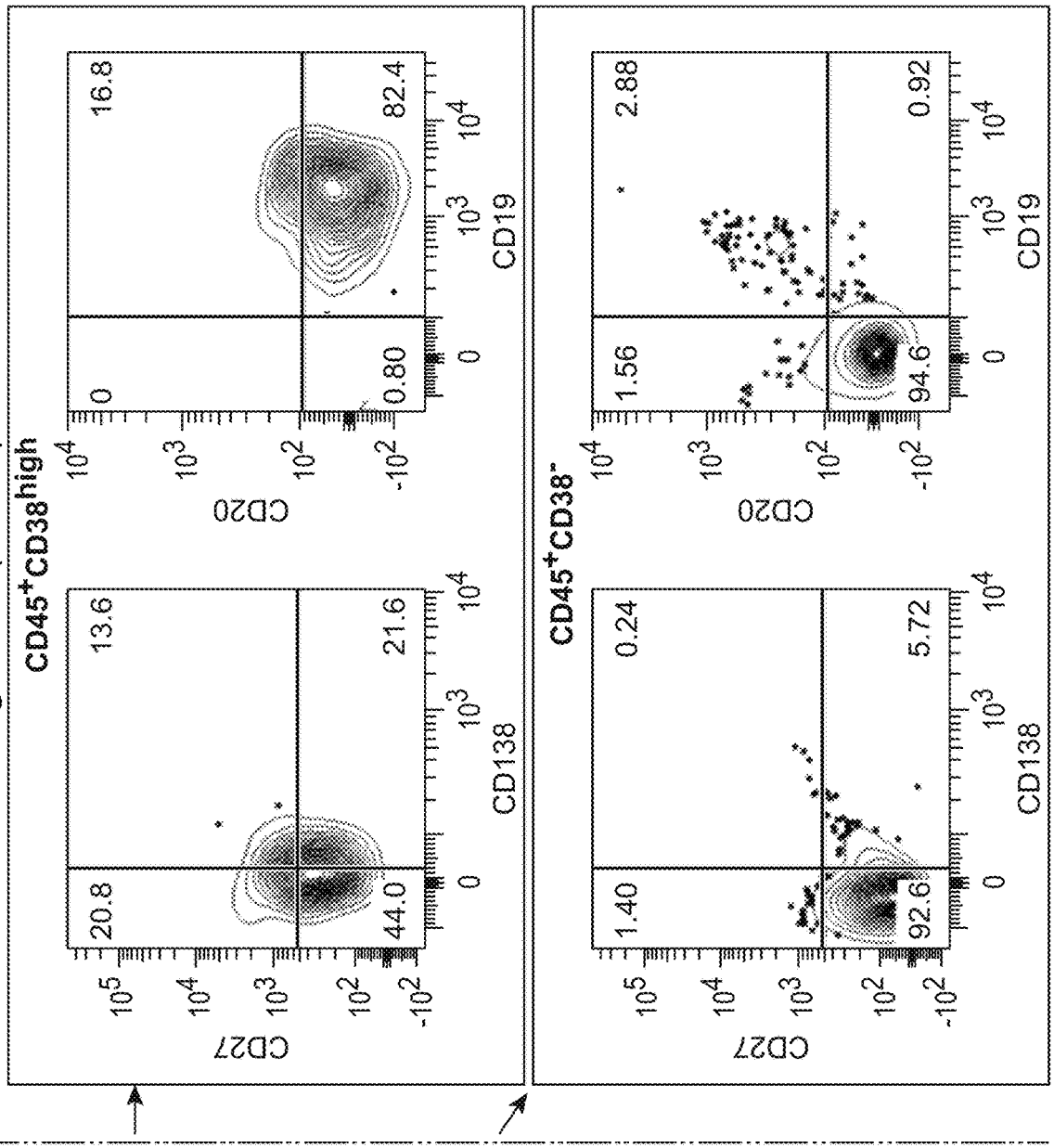

To experimentally evaluate the reciprocal survival associations of PMN and PC signatures, their infiltration of 187 lung adenocarcinomas was assessed using tissue microarray (TMA) analysis. Characteristics of both cell types were observed by H&E staining of tissue sections (FIGS. 27c, 27d), and the presence of tumor infiltrating plasmacytic cells (i.e., plasmablasts or plasma cells) was confirmed in fresh tumor specimens using both flow cytometry (FIG. 27e) and morphological assessment (FIG. 27f). Moreover, we confirmed an elevated presence of plasmacytic cells in non-small cell lung cancer (NSCLC) tumors, as compared to normal adjacent tissues (FIGS. 27g, 27h). In serial lung adenocarcinoma tissue sections, we stained for the presence of MPO (myeloperoxidase) and IGKC (Immunoglobulin kappa constant), markers of PMNs and PCs, respectively (FIG. 28a). Since B-cells express varying levels of IGKC, we also tested for CD20, a surface marker of mature B-cells but not PCs (FIG. 27e). We found <10% overlap with CD20, indicating the high specificity of IGKC for PCs (FIG. 28b; Methods). Next, we quantitated the staining area for each marker in the tissue array (Methods; FIGS. 28c, 28d). While operating on differing scales and measured on independent tumor specimens, fractional levels of these three markers measured in situ on TMAs were comparable to relative infiltrate levels inferred by CIBERSORT (FIG. 24c). Moreover, in both continuous and binary models, we found a strong relationship between inferior survival and a higher ratio of PMN to PC levels in lung adenocarcinoma, whether measured in PRECOG (FIG. 24d), in held-out microarray validation datasets (FIG. 28e), or by surrogate markers in tissue microarray specimens (FIG. 24e). Furthermore, TMA results remained significant in multivariate models incorporating relevant clinical parameters. Together, these data validate the computational approach, and demonstrate that tumor-associated PMNs and PCs exhibit opposite associations with overall survival.

FIGS. 8a-8e: Assessment of TMA markers and staining quantification, and prognostic significance of inferred PMN/PC levels in held-out expression datasets. (FIG. 28a) Representative lung adenocarcinoma tissue sections, stained by an RNA in situ probe targeting IGKC, or antibodies targeting CD20 or MPO. Top: Serial sections in which IGKC and CD20 are high and MPO is low. Bottom: Serial sections in which MPO is high and IGKC/CD20 are low. Staining was quantified by GemIdent image analysis software[4] and post-processing (Methods). (FIG. 28b) Histogram of the spatial overlap between IGKC and CD20 stains in adjacent lung adenocarcinoma tissue sections (median overlap of ~4.8%). (FIG. 28c) Concordance between IGKC staining assessment by a pathologist (R.W.) and by GemIdent (Methods) for 10 randomly selected lung adenocarcinoma specimens. (FIG. 28d) GemIdent was trained to recognize CD20 staining by two different operators, and the results are plotted for all lung adenocarcinoma specimens. (FIG. 28e) Survival analysis of the ratio of PMNs to PCs in held-out lung adenocarcinoma datasets. Plasmacytic cell and neutrophil fractions estimated by CIBERSORT were used to compute their ratio in three lung cancer datasets not included in PRECOG. Patients were stratified into high or low groups based on the median value of the PMN:PC ratio in each dataset. This permitted merging of the three cohorts into one combined dataset of sufficient size for survival analysis. Hazard ratio (HR) with 95% confidence interval is shown along with P value in Cox regression (log-rank test).

Circulating leukocytes, including PMNs and B-lymphocytes contribute to the tumor microenvironment, and leukocyte frequencies of innate and adaptive effectors in peripheral blood can have prognostic value. Therefore, a subset of NSCLC patients from the TMA was examined with available peri-operative complete blood counts to assess the concordance between levels of circulating leukocytes and TALs. While intra-tumoral PMN to PC ratios remained significantly prognostic within this subset, no significant correlation between circulating and infiltrating compartments was found, and no prognostic value from circulating leukocyte levels was found.

While the present disclosure has been described with reference to the specific embodiments thereof, it should be understood by those skilled in the art that various changes may be made and equivalents may be substituted without departing from the true spirit and scope of the present disclosure. In addition, many modifications may be made to adapt a particular situation, material, composition of matter, process, process step or steps, to the objective, spirit and scope of the present disclosure. All such modifications are intended to be within the scope of the claims appended hereto.

What is claimed is:

1. A method comprising:
   (a) providing a biological sample derived from a subject having cancer, the biological sample comprising a plurality of cell populations;
   (b) assaying said biological sample to generate a feature profile, wherein said feature profile comprises a gene expression profile, a genotype profile, a protein expression profile, a protein-protein interaction profile, a protein phosphorylation profile, a cellular electrical activity profile, a chromatin modification profile, a chromosome binding profile, an enzymatic activity profile, a metabolite profile, a nuclear magnetic resonance (NMR) spectrum, an electromagnetic radiation absorbance or emission spectrum, a circular dichroism spectrum, a Raman spectrum, a mass spectrum, a chromatogram, or a combination thereof;
   (c) computer processing said feature profile to determine (i) an estimation of relative proportions of at least one of said plurality of cell populations in said biological sample, and (ii) a significance value for said estimation;
   (d) predicting a clinical outcome of a cancer therapy for said cancer, based at least in part on said estimation of said relative proportions of said at least one of said plurality of cell populations in said biological sample; and
   (e) administering said cancer therapy to said subject based on said predicted clinical outcome of said cancer therapy, wherein said cancer therapy comprises a member selected from the group consisting of a chemotherapy, an immunotherapy, and an immunochemotherapy.

2. The method of claim 1, wherein (b) further comprises assaying deoxyribonucleic acid (DNA) or ribonucleic acid (RNA) of cells in said biological sample.

3. The method of claim 1, wherein (c) further comprises:
   (i) optimizing a regression between a feature profile m and a reference matrix B of feature signatures for a second feature profile, wherein said feature profile m is modeled as a linear combination of said reference matrix B of feature signatures, wherein said optimization of said regression comprises solving for f comprising a set of regression coefficients of said regression, and wherein said optimization of said regression minimizes: a linear loss function; and an L2-norm penalty function; and
   (ii) estimating, based on said optimization of said regression, said relative proportions of said at least one of said plurality of cell populations in said biological sample.

4. The method of claim 1, wherein said feature profile m is said gene expression profile.

5. The method of claim 1, wherein said cancer comprises a blood cancer.

6. The method of claim 1, wherein said biological sample comprises a tumor biopsy.

7. The method of claim 1, wherein said estimation of said relative proportions of said at least one of said plurality of cell populations in said biological sample comprises an estimation of a fractional representation of said at least one of said plurality of cell populations in said biological sample.

8. The method of claim 7, further comprising determining a prognosis for said cancer based at least in part on a comparison between (i) said estimation of said fractional representation of said at least one of said plurality of cell populations in said biological sample and (ii) a reference fractional representation of said at least one of said plurality of cell populations in one or more reference samples.

9. The method of claim 8, wherein said one or more reference samples are derived from a cohort of subjects having said cancer and/or a cohort of subjects without said cancer.

10. The method of claim 7, wherein said clinical outcome of said cancer therapy for said cancer is predicted based at least in part on a comparison between (i) said estimation of said fractional representation of said at least one of said plurality of cell populations in said biological sample and (ii) a reference fractional representation of said at least one of said plurality of cell populations in one or more reference samples.

11. The method of claim 1, wherein said immunochemotherapy comprises a combination of rituximab, cyclophosphamide, doxorubicin, vincristine, and prednisone (R-CHOP).

12. The method of claim 1, wherein said immunotherapy comprises rituximab.

13. The method of claim 1, wherein said subject has received said cancer therapy for said cancer.

14. The method of claim 1, wherein (d) further comprises determining that a first cell population of said plurality of cell populations is undetectable in said biological sample.

15. The method of claim 14, wherein said first cell population is a population of lymphoma cells.

16. The method of claim 14, wherein said first cell population is a population of immune cells.

17. The method of claim 1, wherein (d) further comprises determining said estimation of said fractional representation of a population of cancer cells in said biological sample.

18. The method of claim 17, wherein said population of cancer cells comprises blood cancer cells, breast cancer cells, colon cancer cells, lung cancer cells, prostate cancer cells, hepatocellular cancer cells, gastric cancer cells, pancreatic cancer cells, cervical cancer cells, ovarian cancer cells, liver cancer cells, bladder cancer cells, urinary tract cancer cells, thyroid cancer cells, renal cancer cells, carcinoma cells, melanoma cells, or brain cancer cells.

19. The method of claim 1, wherein (d) further comprises determining said estimation of said fractional representation of a population of tumor infiltrating leukocytes in said biological sample.

20. The method of claim 1, wherein said biological sample comprises a blood sample.

21. The method of claim 1, wherein said cancer therapy comprises said chemotherapy.

22. The method of claim 1, wherein said cancer therapy comprises said immunotherapy.

23. The method of claim 1, wherein said cancer therapy comprises said immunochemotherapy.

* * * * *